US012435134B2

(12) United States Patent
Lee et al.

(10) Patent No.: US 12,435,134 B2
(45) Date of Patent: Oct. 7, 2025

(54) ANTAGONISTS ANTI-CD7 ANTIBODIES

(71) Applicant: KYMAB LIMITED, Cambridge (GB)

(72) Inventors: E-Chiang Lee, Cambridge (GB); Gwenoline Borhis, Cambridge (GB); Cassandra Van Krinks, Cambridge (GB); Lucy Hepburn, Cambridge (GB); Luke Bayliss, Cambridge (GB); Miha Kosmac, Cambridge (GB)

(73) Assignee: KYMAB LIMITED, Cambridge (GB)

( * ) Notice: Subject to any disclaimer, the term of this patent is extended or adjusted under 35 U.S.C. 154(b) by 1028 days.

(21) Appl. No.: 17/604,209

(22) PCT Filed: Apr. 17, 2020

(86) PCT No.: PCT/GB2020/050976
§ 371 (c)(1),
(2) Date: Oct. 15, 2021

(87) PCT Pub. No.: WO2020/212710
PCT Pub. Date: Oct. 22, 2020

(65) Prior Publication Data

US 2022/0324968 A1 Oct. 13, 2022

(30) Foreign Application Priority Data

Apr. 18, 2019 (GB) ..................................... 1905552

(51) Int. Cl.
*C07K 16/28* (2006.01)
*A61K 39/00* (2006.01)
*A61K 39/395* (2006.01)
*A61K 45/06* (2006.01)
*A61P 35/02* (2006.01)

(52) U.S. Cl.
CPC .... *C07K 16/2803* (2013.01); *A61K 39/39558* (2013.01); *A61K 45/06* (2013.01); *A61P 35/02* (2018.01); *A61K 2039/505* (2013.01); *C07K 2317/33* (2013.01); *C07K 2317/34* (2013.01); *C07K 2317/565* (2013.01); *C07K 2317/732* (2013.01); *C07K 2317/734* (2013.01)

(58) Field of Classification Search
CPC ............ C07K 16/2803; C07K 2317/33; C07K 2317/34; C07K 2317/565; C07K 2317/732; C07K 2317/734; C07K 2317/21; C07K 2317/70; C07K 2317/92; C07K 2317/94; A61K 39/39558; A61K 45/06; A61K 2039/505; A61P 35/02
See application file for complete search history.

(56) References Cited

U.S. PATENT DOCUMENTS

2017/0226204 A1* 8/2017 Yang ................. C07K 16/2803

FOREIGN PATENT DOCUMENTS

| | | | | |
|---|---|---|---|---|
| WO | WO 1995/031212 A1 | | 11/1995 | |
| WO | WO-2005040220 A1 | * | 5/2005 | .............. A61P 19/02 |
| WO | WO 2008/003103 A2 | | 1/2008 | |
| WO | WO-2013041844 A2 | * | 3/2013 | ......... A01K 67/0275 |
| WO | WO 2015/103072 A1 | | 7/2015 | |
| WO | WO 2017/220990 A1 | | 12/2017 | |
| WO | WO 2018/029474 A2 | | 2/2018 | |
| WO | WO-2018025178 A1 | * | 2/2018 | .............. A61P 31/00 |

OTHER PUBLICATIONS

Rudikoff et. al. "Single amino acid substituion altering antigen-binding specificity", PNAS vol. 79 pp. 1979-1983 (Year: 1982).*
Almagro et. al., Front. Immunol. 2018; 8:1751 (Year: 2018).*
Chiu ML et al. Antibodies Aug. 2019, 55, 1-80 (Year: 2019).*
Pauza ME, Doumbia SO, Pennell CA. Construction and characterization of human CD7-specific single-chain Fv immunotoxins. J Immunol. Apr. 1, 1997;158(7):3259-69. PMID: 9120282 (Year: 1997).*
Gershoni et al., Epitope Mapping, Biodrugs 2007; 21 (3) (Year: 2007).*
Blythe et al., Benchmarking B cell epitope prediction: Underperformance of existing methods, Protein Science (2005), 14:246-248 p. 246 (Year: 2005).*
Schreiber et al.,3D-Epitope-Explorer (3DEX): Localization of Conformational Epitopes within Three-Dimensional Structures of Proteins, Wiley Interscience, 42-44, 60596, p. 879 (Year: 2005).*
Lichtman MA et al. The Oncologist2017; 22(5); 542-548 (Year: 2017).*
Hanahan D et al. Cell 2011 144(5) p. 646-674 (Year: 2011).*
Lee KW et al. Nature Reviews Cancer Nov. 2011 211-218, p. 211 (Year: 2011).*
Janeway CA Jr, Travers P, Walport M, et al. Immunobiology: The Immune System in Health and Disease. 5th edition. New York: Garland Science; 2001. The structure of a typical antibody molecule. Available from: https://www.ncbi.nlm.nih.gov/books/NBK27144/ (Year: 2001).*
Ostermeier C, Michel H. Improved cloning of antibody variable regions from hybridomas by an antisense-directed RNase H digestion of the P3-X63-Ag8.653 derived pseudogene mRNA. Nucleic Acids Res. May 15, 1996;24(10):1979-80. doi: 10.1093/nar/24.10.1979. PMID: 8657583; PMCID: PMC145887 (Year: 1996).*
NCT03690011 "Cell Therapy for High Risk T-Cell Malignancies Using CD7-Specific CAR Expressed on Autologous T Cells" by Baylor College of Medicine first published Oct. 1, 2018 (Year: 2018).*
Flavell DJ, Cooper S, Morland B, Flavell SU. Characteristics and performance of a bispecific F (ab'gamma)2 antibody for delivering saporin to a CD7+ human acute T-cell leukaemia cell line. Br J Cancer. Aug. 1991;64(2):274-80. doi: 10.1038/bjc.1991.291. PMID: 1716453; PMCID: PMC1977495. (Year: 1991).*

(Continued)

*Primary Examiner* — Janet L Epps-Smith
*Assistant Examiner* — Kathleen Cunningchen
(74) *Attorney, Agent, or Firm* — LATHROP GPM LLP; James H. Velema, Esq.

(57) ABSTRACT

The invention relates to Cluster of Differentiation 7 (CD7) antagonists, such as antibodies and fragments, as well as methods, uses and combinations.

22 Claims, 34 Drawing Sheets

Specification includes a Sequence Listing.

(56) References Cited

OTHER PUBLICATIONS

Aandahl et al., "CD7 Is a Differentiation Marker That Identifies Multiple CD8 T Cell Effector Subsets", J Immunol, Mar. 1, 2003, 170(5): 2349-2355.
Agnusdei et al., "Therapeutic antibody targeting of Notchl in T-acute lymphoblastic leukemia xenografts", Leukemia, Feb. 2014, 28(2): 278-288.
Aldoss et al., "Redirecting T cells to eradicate B-cell acute lymphoblastic leukemia: bispecific", Leukemia, Apr. 2017, 31(4): 777-787.
Barcena et al. "Phenotypic and functional analysis ofT-cell precursors in the human fetal liver and thymus: CD7 expression in the early stages ofT- and myeloid-cell development", Blood, Dec. 1, 1993, 82(11): 3401-3414.
Baum et al., "Therapy with CD7 monoclonal antibody TH-69 is highly effective for xenografted human T-cell ALL", Br J Haematol., Nov. 1996, 95(2): 327-338.
Carriere et al., "Antigenic modulation induced by four monoclonal antibodies adsorbed on gold particles (specificity anti-CD4, anti-CDS, anti-CD7, and anti-150-kDa antigen): Relationship between modulation and cytotoxic activity of immunotoxins", Exp Cell Res., May 1989, 182(1): 114-128.
Cooper et al., "An "off-the-shelf" fratricide-resistant CAR-T for the treatment of T cell hematologic malignancies", Leukemia, Sep. 2018, 32(9): 1970-1983.
Coustan-Smith et al., "Early T-cell precursor leukaemia: a subtype of very high-risk acute lymphoblastic leukaemia", Lancet Oneal., Feb. 2009, 10(2): 147-156.
De Jong et al., "A Novel Platform for the Potentiation of Therapeutic Antibodies Based on Antigen-Dependent Formation of IgG Hexamers at the Cell Surface", PLoS Biol., Jan. 2016, 14(1): e1002344, pp. 1-24.
Deangelo et al. "Nelarabine induces complete remissions in adults with relapsed or refractory", Blood, Jun. 15, 2007, 109(12): 5136-5142.
Diebolder et al. "Complement is activated by IgG hexamers assembled at the cell surface", Science, Mar. 14, 2014, 343(6176): 1260-1263.
Digiammarino et al., (2012) "Design and Generation of DVD-Ig™ Molecules for Dual-Specific Targeting", Therapeutic Proteins, Methods in Molecular Biology (Methods and Protocols), vol. 899, Chapter 9, pp. 145-156, https://doi.org/10.1007/978-1-61779-921-1_9.
Dillon et al., "Systemic lupus erythematosus and C1q: A quantitative ELISA for determining C1q levels in serum", Biotechnol J., Aug. 2009, 4(8): 1210-1214.
Frankel et al., "Therapy of patients with T-cell lymphomas and leukemias using an anti-CD7 monoclonal antibody-ricin A chain immunotoxin", Leuk Lymphoma, Jul. 1997, 26(3-4): 287-298.
Gramatzki et al. (1993), "158: T-ALL therapy in a preclinical model: The CD7 antibody TH-69 is highly active", Annals Hematology, 63(1): A41.
Haapaniemi et al., "CRISPR-Cas9 genome editing induces a p53-mediated DNA damage response", Nat Med., Jul. 2018, 24(7): 927-930.
Hao et al., "Human intrathymic lineage commitment is marked by differential CD7 expression: identification of CD7—lympho-myeloid thymic progenitors", Blood, Feb. 1, 2008, 111(3): 1318-1326.
Heinrich et al., "Characterization of a human T cell-specific chimeric antibody (CD7) with human constant and mouse variable regions", J Immunol., Dec. 1, 1989, 143(11): 3589-3597.
Hirata et al. (1987), "Differential prognosis detected by immunophenotyping in acute lymphoblastic leukemia of childhood with poor prognostic factors", Japanese Journal of Clinical Oncology, 17(3): 229-235.
International Search Report and Written Opinion for PCT International Application No. PCT/GB2020/050976, mailed Jul. 20, 2020.
Jain et al., "Early T-cell precursor acute lymphoblastic leukemia/lymphoma (ETP-ALL/LBL) in adolescents and adults: a high-risk subtype", Blood, Apr. 14, 2016, 127(15): 1863-1869.
Jansen et al. (Mar. 1, 1992) "Successful treatment of human acute T-cell leukemia in SCIO mice using the anti-CD7-deglycosylated ricin A-chain immunotoxin DA7", Cancer Research, 52: 1314-1321.
Jung et al., "CD7 augments T cell proliferation via the interleukin-2 autocrine pathway", Cell Immunol., Apr. 15, 1992, 141(1): 189-199.
Kabat et al., "Attempts to Locate Complementarity-Determining Residues in the Variable Positions of Light and Heavy Chains", (1971) Annals New York Academy of Sciences, 190: 382-391.
Keizer et al., "The High Prevalence of Functional Complement Defects Induced by Chemotherapy", Front Immunol., Oct. 17, 2016, 7(420): 1-14.
Kita et al., "Clinical importance of CD7 expression in acute myelocytic leukemia", Blood, May 1, 1993, 81(9): 2399-2405.
Kola et al., "Epitope mapping of a C5a neutralizing mAb using a combined approach of phage display, synthetic peptides and site directed mutagenesis", Immunotechnology, Jun. 1996, 2(2): 115-126.
Kosicki et al., "Repair of double-strand breaks induced by CRISPR-Cas9 leads to large deletions and complex rearrangements", Nature Biotechnology, Aug. 2018, 36(8): 765-771.
Lee et al., "Antibodies to a conformational epitope on gp41 neutralize HIV-1 by destabilizing the Env spike", Nature communications, Sep. 25, 2015, 6(8167): 1-14.
Lee et al., "Complete humanization of the mouse immunoglobulin loci enables efficient therapeutic antibody discovery", Nat Biotechnol., Apr. 2014, 32(4): 356-363.
Lee et al., "Immunologic characterization of CD7-deficient mice", J Immunol., Jun. 15, 1998, 160(12): 5749-5756.
Lefranc, M. P., "Unique database numbering system for immunogenetic analysis", Immunol. Today, Nov. 1997, 18(11): 509.
Markiewski et al., "The role of complement in inflammatory diseases from behind the scenes into the spotlight", Am J Pathol., Sep. 2007, 171(3): 715-727.
Marks et al., "T-cell acute lymphoblastic leukemia in adults: clinical features, immunophenotype, cytogenetics, and outcome from the large randomized prospective trial (UKALL XII/ECOG 2993)", Blood, Dec. 10, 2009, 114(25): 5136-5145.
Matlung et al., "Neutrophils Kill Antibody-Opsonized Cancer Cells by Trogoptosis", Cell Rep., Jun. 26, 2018, 23(13): 3946-3959, e1-e6.
Niederfellner et al., "Epitope characterization and crystal structure of GA101 provide insights into the molecular basis for type 1/11 distinction of CD20 antibodies", Blood, Jul. 14, 2011, 118(2): 358-367.
Phanse et al., "Analyzing cellular internalization of nanoparticles and bacteria by multi-spectral imaging flow cytometry", J Vis Exp., 2012, (64), e3884, pp. 1-6.
Png et al., "Blockade of CD7 expression in T cells for effective chimeric antigen receptor targeting of T-cell malignancies", Blood Adv., Nov. 28, 2017, 1(25): 2348-2360.
Rabinowich et al., "Signaling via CD7 molecules on human NK cells. Induction of tyrosine phosphorylation and beta 1 integrin-mediated adhesion to fibronectin", J Immunol., Oct. 15, 1994, 153(8): 3504-3513.
Rappl et al., "CD4+CD7-leukemic T cells from patients with Sezary syndrome are protected from galectin-1-triggered T cell death", Leukemia, May 2002, 16(5): 840-845.
Ravandi et al., "Phase II study of alemtuzumab in combination with pentostatin in patients with T-cell neoplasms", J Clin Oncol., Nov. 10, 2009, 27(32): 5425-5430.
Reinhold et al., "CD4+ CD7—T cells: a separate subpopulation of memory T cells?", J Clin Immunol., Jul. 1997, 17(4): 265-271.
Röhrs et al., "Quentmeier H. CD7 in acute myeloid leukemia: correlation with loss of wild-type CEBPA, consequence of epigenetic regulation", J Hematol & Oncol., Apr. 14, 2010, 3: 15.
Sempowski et al., "Resistance of CD7-deficient mice to lipopolysaccharide-induced shock syndromes", J Exp Med., Mar. 15, 1999, 189(6): 1011-1016.
Sharma et al., "Human mouse chimeric CD7 monoclonal antibody (SDZCHH380) for the prophylaxis of kidney transplant rejection: analysis beyond 4 years", Transplant Proc., Mar. 1997, 29(1-2): 323-324.

(56) References Cited

OTHER PUBLICATIONS

Spiess et al., "Alternative molecular formats and therapeutic applications for bispecific antibodies", Mol Immunol., Oct. 2015, 67: 95-106.
Suckau et al., "Molecular epitope identification by limited proteolysis of an immobilized antigen-antibody complex and mass spectrometric peptide mapping", Proceedings of the National Academy of Sciences USA, Dec. 1990, 87(24): 9848-9852.
Tang et al. (2016), "Novel CD7-specific nanobody-based immunotoxins potently enhanced apoptosis of CD7-positive malignant cells", Oncotarget, 7(23): 34070-34083.
Vallera et al. (1996), "Laboratory preparation of a deglycosylated ricin toxin A chain containing immunotoxin directed against a CD7 T lineage differentiation antigen for phase I human clinical studies involving T cell malignancies", Journal of Immunological Methods, 197: 69-83.
Van Vlierberghe et al., "The molecular basis of T cell acute lymphoblastic leukemia", J Clin Invest., Oct. 2012, 122(10): 3398-3406.
Ware et al., "Induction of T cell CD7 gene transcription by nonmitogenic ionomycin-induced transmembrane calcium flux", J Immunol., Oct. 1991, 147(8): 2787-2794.
Ware et al., "T cell CD7 mRNA expression is regulated by both transcriptional and post-transcriptional mechanisms", Int Immunol., Feb. 1993, 5(2): 179-187.
Hamada et al., 633. Myelodysplastic Syndromes: Poster II "CD7 Expression On Blasts Of Myelodysplastic Syndromes Is Associated With Apoptosis Resistance With Decreased Expression of the Proapoptotic Protein Bad and An Independent Unfavorable Prognostic Factor Together With The Revised IPSS Score In Patients", Blood, Nov. 15, 2013, 122(21): 2799.
Satoh et al., "Aggressive characteristics of myeloblasts expressing CD7 in myelodysplastic syndromes", Leukemia Research, 2009, 33: 326-331, Epublished Aug. 20, 2008.

* cited by examiner

A.

B.

B. *In vivo* passage non-relapsed T-ALL cell lines c. *In vivo* passage non-relapsed T-ALL cell lines

SEQUENCE LISTING

```
<160> NUMBER OF SEQ ID NOS: 149

<210> SEQ ID NO 1
<211> LENGTH: 8
<212> TYPE: PRT
<213> ORGANISM: Homo Sapien

<400> SEQUENCE: 1

Gly Phe Ser Phe Ser Val Ala Trp
1               5


<210> SEQ ID NO 2
<211> LENGTH: 10
<212> TYPE: PRT
<213> ORGANISM: Homo Sapien

<400> SEQUENCE: 2

Ile Lys Arg Lys Thr Asp Gly Gly Thr Thr
1               5                   10


<210> SEQ ID NO 3
<211> LENGTH: 20
<212> TYPE: PRT
<213> ORGANISM: Homo Sapien

<400> SEQUENCE: 3

Thr Thr Asp Pro Leu Leu Arg Tyr Ser Asp Trp Leu Ser His Ser Leu
1               5                   10                  15

Met Gly Asp Val
            20


<210> SEQ ID NO 4
<211> LENGTH: 6
<212> TYPE: PRT
<213> ORGANISM: Homo Sapien

<400> SEQUENCE: 4

Ser Val Ala Trp Met Ser
1               5


<210> SEQ ID NO 5
<211> LENGTH: 19
<212> TYPE: PRT
<213> ORGANISM: Homo Sapien

<400> SEQUENCE: 5

Arg Ile Lys Arg Lys Thr Asp Gly Gly Thr Thr Asp Tyr Ala Ala Pro
1               5                   10                  15
```

Val Lys Gly

<210> SEQ ID NO 6
<211> LENGTH: 18
<212> TYPE: PRT
<213> ORGANISM: Homo Sapien

<400> SEQUENCE: 6

Asp Pro Leu Leu Arg Tyr Ser Asp Trp Leu Ser His Ser Leu Met Gly
1               5                   10                  15

Asp Val

<210> SEQ ID NO 7
<211> LENGTH: 129
<212> TYPE: PRT
<213> ORGANISM: Homo Sapien

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Val Ala
            20                  25                  30

Trp Met Ser Trp Val Arg Gln Ala Pro Gly Lys Gly Leu Glu Trp Val
        35                  40                  45

Gly Arg Ile Lys Arg Lys Thr Asp Gly Gly Thr Thr Asp Tyr Ala Ala
    50                  55                  60

Pro Val Lys Gly Arg Phe Ile Ile Ser Arg Asp Asp Ser Ile Lys Ala
65                  70                  75                  80

Leu Tyr Leu Gln Met Asn Ser Leu Lys Thr Glu Asp Thr Ala Val Tyr
                85                  90                  95

Tyr Cys Thr Thr Asp Pro Leu Leu Arg Tyr Ser Asp Trp Leu Ser His
            100                 105                 110

Ser Leu Met Gly Asp Val Trp Gly Gln Gly Thr Thr Val Thr Val Ser
        115                 120                 125

Ser

<210> SEQ ID NO 8
<211> LENGTH: 388
<212> TYPE: DNA
<213> ORGANISM: Homo Sapien

<400> SEQUENCE: 8
gaggtgcagc tggtggagtc tgggggaggc ttggtaaagc ctggggggtc ccttagactc     60
tcctgtgcag cctctggatt cagtttcagt gtcgcctgga tgagctgggt ccgccaggct    120
ccagggaagg ggctggagtg ggttggccgt attaagcgca aaactgatgg tgggacaaca    180
gactacgctg cacccgtgaa aggcagattc atcatctcaa gagatgattc aataaaagcg    240
ctgtatctgc aaatgaacag cctgaaaacc gaggacacag ccgtgtatta ctgtaccaca    300
gatcccttat tacgatattc tgactggtta tcccactccc ttatggggga cgtctggggc    360
caagggacca cggtcaccgt ctcctcag                                        388

<210> SEQ ID NO 9
<211> LENGTH: 458
<212> TYPE: PRT
<213> ORGANISM: Homo Sapien

<400> SEQUENCE: 9

-continued

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Phe Ser Val Ala
            20                  25                  30

Trp Met Ser Trp Val Arg Gln Ala Pro Gly Lys Gly Leu Glu Trp Val
        35                  40                  45

Gly Arg Ile Lys Arg Lys Thr Asp Gly Gly Thr Thr Asp Tyr Ala Ala
    50                  55                  60

Pro Val Lys Gly Arg Phe Ile Ile Ser Arg Asp Asp Ser Ile Lys Ala
65                  70                  75                  80

Leu Tyr Leu Gln Met Asn Ser Leu Lys Thr Glu Asp Thr Ala Val Tyr
                85                  90                  95

Tyr Cys Thr Thr Asp Pro Leu Leu Arg Tyr Ser Asp Trp Leu Ser His
            100                 105                 110

Ser Leu Met Gly Asp Val Trp Gly Gln Gly Thr Thr Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Asp
        355                 360                 365

Glu Leu Thr Lys Asn Gln Val Ser Leu Thr Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
```

```
        420                 425                 430

Asn Val Phe Ser Cys Ser Val Met His Gly Ala Leu His Asn His Tyr
    435                 440                 445

Thr Gln Lys Ser Leu Ser Leu Ser Pro Gly
450                 455
```

<210> SEQ ID NO 10
<211> LENGTH: 1375
<212> TYPE: DNA
<213> ORGANISM: Homo Sapien

<400> SEQUENCE: 10

```
gaggtgcagc tggtggagtc tgggggaggc ttggtaaagc ctgggggtc ccttagactc     60
tcctgtgcag cctctggatt cagtttcagt gtcgcctgga tgagctgggt ccgccaggct    120
ccagggaagg ggctggagtg ggttggccgt attaagcgca aaactgatgg tgggacaaca    180
gactacgctg cacccgtgaa aggcagattc atcatctcaa gagatgattc aataaaagcg    240
ctgtatctgc aaatgaacag cctgaaaacc gaggacacag ccgtgtatta ctgtaccaca    300
gatcccttat tacgatattc tgactggtta tcccactccc ttatggggga cgtctggggc    360
caagggacca cggtcaccgt ctcctcaggc cagcaccaag ggcccctctg tgttccctct    420
ggccccttcc agcaagtcca cctctggcgg aacagccgct ctgggctgcc tcgtgaagga    480
ctacttcccc gagcctgtga ccgtgtcctg gaactctggc gctctgacca gcggagtgca    540
caccttccct gctgtgctgc agtcctccgg cctgtactcc ctgtcctccg tcgtgaccgt    600
gccttccagc tctctgggca cccagaccta catctgcaac gtgaaccaca agccctccaa    660
caccaaggtg gacaagaagg tggaacccaa gtcctgcgac aagacccaca cctgtccccc    720
ttgtcctgcc cctgaactgc tgggcggacc ttccgtgttc ctgttccccc caaagcccaa    780
ggacaccctg atgatctccc ggacccccga agtgacctgc gtggtggtgg atgtgtccca    840
cgaggaccct gaagtgaagt tcaattggta cgtggacggc gtggaagtgc acaacgccaa    900
gaccaagcct agagaggaac agtacaactc cacctaccgg gtggtgtccg tgctgaccgt    960
gctgcaccag gattggctga acggcaaaga gtacaagtgc aaggtgtcca acaaggccct   1020
gcctgccccc atcgaaaaga ccatctccaa ggccaagggc cagccccggg aaccccaggt   1080
gtacacactg cccccctagca gggacgagct gaccaagaac caggtgtccc tgacctgtct   1140
cgtgaaaggc ttctacccct ccgatatcgc cgtggaatgg gagtccaacg gccagcctga   1200
gaacaactac aagaccaccc cccctgtgct ggactccgac ggctcattct tcctgtacag   1260
caagctgaca gtggacaagt cccggtggca gcagggcaac gtgttctcct gctccgtgat   1320
gcacggcgcc ctgcacaacc actacaccca gaagtccctg tccctgagcc ccggc        1375
```

<210> SEQ ID NO 11
<211> LENGTH: 6
<212> TYPE: PRT
<213> ORGANISM: Homo Sapien

<400> SEQUENCE: 11

```
Gln Asn Ile Asn Asn Tyr
1               5
```

<210> SEQ ID NO 12
<211> LENGTH: 3
<212> TYPE: PRT
<213> ORGANISM: Homo Sapien

```
<400> SEQUENCE: 12

Ala Ala Ser
1


<210> SEQ ID NO 13
<211> LENGTH: 13
<212> TYPE: PRT
<213> ORGANISM: Homo Sapien

<400> SEQUENCE: 13

Gln Gln Thr Tyr Ser Ile Pro Leu Thr Phe Gly Gly Gly
1               5                   10


<210> SEQ ID NO 14
<211> LENGTH: 5
<212> TYPE: PRT
<213> ORGANISM: Homo Sapien

<400> SEQUENCE: 14

Asn Asn Tyr Leu Asn
1               5


<210> SEQ ID NO 15
<211> LENGTH: 12
<212> TYPE: PRT
<213> ORGANISM: Homo Sapien

<400> SEQUENCE: 15

Tyr Ala Ala Ser Ser Leu Gln Ser Gly Val Pro Ser
1               5                   10


<210> SEQ ID NO 16
<211> LENGTH: 13
<212> TYPE: PRT
<213> ORGANISM: Homo Sapien

<400> SEQUENCE: 16

Gln Gln Thr Tyr Ser Ile Pro Leu Thr Phe Gly Gly Gly
1               5                   10


<210> SEQ ID NO 17
<211> LENGTH: 107
<212> TYPE: PRT
<213> ORGANISM: Homo Sapien

<400> SEQUENCE: 17

Asp Ile Gln Met Thr Gln Ser Pro Ser Ser Leu Ser Ala Ser Val Gly
1               5                   10                  15

Asp Arg Val Ala Ile Thr Cys Arg Thr Ser Gln Asn Ile Asn Asn Tyr
            20                  25                  30

Leu Asn Trp Tyr Gln Gln Lys Pro Gly Lys Ala Pro Lys Pro Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Thr Leu His Pro
65                  70                  75                  80

Glu Asp Phe Ala Thr Tyr Tyr Cys Gln Gln Thr Tyr Ser Ile Pro Leu
                85                  90                  95

Thr Phe Gly Gly Gly Thr Lys Val Glu Ile Lys
            100                 105
```

<210> SEQ ID NO 18
<211> LENGTH: 321
<212> TYPE: DNA
<213> ORGANISM: Homo Sapien

<400> SEQUENCE: 18
gatatccaga tgacccagtc cccctccagc ctgtctgcct ctgtgggcga cagagtggcc 60
atcacctgtc ggacctccca gaacatcaac aactacctga actggtatca gcagaagccc 120
ggcaaggccc ccaagcccct gatctacgct gcttccagtc tgcagtccgg cgtgccctct 180
agattctccg gctctggctc tggcaccgac ttcaccctga ccatctccac cctgcacccc 240
gaggacttcg ccacctacta ctgccagcag acctactcca tcccctgac ctttggcgga 300 ggcaccaagg tggaaatcaa a 321

<210> SEQ ID NO 19
<211> LENGTH: 214
<212> TYPE: PRT
<213> ORGANISM: Homo Sapien

<400> SEQUENCE: 19

Asp Ile Gln Met Thr Gln Ser Pro Ser Ser Leu Ser Ala Ser Val Gly
1 5 10 15

Asp Arg Val Ala Ile Thr Cys Arg Thr Ser Gln Asn Ile Asn Asn Tyr
20 25 30

Leu Asn Trp Tyr Gln Gln Lys Pro Gly Lys Ala Pro Lys Pro Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Thr Leu His Pro
65 70 75 80

Glu Asp Phe Ala Thr Tyr Tyr Cys Gln Gln Thr Tyr Ser Ile Pro Leu
85 90 95

Thr Phe Gly Gly Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 20
<211> LENGTH: 642
<212> TYPE: DNA
<213> ORGANISM: Homo Sapien

<400> SEQUENCE: 20
gatatccaga tgacccagtc cccctccagc ctgtctgcct ctgtgggcga cagagtggcc 60

```
atcacctgtc ggacctccca gaacatcaac aactacctga actggtatca gcagaagccc    120

ggcaaggccc ccaagcccct gatctacgct gcttccagtc tgcagtccgg cgtgccctct    180

agattctccg gctctggctc tggcaccgac ttcaccctga ccatctccac cctgcacccc    240

gaggacttcg ccacctacta ctgccagcag acctactcca tccccctgac ctttggcgga    300

ggcaccaagg tggaaatcaa acgtacggtg gccgctccct ccgtgttcat cttcccacct    360

tccgacgagc agctgaagtc cggcaccgct tctgtcgtgt gcctgctgaa caacttctac    420

ccccgcgagg ccaaggtgca gtggaaggtg gacaacgccc tgcagtccgg caactcccag    480

gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                       642
```

<210> SEQ ID NO 21
<211> LENGTH: 6
<212> TYPE: PRT
<213> ORGANISM: Homo Sapien

<400> SEQUENCE: 21

```
Gln Ser Val Ser Ser Tyr
1               5
```

<210> SEQ ID NO 22
<211> LENGTH: 3
<212> TYPE: PRT
<213> ORGANISM: Homo Sapien

<400> SEQUENCE: 22

```
Asp Thr Ser
1
```

<210> SEQ ID NO 23
<211> LENGTH: 9
<212> TYPE: PRT
<213> ORGANISM: Homo Sapien

<400> SEQUENCE: 23

```
Gln Gln Arg Arg Asn Trp Pro Leu Thr
1               5
```

<210> SEQ ID NO 24
<211> LENGTH: 11
<212> TYPE: PRT
<213> ORGANISM: Homo Sapien

<400> SEQUENCE: 24

```
Arg Val Ser Gln Ser Val Ser Ser Tyr Leu Ala
1               5                   10
```

<210> SEQ ID NO 25
<211> LENGTH: 7
<212> TYPE: PRT
<213> ORGANISM: Homo Sapien

<400> SEQUENCE: 25

```
Asp Thr Ser Asn Arg Ala Thr
1               5
```

<210> SEQ ID NO 26
<211> LENGTH: 9
<212> TYPE: PRT

<213> ORGANISM: Homo Sapien

<400> SEQUENCE: 26

Gln Gln Arg Arg Asn Trp Pro Leu Thr
1 5

<210> SEQ ID NO 27
<211> LENGTH: 125
<212> TYPE: PRT
<213> ORGANISM: Homo Sapien

<400> SEQUENCE: 27

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Ala Met Ser Trp Val Arg Gln Ala Pro Gly Lys Gly Leu Glu Trp Val
35 40 45

Ser Ser Ile Ser Ala Ser Gly Ala Thr Thr Phe Tyr Ala Asp Pro Val
50 55 60

Lys Gly Arg Phe Thr Ile Ser Arg Asp Asn Ser Lys Lys Thr Leu Tyr
65 70 75 80

Leu Gln Met Asn Ser Leu Arg Ala Glu Asp Thr Ala Val Tyr Tyr Cys
85 90 95

Ala Lys Asp Gln Asp Phe Asp Ile Leu Thr Gly Tyr Leu Asn Trp Phe
100 105 110

Asp Pro Trp Gly Gln Gly Thr Leu Val Thr Val Ser Ser
115 120 125

<210> SEQ ID NO 28
<211> LENGTH: 375
<212> TYPE: DNA
<213> ORGANISM: Homo Sapien

<400> SEQUENCE: 28
gaagtgcagc tggttgaatc tggcggcgga ttggttcagc ctggcggatc tctgagactg 60
tcttgtgccg cctccggctt caccttctcc agatacgcta tgtcctgggt ccgacaggct 120
cctggcaaag gactggaatg ggtgtcctcc atctctgcct ctggcgccac cacctttac 180 gccgatcctg tgaagggcag attcaccatc agccgggaca actccaagaa aaccctgtac 240
ctgcagatga actccctgag agccgaggac accgccgtgt actactgtgc caaggaccag 300
gacttcgaca tcctgaccgg ctacctgaat tggttcgacc cttggggcca gggcacactg 360
gttacagtgt ctagc 375

<210> SEQ ID NO 29
<211> LENGTH: 454
<212> TYPE: PRT
<213> ORGANISM: Homo Sapien

<400> SEQUENCE: 29

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Tyr
20 25 30

Ala Met Ser Trp Val Arg Gln Ala Pro Gly Lys Gly Leu Glu Trp Val
35 40 45

Ser Ser Ile Ser Ala Ser Gly Ala Thr Thr Phe Tyr Ala Asp Pro Val

```
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Asp Phe Asp Ile Leu Thr Gly Tyr Leu Asn Trp Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Gly Ala Leu His Asn His Tyr Thr Gln Lys Ser
        435                 440                 445

Leu Ser Leu Ser Pro Gly
    450
```

<210> SEQ ID NO 30

<211> LENGTH: 1362
<212> TYPE: DNA
<213> ORGANISM: Homo Sapien

<400> SEQUENCE: 30

```
gaagtgcagc tggttgaatc tggcggcgga ttggttcagc ctggcggatc tctgagactg     60

tcttgtgccg cctccggctt caccttctcc agatacgcta tgtcctgggt ccgacaggct    120

cctggcaaag gactggaatg ggtgtcctcc atctctgcct ctggcgccac cacctttac     180

gccgatcctg tgaagggcag attcaccatc agccgggaca actccaagaa aaccctgtac    240

ctgcagatga actccctgag agccgaggac accgccgtgt actactgtgc caaggaccag    300

gacttcgaca tcctgaccgg ctacctgaat tggttcgacc cttggggcca gggcacactg    360

gttacagtgt ctagcgccag caccaagggc ccctctgtgt tccctctggc cccttccagc    420

aagtccacct ctggcggaac agccgctctg ggctgcctcg tgaaggacta cttccccgag    480

cctgtgaccg tgtcctggaa ctctggcgct ctgaccagcg gagtgcacac cttccctgct    540

gtgctgcagt cctccggcct gtactccctg tcctccgtcg tgaccgtgcc ttccagctct    600

ctgggcaccc agacctacat ctgcaacgtg aaccacaagc cctccaacac caaggtggac    660

aagaaggtgg aacccaagtc ctgcgacaag acccacacct gtcccccttg tcctgcccct    720

gaactgctgg gcggaccttc cgtgttcctg ttccccccaa agcccaagga caccctgatg    780

atctcccgga cccccgaagt gacctgcgtg gtggtggatg tgtcccacga ggaccctgaa    840

gtgaagttca attggtacgt ggacggcgtg gaagtgcaca acgccaagac caagcctaga    900

gaggaacagt acaactccac ctaccgggtg gtgtccgtgc tgaccgtgct gcaccaggat    960

tggctgaacg gcaaagagta caagtgcaag gtgtccaaca aggccctgcc tgcccccatc   1020

gaaaagacca tctccaaggc caagggccag ccccgggaac cccaggtgta cacactgccc   1080

cctagcaggg acgagctgac caagaaccag gtgtccctga cctgtctcgt gaaaggcttc   1140

taccccctccg atatcgccgt ggaatgggag tccaacggcc agcctgagaa caactacaag   1200

accacccccc ctgtgctgga ctccgacggc tcattcttcc tgtacagcaa gctgacagtg   1260

gacaagtccc ggtggcagca gggcaacgtg ttctcctgct ccgtgatgca cggcgccctg   1320

cacaaccact acacccagaa gtccctgtcc ctgagccccg gc                      1362
```

<210> SEQ ID NO 31
<211> LENGTH: 6
<212> TYPE: PRT
<213> ORGANISM: Homo Sapien

<400> SEQUENCE: 31

```
Gln Ser Val Ser Ser Tyr
1               5
```

<210> SEQ ID NO 32
<211> LENGTH: 3
<212> TYPE: PRT
<213> ORGANISM: Homo Sapien

<400> SEQUENCE: 32

```
Asp Thr Ser
1
```

<210> SEQ ID NO 33
<211> LENGTH: 9
<212> TYPE: PRT
<213> ORGANISM: Homo Sapien

<400> SEQUENCE: 33

```
Gln Gln Arg Arg Asn Trp Pro Leu Thr
1               5
```

<210> SEQ ID NO 34
<211> LENGTH: 11
<212> TYPE: PRT
<213> ORGANISM: Homo Sapien

<400> SEQUENCE: 34

```
Arg Val Ser Gln Ser Val Ser Ser Tyr Leu Ala
1               5                   10
```

<210> SEQ ID NO 35
<211> LENGTH: 7
<212> TYPE: PRT
<213> ORGANISM: Homo Sapien

<400> SEQUENCE: 35

```
Asp Thr Ser Asn Arg Ala Thr
1               5
```

<210> SEQ ID NO 36
<211> LENGTH: 9
<212> TYPE: PRT
<213> ORGANISM: Homo Sapien

<400> SEQUENCE: 36

```
Gln Gln Arg Arg Asn Trp Pro Leu Thr
1               5
```

<210> SEQ ID NO 37
<211> LENGTH: 107
<212> TYPE: PRT
<213> ORGANISM: Homo Sapien

<400> SEQUENCE: 37

```
Glu Ile Val Leu Thr Gln Ser Pro Ala Thr Leu Ser Leu Ser Pro Gly
1               5                   10                  15

Glu Arg Val Ile Leu Ser Cys Arg Val Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Asn Trp Pro Leu
                85                  90                  95

Thr Phe Gly Gly Gly Thr Lys Val Glu Ile Lys
            100                 105
```

<210> SEQ ID NO 38
<211> LENGTH: 321
<212> TYPE: DNA
<213> ORGANISM: Homo Sapien

<400> SEQUENCE: 38

```
gagatcgtgc tgacccagtc tcctgccaca ctgtcactgt ctccaggcga gagagtgatc      60

ctgtcttgcc gggtgtccca gtccgtgtcc tcttacctgg cttggtatca gcagaagccc     120
```

```
ggccaggctc ctagactgct gatctacgac acctccaaca gagccacagg catccccgcc    180

agattttccg gctctggctc tggcacagac tttaccctga ccatctccag cctggaacct    240

gaggacttcg ccgtgtacta ctgccagcag cggagaaact ggcccctgac atttggcggc    300

ggaacaaagg tggaaatcaa g                                              321
```

<210> SEQ ID NO 39
<211> LENGTH: 214
<212> TYPE: PRT
<213> ORGANISM: Homo Sapien

<400> SEQUENCE: 39

```
Glu Ile Val Leu Thr Gln Ser Pro Ala Thr Leu Ser Leu Ser Pro Gly
1               5                   10                  15

Glu Arg Val Ile Leu Ser Cys Arg Val Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 40
<211> LENGTH: 642
<212> TYPE: DNA
<213> ORGANISM: Homo Sapien

<400> SEQUENCE: 40

```
gagatcgtgc tgacccagtc tcctgccaca ctgtcactgt ctccaggcga gagagtgatc     60

ctgtcttgcc gggtgtccca gtccgtgtcc tcttacctgg cttggtatca gcagaagccc    120

ggccaggctc ctagactgct gatctacgac acctccaaca gagccacagg catccccgcc    180

agattttccg gctctggctc tggcacagac tttaccctga ccatctccag cctggaacct    240

gaggacttcg ccgtgtacta ctgccagcag cggagaaact ggcccctgac atttggcggc    300

ggaacaaagg tggaaatcaa gcgtacggtg gccgctccct ccgtgttcat cttcccacct    360
```

```
tccgacgagc agctgaagtc cggcaccgct tctgtcgtgt gcctgctgaa caacttctac    420

ccccgcgagg ccaaggtgca gtggaaggtg gacaacgccc tgcagtccgg caactcccag    480

gaatccgtga ccgagcagga ctccaaggac agcacctact ccctgtcctc caccctgacc    540

ctgtccaagg ccgactacga gaagcacaag gtgtacgcct gcgaagtgac ccaccagggc    600

ctgtctagcc ccgtgaccaa gtctttcaac cggggcgagt gt                        642


<210> SEQ ID NO 41
<211> LENGTH: 8
<212> TYPE: PRT
<213> ORGANISM: Homo Sapien

<400> SEQUENCE: 41

Gly Leu Thr Phe Asn Asn Tyr Ala
1               5


<210> SEQ ID NO 42
<211> LENGTH: 8
<212> TYPE: PRT
<213> ORGANISM: Homo Sapien

<400> SEQUENCE: 42

Ile Ser Gly Ser Gly Gly Ser Thr
1               5


<210> SEQ ID NO 43
<211> LENGTH: 15
<212> TYPE: PRT
<213> ORGANISM: Homo Sapien

<400> SEQUENCE: 43

Ala Lys Gly Gly Leu Leu Tyr Phe Gly Glu Phe His Phe Asp Tyr
1               5                   10                  15


<210> SEQ ID NO 44
<211> LENGTH: 4
<212> TYPE: PRT
<213> ORGANISM: Homo Sapien

<400> SEQUENCE: 44

Asn Asn Tyr Ala
1


<210> SEQ ID NO 45
<211> LENGTH: 17
<212> TYPE: PRT
<213> ORGANISM: Homo Sapien

<400> SEQUENCE: 45

Thr Ile Ser Gly Ser Gly Gly Ser Thr Tyr Tyr Ala Asp Ser Ala Lys
1               5                   10                  15

Gly


<210> SEQ ID NO 46
<211> LENGTH: 13
<212> TYPE: PRT
<213> ORGANISM: Homo Sapien

<400> SEQUENCE: 46

Gly Gly Leu Leu Tyr Phe Gly Glu Phe His Phe Asp Tyr
1               5                   10
```

<210> SEQ ID NO 47
<211> LENGTH: 122
<212> TYPE: PRT
<213> ORGANISM: Homo Sapien

<400> SEQUENCE: 47

Glu Val Gln Leu Val Glu Ser Gly Gly Gly Leu Val Gln Leu Gly Gly
1               5                   10                  15

Ser Leu Arg Leu Ser Cys Ala Ala Ser Gly Leu Thr Phe Asn Asn Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Leu Leu Tyr Phe Gly Glu Phe His Phe Asp Tyr Trp
            100                 105                 110

Gly Gln Gly Thr Leu Val Thr Val Ser Ser
        115                 120

<210> SEQ ID NO 48
<211> LENGTH: 366
<212> TYPE: DNA
<213> ORGANISM: Homo Sapien

<400> SEQUENCE: 48
gaggtgcagc tggtggagtc tgggggaggc ttggtacagc ttggggggtc cctgagactc     60
tcctgtgcag cctctggact cacctttaac aactatgcca tgagctgggt ccgccaggct    120
ccagggaagg ggctggagtg ggtctcaact attagtggaa gtggtggcag cacatactac    180
gcagactccg cgaagggccg gttcaccatc tccagagaca attccaagaa cacgctgtat    240
ctgcaaatga acagcctgag agccgaggac acggccgtat attactgtgc gaaagggggc    300
ttactatact tcggggagtt ccactttgac tactggggcc agggaaccct ggtcaccgtc    360
tcctca                                                               366

<210> SEQ ID NO 49
<211> LENGTH: 451
<212> TYPE: PRT
<213> ORGANISM: Homo Sapien

<400> SEQUENCE: 49

Glu Val Gln Leu Val Glu Ser Gly Gly Gly Leu Val Gln Leu Gly Gly
1               5                   10                  15

Ser Leu Arg Leu Ser Cys Ala Ala Ser Gly Leu Thr Phe Asn Asn Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Gly Ser Thr Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Gly Gly Leu Leu Tyr Phe Gly Glu Phe His Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Gly Ala Leu His Asn His Tyr Thr Gln Lys Ser Leu Ser Leu
        435                 440                 445

Ser Pro Gly
    450
```

<210> SEQ ID NO 50
<211> LENGTH: 1353
<212> TYPE: DNA
<213> ORGANISM: Homo Sapien

<400> SEQUENCE: 50

```
gaggtgcagc tggtggagtc tgggggaggc ttggtacagc ttgggggtc cctgagactc      60
```

```
tcctgtgcag cctctggact cacctttaac aactatgcca tgagctgggt ccgccaggct    120

ccagggaagg ggctggagtg ggtctcaact attagtggaa gtggtggcag cacatactac    180

gcagactccg cgaagggccg gttcaccatc tccagagaca attccaagaa cacgctgtat    240

ctgcaaatga acagcctgag agccgaggac acggccgtat attactgtgc gaaagggggc    300

ttactatact tcggggagtt ccactttgac tactggggcc agggaaccct ggtcaccgtc    360

tcctcagcca gcaccaaggg cccctctgtg ttccctctgg ccccttccag caagtccacc    420

tctggcggaa cagccgctct gggctgcctc gtgaaggact acttccccga gcctgtgacc    480

gtgtcctgga actctggcgc tctgaccagc ggagtgcaca ccttccctgc tgtgctgcag    540

tcctccggcc tgtactccct gtcctccgtc gtgaccgtgc cttccagctc tctgggcacc    600

cagacctaca tctgcaacgt gaaccacaag ccctccaaca ccaaggtgga caagaaggtg    660

gaacccaagt cctgcgacaa gacccacacc tgtccccctt gtcctgcccc tgaactgctg    720

ggcggacctt ccgtgttcct gttcccccca aagcccaagg acaccctgat gatctcccgg    780

acccccgaag tgacctgcgt ggtggtggat gtgtcccacg aggaccctga agtgaagttc    840

aattggtacg tggacggcgt ggaagtgcac aacgccaaga ccaagcctag agaggaacag    900

tacaactcca cctaccgggt ggtgtccgtg ctgaccgtgc tgcaccagga ttggctgaac    960

ggcaaagagt acaagtgcaa ggtgtccaac aaggccctgc ctgcccccat cgaaaagacc   1020

atctccaagg ccaagggcca gccccgggaa ccccaggtgt acacactgcc ccctagcagg   1080

gacgagctga ccaagaacca ggtgtccctg acctgtctcg tgaaaggctt ctacccctcc   1140

gatatcgccg tggaatggga gtccaacggc cagcctgaga acaactacaa gaccaccccc   1200

cctgtgctgg actccgacgg ctcattcttc ctgtacagca agctgacagt ggacaagtcc   1260

cggtggcagc agggcaacgt gttctcctgc tccgtgatgc acggcgccct gcacaaccac   1320

tacacccaga agtccctgtc cctgagcccc ggc                                 1353
```

```
<210> SEQ ID NO 51
<211> LENGTH: 6
<212> TYPE: PRT
<213> ORGANISM: Homo Sapien

<400> SEQUENCE: 51

Gln Gly Ile Ser Asn Tyr
1               5


<210> SEQ ID NO 52
<211> LENGTH: 3
<212> TYPE: PRT
<213> ORGANISM: Homo Sapien

<400> SEQUENCE: 52

Ala Ala Ser
1


<210> SEQ ID NO 53
<211> LENGTH: 9
<212> TYPE: PRT
<213> ORGANISM: Homo Sapien

<400> SEQUENCE: 53

Gln His Tyr Asn Ser Tyr Pro Leu Thr
1               5


<210> SEQ ID NO 54
```

<211> LENGTH: 11
<212> TYPE: PRT
<213> ORGANISM: Homo Sapien

<400> SEQUENCE: 54

Arg Ala Ser Gln Gly Ile Ser Asn Tyr Leu Ala
1               5                   10

<210> SEQ ID NO 55
<211> LENGTH: 7
<212> TYPE: PRT
<213> ORGANISM: Homo Sapien

<400> SEQUENCE: 55

Ala Ala Ser Ser Leu Gln Ser
1               5

<210> SEQ ID NO 56
<211> LENGTH: 9
<212> TYPE: PRT
<213> ORGANISM: Homo Sapien

<400> SEQUENCE: 56

Gln His Tyr Asn Ser Tyr Pro Leu Thr
1               5

<210> SEQ ID NO 57
<211> LENGTH: 107
<212> TYPE: PRT
<213> ORGANISM: Homo Sapien

<400> SEQUENCE: 57

Asp Ile Gln Met Thr Gln Ser Pro Ser Ser Leu Ser Ala Ser Val Gly
1               5                   10                  15

Asp Arg Val Thr Ile Ile Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Asn Ser Tyr Pro Leu
                85                  90                  95

Thr Phe Gly Gly Gly Thr Lys Val Glu Ile Lys
            100                 105

<210> SEQ ID NO 58
<211> LENGTH: 321
<212> TYPE: DNA
<213> ORGANISM: Homo Sapien

<400> SEQUENCE: 58
gacatccaga tgacccagtc tccatcctca ctgtctgcat ctgtaggaga cagagtcacc      60
atcatttgtc gggcgagtca gggcattagc aattatttag cctggtttca gcagaaacca     120
gggaaagccc ctaagtccct gatctatgct gcatccagtt tgcaaagtgg ggtcccatca     180
aagttcagcg gcagtggatc tgggacagat ttcactctca ccatcagcag cctgcagcct     240
gaagattttg caacttatta ctgccaacat tataatagtt acccgctcac tttcggcgga     300
gggaccaagg tggagatcaa a                                               321

<210> SEQ ID NO 59
<211> LENGTH: 214
<212> TYPE: PRT
<213> ORGANISM: Homo Sapien

<400> SEQUENCE: 59

```
Asp Ile Gln Met Thr Gln Ser Pro Ser Ser Leu Ser Ala Ser Val Gly
1               5                   10                  15

Asp Arg Val Thr Ile Ile Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 60
<211> LENGTH: 642
<212> TYPE: DNA
<213> ORGANISM: Homo Sapien

<400> SEQUENCE: 60

```
gacatccaga tgacccagtc tccatcctca ctgtctgcat ctgtaggaga cagagtcacc      60

atcatttgtc gggcgagtca gggcattagc aattatttag cctggtttca gcagaaacca     120

gggaaagccc ctaagtccct gatctatgct gcatccagtt tgcaaagtgg ggtcccatca     180

aagttcagcg gcagtggatc tgggacagat ttcactctca ccatcagcag cctgcagcct     240

gaagattttg caacttatta ctgccaacat tataatagtt acccgctcac tttcggcgga     300

gggaccaagg tggagatcaa acgtacggtg gccgctccct ccgtgttcat cttcccacct     360

tccgacgagc agctgaagtc cggcaccgct tctgtcgtgt gcctgctgaa caacttctac     420

ccccgcgagg ccaaggtgca gtggaaggtg gacaacgccc tgcagtccgg caactcccag     480

gaatccgtga ccgagcagga ctccaaggac agcacctact ccctgtcctc caccctgacc     540

ctgtccaagg ccgactacga gaagcacaag gtgtacgcct gcgaagtgac ccaccagggc     600
```

ctgtctagcc ccgtgaccaa gtctttcaac cggggcgagt gt 642

<210> SEQ ID NO 61
<211> LENGTH: 8
<212> TYPE: PRT
<213> ORGANISM: Homo Sapien

<400> SEQUENCE: 61

Gly Val Thr Phe Ser Asn Ala Trp
1 5

<210> SEQ ID NO 62
<211> LENGTH: 10
<212> TYPE: PRT
<213> ORGANISM: Homo Sapien

<400> SEQUENCE: 62

Ile Lys Ser Lys Thr Asp Gly Gly Thr Thr
1 5 10

<210> SEQ ID NO 63
<211> LENGTH: 11
<212> TYPE: PRT
<213> ORGANISM: Homo Sapien

<400> SEQUENCE: 63

Thr Ile Glu Ala Val Ala Gly His Phe Asp Tyr
1 5 10

<210> SEQ ID NO 64
<211> LENGTH: 6
<212> TYPE: PRT
<213> ORGANISM: Homo Sapien

<400> SEQUENCE: 64

Ser Asn Ala Trp Met Ser
1 5

<210> SEQ ID NO 65
<211> LENGTH: 19
<212> TYPE: PRT
<213> ORGANISM: Homo Sapien

<400> SEQUENCE: 65

Arg Ile Lys Ser Lys Thr Asp Gly Gly Thr Thr Asp Tyr Ala Ala Pro
1 5 10 15

Val Lys Gly

<210> SEQ ID NO 66
<211> LENGTH: 9
<212> TYPE: PRT
<213> ORGANISM: Homo Sapien

<400> SEQUENCE: 66

Glu Ala Val Ala Gly His Phe Asp Tyr
1 5

<210> SEQ ID NO 67
<211> LENGTH: 120
<212> TYPE: PRT
<213> ORGANISM: Homo Sapien

<400> SEQUENCE: 67

Glu Val Gln Leu Val Glu Ser Gly Gly Gly Leu Val Lys Pro Gly Gly

```
1               5                   10                  15

Ser Pro Arg Leu Ser Cys Ala Ala Tyr Gly Val Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ile Glu Ala Val Ala Gly His Phe Asp Tyr Trp Gly Gln
            100                 105                 110

Gly Thr Leu Val Thr Val Ser Ser
        115                 120


<210> SEQ ID NO 68
<211> LENGTH: 360
<212> TYPE: DNA
<213> ORGANISM: Homo Sapien

<400> SEQUENCE: 68

gaggtgcagt tggtggagtc tgggggaggc ttggtaaagc ctgggggtc ccctagactc     60

tcctgtgcag cctatggagt cactttcagt aacgcctgga tgagttgggt ccgccaggct    120

ccagggaagg ggctggagtg ggttggccgt attaaaagca aaactgatgg tgggacaaca    180

gactatgctg cacccgtgaa aggcagattc accatctcaa gagatgattc aaaaaacacg    240

ctgtatctgc aaatgaacag cctgaaaacc gaggacacag ccgtgtatta ctgtaccata    300

gaagcagtgg ctggtcactt tgactactgg ggccagggaa ccctggtcac cgtctcctca    360


<210> SEQ ID NO 69
<211> LENGTH: 449
<212> TYPE: PRT
<213> ORGANISM: Homo Sapien

<400> SEQUENCE: 69

Glu Val Gln Leu Val Glu Ser Gly Gly Gly Leu Val Lys Pro Gly Gly
1               5                   10                  15

Ser Pro Arg Leu Ser Cys Ala Ala Tyr Gly Val Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ile Glu Ala Val Ala Gly His Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Gly Ala Leu His Asn His Tyr Thr Gln Lys Ser Leu Ser Leu Ser Pro
435 440 445

Gly

<210> SEQ ID NO 70
<211> LENGTH: 1347
<212> TYPE: DNA
<213> ORGANISM: Homo Sapien

<400> SEQUENCE: 70
gaggtgcagt tggtggagtc tgggggaggc ttggtaaagc ctgggggtc ccctagactc 60 tcctgtgcag cctatggagt cactttcagt aacgcctgga tgagttgggt ccgccaggct 120
ccagggaagg ggctggagtg ggttggccgt attaaaagca aaactgatgg tgggacaaca 180
gactatgctg cacccgtgaa aggcagattc accatctcaa gagatgattc aaaaaacacg 240
ctgtatctgc aaatgaacag cctgaaaacc gaggacacag ccgtgtatta ctgtaccata 300
gaagcagtgg ctggtcactt tgactactgg ggccagggaa ccctggtcac cgtctcctca 360
gccagcacca agggcccctc tgtgttccct ctggcccctt ccagcaagtc cacctctggc 420

```
ggaacagccg ctctgggctg cctcgtgaag gactacttcc ccgagcctgt gaccgtgtcc    480

tggaactctg gcgctctgac cagcggagtg cacaccttcc ctgctgtgct gcagtcctcc    540

ggcctgtact ccctgtcctc cgtcgtgacc gtgccttcca gctctctggg cacccagacc    600

tacatctgca acgtgaacca caagccctcc aacaccaagg tggacaagaa ggtggaaccc    660

aagtcctgcg acaagaccca cacctgtccc ccttgtcctg cccctgaact gctgggcgga    720

ccttccgtgt tcctgttccc cccaaagccc aaggacaccc tgatgatctc ccggaccccc    780

gaagtgacct gcgtggtggt ggatgtgtcc cacgaggacc ctgaagtgaa gttcaattgg    840

tacgtggacg gcgtggaagt gcacaacgcc aagaccaagc ctagagagga acagtacaac    900

tccacctacc gggtggtgtc cgtgctgacc gtgctgcacc aggattggct gaacggcaaa    960

gagtacaagt gcaaggtgtc caacaaggcc ctgcctgccc ccatcgaaaa gaccatctcc   1020

aaggccaagg gccagccccg ggaaccccag gtgtacacac tgccccctag cagggacgag   1080

ctgaccaaga accaggtgtc cctgacctgt ctcgtgaaag gcttctaccc ctccgatatc   1140

gccgtggaat gggagtccaa cggccagcct gagaacaact acaagaccac cccccctgtg   1200

ctggactccg acggctcatt cttcctgtac agcaagctga cagtggacaa gtcccggtgg   1260

cagcagggca acgtgttctc ctgctccgtg atgcacggcg ccctgcacaa ccactacacc   1320

cagaagtccc tgtccctgag ccccggc                                       1347
```

<210> SEQ ID NO 71
<211> LENGTH: 6
<212> TYPE: PRT
<213> ORGANISM: Homo Sapien

<400> SEQUENCE: 71

```
Gln Ser Ile Ser Ser Trp
1               5
```

<210> SEQ ID NO 72
<211> LENGTH: 3
<212> TYPE: PRT
<213> ORGANISM: Homo Sapien

<400> SEQUENCE: 72

```
Lys Ala Ser
1
```

<210> SEQ ID NO 73
<211> LENGTH: 9
<212> TYPE: PRT
<213> ORGANISM: Homo Sapien

<400> SEQUENCE: 73

```
Gln Gln Tyr Asn Asn Tyr Ser Pro Thr
1               5
```

<210> SEQ ID NO 74
<211> LENGTH: 11
<212> TYPE: PRT
<213> ORGANISM: Homo Sapien

<400> SEQUENCE: 74

```
Arg Ala Ser Gln Ser Ile Ser Ser Trp Leu Ala
1               5                   10
```

<210> SEQ ID NO 75

<211> LENGTH: 7
<212> TYPE: PRT
<213> ORGANISM: Homo Sapien

<400> SEQUENCE: 75

Lys Ala Ser Ser Leu Glu Ser
1               5

<210> SEQ ID NO 76
<211> LENGTH: 9
<212> TYPE: PRT
<213> ORGANISM: Homo Sapien

<400> SEQUENCE: 76

Gln Gln Tyr Asn Asn Tyr Ser Pro Thr
1               5

<210> SEQ ID NO 77
<211> LENGTH: 107
<212> TYPE: PRT
<213> ORGANISM: Homo Sapien

<400> SEQUENCE: 77

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Asn Tyr Ser Pro
                85                  90                  95

Thr Phe Gly Gln Gly Thr Lys Val Glu Ile Lys
            100                 105

<210> SEQ ID NO 78
<211> LENGTH: 321
<212> TYPE: DNA
<213> ORGANISM: Homo Sapien

<400> SEQUENCE: 78
gacatccaga tgacccagtc tccttccacc ctgtctgcat ctgtaggaga cagagtcacc      60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataataatt attctccgac gttcggccag     300
gggaccaagg tggaaatcaa a                                               321

<210> SEQ ID NO 79
<211> LENGTH: 214
<212> TYPE: PRT
<213> ORGANISM: Homo Sapien

<400> SEQUENCE: 79

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Asn Tyr Ser Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 80
<211> LENGTH: 642
<212> TYPE: DNA
<213> ORGANISM: Homo Sapien

<400> SEQUENCE: 80
gacatccaga tgacccagtc tccttccacc ctgtctgcat ctgtaggaga cagagtcacc 60
atcacttgcc gggccagtca gagtattagt agctggttgg cctggtatca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgccaacag tataataatt attctccgac gttcggccag 300
gggaccaagg tggaaatcaa acgtacggtg gccgctccct ccgtgttcat cttcccacct 360
tccgacgagc agctgaagtc cggcaccgct tctgtcgtgt gcctgctgaa caacttctac 420
ccccgcgagg ccaaggtgca gtggaaggtg gacaacgccc tgcagtccgg caactcccag 480
gaatccgtga ccgagcagga ctccaaggac agcacctact ccctgtcctc caccctgacc 540
ctgtccaagg ccgactacga gaagcacaag gtgtacgcct gcgaagtgac ccaccagggc 600
ctgtctagcc ccgtgaccaa gtctttcaac cggggcgagt gt 642

<210> SEQ ID NO 81
<211> LENGTH: 723
<212> TYPE: DNA
<213> ORGANISM: Homo Sapien

<400> SEQUENCE: 81
atggccgggc ctccgaggct cctgctgctg cccctgcttc tggcgctggc tcgcggcctg 60

```
cctggggccc tggctgccca agaggtgcag cagtctcccc actgcacgac tgtccccgtg    120

ggagcctccg tcaacatcac ctgctccacc agcgggggcc tgcgtgggat ctacctgagg    180

cagctcgggc cacagcccca agacatcatt tactacgagg acggggtggt gcccactacg    240

gacagacggt tccggggccg catcgacttc tcagggtccc aggacaacct gactatcacc    300

atgcaccgcc tgcagctgtc ggacactggc acctacacct gccaggccat cacggaggtc    360

aatgtctacg gctccggcac cctggtcctg gtgacagagg aacagtccca aggatggcac    420

agatgctcgg acgccccacc aagggcctct gccctccctg ccccaccgac aggctccgcc    480

ctccctgacc cgcagacagc ctctgccctc cctgacccgc cagcagcctc tgccctccct    540

gcggccctgg cggtgatctc cttcctcctc gggctgggcc tgggggtggc gtgtgtgctg    600

gcgaggacac agataaagaa actgtgctcg tggcgggata agaattcggc ggcatgtgtg    660

gtgtacgagg acatgtcgca cagccgctgc aacacgctgt cctcccccaa ccagtaccag    720

tga                                                                  723
```

<210> SEQ ID NO 82
<211> LENGTH: 238
<212> TYPE: PRT
<213> ORGANISM: Homo Sapien

<400> SEQUENCE: 82

```
Met Ala Gly Pro Pro Arg Leu Leu Leu Leu Pro Leu Leu Leu Ala Leu
1               5                   10                  15

Ala Arg Gly Leu Pro Gly Ala Leu Ala Ala Gln Glu Val Gln Gln Ser
            20                  25                  30

Pro His Cys Thr Thr Val Pro Val Gly Ala Ser Val Asn Ile Thr Cys
        35                  40                  45

Ser Thr Ser Gly Gly Leu Arg Gly Ile Tyr Leu Arg Gln Leu Gly Pro
    50                  55                  60

Gln Pro Gln Asp Ile Ile Tyr Tyr Glu Asp Gly Val Val Pro Thr Thr
65                  70                  75                  80

Asp Arg Arg Phe Arg Gly Arg Ile Asp Phe Ser Gly Ser Gln Asp Asn
                85                  90                  95

Leu Thr Ile Thr Met His Arg Leu Gln Leu Ser Asp Thr Gly Thr Tyr
            100                 105                 110

Thr Cys Gln Ala Ile Thr Glu Val Asn Val Tyr Gly Ser Gly Thr Leu
        115                 120                 125

Val Leu Val Thr Glu Glu Gln Ser Gln Gly Trp His Arg Cys Ser Asp
    130                 135                 140

Ala Pro Pro Arg Ala Ser Ala Leu Pro Ala Pro Pro Thr Gly Ser Ala
145                 150                 155                 160

Leu Pro Asp Pro Gln Thr Ala Ser Ala Leu Pro Asp Pro Pro Ala Ala
                165                 170                 175

Ser Ala Leu Pro Ala Ala Leu Ala Val Ile Ser Phe Leu Leu Gly Leu
            180                 185                 190

Gly Leu Gly Val Ala Cys Val Leu Ala Arg Thr Gln Ile Lys Lys Leu
        195                 200                 205

Cys Ser Trp Arg Asp Lys Asn Ser Ala Ala Cys Val Val Tyr Glu Asp
    210                 215                 220

Met Ser His Ser Arg Cys Asn Thr Leu Ser Ser Pro Asn Gln
225                 230                 235
```

<210> SEQ ID NO 83
<211> LENGTH: 723
<212> TYPE: DNA
<213> ORGANISM: Macaca fascicularis

<400> SEQUENCE: 83
atggccgggc tcccgaggct cctgctgctg cccctcctcc tggcgctggc tcgtggcctg 60
cctggggccc tggccgccca agaggtgcag cagtctcccc actgcacgat tgcccccgtg 120
ggaggctccg tcaacatcac ctgctccacc agcggggaac tgcatgggat ctacctgagg 180
cagctcgggc cacagcccca aaacatcatt tactacgagg acagggtggt gcccactacg 240
gacaaacggt tccagggccg cattgacttc tcggggtccc aggacaacct gactattacc 300
atgcaccacc tgcagccgtc ggacactggc acctacacct gccaggccgt cacggagatc 360
aatgtctacg gctccggtac cctggtcctg gtgacagagg aacagtccca aggattgcac 420
agatgctcgg acgccccgcc gacaggctct gccctccctg tcccgccgac aacctctgcc 480
ctccctgccc tgccaacagc ctctgccctc cctgccctgc cgacagcctc tgccctccct 540
gtggccctgg cagtggtctc cttcctcctc gggctggccc tgggggtggc ctgtgtgctg 600
gtgaggacgc agatgaagaa actgtgctcg tcgcgggata agaattcggc agcgtgtgtg 660
gtgtacgagg acatgtcccg cagccgctgc aacacgctgt cctcccccaa ccagtaccag 720
tga 723

<210> SEQ ID NO 84
<211> LENGTH: 240
<212> TYPE: PRT
<213> ORGANISM: Macaca fascicularis

<400> SEQUENCE: 84

Met Ala Gly Leu Pro Arg Leu Leu Leu Leu Pro Leu Leu Leu Ala Leu
1               5                   10                  15

Ala Arg Gly Leu Pro Gly Ala Leu Ala Ala Gln Glu Val Gln Gln Ser
            20                  25                  30

Pro His Cys Thr Ile Ala Pro Val Gly Gly Ser Val Asn Ile Thr Cys
        35                  40                  45

Ser Thr Ser Gly Glu Leu His Gly Ile Tyr Leu Arg Gln Leu Gly Pro
    50                  55                  60

Gln Pro Gln Asn Ile Ile Tyr Tyr Glu Asp Arg Val Val Pro Thr Thr
65                  70                  75                  80

Asp Lys Arg Phe Gln Gly Arg Ile Asp Phe Ser Gly Ser Gln Asp Asn
                85                  90                  95

Leu Thr Ile Thr Met His His Leu Gln Pro Ser Asp Thr Gly Thr Tyr
            100                 105                 110

Thr Cys Gln Ala Val Thr Glu Ile Asn Val Tyr Gly Ser Gly Thr Leu
        115                 120                 125

Val Leu Val Thr Glu Glu Gln Ser Gln Gly Leu His Arg Cys Ser Asp
    130                 135                 140

Ala Pro Pro Thr Gly Ser Ala Leu Pro Val Pro Pro Thr Thr Ser Ala
145                 150                 155                 160

Leu Pro Ala Leu Pro Thr Ala Ser Ala Leu Pro Ala Leu Pro Thr Ala
                165                 170                 175

Ser Ala Leu Pro Val Ala Leu Ala Val Val Ser Phe Leu Leu Gly Leu
            180                 185                 190

Ala Leu Gly Val Ala Cys Val Leu Val Arg Thr Gln Met Lys Lys Leu
        195                 200                 205

```
Cys Ser Ser Arg Asp Lys Asn Ser Ala Ala Cys Val Val Tyr Glu Asp
    210                 215                 220

Met Ser Arg Ser Arg Cys Asn Thr Leu Ser Ser Pro Asn Gln Tyr Gln
225                 230                 235                 240
```

<210> SEQ ID NO 85
<211> LENGTH: 630
<212> TYPE: DNA
<213> ORGANISM: Rattus norvegicus

<400> SEQUENCE: 85

```
atgactcagg cactgttggc tttgctactt acactggcta gaatcctgcc tggccccctg      60

gatgcccaag aggtacatca gtctccccga gtcgtgatcg cctccgaggg agagtccatc     120

aacatcacct gctctacaag aggggatttg gaagggctca taatgaagcg gatctggcca     180

caggcttcca atgtgattta ctttgaagac gaattggagc ccacagtaga cagtgccttc     240

tcaggccgaa ttaatttctc tggtcccag aagaatctga ccatcatcat gagccttctc      300

caggaggcag acactggagc ctacacctgc gaggccgtca gaaaagtcag tgtccatggc     360

ttgttcacca cggttgtggt gaaagaaaaa ctatcccatg aagcgtacag atcccaggaa     420

cctctgcaga catcagtttc cctcccagct gccattgctg taagcttctt cctcactggg     480

ctgatccttg ggtgctgtg cagcatgctg aggaagacgc agatcaagaa actgtgtgcc      540

tcagggaata aggactctct gtgcgtcgtg tatgaagaca tgtcctgcag caaccgcaag     600

ataccatgta cccccaacca gtaccaatga                                      630
```

<210> SEQ ID NO 86
<211> LENGTH: 209
<212> TYPE: PRT
<213> ORGANISM: Rattus norvegicus

<400> SEQUENCE: 86

```
Met Thr Gln Ala Leu Leu Ala Leu Leu Leu Thr Leu Ala Arg Ile Leu
1               5                   10                  15

Pro Gly Pro Leu Asp Ala Gln Glu Val His Gln Ser Pro Arg Val Val
            20                  25                  30

Ile Ala Ser Glu Gly Glu Ser Ile Asn Ile Thr Cys Ser Thr Arg Gly
        35                  40                  45

Asp Leu Glu Gly Leu Ile Met Lys Arg Ile Trp Pro Gln Ala Ser Asn
    50                  55                  60

Val Ile Tyr Phe Glu Asp Glu Leu Glu Pro Thr Val Asp Ser Ala Phe
65                  70                  75                  80

Ser Gly Arg Ile Asn Phe Ser Gly Ser Gln Lys Asn Leu Thr Ile Ile
                85                  90                  95

Met Ser Leu Leu Gln Glu Ala Asp Thr Gly Ala Tyr Thr Cys Glu Ala
            100                 105                 110

Val Arg Lys Val Ser Val His Gly Leu Phe Thr Thr Val Val Val Lys
        115                 120                 125

Glu Lys Leu Ser His Glu Ala Tyr Arg Ser Gln Glu Pro Leu Gln Thr
    130                 135                 140

Ser Val Ser Leu Pro Ala Ala Ile Ala Val Ser Phe Phe Leu Thr Gly
145                 150                 155                 160

Leu Ile Leu Gly Val Leu Cys Ser Met Leu Arg Lys Thr Gln Ile Lys
                165                 170                 175

Lys Leu Cys Ala Ser Gly Asn Lys Asp Ser Leu Cys Val Val Tyr Glu
```

```
            180                 185                 190

Asp Met Ser Cys Ser Asn Arg Lys Ile Pro Cys Thr Pro Asn Gln Tyr
        195                 200                 205

Gln


<210> SEQ ID NO 87
<211> LENGTH: 990
<212> TYPE: DNA
<213> ORGANISM: Homo Sapien

<400> SEQUENCE: 87

gcctccacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240

tacatctgca acgtgaatca caagcccagc aacaccaagg tggacaagaa agttgagccc     300

aaatcttgtg acaaaactca cacatgccca ccgtgcccag cacctgaact cctgggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacaac     540

agcacgtacc gggtggtcag cgtcctcacc gtcctgcacc aggactggct gaatggcaag     600

gagtacaagt gcaaggtctc caacaaagcc ctcccagccc ccatcgagaa aaccatctcc     660

aaagccaaag ggcagccccg agaaccacag gtgtacaccc tgcccccatc ccgggatgag     720

ctgaccaaga accaggtcag cctgacctgc ctggtcaaag gcttctatcc cagcgacatc     780

gccgtggagt gggagagcaa tgggcagccg gagaacaact acaagaccac gcctcccgtg     840

ctggactccg acggctcctt cttcctctac agcaagctca ccgtggacaa gagcaggtgg     900

cagcagggga acgtcttctc atgctccgtg atgcatgagg ctctgcacaa ccactacacg     960

cagaagagcc tctccctgtc tccgggtaaa                                      990


<210> SEQ ID NO 88
<211> LENGTH: 330
<212> TYPE: PRT
<213> ORGANISM: Homo Sapien

<400> SEQUENCE: 88

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 89
<211> LENGTH: 990
<212> TYPE: DNA
<213> ORGANISM: Homo Sapien

<400> SEQUENCE: 89

```
gcctccacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900
```

cagcagggga acgtcttctc atgctccgtg atgcatgagg ctctgcacaa ccactacacg 960
cagaagagcc tctccctgtc tccgggtaaa 990

<210> SEQ ID NO 90
<211> LENGTH: 330
<212> TYPE: PRT
<213> ORGANISM: Homo Sapien

<400> SEQUENCE: 90

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 91
<211> LENGTH: 990
<212> TYPE: DNA

<213> ORGANISM: Homo Sapien

<400> SEQUENCE: 91

```
gcctccacca agggcccatc ggtcttcccc ctggcaccct cctccaagag cacctctggg     60
ggcacagcgg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagag agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggtaaa                                     990
```

<210> SEQ ID NO 92
<211> LENGTH: 330
<212> TYPE: PRT
<213> ORGANISM: Homo Sapien

<400> SEQUENCE: 92

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 93
<211> LENGTH: 990
<212> TYPE: DNA
<213> ORGANISM: Homo Sapien

<400> SEQUENCE: 93

```
gcctccacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240

tacatctgca acgtgaatca caagcccagc aacaccaagg tggacaagaa agttgagccc     300

aaatcttgtg acaaaactca cacatgccca ccgtgcccag cacctgaact cctgggggga     360

ccgtcagtct tcctcttccc cccaaaaccc aaggacaccc tcatgatctc ccggacccct     420

gaggtcacat gcgtggtggt ggacgtgagc cacgaagacc ctgaggtcaa gttcaactgg     480

tacgtggacg gcgtggaggt gcataatgcc aagacaaagc cgcgggagga gcagtacaac     540

agcacgtacc gtgtggtcag cgtcctcacc gtcctgcacc aggactggct gaatggcaag     600

gagtacaagt gcaaggtctc caacaaagcc ctcccagccc ccatcgagaa aaccatctcc     660

aaagccaaag ggcagccccg agaaccacag gtgtacaccc tgcccccatc ccgggatgag     720

ctgaccaaga accaggtcag cctgacctgc ctggtcaaag gcttctatcc cagcgacatc     780

gccgtggagt gggagagcaa tgggcagccg gagaacaact acaagaccac gcctcccgtg     840

ctggactccg acggctcctt cttcctctac agcaagctca ccgtggacaa gagcaggtgg     900

cagcagggga acatcttctc atgctccgtg atgcatgagg ctctgcacaa ccactacacg     960

cagaagagcc tctccctgtc tccgggtaaa                                      990
```

<210> SEQ ID NO 94
<211> LENGTH: 330
<212> TYPE: PRT
<213> ORGANISM: Homo Sapien

<400> SEQUENCE: 94

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Ile Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 95
<211> LENGTH: 990
<212> TYPE: DNA
<213> ORGANISM: Homo Sapien

<400> SEQUENCE: 95

```
gcctccacca agggcccatc ggtcttcccc ctggcaccct cctccaagag cacctctggg      60

ggcacagcgg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacccagacc     240
```

```
tacatctgca acgtgaatca caagcccagc aacaccaagg tggacaagaa agtggagccc    300

aaatcttgtg acaaaactca cacatgccca ccgtgcccag cacctgaact cgcgggggca    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990
```

<210> SEQ ID NO 96
<211> LENGTH: 330
<212> TYPE: PRT
<213> ORGANISM: Homo Sapien

<400> SEQUENCE: 96

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 97
<211> LENGTH: 978
<212> TYPE: DNA
<213> ORGANISM: Homo Sapien

<400> SEQUENCE: 97

gcctccacca agggcccatc ggtcttcccc ctggcgccct gctccaggag cacctccgag      60

agcacagccg ccctgggctg cctggtcaag gactacttcc ccgaaccggt gacggtgtcg     120

tggaactcag gcgctctgac cagcggcgtg cacaccttcc cagctgtcct acagtcctca     180

ggactctact ccctcagcag cgtggtgacc gtgccctcca gcaacttcgg cacccagacc     240

tacacctgca acgtagatca caagcccagc aacaccaagg tggacaagac agttgagcgc     300

aaatgttgtg tcgagtgccc accgtgccca gcaccacctg tggcaggacc gtcagtcttc     360

ctcttccccc caaaacccaa ggacaccctc atgatctccc ggacccctga ggtcacgtgc     420

gtggtggtgg acgtgagcca cgaagacccc gaggtccagt tcaactggta cgtggacggc     480

gtggaggtgc ataatgccaa gacaaagcca cgggaggagc agttcaacag cacgttccgt     540

gtggtcagcg tcctcaccgt tgtgcaccag gactggctga acggcaagga gtacaagtgc     600

aaggtctcca acaaaggcct cccagccccc atcgagaaaa ccatctccaa aaccaaaggg     660

cagccccgag aaccacaggt gtacaccctg cccccatccc gggaggagat gaccaagaac     720

caggtcagcc tgacctgcct ggtcaaaggc ttctacccca gcgacatcgc cgtggagtgg     780

gagagcaatg ggcagccgga gaacaactac aagaccacac ctcccatgct ggactccgac     840

ggctccttct tcctctacag caagctcacc gtggacaaga gcaggtggca gcaggggaac     900

gtcttctcat gctccgtgat gcatgaggct ctgcacaacc actacacgca gaagagcctc     960

tccctgtctc cgggtaaa                                                   978


<210> SEQ ID NO 98
<211> LENGTH: 326
<212> TYPE: PRT
<213> ORGANISM: Homo Sapien

<400> SEQUENCE: 98

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 99
<211> LENGTH: 978
<212> TYPE: DNA
<213> ORGANISM: Homo Sapien

<400> SEQUENCE: 99

gcctccacca agggcccatc ggtcttcccc ctggcgccct gctccaggag cacctccgag      60

agcacagcgg ccctgggctg cctggtcaag gactacttcc ccgaaccggt gacggtgtcg     120

tggaactcag gcgctctgac cagcggcgtg cacaccttcc cggctgtcct acagtcctca     180

ggactctact ccctcagcag cgtggtgacc gtgacctcca gcaacttcgg cacccagacc     240

tacacctgca acgtagatca caagcccagc aacaccaagg tggacaagac agttgagcgc     300

aaatgttgtg tcgagtgccc accgtgccca gcaccacctg tggcaggacc gtcagtcttc     360

ctcttccccc caaaacccaa ggacaccctc atgatctccc ggacccctga ggtcacgtgc     420

gtggtggtgg acgtgagcca cgaagacccc gaggtccagt tcaactggta cgtggacggc     480

atggaggtgc ataatgccaa gacaaagcca cgggaggagc agttcaacag cacgttccgt     540
```

```
gtggtcagcg tcctcaccgt cgtgcaccag gactggctga acggcaagga gtacaagtgc    600

aaggtctcca acaaaggcct cccagccccc atcgagaaaa ccatctccaa aaccaaaggg    660

cagccccgag aaccacaggt gtacaccctg cccccatccc gggaggagat gaccaagaac    720

caggtcagcc tgacctgcct ggtcaaaggc ttctacccca gcgacatcgc cgtggagtgg    780

gagagcaatg ggcagccgga gaacaactac aagaccacac ctcccatgct ggactccgac    840

ggctccttct tcctctacag caagctcacc gtggacaaga gcaggtggca gcaggggaac    900

gtcttctcat gctccgtgat gcatgaggct ctgcacaacc actacacaca gaagagcctc    960

tccctgtctc cgggtaaa                                                  978


<210> SEQ ID NO 100
<211> LENGTH: 326
<212> TYPE: PRT
<213> ORGANISM: Homo Sapien

<400> SEQUENCE: 100

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Met Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
```

```
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 101
<211> LENGTH: 978
<212> TYPE: DNA
<213> ORGANISM: Homo Sapien

<400> SEQUENCE: 101

```
gcctccacca agggcccatc ggtcttcccc ctggcgccct gctccaggag cacctccgag     60

agcacagcgg ccctgggctg cctggtcaag gactacttcc ccgaaccggt gacggtgtcg    120

tggaactcag gcgctctgac cagcggcgtg cacaccttcc cagctgtcct acagtcctca    180

ggactctact ccctcagcag cgtggtgacc gtgccctcca gcagcttggg cacccagacc    240

tacacctgca acgtagatca caagcccagc aacaccaagg tggacaagac agttgagcgc    300

aaatgttgtg tcgagtgccc accgtgccca gcaccacctg tggcaggacc gtcagtcttc    360

ctcttccccc caaaacccaa ggacaccctc atgatctccc ggacccctga ggtcacgtgc    420

gtggtggtgg acgtgagcca cgaagacccc gaggtccagt tcaactggta cgtggacggc    480

gtggaggtgc ataatgccaa gacaaagcca cgggaggagc agttcaacag cacgttccgt    540

gtggtcagcg tcctcaccgt tgtgcaccag gactggctga acggcaagga gtacaagtgc    600

aaggtctcca acaaaggcct cccagccccc atcgagaaaa ccatctccaa aaccaaaggg    660

cagccccgag aaccacaggt gtacaccctg cccccatccc gggaggagat gaccaagaac    720

caggtcagcc tgacctgcct ggtcaaaggc ttctacccca gcgacatcgc cgtggagtgg    780

gagagcaatg ggcagccgga gaacaactac aagaccacac ctcccatgct ggactccgac    840

ggctccttct tcctctacag caagctcacc gtggacaaga gcaggtggca gcaggggaac    900

gtcttctcat gctccgtgat gcatgaggct ctgcacaacc actacacgca gaagagcctc    960

tccctgtctc cgggtaaa                                                  978
```

<210> SEQ ID NO 102
<211> LENGTH: 326
<212> TYPE: PRT
<213> ORGANISM: Homo Sapien

<400> SEQUENCE: 102

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110
```

```
Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 103
<211> LENGTH: 978
<212> TYPE: DNA
<213> ORGANISM: Homo Sapien

<400> SEQUENCE: 103

```
gcctccacca agggcccatc ggtcttcccc ctggcgccct gctccaggag cacctccgag     60

agcacagcgg ccctgggctg cctggtcaag gactacttcc ccgaaccggt gacggtgtcg    120

tggaactcag gcgctctgac cagcggcgtg cacaccttcc cggctgtcct acagtcctca    180

ggactctact ccctcagcag cgtggtgacc gtgccctcca gcaacttcgg cacccagacc    240

tacacctgca acgtagatca caagcccagc aacaccaagg tggacaagac agttgagcgc    300

aaatgttgtg tcgagtgccc accgtgccca gcaccacctg tggcaggacc gtcagtcttc    360

ctcttccccc caaaacccaa ggacaccctc atgatctccc ggacccctga ggtcacgtgc    420

gtggtggtgg acgtgagcca cgaagacccc gaggtccagt tcaactggta cgtggacggc    480

gtggaggtgc ataatgccaa gacaaagcca cgggaggagc agttcaacag cacgttccgt    540

gtggtcagcg tcctcaccgt cgtgcaccag gactggctga acggcaagga gtacaagtgc    600

aaggtctcca acaaaggcct cccagccccc atcgagaaaa ccatctccaa aaccaaaggg    660

cagccccgag aaccacaggt gtacaccctg cccccatccc gggaggagat gaccaagaac    720

caggtcagcc tgacctgcct ggtcaaaggc ttctacccca gcgacatctc cgtggagtgg    780

gagagcaatg ggcagccgga gaacaactac aagaccacac ctcccatgct ggactccgac    840

ggctccttct tcctctacag caagctcacc gtggacaaga gcaggtggca gcaggggaac    900
```

gtcttctcat gctccgtgat gcatgaggct ctgcacaacc actacacaca gaagagcctc 960
tccctgtctc cgggtaaa 978

<210> SEQ ID NO 104
<211> LENGTH: 326
<212> TYPE: PRT
<213> ORGANISM: Homo Sapien

<400> SEQUENCE: 104

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Pro Val Ala Gly Pro Ser Val Phe Leu Phe Pro Pro Lys Pro Lys Asp
115 120 125

Thr Leu Met Ile Ser Arg Thr Pro Glu Val Thr Cys Val Val Val Asp
130 135 140

Val Ser His Glu Asp Pro Glu Val Gln Phe Asn Trp Tyr Val Asp Gly
145 150 155 160

Val Glu Val His Asn Ala Lys Thr Lys Pro Arg Glu Glu Gln Phe Asn
165 170 175

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ala Pro Ile Glu Lys Thr Ile Ser Lys Thr Lys Gly Gln Pro Arg Glu
210 215 220

Pro Gln Val Tyr Thr Leu Pro Pro Ser Arg Glu Glu Met Thr Lys Asn
225 230 235 240

Gln Val Ser Leu Thr Cys Leu Val Lys Gly Phe Tyr Pro Ser Asp Ile
245 250 255

Ser Val Glu Trp Glu Ser Asn Gly Gln Pro Glu Asn Asn Tyr Lys Thr
260 265 270

Thr Pro Pro Met Leu Asp Ser Asp Gly Ser Phe Phe Leu Tyr Ser Lys
275 280 285

Leu Thr Val Asp Lys Ser Arg Trp Gln Gln Gly Asn Val Phe Ser Cys
290 295 300

Ser Val Met His Glu Ala Leu His Asn His Tyr Thr Gln Lys Ser Leu
305 310 315 320

Ser Leu Ser Pro Gly Lys
325

<210> SEQ ID NO 105
<211> LENGTH: 981

<212> TYPE: DNA
<213> ORGANISM: Homo Sapien

<400> SEQUENCE: 105
gcttccacca agggcccatc cgtcttcccc ctggcgccct gctccaggag cacctccgag 60
agcacagccg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacgaagacc 240
tacacctgca acgtagatca caagcccagc aacaccaagg tggacaagag agttgagtcc 300
aaatatggtc ccccatgccc atcatgccca gcacctgagt tcctgggggg accatcagtc 360
ttcctgttcc ccccaaaacc caaggacact ctcatgatct cccggacccc tgaggtcacg 420
tgcgtggtgg tggacgtgag ccaggaagac cccgaggtcc agttcaactg gtacgtggat 480
ggcgtggagg tgcataatgc caagacaaag ccgcgggagg agcagttcaa cagcacgtac 540
cgtgtggtca gcgtcctcac cgtcctgcac caggactggc tgaacggcaa ggagtacaag 600
tgcaaggtct ccaacaaagg cctcccgtcc tccatcgaga aaaccatctc caaagccaaa 660
gggcagcccc gagagccaca ggtgtacacc ctgcccccat cccaggagga gatgaccaag 720
aaccaggtca gcctgacctg cctggtcaaa ggcttctacc ccagcgacat cgccgtggag 780
tgggagagca atgggcagcc ggagaacaac tacaagacca cgcctcccgt gctggactcc 840
gacggctcct tcttcctcta cagcaggcta accgtggaca agagcaggtg gcaggagggg 900
aatgtcttct catgctccgt gatgcatgag gctctgcaca accactacac acagaagagc 960
ctctccctgt ctctgggtaa a 981

<210> SEQ ID NO 106
<211> LENGTH: 327
<212> TYPE: PRT
<213> ORGANISM: Homo Sapien

<400> SEQUENCE: 106

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Lys Thr
65 70 75 80

Tyr Thr Cys Asn Val Asp His Lys Pro Ser Asn Thr Lys Val Asp Lys
85 90 95

Arg Val Glu Ser Lys Tyr Gly Pro Pro Cys Pro Ser Cys Pro Ala Pro
100 105 110

Glu Phe Leu Gly Gly Pro Ser Val Phe Leu Phe Pro Pro Lys Pro Lys
115 120 125

Asp Thr Leu Met Ile Ser Arg Thr Pro Glu Val Thr Cys Val Val Val
130 135 140

Asp Val Ser Gln Glu Asp Pro Glu Val Gln Phe Asn Trp Tyr Val Asp
145 150 155 160

Gly Val Glu Val His Asn Ala Lys Thr Lys Pro Arg Glu Glu Gln Phe
165 170 175

```
Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 107
<211> LENGTH: 981
<212> TYPE: DNA
<213> ORGANISM: Homo Sapien

<400> SEQUENCE: 107

```
gcttccacca agggcccatc cgtcttcccc ctggcgccct gctccaggag cacctccgag      60

agcacagccg ccctgggctg cctggtcaag gactacttcc ccgaaccggt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacgaagacc     240

tacacctgca acgtagatca caagcccagc aacaccaagg tggacaagag agttgagtcc     300

aaatatggtc ccccgtgccc atcatgccca gcacctgagt tcctgggggg accatcagtc     360

ttcctgttcc ccccaaaacc caaggacact ctcatgatct cccggacccc tgaggtcacg     420

tgcgtggtgg tggacgtgag ccaggaagac cccgaggtcc agttcaactg gtacgtggat     480

ggcgtggagg tgcataatgc caagacaaag ccgcgggagg agcagttcaa cagcacgtac     540

cgtgtggtca gcgtcctcac cgtcgtgcac caggactggc tgaacggcaa ggagtacaag     600

tgcaaggtct ccaacaaagg cctcccgtcc tccatcgaga aaaccatctc caaagccaaa     660

gggcagcccc gagagccaca ggtgtacacc ctgcccccat cccaggagga gatgaccaag     720

aaccaggtca gcctgacctg cctggtcaaa ggcttctacc ccagcgacat cgccgtggag     780

tgggagagca atgggcagcc ggagaacaac tacaagacca cgcctcccgt gctggactcc     840

gacggctcct tcttcctcta cagcaggcta accgtggaca agagcaggtg gcaggagggg     900

aatgtcttct catgctccgt gatgcatgag gctctgcaca accactacac gcagaagagc     960

ctctccctgt ctctgggtaa a                                                981
```

<210> SEQ ID NO 108
<211> LENGTH: 327
<212> TYPE: PRT
<213> ORGANISM: Homo Sapien

<400> SEQUENCE: 108

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 109
<211> LENGTH: 981
<212> TYPE: DNA
<213> ORGANISM: Homo Sapien

<400> SEQUENCE: 109

```
gcttccacca agggcccatc cgtcttcccc ctggcgccct gctccaggag cacctccgag      60

agcacagccg ccctgggctg cctggtcaag gactacttcc ccgaaccggt gacggtgtcg     120

tggaactcag gcgccctgac cagcggcgtg cacaccttcc cggctgtcct acagtcctca     180
```

```
ggactctact ccctcagcag cgtggtgacc gtgccctcca gcagcttggg cacgaagacc    240

tacacctgca acgtagatca caagcccagc aacaccaagg tggacaagag agttgagtcc    300

aaatatggtc ccccatgccc atcatgccca gcacctgagt tcctgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtcc tccatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggctcct tcttcctcta cagcaagctc accgtggaca agagcaggtg gcaggagggg    900

aacgtcttct catgctccgt gatgcatgag gctctgcaca accactacac gcagaagagc    960

ctctccctgt ctctgggtaa a                                              981


<210> SEQ ID NO 110
<211> LENGTH: 327
<212> TYPE: PRT
<213> ORGANISM: Homo Sapien

<400> SEQUENCE: 110

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
```

```
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 111
<211> LENGTH: 981
<212> TYPE: DNA
<213> ORGANISM: Artificial Sequence
<220> FEATURE:
<223> OTHER INFORMATION: Human IgG4-PE constant region

<400> SEQUENCE: 111

gcctccacca agggcccatc cgtcttcccc ctggcgccct gctccaggag cacctccgag      60

agcacggccg ccctgggctg cctggtcaag gactacttcc ccgaaccagt gacggtgtcg     120

tggaactcag gcgccctgac cagcggcgtg cacaccttcc cggctgtcct acagtcctca     180

ggactctact ccctcagcag cgtggtgacc gtgccctcca gcagcttggg cacgaagacc     240

tacacctgca acgtagatca caagcccagc aacaccaagg tggacaagag agttgagtcc     300

aaatatggtc ccccatgccc accatgccca gcgcctgaat ttgagggggg accatcagtc     360

ttcctgttcc ccccaaaacc caaggacact ctcatgatct cccggacccc tgaggtcacg     420

tgcgtggtgg tggacgtgag ccaggaagac cccgaggtcc agttcaactg gtacgtggat     480

ggcgtggagg tgcataatgc caagacaaag ccgcgggagg agcagttcaa cagcacgtac     540

cgtgtggtca gcgtcctcac cgtcctgcac caggactggc tgaacggcaa ggagtacaag     600

tgcaaggtct ccaacaaagg cctcccgtca tcgatcgaga aaaccatctc caaagccaaa     660

gggcagcccc gagagccaca ggtgtacacc ctgcccccat cccaggagga gatgaccaag     720

aaccaggtca gcctgacctg cctggtcaaa ggcttctacc ccagcgacat cgccgtggag     780

tgggagagca atgggcagcc ggagaacaac tacaagacca cgcctcccgt gctggactcc     840

gacggatcct tcttcctcta cagcaggcta accgtggaca agagcaggtg gcaggagggg     900

aatgtcttct catgctccgt gatgcatgag gctctgcaca accactacac acagaagagc     960

ctctccctgt ctctgggtaa a                                               981


<210> SEQ ID NO 112
<211> LENGTH: 981
<212> TYPE: DNA
<213> ORGANISM: Artificial Sequence
<220> FEATURE:
<223> OTHER INFORMATION: Human IgG4-PE constant region

<400> SEQUENCE: 112

gcctccacca agggacctag cgtgttccct ctcgcccct gttccaggtc cacaagcgag       60

tccaccgctg ccctcggctg tctggtgaaa gactactttc ccgagcccgt gaccgtctcc     120

tggaatagcg gagccctgac ctccggcgtg cacacatttc ccgccgtgct gcagagcagc     180
```

```
ggactgtata gcctgagcag cgtggtgacc gtgcccagct ccagcctcgg caccaaaacc    240

tacacctgca acgtggacca caagccctcc aacaccaagg tggacaagcg ggtggagagc    300

aagtacggcc ccccttgccc tccttgtcct gcccctgagt tcgagggagg accctccgtg    360

ttcctgtttc cccccaaacc caaggacacc ctgatgatct cccggacacc cgaggtgacc    420

tgtgtggtcg tggacgtcag ccaggaggac cccgaggtgc agttcaactg gtatgtggac    480

ggcgtggagg tgcacaatgc caaaaccaag cccagggagg agcagttcaa ttccacctac    540

agggtggtga gcgtgctgac cgtcctgcat caggattggc tgaacggcaa ggagtacaag    600

tgcaaggtgt ccaacaaggg actgcccagc tccatcgaga agaccatcag caaggctaag    660

ggccagccga gggagcccca ggtgtatacc ctgcctccta gccaggaaga gatgaccaag    720

aaccaagtgt ccctgacctg cctggtgaag ggattctacc cctccgacat cgccgtggag    780

tgggagagca atggccagcc cgagaacaac tacaaaacaa cccctcccgt gctcgatagc    840

gacggcagct tctttctcta cagccggctg acagtggaca agagcaggtg gcaggagggc    900

aacgtgttct cctgttccgt gatgcacgag gccctgcaca atcactacac ccagaagagc    960

ctctccctgt ccctgggcaa g                                              981
```

<210> SEQ ID NO 113
<211> LENGTH: 981
<212> TYPE: DNA
<213> ORGANISM: Artificial Sequence
<220> FEATURE:
<223> OTHER INFORMATION: Human IgG4-PE constant region

<400> SEQUENCE: 113

```
gccagcacca agggcccttc cgtgttcccc ctggcccctt gcagcaggag cacctccgaa     60

tccacagctg ccctgggctg tctggtgaag gactactttc ccgagcccgt gaccgtgagc    120

tggaacagcg gcgctctgac atccggcgtc cacacctttc ctgccgtcct gcagtcctcc    180

ggcctctact ccctgtcctc cgtggtgacc gtgcctagct cctccctcgg caccaagacc    240

tacacctgta acgtggacca caaaccctcc aacaccaagg tggacaaacg ggtcgagagc    300

aagtacggcc ctccctgccc tccttgtcct gcccccgagt tcgaaggcgg acccagcgtg    360

ttcctgttcc ctcctaagcc caaggacacc ctcatgatca gccggacacc cgaggtgacc    420

tgcgtggtgg tggatgtgag ccaggaggac cctgaggtcc agttcaactg gtatgtggat    480

ggcgtggagg tgcacaacgc caagacaaag ccccgggaag agcagttcaa ctccacctac    540

agggtggtca gcgtgctgac cgtgctgcat caggactggc tgaacggcaa ggagtacaag    600

tgcaaggtca gcaataaggg actgcccagc agcatcgaga agaccatctc caaggctaaa    660

ggccagcccc gggaacctca ggtgtacacc ctgcctccca gccaggagga gatgaccaag    720

aaccaggtga gcctgacctg cctggtgaag ggattctacc cttccgacat cgccgtggag    780

tgggagtcca acggccagcc cgagaacaat tataagacca cccctcccgt cctcgacagc    840

gacggatcct tctttctgta ctccaggctg accgtggata agtccaggtg gcaggaaggc    900

aacgtgttca gctgctccgt gatgcacgag gccctgcaca atcactacac ccagaagtcc    960

ctgagcctgt ccctgggaaa g                                              981
```

<210> SEQ ID NO 114
<211> LENGTH: 327
<212> TYPE: PRT
<213> ORGANISM: Artificial Sequence
<220> FEATURE:

<223> OTHER INFORMATION: Human IgG4-PE constant region

<400> SEQUENCE: 114

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 115
<211> LENGTH: 981
<212> TYPE: DNA
<213> ORGANISM: Artificial Sequence
<220> FEATURE:
<223> OTHER INFORMATION: Inactivated Human IgG4

<400> SEQUENCE: 115

```
gcctccacca agggcccatc cgtcttcccc ctggcgccct gctccaggag cacctccgag     60
```

```
agcacggccg ccctgggctg cctggtcaag gactacttcc ccgaaccagt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacgaagacc    240

tacacctgca acgtagatca caagcccagc aacaccaagg tggacaagag agttgagtcc    300

aaatatggtc ccccatgccc accatgccca gcgcctccag ttgcgggggg accatcagtc    360

ttcctgttcc ccccaaaacc caaggacact ctcatgatct cccggacccc tgaggtcacg    420

tgcgtggtgg tggacgtgag ccaggaagac cccgaggtcc agttcaactg gtacgtggat    480

ggcgtggagg tgcataatgc caagacaaag ccgcgggagg agcagttcaa cagcacgtac    540

cgtgtggtca gcgtcctcac cgtcctgcac caggactggc tgaacggcaa ggagtacaag    600

tgcaaggtct ccaacaaagg cctcccgtca tcgatcgaga aaaccatctc caaagccaaa    660

gggcagcccc gagagccaca ggtgtacacc ctgcccccat cccaggagga gatgaccaag    720

aaccaggtca gcctgacctg cctggtcaaa ggcttctacc ccagcgacat cgccgtggag    780

tgggagagca atgggcagcc ggagaacaac tacaagacca cgcctcccgt gctggactcc    840

gacggatcct tcttcctcta cagcaggcta accgtggaca agagcaggtg gcaggagggg    900

aatgtcttct catgctccgt gatgcatgag gctctgcaca accactacac acagaagagc    960

ctctccctgt ctctgggtaa a                                              981
```

```
<210> SEQ ID NO 116
<211> LENGTH: 327
<212> TYPE: PRT
<213> ORGANISM: Artificial Sequence
<220> FEATURE:
<223> OTHER INFORMATION: Inactivated Human IgG4

<400> SEQUENCE: 116

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
```

```
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 117
<211> LENGTH: 321
<212> TYPE: DNA
<213> ORGANISM: Homo Sapien

<400> SEQUENCE: 117

cgtacggtgg ccgctccctc cgtgttcatc ttcccacctt ccgacgagca gctgaagtcc      60

ggcaccgctt ctgtcgtgtg cctgctgaac aacttctacc cccgcgaggc caaggtgcag     120

tggaaggtgg acaacgccct gcagtccggc aactcccagg aatccgtgac cgagcaggac     180

tccaaggaca gcacctactc cctgtcctcc accctgaccc tgtccaaggc cgactacgag     240

aagcacaagg tgtacgcctg cgaagtgacc caccagggcc tgtctagccc cgtgaccaag     300

tctttcaacc ggggcgagtg t                                               321


<210> SEQ ID NO 118
<211> LENGTH: 107
<212> TYPE: PRT
<213> ORGANISM: Homo Sapien

<400> SEQUENCE: 118

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 119
<211> LENGTH: 321
<212> TYPE: DNA
```

<213> ORGANISM: Homo Sapien

<400> SEQUENCE: 119

```
cgaactgtgg ctgcaccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggag    180

agcaaggaca gcacctacag cctcagcagc accctgacgc tgagcaaagc agactacgag    240

aaacacaaag tctacgccgg cgaagtcacc catcagggcc tgagctcgcc cgtcacaaag    300

agcttcaaca ggggagagtg t                                              321
```

<210> SEQ ID NO 120
<211> LENGTH: 107
<212> TYPE: PRT
<213> ORGANISM: Homo Sapien

<400> SEQUENCE: 120

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105
```

<210> SEQ ID NO 121
<211> LENGTH: 321
<212> TYPE: DNA
<213> ORGANISM: Homo Sapien

<400> SEQUENCE: 121

```
cgaactgtgg ctgcaccatc tgtcttcatc ttcccgccat ctgatgagca gttgaaatct     60

ggaactgcct ctgttgtgtg cctgctgaat aacttctatc ccagagaggc caaagtacag    120

cggaaggtgg ataacgccct ccaatcgggt aactcccagg agagtgtcac agagcaggag    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg t                                              321
```

<210> SEQ ID NO 122
<211> LENGTH: 107
<212> TYPE: PRT
<213> ORGANISM: Homo Sapien

<400> SEQUENCE: 122

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 123
<211> LENGTH: 321
<212> TYPE: DNA
<213> ORGANISM: Homo Sapien

<400> SEQUENCE: 123
cgaactgtgg ctgcaccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcagc accctgacgc tgagcaaagc agactacgag 240
aaacacaaac tctacgcctg cgaagtcacc catcagggcc tgagctcgcc cgtcacaaag 300
agcttcaaca ggggagagtg t 321

<210> SEQ ID NO 124
<211> LENGTH: 107
<212> TYPE: PRT
<213> ORGANISM: Homo Sapien

<400> SEQUENCE: 124

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 125
<211> LENGTH: 321
<212> TYPE: DNA
<213> ORGANISM: Homo Sapien

<400> SEQUENCE: 125
cgaactgtgg ctgcaccatc tgtcttcatc ttcccgccat ctgatgagca gttgaaatct 60
ggaactgcct ctgttgtgtg cctgctgaat aacttctatc ccagagaggc caaagtacag 120
tggaaggtgg ataacgccct ccaatcgggt aactcccagg agagtgtcac agagcaggac 180
agcaaggaca gcacctacag cctcagcaac accctgacgc tgagcaaagc agactacgag 240
aaacacaaag tctacgcctg cgaagtcacc catcagggcc tgagctcgcc cgtcacaaag 300
agcttcaaca ggggagagtg c 321

<210> SEQ ID NO 126
<211> LENGTH: 107
<212> TYPE: PRT
<213> ORGANISM: Homo Sapien

<400> SEQUENCE: 126

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Asn Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 127
<211> LENGTH: 312
<212> TYPE: DNA
<213> ORGANISM: Homo Sapien

<400> SEQUENCE: 127
cccaaggcca accccacggt cactctgttc ccgccctcct ctgaggagct ccaagccaac 60
aaggccacac tagtgtgtct gatcagtgac ttctacccgg gagctgtgac agtggcttgg 120
aaggcagatg gcagccccgt caaggcggga gtggagacga ccaaaccctc caaacagagc 180
aacaacaagt acgcggccag cagctacctg agcctgacgc ccgagcagtg gaagtcccac 240
agaagctaca gctgccaggt cacgcatgaa gggagcaccg tggagaagac agtggcccct 300
acagaatgtt ca 312

<210> SEQ ID NO 128
<211> LENGTH: 104
<212> TYPE: PRT
<213> ORGANISM: Homo Sapien

<400> SEQUENCE: 128

Pro Lys Ala Asn Pro Thr Val Thr Leu Phe Pro Pro Ser Ser Glu Glu
1 5 10 15

Leu Gln Ala Asn Lys Ala Thr Leu Val Cys Leu Ile Ser Asp Phe Tyr
20 25 30

Pro Gly Ala Val Thr Val Ala Trp Lys Ala Asp Gly Ser Pro Val Lys
35 40 45

Ala Gly Val Glu Thr Thr Lys Pro Ser Lys Gln Ser Asn Asn Lys Tyr
50 55 60

Ala Ala Ser Ser Tyr Leu Ser Leu Thr Pro Glu Gln Trp Lys Ser His
65 70 75 80

Arg Ser Tyr Ser Cys Gln Val Thr His Glu Gly Ser Thr Val Glu Lys
85 90 95

Thr Val Ala Pro Thr Glu Cys Ser
100

<210> SEQ ID NO 129
<211> LENGTH: 318
<212> TYPE: DNA
<213> ORGANISM: Homo Sapien

<400> SEQUENCE: 129
ggtcagccca aggccaaccc cactgtcact ctgttcccgc cctcctctga ggagctccaa 60
gccaacaagg ccacactagt gtgtctgatc agtgacttct acccgggagc tgtgacagtg 120
gcctggaagg cagatggcag ccccgtcaag gcgggagtgg agaccaccaa accctccaaa 180
cagagcaaca acaagtacgc ggccagcagc tacctgagcc tgacgcccga gcagtggaag 240
tcccacagaa gctacagctg ccaggtcacg catgaaggga gcaccgtgga gaagacagtg 300
gcccctacag aatgttca 318

<210> SEQ ID NO 130
<211> LENGTH: 318
<212> TYPE: DNA
<213> ORGANISM: Homo Sapien

<400> SEQUENCE: 130
ggtcagccca aggccaaccc cactgtcact ctgttcccgc cctcctctga ggagctccaa 60
gccaacaagg ccacactagt gtgtctgatc agtgacttct acccgggagc tgtgacagtg 120
gcctggaagg cagatggcag ccccgtcaag gcgggagtgg agaccaccaa accctccaaa 180
cagagcaaca acaagtacgc ggccagcagc tacctgagcc tgacgcccga gcagtggaag 240
tcccacagaa gctacagctg ccaggtcacg catgaaggga gcaccgtgga gaagacagtg 300
gcccctacag aatgttca 318

<210> SEQ ID NO 131
<211> LENGTH: 106
<212> TYPE: PRT
<213> ORGANISM: Homo Sapien

<400> SEQUENCE: 131

Gly Gln Pro Lys Ala Asn Pro Thr Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Gly Ser Pro
35 40 45

Val Lys Ala Gly Val Glu Thr Thr Lys Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Arg Ser Tyr Ser Cys Gln Val Thr His Glu Gly Ser Thr Val
85 90 95

Glu Lys Thr Val Ala Pro Thr Glu Cys Ser
100 105

<210> SEQ ID NO 132
<211> LENGTH: 318
<212> TYPE: DNA
<213> ORGANISM: Homo Sapien

<400> SEQUENCE: 132
ggccagccta aggccgctcc ttctgtgacc ctgttccccc catcctccga ggaactgcag 60
gctaacaagg ccaccctcgt gtgcctgatc agcgacttct accctggcgc cgtgaccgtg 120
gcctggaagg ctgatagctc tcctgtgaag gccggcgtgg aaaccaccac cccttccaag 180
cagtccaaca acaaatacgc cgcctcctcc tacctgtccc tgacccctga gcagtggaag 240
tcccaccggt cctacagctg ccaagtgacc cacgagggct ccaccgtgga aaagaccgtg 300
gctcctaccg agtgctcc 318

<210> SEQ ID NO 133
<211> LENGTH: 318
<212> TYPE: DNA
<213> ORGANISM: Homo Sapien

<400> SEQUENCE: 133
ggccagccta aagctgcccc cagcgtcacc ctgtttcctc cctccagcga ggagctccag 60
gccaacaagg ccaccctcgt gtgcctgatc tccgacttct atcccggcgc tgtgaccgtg 120
gcttggaaag ccgactccag ccctgtcaaa gccggcgtgg agaccaccac accctccaag 180
cagtccaaca acaagtacgc cgcctccagc tatctctccc tgacccctga gcagtggaag 240
tcccaccggt cctactcctg tcaggtgacc cacgagggct ccaccgtgga aaagaccgtc 300
gcccccaccg agtgctcc 318

<210> SEQ ID NO 134
<211> LENGTH: 106
<212> TYPE: PRT
<213> ORGANISM: Homo Sapien

<400> SEQUENCE: 134

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Arg Ser Tyr Ser Cys Gln Val Thr His Glu Gly Ser Thr Val
85 90 95

Glu Lys Thr Val Ala Pro Thr Glu Cys Ser
100 105

<210> SEQ ID NO 135
<211> LENGTH: 318
<212> TYPE: DNA
<213> ORGANISM: Homo Sapien

<400> SEQUENCE: 135
ggtcagccca aggctgcccc ctcggtcact ctgttcccgc cctcctctga ggagcttcaa 60
gccaacaagg ccacactggt gtgtctcata agtgacttct acccgggagc cgtgacagtg 120
gcctggaagg cagatagcag ccccgtcaag gcgggagtgg agaccaccac accctccaaa 180
caaagcaaca acaagtacgc ggccagcagc tatctgagcc tgacgcctga gcagtggaag 240
tcccacagaa gctacagctg ccaggtcacg catgaaggga gcaccgtgga gaagacagtg 300
gcccctacag aatgttca 318

<210> SEQ ID NO 136
<211> LENGTH: 106
<212> TYPE: PRT
<213> ORGANISM: Homo Sapien

<400> SEQUENCE: 136

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Arg Ser Tyr Ser Cys Gln Val Thr His Glu Gly Ser Thr Val
85 90 95

Glu Lys Thr Val Ala Pro Thr Glu Cys Ser
100 105

<210> SEQ ID NO 137
<211> LENGTH: 312
<212> TYPE: DNA
<213> ORGANISM: Homo Sapien

<400> SEQUENCE: 137
cccaaggctg ccccctcggt cactctgttc ccaccctcct ctgaggagct tcaagccaac 60
aaggccacac tggtgtgtct cataagtgac ttctacccgg gagccgtgac agttgcctgg 120
aaggcagata gcagccccgt caaggcgggg gtggagacca ccacaccctc caaacaaagc 180
aacaacaagt acgcggccag cagctacctg agcctgacgc ctgagcagtg gaagtcccac 240
aaaagctaca gctgccaggt cacgcatgaa gggagcaccg tggagaagac agttgcccct 300
acggaatgtt ca 312

<210> SEQ ID NO 138
<211> LENGTH: 104
<212> TYPE: PRT
<213> ORGANISM: Homo Sapien

<400> SEQUENCE: 138

Pro Lys Ala Ala Pro Ser Val Thr Leu Phe Pro Pro Ser Ser Glu Glu
1 5 10 15

Leu Gln Ala Asn Lys Ala Thr Leu Val Cys Leu Ile Ser Asp Phe Tyr
20 25 30

Pro Gly Ala Val Thr Val Ala Trp Lys Ala Asp Ser Ser Pro Val Lys
35 40 45

Ala Gly Val Glu Thr Thr Thr Pro Ser Lys Gln Ser Asn Asn Lys Tyr
50 55 60

Ala Ala Ser Ser Tyr Leu Ser Leu Thr Pro Glu Gln Trp Lys Ser His
65 70 75 80

Lys Ser Tyr Ser Cys Gln Val Thr His Glu Gly Ser Thr Val Glu Lys
85 90 95

Thr Val Ala Pro Thr Glu Cys Ser
100

<210> SEQ ID NO 139
<211> LENGTH: 318
<212> TYPE: DNA
<213> ORGANISM: Homo Sapien

<400> SEQUENCE: 139
ggtcagccca aggctgcccc ctcggtcact ctgttcccac cctcctctga ggagcttcaa 60
gccaacaagg ccacactggt gtgtctcata agtgacttct acccggggcc agtgacagtt 120
gcctggaagg cagatagcag ccccgtcaag gcgggggtgg agaccaccac accctccaaa 180
caaagcaaca acaagtacgc ggccagcagc tacctgagcc tgacgcctga gcagtggaag 240
tcccacaaaa gctacagctg ccaggtcacg catgaaggga gcaccgtgga gaagacagtg 300
gcccctacgg aatgttca 318

<210> SEQ ID NO 140
<211> LENGTH: 106
<212> TYPE: PRT
<213> ORGANISM: Homo Sapien

<400> SEQUENCE: 140

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Pro Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Lys Ser Tyr Ser Cys Gln Val Thr His Glu Gly Ser Thr Val
85 90 95

Glu Lys Thr Val Ala Pro Thr Glu Cys Ser
100 105

<210> SEQ ID NO 141
<211> LENGTH: 318
<212> TYPE: DNA
<213> ORGANISM: Homo Sapien

<400> SEQUENCE: 141
ggtcagccca aggctgcccc ctcggtcact ctgttcccac cctcctctga ggagcttcaa 60
gccaacaagg ccacactggt gtgtctcata agtgacttct acccgggagc cgtgacagtg 120
gcctggaagg cagatagcag ccccgtcaag gcgggagtgg agaccaccac accctccaaa 180
caaagcaaca acaagtacgc ggccagcagc tacctgagcc tgacgcctga gcagtggaag 240
tcccacaaaa gctacagctg ccaggtcacg catgaaggga gcaccgtgga gaagacagtg 300
gcccctacag aatgttca 318

<210> SEQ ID NO 142
<211> LENGTH: 106
<212> TYPE: PRT
<213> ORGANISM: Homo Sapien

<400> SEQUENCE: 142

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 143
<211> LENGTH: 318
<212> TYPE: DNA
<213> ORGANISM: Homo Sapien

<400> SEQUENCE: 143

ggtcagccca aggctgcccc ctcggtcact ctgttcccgc cctcctctga ggagcttcaa      60

gccaacaagg ccacactggt gtgtctcata agtgacttct acccgggagc cgtgacagtg     120

gcctggaagg cagatagcag ccccgtcaag gcgggagtgg agaccaccac accctccaaa     180

caaagcaaca acaagtacgc ggccagcagc tacctgagcc tgacgcctga gcagtggaag     240

tcccacagaa gctacagctg ccaggtcacg catgaaggga gcaccgtgga gaagacagtg     300

gcccctacag aatgttca                                                   318


<210> SEQ ID NO 144
<211> LENGTH: 106
<212> TYPE: PRT
<213> ORGANISM: Homo Sapien

<400> SEQUENCE: 144

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 145
<211> LENGTH: 318
<212> TYPE: DNA
<213> ORGANISM: Homo Sapien

<400> SEQUENCE: 145
```

```
ggtcagccca aggctgcccc atcggtcact ctgttcccgc cctcctctga ggagcttcaa     60

gccaacaagg ccacactggt gtgcctgatc agtgacttct acccgggagc tgtgaaagtg    120

gcctggaagg cagatggcag ccccgtcaac acgggagtgg agaccaccac accctccaaa    180

cagagcaaca acaagtacgc ggccagcagc tacctgagcc tgacgcctga gcagtggaag    240

tcccacagaa gctacagctg ccaggtcacg catgaaggga gcaccgtgga gaagacagtg    300

gcccctgcag aatgttca                                                   318


<210> SEQ ID NO 146
<211> LENGTH: 106
<212> TYPE: PRT
<213> ORGANISM: Homo Sapien

<400> SEQUENCE: 146

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105


<210> SEQ ID NO 147
<211> LENGTH: 318
<212> TYPE: DNA
<213> ORGANISM: Homo Sapien

<400> SEQUENCE: 147

ggtcagccca aggctgcccc atcggtcact ctgttcccac cctcctctga ggagcttcaa     60

gccaacaagg ccacactggt gtgtctcgta agtgacttct acccgggagc cgtgacagtg    120

gcctggaagg cagatggcag ccccgtcaag gtgggagtgg agaccaccaa accctccaaa    180

caaagcaaca acaagtatgc ggccagcagc tacctgagcc tgacgcccga gcagtggaag    240

tcccacagaa gctacagctg ccgggtcacg catgaaggga gcaccgtgga gaagacagtg    300

gcccctgcag aatgctct                                                   318


<210> SEQ ID NO 148
<211> LENGTH: 106
<212> TYPE: PRT
<213> ORGANISM: Homo Sapien

<400> SEQUENCE: 148

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
```

-continued

```
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105


<210> SEQ ID NO 149
<211> LENGTH: 318
<212> TYPE: DNA
<213> ORGANISM: Homo Sapien

<400> SEQUENCE: 149

ggtcagccca aggctgcccc ctcggtcact ctgttcccac cctcctctga ggagcttcaa      60

gccaacaagg ccacactggt gtgtctcgta agtgacttca acccgggagc cgtgacagtg     120

gcctggaagg cagatggcag ccccgtcaag gtgggagtgg agaccaccaa accctccaaa     180

caaagcaaca acaagtatgc ggccagcagc tacctgagcc tgacgcccga gcagtggaag     240

tcccacagaa gctacagctg ccgggtcacg catgaaggga gcaccgtgga gaagacagtg     300

gcccctgcag aatgctct                                                   318
```

ANTAGONISTS ANTI-CD7 ANTIBODIES

RELATED APPLICATIONS

This application is a 35 U.S.C. § 371 filing of International Patent Application No. PCT/GB2020/050976, filed Apr. 17, 2020, which claims priority to Great Britain Patent Application No. 1905552.4, filed Apr. 18, 2019, the entire disclosures of which are hereby incorporated herein by reference.

FIELD OF THE INVENTION

The invention relates to Cluster of Differentiation 7 (CD7)-expressing cell depletion or CD7 antagonism, such as antibodies and fragments, as well as methods, uses and combinations.

BACKGROUND

CD7 is a type I transmembrane protein expressed on the surface of T and NK lineage cells. CD7 is highly expressed in T-ALL cells. CD7 has been shown to be a validated biomarker for diagnosis of T-ALL. In addition, it is expressed in all CEBPA double mutated AML cases comprising 5-14% AML patients. It is also expressed in subset of MDS (Myelodysplastic syndromes) blasts. Based on these observations, it would be desirable to target CD7 with a ligand, such as an antibody, to kill tumour cells to treat these malignant diseases.

T-ALL is an uncommon aggressive leukaemia resulting from the malignant transformation of T cell progenitors. Rates of relapsed and refractory T-ALLs under current standard of care from multi-centre clinical trials are 20% in children and 40% in adults. Among relapsed patients, only 5% survive for more than 5 years. There is obviously high medical need for those T-ALL patients who are therapy resistant or who relapse after initial treatment.

STATEMENT OF INVENTION

In a first configuration the invention provides:

An antibody or fragment comprising a binding site which specifically binds to CD7 (Cluster of Differentiation 7), wherein the binding site comprises a VH domain that is encoded by a nucleotide sequence that is derived from the recombination of a human VH gene segment, DH gene segment and JH gene segment, wherein the VH gene segment is selected from IGHV3-15 and IGHV3-23.

In a second configuration the invention provides:

An antibody or fragment which specifically binds to CD7 and comprises a VH domain which comprises a CDRH3 sequence of an antibody selected from G09, F05, C02 and E04; or said sequence comprising 3, 2 or 1 amino acid substitution(s).

In a third configuration the invention provides:

An antibody or fragment (optionally according to any preceding claim) which specifically binds to CD7 and comprises a VL domain which comprises a CDRL3 sequence selected from SEQ ID NO: 13, 16, 33, 36, 53, 56, 73 and 76, or said selected CDRL3 sequence comprising 3, 2 or 1 amino acid substitution(s).

In a fourth configuration the invention provides:

An antibody or fragment comprising a binding site which specifically binds to CD7, wherein the binding site comprises a VL domain that comprises the amino acid sequence of a VL domain of an antibody selected from G09, F05, C02 and E04; or an amino acid that is at least 70% identical thereto.

In a fifth configuration the invention provides:

An antibody or fragment which specifically binds to CD7 and comprises the heavy chain amino acid sequence of an antibody selected from G09, F05, C02 and E04; or an amino acid that is at least 70% identical thereto.

In a sixth configuration the invention provides:

An antibody or fragment which specifically binds to CD7 and comprises the light chain amino acid sequence of an antibody selected from G09, F05, C02 and E04; or an amino acid that is at least 70% identical thereto.

In a seventh configuration the invention provides:

An antibody or fragment which specifically binds to a human CD7 epitope that is identical to an epitope to which the antibody of any preceding claim binds.

In a eighth configuration the invention provides:

An antibody or fragment which competes for binding to human CD7 with the antibody of any preceding configuration.

In a ninth configuration the invention provides:

A combination of an amount of an anti-CD7 antibody or fragment of the invention and an amount of a chemotherapeutic agent.

In a tenth configuration the invention provides:

Use of the antibody, fragment or combination of the invention in the manufacture of a medicament for administration to a subject for treating or preventing a CD7-mediated disease or condition, optionally a cancer.

In a eleventh configuration the invention provides:

A method of treating or preventing a CD7-mediated disease or condition in a subject (optionally a cancer), the method comprising administering to said subject a therapeutically effective amount of an antibody, fragment or combination of the invention, wherein the CD7-mediated disease or condition is thereby treated or prevented.

In a twefth configuration the invention provides:

A pharmaceutical composition comprising the antibody, fragment or combination.

In a thirteenth configuration the invention provides:

A nucleic acid that encodes a VH domain and/or a VL domain of an antibody or fragment of the invention.

In a fourteenth configuration the invention provides:

A nucleic acid that encodes a VH domain comprising the amino acid sequence of a VH domain of an antibody selected from G09, F05, C02 and E04; or an amino acid that is at least 70% identical thereto.

In a fifteenth configuration the invention provides:

A nucleic acid that encodes a VL domain comprising the amino acid sequence of a VL domain of an antibody selected from G09, F05, C02 and E04; or an amino acid that is at least 70% identical thereto.

In a sixteenth configuration the invention provides:

A nucleic acid comprising (a) a nucleotide sequence that is at least 70% identical to the sequence of SEQ ID NO: 10; and/or (b) a nucleotide sequence that is at least 70% identical to the sequence of SEQ ID NO: 20.

In a seventeenth configuration the invention provides:

A nucleic acid that encodes a heavy chain and/or a light chain of an antibody or fragment of the invention.

In a eighteenth configuration the invention provides:

A nucleic acid that encodes a heavy chain comprising an amino acid sequence that is at least 70% identical to SEQ ID NO: 8.

In a nineteenth configuration the invention provides:

A nucleic acid that encodes a light chain comprising an amino acid sequence that is at least 70% identical to SEQ ID NO: 18.

In a twentieth configuration the invention provides:

A nucleic acid (eg, in a host cell, eg, a CHO or HEK293 or Cos cell) comprising (a) a nucleotide sequence that is at least 70% identical to a heavy chain sequence selected of an antibody selected from G09, F05, C02 and E04; and/or (b) a nucleotide sequence that is at least 70% identical to a sequence selected of an antibody selected from G09, F05, C02 and E04.

In a twenty-first configuration the invention provides:

A vector comprising the nucleic acid(s); optionally wherein the vector is a CHO or HEK293 vector.

In a twenty-second configuration the invention provides:

A host cell comprising the nucleic acid(s) or the vector of the invention.

In a twenty-third configuration the invention provides:

An antibody, fragment, combination, vector, host cell, use or method as herein described.

In a twenty-fourth configuration the invention provides:

A method of diagnosing a CD7-mediated disease or condition in a subject (optionally a cancer), the method comprising combining an antibody or fragment of the invention with an isolated cell sample (eg, a blood or serum sample) and determining that cells comprised by the sample are specifically bound by the antibody or fragment.

Also provided is:

An in vitro assay for detecting CD7-positive cells in a sample, the assay comprising combining an antibody or fragment of the invention with an isolated cell sample (eg, a blood or serum sample) and determining that cells comprised by the sample are specifically bound by the antibody or fragment.

DETAILED DESCRIPTION

Definitions

Figure 1:
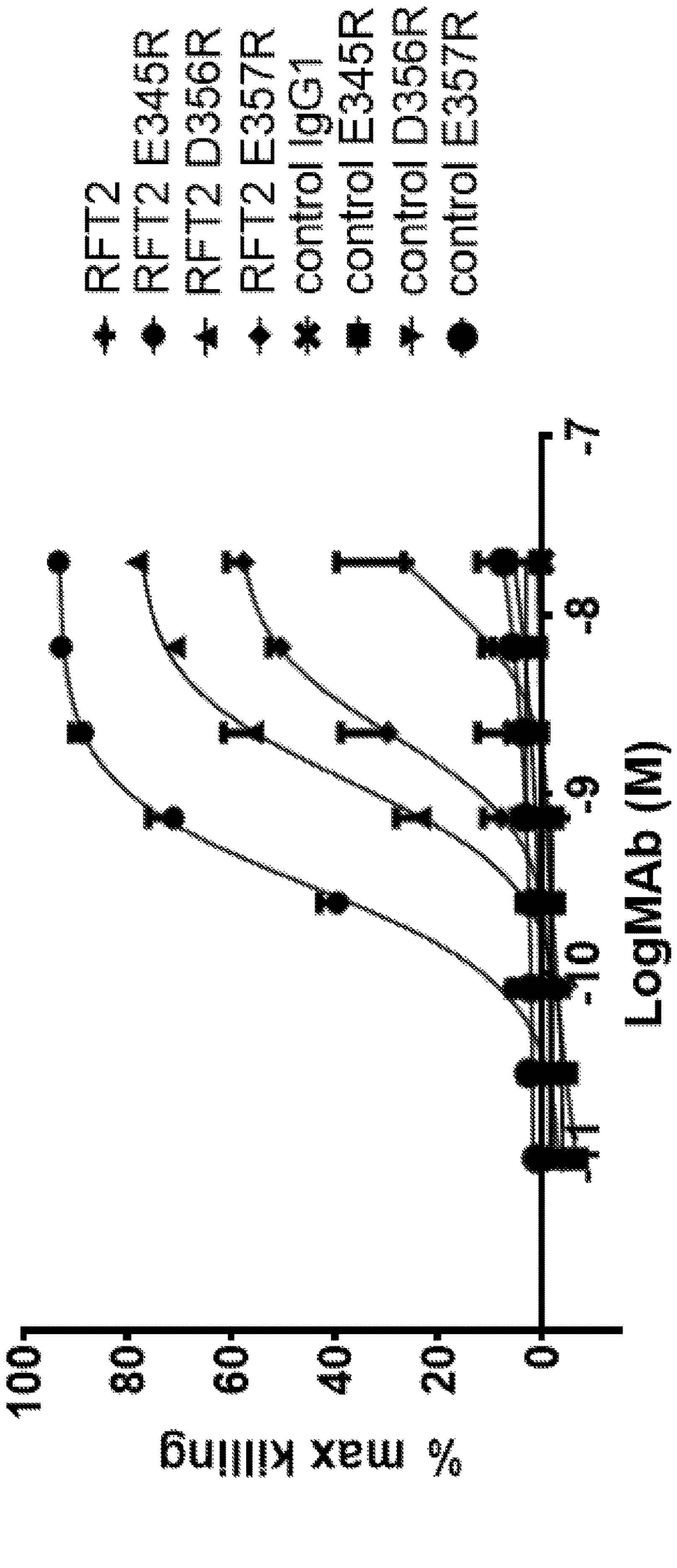
FIG. 1: Effect of IgG1 Fc variant on CDC activity of the anti-CD7 benchmark monoclonal antibody, RFT2. CEM cells were plated at 1,750 cells/well in a 384-well plate and human complement serum added at a 1/16 final concentration. Titrations of each RFT2 IgG1 variant as well as an isotype control were added and incubated for 2 hours at 37° C. CellTiter-Glo® was added and luminescence read on an Envision plate reader. Percentage killing was calculated for each antibody based on signal from wells without antibody and with/without cells. Error bars represent standard deviation of 3 replicates for each point. RFT2 E345R induced potent and maximum killing significantly greater than other variants. Data was analyzed using GraphPad Prism v7.02, where log antibody concentration (M) was plotted against % killing (mean±standard deviation) and a 4-parameter logistic curve fit was applied to data, allowing calculation of $EC_{50}$ values. The statistical comparison of the antibodies is shown in Table 6. RFT is discussed in J Immunol. 1989 Dec. 1; 143(11):3589-97, "Characterization of a human T cell-specific chimeric antibody (CD7) with human constant and mouse variable regions", Heinrich G et al.

Unless otherwise defined herein, scientific and technical terms shall have the meanings that are commonly understood by those of ordinary skill in the art. Further, unless otherwise required by context, singular terms shall include pluralities and plural terms shall include the singular.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia and is used herein to indicate a non-limiting example. Thus, the abbreviation "e.g." is synonymous with the term "for example." In the specification and claims, the term "about" is used to modify, for example, the quantity of an ingredient in a composition, concentration, volume, process temperature, process time, yield, flow rate, pressure, and like values, and ranges thereof, employed in describing the embodiments of the disclosure. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

As used herein, "administer" or "administration" refers to the act of injecting or otherwise physically delivering a substance as it exists outside the body (e.g., an anti-hCD7 antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

The term "antibody", "immunoglobulin" or "Ig" may be used interchangeably herein and means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', $F(ab')_2$, and Fv fragments), single chain Fv (scFv) mutants, multispecific antibodies such as bispecific antibodies (including dual binding antibodies), chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. The term "antibody" can also refer to a Y-shaped glycoprotein with a molecular weight of approximately 150 kDa that is made up of four polypeptide chains: two light (L) chains and two heavy (H) chains. There are five types of mammalian Ig heavy chain isotypes denoted by the Greek letters alpha (α), delta (δ), epsilon (ε), gamma (γ), and mu (μ). The type of heavy chain defines the class of antibody, i.e., IgA, IgD, IgE, IgG, and IgM, respectively. The γ and α classes are further divided into subclasses on the basis of differences in the constant domain sequence and function, e.g., IgG1, hIgG2, mIgG2A, mIgG2B, IgG3, IgG4, IgA1 and IgA2. In mammals, there are two types of immunoglobulin light chains, λ and κ. The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. An example of antibodies are heavy chain-only (ie, H2) antibodies that comprise a dimer of a heavy chain (5'-VH-(optional Hinge)-CH2-CH3-3') and are devoid of a light chain.

The antibodies described herein may be oligoclonal, polyclonal, monoclonal (including full-length monoclonal antibodies), camelised, chimeric, CDR-grafted, multi-specific, bi-specific (including dual-binding antibodies), catalytic, chimeric, humanized, fully human, anti-idiotypic, including antibodies that can be labelled in soluble or bound form as well as fragments, variants or derivatives thereof, either alone or in combination with other amino acid sequences provided by known techniques. An antibody may be from any species. Antibodies described herein can be naked or conjugated to other molecules such as toxins, radioisotopes, etc.

The term "antigen binding site," "antigen binding domain," "antigen binding region," "antigen binding fragment," and similar terms refer to that portion of an antibody which comprises the amino acid residues that interact with an antigen and confer on the binding agent its specificity and affinity for the antigen (e.g. the complementarity determining regions (CDRs)). The antigen binding region can be derived from any animal species, such as rodents (e.g. rabbit, rat or hamster) and humans. Preferably, the antigen binding region will be of human origin.

Antigen binding fragments described herein can include single-chain Fvs (scFv), single-chain antibodies, single domain antibodies, domain antibodies, Fv fragments, Fab fragments, F(ab') fragments, $F(ab')_2$ fragments, antibody fragments that exhibit the desired biological activity, disulfide-stabilised variable region (dsFv), dimeric variable region (diabody), anti-idiotypic (anti-Id) antibodies (including, e.g. anti-Id antibodies to antibodies), intrabodies, linear antibodies, single-chain antibody molecules and multispecific antibodies formed from antibody fragments and epitope-binding fragments of any of the above. In particular, antibodies and antibody fragments described herein can include immunoglobulin molecules and immunologically active fragments of immunoglobulin molecules, i.e., molecules that contain an antigen-binding site. Digestion of antibodies with the enzyme, papain, results in two identical antigen-binding fragments, known also as "Fab" fragments, and a "Fc" fragment, having no antigen-binding activity but having the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulfides. The effector functions of antibodies are determined by sequences in the Fc region, the region which is also recognized by Fc receptors (FcR) found on certain types of cells. Digestion of antibodies with the enzyme, pepsin, results in a $F(ab')_2$ fragment in which the two arms of the antibody molecule remain linked and comprise two-antigen binding sites. The $F(ab')_2$ fragment has the ability to crosslink antigen.

The term "derived from the recombination of" in relation to gene segments will be readily apparent to the skilled person, who will understand that B-cells recombine their variable region gene segments to produce coding sequence for variable domains. For example "derived from the recombination of a human VH gene segment, DH gene segment and JH gene segment" relates to the recombination of one human VH gene segment, with one DH gene segment and one JH gene segment together to form a rearranged VDJ sequence encoding a heavy chain antibody variable domain. Junctional and somatic hypermutation may also be features of the process, whereby the resulting recombined VDJ sequence includes one or more nucleotide additions, substitutions or deletions (eg, p-additions and/or n-additions) that are not comprised by the germline V, D and J sequences. The equivalent will be said of VK and JK gene segments for a kappa light chain variable domain, and of VA and JA for a lambda light chain variable domain. It is intended that any post-translational modifications may additionally encompassed in variable domains.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "monoclonal antibody" as used herein refers to an antibody obtained from a population of substantially homogeneous antibodies, i.e. the individual antibodies comprising the population are identical except for possible naturally occurring mutations and/or post-translation modifications (e.g. isomerizations, amidations) that may be present in minor amounts. Monoclonal antibodies are highly specific and are directed against a single antigentic determinant or epitope. In contrast, polyclonal antibody preparations typically include different antibodies directed against different antigenic determinants (or epitopes). The term "monoclonal antibody" as used herein encompasses both intact and full-length monoclonal antibodies as well as antibody fragments (such as Fab, Fab', $F(ab')_2$, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, hybridoma, phage selection, recombinant expression, and transgenic animals.

The monoclonal antibodies herein can include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies that exhibit the desired biological activity.

The term "humanised antibody" refers to a subset of chimeric antibodies in which a "hypervariable region" from a non-human immunoglobulin (the donor antibody) replaces residues from a hypervariable region in a human immunoglobulin (recipient antibody). In general, a humanized antibody will include substantially all of at least one, and typically two, variable domains, in which all or substantially all of the hypervariable loops correspond to those of a non-human immunoglobulin sequence, and all or substantially all of the framework regions are those of a human immunoglobulin sequence, although the framework regions may include one or more substitutions that improve antibody performance, such as binding affinity, isomerization, immunogenicity, etc.

Where utilised: ScFv is single variable fragment; Fc is fragment crystallisable; Fab is fragment antigen-binding, mAB is monoclonal antibody, dAb is domain antibody; sc is single chain; KIH is knobs-into-holes; TCR is T cell receptor; DT is dual targeting; IgG is Immunoglobulin G; Fv is variable fragment The term "bispecific antibody" means an antibody which comprises specificity for two target molecules, and includes, but is not limited to, formats such as Dual-Variable-Domain Immunoglobulins (DVD-Ig™) (see DiGiammarino et al., "Design and generation of DVD-Ig™ molecules for dual-specific targeting", Meth. Mo. Biol., 2012, 889, 145-156), $mAb^2$ (see WO2008/003103, the description of the $mAb^2$ format is incorporated herein by reference), FIT-Ig® (see WO2015/103072, the description of the Fabs-In-Tandem Immunoglobulin (FIT-Ig®) scaffold is incorporated herein by reference), mAb-dAb, dock and lock, Fab-arm exchange, strand-exchange engineered domain body (SEEDbody), Trifunctional antibodies (Triomab), LUZ-Y, Fc domain with antigen-binding sites (Fcab), κλ-body, orthogonal Fab, scDiabody-Fc, diabody-Fc, tandem scFv-Fc, Fab-scFv-Fc, Fab-scFv, intrabody, Bi-specific T-cell engager (BiTE), diabody, dual affinity retargeting antibody (DART), Tandem Diabody (TandAb®), scDiabody, scDiabody-CH3, Diabody-CH3, Triple body, Miniantibody, minibody, trimeric bispecific minibody (TriBi minibody), scFv-CH3 KIH, scFv-CH-CL-scFv, F(ab')2-scFv, scFv-KIH, Fab-scFv-Fc, tetravalent heavy chain-only antibodies (HCab), Immune-mobilizing monoclonal TCRs Against Cancer (ImmTAC), knobs-in-holes, knobs-in-holes with common light chain, knobs-in-holes with common light chain and charge pairs, charge pairs, charge pairs with common light chain, DT-IgG, DutaMab™, IgG(H)-scFv, scrv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and Zybody™, For a review of bispecific formats, see Spiess, C., et al., Mol. Immunol. (2015). In another embodiment, the bispecific molecule comprises an antibody which is fused to another non-Ig format, for example a T-cell receptor binding domain; an immunoglobulin superfamily domain; an agnathan variable lymphocyte receptor; a fibronectin domain (e.g. an Adnectin™); an antibody constant domain (e.g. a $CH_3$ domain, e.g., a $CH_2$ and/or $CH_3$ of an Fcab™) wherein the constant domain is not a functional $CH_1$ domain; an scFv; an $(scFv)_2$; an sc-diabody; an scFab; a centyrin and an epitope binding domain derived from a scaffold selected from CTLA-4 (Evibody™); a lipocalin domain; Protein A such as Z-domain of Protein A (e.g. an Affibody™ or SpA); an A-domain (e.g. an Avimer™ or Maxibody™); a heat shock protein (such as and epitope binding domain derived from GroEI and GroES); a transferrin domain (e.g. a trans-body); ankyrin repeat protein (e.g. a DARPin™); peptide aptamer; C-type lectin domain (e.g. Tetranectin™); human γ-crystallin or human ubiquitin (an affilin); a PDZ domain; scorpion toxin; and a kunitz type domain of a human protease inhibitor.

In one embodiment, the bispecific antibody is a $mAb^2$. A $mAb^2$ comprises a $V_H$ and $V_L$ domain from an intact antibody, fused to a modified constant region, which has been engineered to form an antigen-binding site, known as an "Fcab". The technology behind the Fcab/$mAb^2$ format is described in more detail in WO2008/003103, and the description of the $mAb^2$ format is incorporated herein by reference.

In another embodiment, the bispecific antibody is a "dual binding antibody". As used herein, the term "dual binding antibody" is a bispecific antibody wherein both antigen-binding domains are formed by a $V_H/V_L$ pair, and includes FIT-Ig (see WO2015/103072, incorporated herein by reference), mAb-dAb, dock and lock, Fab-arm exchange, SEED-body, Triomab, LUZ-Y, Fcab, KA-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-CH3, Diabody-CH3, Triple body, Miniantibody, minibody, scFv-$CH_3$ KIH, scFv-CH-CL-scFv, $F(ab')_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG (L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv and scFv4-Ig.

The term "hypervariable region", "CDR region" or "CDR" refers to the regions of an antibody variable domain which are hypervariable in sequence and/or form structurally defined loops. Generally, antigen binding sites of an antibody include six hypervariable regions: three in the $V_H$ (CDRH1, CDRH2, CDRH3), and three in the $V_L$ (CDRL1, CDRL2, CDRL3). These regions of the heavy and light chains of an antibody confer antigen-binding specificity to the antibody. CDRs may be defined according to the Kabat system (see Kabat, E. A. et al., 1991, "Sequences of Proteins of Immunological Interest", $5^{th}$ edit., NIH Publication no. 91-3242, U.S. Department of Health and Human Services). Other systems may be used to define CDRs, which as the system devised by Chothia et al (see Chothia, C. & Lesk, A. M., 1987, "Canonical structures for the hypervariable regions of immunoglobulins", J. Mol. Biol., 196, 901-917) and the IMGT system (see Lefranc, M. P., 1997, "Unique database numbering system for immunogenetic analysis", Immunol. Today, 18, 50). An antibody typically contains 3 heavy chain CDRs and 3 light chain CDRs. The term CDR or CDRs is used here to indicate one or several of these regions. A person skilled in the art is able to readily compare the different systems of nomenclature and determine whether a particular sequence may be defined as a CDR.

A "human antibody" is an antibody that possesses an amino-acid sequence corresponding to that of an antibody produced by a human and/or has been made using any of the techniques for making human antibodies and specifically excludes a humanized antibody comprising non-human antigen-binding residues. The term "specifically binds to" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g. by a radioimmunoassay (RIA).

An antibody or a fragment thereof that specifically binds to a human CD7 (hCD7) antigen may be cross-reactive with related antigens. Preferably, an antibody or a fragment thereof that specifically binds to a hCD7 antigen does not cross-react with other antigens (but may optionally cross-react with CD7 of a different species, e.g. rhesus, or murine). An antibody or a fragment thereof that specifically binds to a hCD7 antigen can be identified, for example, by immunoassays, BIAcore™, or other techniques known to those of skill in the art. An antibody or a fragment thereof binds specifically to a CD7 antigen when it binds to a hCD7 antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times (such as more than 15 times, more than 20 times, more than 50 times or more than 100 times) background. See, e.g. Paul, ed., 1989, Fundamental Immunology Second Edition, Raven Press, New York at pages 332-336 for a discussion regarding antibody specificity.

The term "aliphatic amino acid" means that the amino acid R groups are nonpolar and hydrophobic. Hydrophobicity increases with increasing number of C atoms in the hydrocarbon chain. Glycine, Alanine, Valine, Leucine and Isoleucine are aliphatic amino acids.

The term "aromatic amino acid" means that the amino acid R groups contain an aromatic ring system. Phenylalanine, Tyrosine and Tryptophan are aromatic amino acids.

The term "hydroxyl-containing amino acid" means that the amino acid R groups contain a hydroxyl group and are hydrophilic. Serine, Cysteine, Threonine and Methionine are hydroxyl-containing amino acids.

The term "basic amino acid" means that the amino acid R groups are nitrogen containing and are basic at neutral pH. Histidine, Lysine and Arginine are basic amino acids.

The term "cyclic amino acid" means that the amino acid R groups have an aliphatic cyclic structure. Proline is the only cyclic aliphatic amino acid.

The term "acidic amino acid" means that the amino acid R groups are polar and are negatively charged at physiological pH. Aspartate and Glutamate are acidic amino acids.

The term "amide amino acid" means that the amino acid R groups contain an amide group. Asparagine and Glutamine are amide amino acids.

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g. the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, a "buffer" refers to a chemical agent that is able to absorb a certain quantity of acid or base without undergoing a strong variation in pH.

As used herein, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

The term "chemotherapeutic agent" or "chemotherapy" refers to a therapeutic agent whose primary purpose is to destroy cancer cells, typically by interfering with the tumour cell's ability to grow or multiply. There are many different types of chemotherapeutic agents, with more than 50 approved chemotherapy drugs available. Chemotherapeutic drugs can be classified based on how they work. Alkylating drugs kill cancer cells by directly attacking DNA, the genetic material of the genes. Cyclophosphamide is an alkylating drug. Antimetabolites interfere with the production of DNA and keep cells from growing and multiplying. An example of an antimetabolite is 5-fluorouracil (5-FU). Anti-tumour antibiotics are made from natural substances such as fungi in the soil. They interfere with important cell functions, including production of DNA and cell proteins. Doxorubicin and bleomycin belong to this group of chemotherapy drugs. Plant alkaloids prevent cells from dividing normally. Vinblastine and vincristine are plant alkaloids obtained from the periwinkle plant. Steroid hormones slow the growth of some cancers that depend on hormones. For example, tamoxifen is used to treat breast cancers that depend on the hormone estrogen for growth. DNA damage response (DDR) inhibitors, such as PARP inhibitors, block DNA repair mechanisms following single or double stranded breaks.

Examples of chemotherapeutic agents include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see, U.S. Pat. No. 4,675,187), Melphalan, and other related nitrogen mustards. Suitable toxins and chemotherapeutic agents are described in Remington's Pharmaceutical Sciences, 19th Ed. (Mack Publishing Co. 1995), and in Goodman and Gilman's The Pharmacological Basis of Therapeutics, $7^{th}$ Ed. (MacMillan Publishing Co. 1985). Another example of chemotherapeutic agents is the class of antibody-conjugated toxins, including, but not limited to pyrrolobenzodiazepiness, maytansanoids, calicheamicin, etc. Other suitable toxins and/or chemotherapeutic agents are known to those of skill in the art.

As used herein, the term "composition" is intended to encompass a product containing the specified ingredients (e.g. an antibody of the invention) in, optionally, the specified amounts, as well as any product which results, directly or indirectly, from combination of the specified ingredients in, optionally, the specified amounts.

As used herein the term "comprising" or "comprises" is used with reference to antibodies, fragments, uses, compositions, methods, and respective component(s) thereof, that are essential to the method or composition, yet open to the inclusion of unspecified elements, whether essential or not.

The term "consisting of" refers to antibodies, fragments, uses, compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

In the context of a polypeptide, the term "derivative" as used herein includes a polypeptide that comprises an amino acid sequence of a hCD7 polypeptide, a fragment of a hCD7 polypeptide, or an antibody or fragment that specifically binds to a hCD7 polypeptide which has been altered by the introduction of amino acid residue substitutions, deletions or additions. The term "derivative" as used herein also includes a hCD7 polypeptide, a fragment of a hCD7 polypeptide, or an antibody that specifically binds to a hCD7 polypeptide which has been chemically modified, e.g. by the covalent attachment of any type of molecule to the polypeptide. For example, but not by way of limitation, a hCD7 polypeptide, a fragment of a hCD7 polypeptide, or a hCD7 antibody may be chemically modified, e.g. by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a hCD7 polypeptide, a fragment of a hCD7 polypeptide, or a hCD7 antibody may be chemically modified by chemical modifications using techniques known to those of skill in the art, including, but not limited to specific chemical cleavage, acetylation, formulation, metabolic synthesis of tunicamycin, etc. Further, a derivative of a hCD7 polypeptide, a fragment of a hCD7 polypeptide, or a hCD7 antibody may contain one or more non-classical amino acids. A polypeptide derivative possesses a similar or identical function as a hCD7 polypeptide, a fragment of a hCD7 polypeptide, or a hCD7 antibody described herein.

The term "effector function" (or "effector-enabled") as used herein refers to one or more of antibody dependant cell mediated cytotoxic activity (ADCC), complement-dependant cytotoxic activity (CDC) mediated responses, Fc-mediated phagocytosis, antibody dependant cellular phagocytosis (ADCP) or antibody-dependent trogocytosis and antibody recycling via the FcRn receptor.

An "effective amount" refers to an amount effective, at dosages and for periods of time necessary, to achieve the desired effect, including a therapeutic or prophylactic result. A "therapeutically effective amount" refers to the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which toxic or detrimental effects of the antibody are outweighed by the therapeutically beneficial effects. A "prophylactically effective amount" refers to an amount effective, at the dosages and for periods of time necessary, to achieve the desired prophylactic result. In some embodiments, the effective amount of an antibody of the invention is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein). In some embodiments, "effective amount" as used herein also refers to the amount of an antibody of the invention to achieve a specified result (e.g. inhibition of a hCD7 biological activity of a cell). The term "epitope" as used herein refers to a localized region on the surface of an antigen, such as hCD7 polypeptide or hCD7 polypeptide fragment, that is capable of being bound to one or more antigen binding regions of an antibody, and that has antigenic or immunogenic activity in an animal, preferably a mammal, and most preferably in a human, that is capable of eliciting an immune response. An epitope having immunogenic activity is a portion of a polypeptide that elicits an antibody response in an animal. An epitope having antigenic activity is a portion of a polypeptide to which an antibody specifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three-dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a hCD7 epitope is a three-dimensional surface feature of a hCD7 polypeptide (e.g. in a trimeric form of a hCD7 polypeptide). In other embodiments, a hCD7 epitope is linear feature of a hCD7 polypeptide (e.g. in a trimeric form or monomeric form of the hCD7 polypeptide). Antibodies provided herein may specifically bind to an epitope of the monomeric (denatured) form of hCD7, an epitope of the trimeric (native) form of hCD7, or both the monomeric (denatured) form and the trimeric (native) form of hCD7. In specific embodiments, the antibodies provided herein specifically bind to an epitope of the trimeric form of hCD7 but do not specifically bind the monomeric form of hCD7.

The term "excipients" as used herein refers to inert substances which are commonly used as a diluent, vehicle, preservatives, binders, or stabilizing agent for drugs and includes, but not limited to, proteins (e.g. serum albumin, etc.), amino acids (e.g. aspartic acid, glutamic acid, lysine, arginine, glycine, histidine, etc.), fatty acids and phospholipids (e.g. alkyl sulfonates, caprylate, etc.), surfactants (e.g. SDS, polysorbate, nonionic surfactant, etc.), saccharides (e.g. sucrose, maltose, trehalose, etc.) and polyols (e.g. mannitol, sorbitol, etc.). See, also, Remington's Pharmaceutical Sciences (1990) Mack Publishing Co., Easton, Pa., which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, CD7 fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a hCD7 polypeptide or an antibody that specifically binds to a hCD7 polypeptide. In a specific embodiment, a fragment of a hCD7 polypeptide or an antibody that specifically binds to a hCD7 antigen retains at least 1, at least 2, or at least 3 functions of the polypeptide or antibody.

The term "free" can refer to a polypeptide, for example, CD7 or fragments and variants thereof, that is combined with a buffer, wherein the polypeptide is not associated with a cell surface or cell membrane. As such, the term "free" can refer to a polypeptide that is capable of surface expression (i.e. includes one or more transmembrane domains or membrane association domains), but that is not, in its present state, expressed on the surface of a cell or bound to a protein that is expressed on the surface of a cell. A free polypeptide can also refer to a free recombinant or native or unbound polypeptide. In the context of phage display, a free antigen can be selected in solution (referred to herein as a "soluble selection") or adsorbed to a surface, for example, adsorbed to the surface of a 96-well plate (referred to herein as "biopanning selection").

The term "fusion protein" as used herein refers to a polypeptide that comprises an amino acid sequence of an antibody and an amino acid sequence of a heterologous polypeptide or protein (i.e. a polypeptide or protein not normally a part of the antibody (e.g. a non-anti-CD7 antigen antibody)). The term "fusion" when used in relation to CD7 or to an anti-CD7 antibody refers to the joining of a peptide or polypeptide, or fragment, variant and/or derivative thereof, with a heterologous peptide or polypeptide. Preferably, the fusion protein retains the biological activity of the CD7 or anti-CD7 antibody. In certain embodiments, the fusion protein comprises a CD7 antibody VH domain, VL domain, VH CDR (one, two or three VH CDRs), and/or VL CDR (one, two or three VL CDRs), wherein the fusion protein specifically binds to a CD7 epitope.

The term "heavy chain" when used with reference to an antibody refers to five distinct types, called alpha (α), delta (δ), epsilon (ε), gamma (γ) and mu (μ), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG2, IgG3 and IgG4. Preferably the heavy chain is a human heavy chain. In the human population, multiple heavy chain constant region alleles, of each immunoglobulin or immunoglobulin subclass, exist. The nucleotide and amino acid sequences of these allelic variants are accessible on publicly available databases such as IMGT, ENSEMBL Swiss-Prot and Uniprot. Allelic variants may also be identified in various genome sequencing projects. In one embodiment, the antibodies and antibody fragments disclosed herein comprise a heavy chain encoded by a IgG1 constant region allele, which includes, but is not limited to, human IGHG1*01, IGHG1*02, IGHG1*03, IGHG1*04 and IGHG1*05. In one embodiment, the antibodies and antibody fragments disclosed herein comprise a protein encoded by a IgG2 constant region allele, which includes, but is not limited to, human IGHG2*01, IGHG2*02, IGHG2*03, IGHG2*04, IGHG2*05 and IGHG2*06. In one embodiment, the antibodies or antibody fragments disclosed herein comprise a protein encoded by a IgG3 constant region allele, which includes but is not limited to human IGHG3*01, IGHG3*02, IGHG3*03, IGHG3*04, IGHG3*05, IGHG3*06, IGHG3*07, IGHG3*08, IGHG3*09, IGHG3*10, IGHG3*11, IGHG3*12, IGHG3*13, IGHG3*14, IGHG3*15, IGHG3*16, IGHG3*17, IGHG3*18 and IGHG3*19. In one embodiment, the antibodies or antibody fragments disclosed herein comprise a protein encoded by a IgG4 constant region allele, which includes but is not limited to human IGHG4*01 (see, eg, the sequence table herein), IGHG4*02 (see, eg, the sequence table herein), IGHG4*03 (see, eg, the sequence table herein) and IGHG4*04 (see, eg, the sequence table herein). In another example, the heavy chain is a disabled IgG isotype, e.g. a disabled IgG4. In certain embodiments, the antibodies of the invention comprise a human gamma 4 constant region. In another embodiment, the heavy chain constant region does not bind Fc-γ receptors, and e.g. comprises a Leu235Glu mutation. In another embodiment, the heavy chain constant region comprises a Ser228Pro mutation to increase stability. In another embodiment, the heavy chain constant region is IgG4-PE (see, eg, the sequence table herein). In another embodiment, the antibodies and antibody fragments disclosed herein comprise a heavy chain constant region encoded by a murine IgG1 constant region allele, which includes but is not limited to mouse IGHG1*01 or IGHG1*02. In one embodiment, the antibodies and antibody fragments disclosed herein comprise a heavy chain constant region encoded by a murine IgG2 constant region allele, which includes, but is not limited to, mouse IGHG2A*01, IGHG2A*02, IGHG2B*01, IGHG2B*02, IGHG2C*01, IGHG2C*02 or IGHG2C*03. In one embodiment, the antibodies or antibody fragments disclosed herein comprise a protein encoded by a murine IgG3 constant region allele, which includes but is not limited to mouse IGHG3*01.

The term "host" as used herein refers to an animal, preferably a mammal, and most preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "in combination" in the context of the administration of other therapies refers to the use of more than one therapy. The use of the term "in combination" does not restrict the order in which therapies are administered to a subject with a disease. A first therapy can be administered before (e.g. 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g. 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a CD7-mediated disease. Any additional therapy can be administered in any order with the other additional therapies. In certain embodiments, the antibodies of the invention can be administered in combination with one or more therapies (e.g. therapies that are not the antibodies of the invention that are currently administered to prevent, treat, manage, and/or ameliorate a CD7-mediated disease. Non-limiting examples of therapies that can be administered in combination with an antibody of the invention include analgesic agents, anaesthetic agents, antibiotics, or immunomodulatory agents or any other agent listed in the U.S. Pharmacopoeia and/or Physician's Desk Reference.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g. the blood in a vein. A common, but non-limiting example of an injection device is a needle and syringe. As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

An "isolated" or "purified" antibody or protein is one that has been identified, separated and/or recovered from a component of its production environment (e.g. natural or recombinant). For example, the antibody or protein is substantially free of cellular material or other contaminating proteins from the cell or tissue source from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e. culture medium represents less than about 20%, 10%, or 5% of the volume of the protein preparation. When the antibody is produced by chemical synthesis, it is preferably substantially free of chemical precursors or other chemicals, i.e., it is separated from chemical precursors or other chemicals which are involved in the synthesis of the protein. Accordingly, such preparations of the antibody have less than about 30%, 20%, 10%, 5% (by dry weight) of chemical precursors or compounds other than the antibody of interest. In a preferred embodiment, antibodies of the invention are isolated or purified.

The terms "Kabat numbering," and like terms are recognized in the art and refer to a system of numbering amino acid residues which are more variable (i.e. hypervariable)

than other amino acid residues in the heavy chain variable regions of an antibody, or an antigen binding portion thereof (Kabat et al., (1971) Ann. NY Acad. Sci., 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3.

“Label” or “labelled” as used herein refers to the addition of a detectable moiety to a polypeptide, for example, a radiolabel, fluorescent label, enzymatic label, chemiluminescent label or a biotinyl group or gold. Radioisotopes or radionuclides may include $^{3}$H, $^{14}$C, $^{15}$N, $^{35}$S, $^{90}$Y, $^{99}$Tc, $^{115}$In, $^{125}$I, $^{131}$I, fluorescent labels may include rhodamine, lanthanide phosphors or FITC and enzymatic labels may include horseradish peroxidase, β-galactosidase, luciferase, alkaline phosphatase. Additional labels include, by way of illustration and not limitation: enzymes, such as glucose-6-phosphate dehydrogenase (“G6PDH”), alpha-D-galactosidase, glucose oxydase, glucose amylase, carbonic anhydrase, acetylcholinesterase, lysozyme, malate dehydrogenase and peroxidase; dyes (e.g. cyanine dyes, e.g. Cy5™, Cy5.5™. or Cy7™); additional fluorescent labels or fluorescers include, such as fluorescein and its derivatives, fluorochrome, GFP (GFP for “Green Fluorescent Protein”), other fluorescent proteins (e.g. mCherry, mTomato), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cisbio Assays); chemoluminescent labels or chemiluminescers, such as isoluminol, luminol and the dioxetanes; sensitisers; coenzymes; enzyme substrates; particles, such as latex or carbon particles; metal sol; crystallite; liposomes; cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The term “light chain” when used in reference to an antibody refers to the immunoglobulin light chains, of which there are two types in mammals, lambda (Λ) and kappa (κ). Preferably, the light chain is a human light chain. Preferably the light chain constant region is a human constant region. In the human population, multiple light chain constant region alleles exist. The nucleotide and amino acid sequences of these allelic variants are accessible on publicly available databases such as IMGT, ENSEMBL, Swiss-Prot and Uniprot. In one embodiment, the antibodies or antibody fragments disclosed herein comprise a protein encoded by a human κ constant region allele, which includes, but is not limited to, IGKC*01 (see, eg, the sequence table herein), IGKC*02 (see, eg, the sequence table herein), IGKC*03 (see, eg, the sequence table herein), IGKC*04 (see, eg, the sequence table herein) and IGKC*05 (see, eg, the sequence table herein). In one embodiment, the antibodies or antibody fragments disclosed herein comprise a protein encoded by a human Λ constant region allele, which includes but is not limited to IGLC1*01 (see, eg, the sequence table herein), IGLC1*02 (see, eg, the sequence table herein), IGLC2*01 (see, eg, the sequence table herein), IGLC2*02 (see, eg, the sequence table herein), IGLC2*03 (see, eg, the sequence table herein), IGLC3*01 (see, eg, the sequence table herein), IGLC3*02 (see, eg, the sequence table herein), IGLC3*03 (see, eg, the sequence table herein), IGLC3*04 (see, eg, the sequence table herein), IGLC6*01 (see, eg, the sequence table herein), IGLC7*01 (see, eg, the sequence table herein), IGLC7*02 (see, eg, the sequence table herein), IGLC7*03 (see, eg, the sequence table herein). In another embodiment, the antibodies and antibody fragments disclosed herein comprise a light chain constant region encoded by a mouse K constant region allele, which includes, but is not limited to, IGKC*01, IGKC*03 or IGKC*03. In another embodiment, the antibodies and antibody fragments disclosed herein comprise a light chain constant region encoded by a mouse Λ constant region allele, which includes, but is not limited to, IGLC1*01, IGLC2*01 or IGLC3*01.

“Percent (%) amino acid sequence identity” and “homology” with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEG ALIGN™ (DNASTAR) software. In one embodiment, the % homology is about 70%. In one embodiment, the % homology is about 75%. In one embodiment, the % homology is about 80%. In one embodiment, the % homology is about 85%. In one embodiment, the % homology is about 90%. In one embodiment, the % homology is about 92%. In one embodiment, the % homology is about 95%. In one embodiment, the % homology is about 97%. In one embodiment, the % homology is about 98%. In one embodiment, the % homology is about 99%. In one embodiment, the % homology is 100%.

The term “naturally occurring” or “native” when used in connection with biological materials such as nucleic acid molecules, polypeptides, host cells, and the like, refers to those which are found in nature and not manipulated by a human being.

As used herein, “packaging” refers to how the components are organized and/or restrained into a unit fit for distribution and/or use. Packaging can include, e.g. boxes, bags, syringes, ampoules, vials, tubes, clamshell packaging, barriers and/or containers to maintain sterility, labelling, etc.

The term “pharmaceutically acceptable” as used herein means being approved by a regulatory agency of the Federal or a state government, or listed in the U.S. Pharmacopeia, European Pharmacopeia or other generally recognized Pharmacopeia for use in animals, and more particularly in humans.

As used herein, the term “polynucleotide,” “nucleotide”, “nucleic acid” “nucleic acid molecule” and other similar terms are used interchangeable and include DNA, RNA, mRNA and the like.

As used herein, the terms “prevent”, “preventing”, and “prevention” refer to the total or partial inhibition of the development, recurrence, onset or spread of a hCD7-mediated disease and/or symptom related thereto, resulting from the administration of a therapy or combination of therapies provided herein (e.g. a combination of prophylactic or therapeutic agents, such as an antibody of the invention).

The term "soluble" refers to a polypeptide, such as CD7 and variants or fragments thereof, that is lacking one or more transmembrane or cytoplasmic domains found in the native or membrane-associated form. In one embodiment, the "soluble" form of CD7 lacks both a transmembrane domain and cytoplasmic domain.

The term "subject" or "patient" refers to any animal, including, but not limited to, mammals. As used herein, the term "mammal" refers to any vertebrate animal that suckle their young and either give birth to living young (eutharian or placental mammals) or are egg-laying (metatharian or nonplacental mammals). Examples of mammalian species include, but are not limited to, humans and other primates, including non-human primates such as chimpanzees and other apes and monkey species; farm animals such as cattle, sheep, pigs, goats and horses; domestic mammals such as dogs and cats; laboratory animals including rodents such as mice, rats (including cotton rats) and guinea pigs; birds, including domestic, wild and game birds such as chickens, turkeys and other gallinaceous birds, ducks, geese, and the like.

As used herein "substantially all" refers to refers to at least about 60%, at least about 70%, at least about 75%, at least about 80%, at least about 85%, at least about 90%, at least about 95%, at least about 98%, at least about 99%, or about 100%.

As used herein, the term "therapeutic agent" refers to any agent that can be used in the treatment, management or amelioration of a CD7-mediated disease and/or a symptom related thereto. In certain embodiments, the term "therapeutic agent" refers to an antibody of the invention. In certain other embodiments, the term "therapeutic agent" refers to an agent other than an antibody of the invention. Preferably, a therapeutic agent is an agent which is known to be useful for, or has been or is currently being used for the treatment, management or amelioration of a CD7-mediated disease or one or more symptoms related thereto. In specific embodiments, the therapeutic agent is a fully human anti-CD7 antibody, such as a fully human anti-CD7 monoclonal antibody.

As used herein, the term "therapy" refers to any protocol, method and/or agent that can be used in the prevention, management, treatment and/or amelioration of a CD7-mediated disease (e.g. cancer). In certain embodiments, the terms "therapies" and "therapy" refer to a biological therapy, supportive therapy, and/or other therapies useful in the prevention, management, treatment and/or amelioration of a CD7-mediated disease known to one of skill in the art such as medical personnel. The terms "treat", "treatment" and "treating" refer to the reduction or amelioration of the progression, severity, and/or duration of a hCD7-mediated disease (e.g. cancer) resulting from the administration of one or more therapies (including, but not limited to, the administration of one or more prophylactic or therapeutic agents, such as an antibody of the invention).

The term "variable region" or "variable domain" refers to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the CD7 and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) $5^{th}$ ed. ("Kabat et al."). In preferred embodiments, the variable region is a human variable region.

Definitions of common terms in cell biology and molecular biology can be found in "The Merck Manual of Diagnosis and Therapy", $19^{th}$ Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (Eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et al., ed., John Wiley and Sons, Inc.), Current Protocols in Cell Biology (CPCB) (Juan S. Bonifacino et al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

Target Rationale

CD7 is a 40 kDa transmembrane glycoprotein of the Ig superfamily (1). It is expressed on the surface of peripheral blood T-cells, NK cells, thymocytes, and bone marrow $CD34^{+}$ $CD38^{-}$ cells early during T-cell ontogeny (2). CD7 is expressed on most T cells except late memory T cells and effector $CD8^{+}$ T cells. CD7 expression is reported during early T cell development. However, it is not expressed in the haemopoietic lineage stem cells (HSCs) (2,3), suggesting HSCs would not be affected by anti-CD7 antibody. While most peripheral T-cells are typically CD7 positive, the absence of CD7 from a small subset of circulating $CD4^{+}$ memory cells ($CD4^{+}CD45RA^{-}$ $CD45R0^{+}$) has been reported (4).

The natural ligand for CD7 has not yet been identified. CD7 has been demonstrated to act as a costimulatory molecule, and anti-CD7 monoclonal antibodies (mAbs) have been reported to be mitogenic, increase calcium flux and augment IL-2 production (5). CD7 binds to the phosphatidylinositol 3-kinase (PI 3-kinase) by means of a cytoplasmic tyrosine based YEDM motif and associates with a type II PI 4-kinase (6). However, the exact signalling mechanisms are still unknown. No major phenotypic abnormalities have been identified in CD7-deficient mice although some labs have reported relatively minor immune system defects such as reduced antigen-specific T-cell triggering, defective generation of antigen-specific cytotoxic T cells and protection from lipopolysaccharide-induced shock syndrome (7,8).

CD7 can be rapidly internalized following antibody binding as demonstrated on the human T-ALL cell line, CEM cells, where in excess of 50% of cell surface CD7 was internalized within 30 minutes (9), following ligation with an antibody. In a clinical study with the mouse-human chimeric antibody RFT2, the half-life of the antibody in humans was reported to be around 12 hours (10). Following internalization, the intracellular pathway of internalized CD7 is not well described as it can be recycled to the cell membrane or directly sent to lysosomes for degradation. This rapid internalization might affect the pharmacokinetic and pharmacodynamic profile of monoclonal antibodies in patients following treatment.

CD7 in T-ALL and AML

CD7 is highly expressed on malignant immature T-cells and is generally absent on malignant mature T-cells, such as $CD4^+$ Sezary leukaemia and HTLV-$1^+$ adult T-cell leukaemia cells (11). In leukemic cells from diagnostic bone marrow samples obtained from patients with T-ALL, the median percentage of CD7 expression was >99% (12). High CD7 expression levels was also observed in samples collected from patients with relapsed T-ALL. CD7 expression level in leukemic cell at diagnosis or relapse consistently exceeded that measured in residual normal T cells in the same samples, and standard of care (SoC) chemotherapy does not affect CD7 expression in leukemic cells. In the bone marrow samples collected during chemotherapy that contained minimal residual disease (MRD), >99% of residual leukemic cells were $CD7^+$. As CD7 expression levels remain high during therapy (12), CD7 is an excellent flow cytometry biomarker for diagnosis of T-ALL (Table 5).

In addition to T-ALL, CD7 is expressed on leukemic cells in 15% of acute myeloid leukaemia (AML) cases (13). CD7 expression in this subset of AML cases is correlated with loss of wild-type CCAAT/enhancer-binding protein alpha (CEBPA) gene due to mutations or silencing by epigenetic mechanisms (14). This mutation or epigenetic screening in AML has a potential clinical importance, allowing a subset of AML to be stratified for CD7-targeted therapy.

In summary, a cell-depletion strategy using anti-CD7 monoclonal antibody is promising to address an unmet medical need in adult T-ALL and $CD7^+$ AML conditions, and also other $CD7^+$ cancers.

Normal T-cell development is a strictly regulated process in which T progenitor cells migrate from the bone marrow to thymus and differentiate toward mature and functional T cells. During this differentiation process, dysregulation of oncogenes and tumour suppressor genes can drive immature thymocytes into uncontrolled clonal expansion and cause T-ALL (22). T-ALL accounts for about 20% of all cases of ALL and is more common in adults than children, although the incidence diminishes with increasing age. Patients typically present with a high white blood cell count and may also present with organmegaly, particularly mediastinal enlargement. Despite improved knowledge of T-ALL disease biology, standard of care (SoC) remains largely unchanged over the last decade, and still consists of intensive multi-agent chemotherapy potentially followed by autologous haematopoietic stem cell transplantation. With this SoC, 20% in children and 40% in adults receiving treatment relapse (23,24). Long term survival in the relapsed and refractory setting is very poor with fewer than 5% of patients subsequently achieving secondary responses. Many patients with refractory or relapsed B-cell lymphoblastic leukaemia have achieved complete remission with a prolonged survival rate after receiving the new generation of targeted therapies (25). However, there is little new drug developmental activity for the T-ALL treatment probably due to its relatively small patient population size.

T-ALL malignancies represent a group of hematologic cancers with high rates of relapse and mortality in patients for whom no effective targeted therapy exists. There is still a high unmet medical need to improve the clinical outcome of patients with relapsed and refractory T-ALL.

Thus, in one aspect the invention is useful for treating T-ALL, such as refractory T-ALL.

The invention, thus, provides various anti-CD7 antibodies and fragments (such as Fab or scFv fragments), uses, and methods. Examples are set out in the following numbered Clauses.

1. An antibody or fragment comprising a binding site which specifically binds to CD7 (Cluster of Differentiation 7), wherein the binding site comprises a VH domain that is encoded by a nucleotide sequence that is derived from the recombination of a human VH gene segment, DH gene segment and JH gene segment, wherein the VH gene segment is selected from IGHV3-15 and IGHV3-23.

In an example, the VH gene segment is IGHV3-15*01 or IGHV3-23*04. For example, the DH gene segment and JH gene segments are human gene segments.

In an example, specific binding is with a KD, $K_{off}$ and/or $K_{on}$ as described further below. In an example, specific binding is with a KD from 1 pM to 5 nM.

The skilled person is familiar with databases and other sources for human and other species of antibody gene segments. For example, the IMGT database is a suitable source, eg, the version as at 1 Sep. 2018.

Reference is made to the Examples, showing antibodies that are based on IGHV3-15 or IGHV3-23. Surprisingly, these human VH gene segments produce anti-CD7 antibodies which have desirable anti-CD7 properties, such as those described in the Examples.

2. The antibody or fragment according to Clause 1, wherein the DH gene segment is a human gene segment selected from IGHD3-9, IGHD3-10 and IGH6-19.

In an example, the DH gene segment is a human gene segment selected from IGHD3-9*01, IGHD3-10*01 and IGH6-19*01.

3. The antibody or fragment according to Clause 1 or 2, wherein the JH gene segment is a human gene segment selected from IGHJ6, IGHJ4 and IGHJ5.

In an example, the JH gene segment is a human gene segment selected from IGHJ6*02, IGHJ4*02 and IGHJ5*02.

4. The antibody or fragment according to any preceding Clause, wherein the binding site comprises a CDRH3 sequence selected from SEQ ID NO: 3, 6, 23, 26, 43, 46, 63 and 66.

5. The antibody or fragment according to any preceding Clause, wherein the binding site comprises (i) a VH domain comprising SEQ ID NO: 7 paired with a VL domain comprising SEQ ID NO: 17; (ii) a VH domain comprising SEQ ID NO: 27 paired with a VL domain comprising SEQ ID NO: 37; (iii) a VH domain comprising SEQ ID NO: 47 paired with a VL domain comprising SEQ ID NO: 57; or (iv) a VH domain comprising SEQ ID NO: 67 paired with a VL domain comprising SEQ ID NO: 77.

6. The antibody or fragment according to any preceding Clause, wherein the binding site comprises a VH domain comprising SEQ ID NO: 7.
7. The antibody or fragment according to any preceding Clause, wherein the binding site comprises a VH domain comprising SEQ ID NO: 7 paired with a VL domain comprising SEQ ID NO: 17.
8. An antibody or fragment which specifically binds to CD7 and comprises the CDRH3 sequence of an anti-CD7 antibody according to any preceding Clause, or said CDRH3 sequence comprising 3, 2 or 1 amino acid substitution(s).
9. An antibody or fragment (optionally according to any preceding Clause) which specifically binds to CD7 and comprises a VH domain which comprises a CDRH3 sequence of an antibody selected from G09, F05, C02 and E04; or said sequence comprising 3, 2 or 1 amino acid substitution(s).
10. The antibody or fragment according to Clause 9, wherein the VH domain comprises (i) a CDRH3 sequence of an antibody selected from G09, F05, C02 and E04; or said CDRH3 sequence comprising 3, 2 or 1 amino acid substitution(s); and (ii) a CDRH1 sequence of said selected antibody; or said CDRH1 sequence comprising 3, 2 or 1 amino acid substitution(s).
11. The antibody or fragment according to Clause 9 or 10, wherein the VH domain comprises (iii) a CDRH3 sequence of an antibody selected from G09, F05, C02 and E04; or said CDRH3 sequence comprising 3, 2 or 1 amino acid substitution(s); and (iv) a CDRH2 sequence of said selected antibody; or said CDRH2 sequence comprising 3, 2 or 1 amino acid substitution(s).
12. An antibody or fragment (optionally according to any preceding Clause) comprising a binding site which specifically binds to CD7, wherein the binding site comprises a VH domain that comprises the amino acid sequence of a VH domain of an antibody selected from G09, F05, C02 and E04; or an amino acid that is at least 70% identical thereto.

For example, the identity is at least 85%. For example, the identity is at least 90%. For example, the identity is at least 95%.

13. The antibody or fragment according to Clause 9, 10, 11 or 12, wherein the selected antibody is G09.
14. The antibody or fragment according to any preceding Clause comprising first and second copies of said VH domain.

In an example, the antibody or fragment comprises a binding site comprising a VH domain of the invention paired with a VL domain of the invention, wherein the binding site is capable of specifically binding to CD7 (eg, mature CD7, eg human and/or cynomolgus monkey CD7). For example, the antibody or fragment comprise two of such binding sites.

15. An antibody or fragment (optionally according to any preceding Clause) comprising a binding site which specifically binds to CD7, wherein the binding site comprises a VL domain that is encoded by a nucleotide sequence that is derived from the recombination of a human VL gene segment and JL gene segment, wherein the VL gene segment is selected from IGKV1D-39, IGKV1-39, IGKV3-11, IGKV1-16 and IGKV1-5.

In an example, the VL gene segment is selected from IGKV1D-39*01, IGKV1-39*01, IGKV3-11*01, IGKV1-16*02 and IGKV1-5*03; or is selected from IGKV1D-39*01, IGKV3-11*01, IGKV1-16*02 and IGKV1-5*03.

16. The antibody or fragment according to Clause 15, wherein the VL is a VK and the JL gene segment is a human gene segment selected from IGKJ1 and IGKJ4.

In an example, the VL is a VK and the JL gene segment is a human gene segment selected from IGKJ1*01 and IGKJ4*01.

17. An antibody or fragment which specifically binds to CD7 and comprises the CDRL3 sequence of an anti-CD7 antibody according to any preceding Clause, or said CDRL3 sequence comprising 3, 2 or 1 amino acid substitution(s).
18. An antibody or fragment (optionally according to any preceding Clause) which specifically binds to CD7 and comprises a VL domain which comprises a CDRL3 sequence selected from SEQ ID NO: 13, 16, 33, 36, 53, 56, 73 and 76, or said selected CDRL3 sequence comprising 3, 2 or 1 amino acid substitution(s).
19. An antibody or fragment (optionally according to any preceding Clause) which specifically binds to Cluster of Differentiation 7 (CD7) and comprises a VL domain which comprises a CDRL3 (and optionally a CDRH3) sequence of an antibody selected from G09, F05, C02 and E04; or said sequence(s) each comprising 3, 2 or 1 amino acid substitution(s).
20. The antibody or fragment according to Clause 19, wherein the VL domain comprises (i) a CDRL3 sequence (and optionally a CDRH3) of an antibody selected from G09, F05, C02 and E04; or said CDR3 sequence(s) each comprising 3, 2 or 1 amino acid substitution(s); and (ii) a CDRL1 (and optionally a CDRH1) sequence of said selected antibody; or said CDR1 sequence(s) each comprising 3, 2 or 1 amino acid substitution(s).

Preferably, the selected antibody herein is G09 or comprises the variable domains of G09.

21. The antibody or fragment according to Clause 19 or 20, wherein the VL domain comprises (iii) a CDRL3 (and optionally a CDRH3) sequence of an antibody selected from G09, F05, C02 and E04; or said CDR3 sequence(s) each comprising 3, 2 or 1 amino acid substitution(s); and (iv) a CDRL2 (and optionally a CDRH2) sequence of said selected antibody; or said CDR2 sequence(s) each comprising 3, 2 or 1 amino acid substitution(s).
22. An antibody or fragment (optionally according to any preceding Clause) comprising a binding site which specifically binds to CD7, wherein the binding site comprises a VL domain that comprises the amino acid sequence of a VL domain of an antibody selected from G09, F05, C02 and E04; or an amino acid that is at least 70% identical thereto.

Optionally, there is provided an antibody or fragment (optionally according to any preceding Clause) comprising a binding site which specifically binds to Cluster of Differentiation 7 (CD7), wherein the binding site comprises a VL domain that comprises the amino acid sequence of a VL domain of an antibody selected from G09, F05, C02 and E04; or an amino acid that is at least 70, 80, 85, 90, 95, 96, 97, 98 or 99% identical thereto.

For example, the identity is at least 85%. For example, the identity is at least 90%. For example, the identity is at least 95%.

Optionally, the antibody or fragment comprises first and second copies of said VL domain.

In an example, the antibody or fragment comprises a binding site comprising a VL domain of the invention paired with a VH domain, wherein the binding site is capable of specifically binding to CD7 (eg, mature CD7, eg human and/or cynomolgus monkey CD7). For example, the antibody or fragment comprise two of such binding sites.

23. An antibody or fragment (optionally according to any preceding Clause) which specifically binds to Cluster of Differentiation 7 (CD7) and comprises the heavy chain amino acid sequence of an antibody selected from G09, F05, C02 and E04; or an amino acid that is at least 70, 80, 85, 90, 95, 96, 97, 98 or 99% identical thereto.

For example, the identity is at least 85%. For example, the identity is at least 90%. For example, the identity is at least 95%.

24. An antibody or fragment (optionally according to any preceding Clause) which specifically binds to Cluster of Differentiation 7 (CD7) and comprises the light chain amino acid sequence of an antibody selected from G09, F05, C02 and E04; or an amino acid that is at least 70, 80, 85, 90, 95, 96, 97, 98 or 99% identical thereto.

For example, the identity is at least 85%. For example, the identity is at least 90%. For example, the identity is at least 95%.

25. The antibody or fragment of Clause 23, comprising the light chain amino acid sequence of said selected antibody; or an amino acid that is at least 70, 80, 85, 90, 95, 96, 97, 98 or 99% identical thereto.

For example, the identity is at least 85%. For example, the identity is at least 90%. For example, the identity is at least 95%.

26. An antibody or fragment (optionally according to any preceding Clause) which specifically binds to a human CD7 epitope that is identical to an epitope to which the antibody of any preceding Clause binds.

27. The antibody or fragment according to Clause 26, wherein the epitope is identified by unrelated amino acid scanning, or by X-ray crystallography.

Contact amino acid residues involved in the interaction of antibody and antigen may be determined by various known methods to those skilled in the art.

In one embodiment, sequential replacement of the amino acids of the antigen sequence (using standard molecular biology techniques to mutate the DNA of the coding sequence of the antigen), in this case CD7 with Alanine (a.k.a Alanine scan), or another unrelated amino acid, may provide residues whose mutation would reduce or ablate the ability of the antibody to recognise the antigen in question. Binding may be assessed using standard techniques, such as, but not limited to, SPR, HTRF, ELISA (which are described elsewhere herein). Other substitutions could be made to enhance the disruption of binding such as changing the charge on the side chain of antigen sequence amino acids (e.g. Lysine change to glutamic acid), switching polar and non-polar residues (e.g. Serine change to leucine). The alanine scan or other amino substitution method may be carried out either with recombinant soluble antigen, or where the target is a cell membrane target, directly on cells using transient or stable expression of the mutated versions.

In one embodiment, protein crystallography may be used to determine contact residues between antibody and antigen (i.e. to determine the epitope to which the antibody binds), crystallography allows the direct visualisation of contact residues involved in the antibody-antigen interaction. As well as standard X-ray crystallography, cryo-electro microscopy has been used to determine contact residues between antibodies and HIV capsid protein (see Lee, Jeong Hyun, et al. "Antibodies to a conformational epitope on gp41 neutralize HIV-1 by destabilizing the Env spike.", Nature communications, 6, (2015)).

In one embodiment, if the antibody recognises a linear epitope, short peptides based on the antigen sequence can be produced and binding of the antibody to these peptides can be assessed using standard techniques, such as, but not limited to, SPR, HTRF, ELISA (which are described elsewhere herein). Further investigation of the epitope could be provided by performing an Alanine scan on any peptides that show binding. Alternative to linear peptides, conformational scans could be carried out using Pepscan technology using their chemical linkage of peptides onto scaffolds, which has been used to determine discontinuous epitopes on CD20 targeting antibodies (Niederfellner, Gerhard, et al. "Epitope characterization and crystal structure of GA101 provide insights into the molecular basis for type I/II distinction of CD20 antibodies.", Blood, 118.2, (2011), 358-367).

In one embodiment, limited proteolytic digestion and mass spectrophotometry can be used to identify binding epitopes. The antibody-antigen complex is digested by a protease, such as, but not limited to, trypsin. The digested complex peptides are compared to antibody-alone and antigen-alone digestion mass spectrophotometry to determine if a particular epitope is protected by the complexation. Further work involving amino acid substitution, competition binding, may then be employed to narrow down to individual amino acid residues involved in the interaction (see, for example, Suckau, Detlev, et al. "Molecular epitope identification by limited proteolysis of an immobilized antigen-antibody complex and mass spectrometric peptide mapping.", Proceedings of the National Academy of Sciences, 87.24, (1990), 9848-9852).

Thus, in one embodiment, the contact residues of the epitope are identified with an unrelated amino acid scan (e.g. alanine scan). In another embodiment, an unrelated amino acid scan (e.g. alanine scan) is carried out using a technique selected from SPR, HTRF, ELISA, X-ray crystallography, cryo-electro microscopy and a combination of limited proteolytic digestion and mass spectrometry. In one embodiment, the unrelated amino acid scan (e.g. alanine scan) is carried out using HTRF. In one embodiment, the unrelated amino acid scan (e.g. alanine scan) is carried out using ELISA. When the alanine scan is carried out with either ELISA or HTRF, an amino acid residue is identified as contributing to the epitope if the reduction in signal is at least 25%. In one embodiment, the reduction in signal is at least 30%. In one embodiment, the reduction in signal is at least 35%. In one embodiment, the reduction in signal is at least 40%. In one embodiment, the reduction in signal is at least 45%. In one embodiment, the reduction in signal is at least 50%. In one embodiment, the reduction in signal is at least 55%. In one embodiment, the reduction in signal is at least 60%. In one embodiment, the reduction in signal is at least 70%. In one embodiment, the reduction in signal is at least 75%. In one embodiment, the reduction in signal is at least 80%. In one embodiment, the reduction in signal is at least 85%. In one embodiment, the reduction in signal is at least 90%. When the alanine scan is carried out with SPR, an amino acid residue is identified as contributing to the epitope if there is at least a 10-fold reduction in affinity. In one embodiment, the reduction in affinity is at least 15-fold. In one embodiment, the reduction in affinity is at least 20-fold. In one embodiment, the reduction in affinity is at least 30-fold. In one embodiment, the reduction in affinity is at least 40-fold. In one embodiment, the reduction in affinity is at least 50-fold. In one embodiment, the reduction in affinity is at least 100-fold.

In one embodiment, the contact residues of the epitope are identified by X-ray crystallography. In one embodiment, the contact residues of the epitope are identified by cryo-electro microscopy. In one embodiment, the contact residues of the epitope are identified by a combination of limited proteolytic digestion and mass spectrometry.

28. The antibody or fragment according to Clause 27, wherein the contact residues of the epitope are defined by a reduction in affinity of at least 10-fold in an unrelated amino acid scan, e.g. an alanine scan as determined by SPR.

In one embodiment, the reduction in affinity is at least 15-fold. In one embodiment, the reduction in affinity is at least 20-fold. In one embodiment, the reduction in affinity is at least 30-fold. In one embodiment, the reduction in affinity is at least 40-fold. In one embodiment, the reduction in affinity is at least 50-fold. In one embodiment, the reduction in affinity is at least 100-fold. SPR may be carried out as described herein.

29. An antibody or fragment (optionally according to any preceding Clause) which competes for binding to human CD7 with the antibody of any preceding Clause.

Optionally, competition is determined by surface plasmon resonance (SPR) or ELISA. The skilled person will be familiar with these techniques and standard conditions, for example.

In one embodiment, the antibody or fragment competes (e.g. in a dose-dependent manner) with hCD7 (or a fusion protein thereof) for binding to cell surface-expressed hCD7. In one embodiment, the antibody or fragment competes (e.g. in a dose-dependent manner) with hCD7 (or a fusion protein thereof) for binding to soluble hCD7.

Optionally, the competition for binding to hCD7 is conducted using SPR. SPR may be carried out as described herein.

30. The antibody or fragment according to any preceding Clause which specifically binds to human CD7 comprising SEQ ID NO: 82; and/or a cynomolgus CD7 comprising SEQ ID NO: 85; and/or a rat CD7 comprising SEQ ID NO: 86.

In an example, CD7 herein is a human, mouse or cynomolgus monkey CD7.

In one embodiment, the antibody or fragment binds to cynomolgus CD7 with an affinity of less than 1 nM (e.g. from 1 nM to 0.01 pM or from 1 nM to 0.1 pM, or from 1 nM to 1 pM). In one embodiment, the antibody or fragment binds to cynomolgus CD7 with an affinity of less than 10 nM (e.g. from 10 nM to 0.01 pM or from 10 nM to 0.1 pM, or from 10 nM to 1 pM). In one embodiment, the antibody or fragment binds to cynomolgus CD7 with an affinity of less than 0.1 nM (e.g. from 0.1 nM to 0.01 pM or from 0.1 nM to 0.1 pM, or from 0.1 nM to 1 pM). In one embodiment, the antibody or fragment binds to cynomolgus CD7 with an affinity of less than 0.01 nM (e.g. from 0.011 nM to 0.01 pM or from 0.01 nM to 0.1 pM).

In one embodiment, the antibody or fragment binds to cynomolgus CD7 with an affinity of within 2-fold of the affinity to hCD7. In one embodiment, the antibody or fragment binds to cynomolgus CD7 with an affinity of within 4-fold of the affinity to hCD7. In one embodiment, the antibody or fragment binds to cynomolgus CD7 with an affinity of within 5-fold of the affinity to hCD7. In one embodiment, the antibody or fragment binds to cynomolgus CD7 with an affinity of within 6-fold of the affinity to hCD7. In one embodiment, the antibody or fragment binds to cynomolgus CD7 with an affinity of within 8-fold of the affinity to hCD7. In one embodiment, the antibody or fragment binds to cynomolgus CD7 with an affinity of within 10-fold of the affinity to hCD7. "hCD7" herein is a human CD7, eg, a human CD7 disclosed herein.

In one embodiment, the antibody or fragment does not detectably bind to cynomolgus CD7. In one embodiment, the antibody or fragment does not detectably bind to murine (eg, mouse and/or rat) CD7.

In one embodiment, the antibody or fragment binds to murine (eg, mouse and/or rat) CD7 with an affinity of less than 1 nM (e.g. from 1 nM to 0.01 pM or from 1 nM to 0.1 pM, or from 1 nM to 1 pM). In one embodiment, the antibody or fragment binds to murine CD7 with an affinity of less than 10 nM (e.g. from 10 nM to 0.01 pM or from 10 nM to 0.1 pM, or from 10 nM to 1 pM). In one embodiment, the antibody or fragment binds to murine CD7 with an affinity of less than 0.1 nM (e.g. from 0.1 nM to 0.01 pM or from 0.1 nM to 0.1 pM, or from 0.1 nM to 1 pM). In one embodiment, the antibody or fragment binds to murine CD7 with an affinity of less than 0.01 nM (e.g. from 0.011 nM to 0.01 pM or from 0.01 nM to 0.1 pM).

Optionally, the antibody or fragment comprises an effector-enabled constant region, such as a human constant region, for example an IgG1 constant region. Optionally, the antibody or fragment comprises a murine (eg, mouse and/or rat) constant region. Optionally, the antibody or fragment comprises any of the heavy chain constant region sequences described herein.

31. The antibody or fragment according to any preceding Clause, wherein the antibody or fragment comprises a human constant region, e.g. an IgG1 constant region.

Optionally, the constant region is an IgG1 constant region, optionally the constant region comprises any IgG1 constant region amino acid sequence disclosed herein. Optionally, the constant region is an IgG2 constant region, optionally the constant region comprises any IgG1 constant region amino acid sequence disclosed herein. Optionally, the constant region is an IgG1 constant region, optionally the constant region comprises any IgG3 constant region amino acid sequence disclosed herein. Optionally, the constant region is an IgG1 constant region, optionally the constant region comprises any IgG4 constant region amino acid sequence disclosed herein.

In an example (optionally in addition to the heavy chain region as per the paragraph immediately above), the constant region comprises a light chain constant region, the light chain constant region comprising any light chain constant region amino acid sequence disclosed herein.

32. The antibody or fragment according to Clause 31, wherein the constant region is an IgG1 constant region, optionally the constant region comprises the amino acid sequence of SEQ ID NO: 88, 90, 92, 94 or 96 (eg, SEQ ID NO: 88).

In other embodiments, the antibody or fragment is any of the isotypes or constant regions as defined herein. In one embodiment, the constant region is wild-type human IgG1. For example, the constant region is an effector-enabled IgG1 constant region, optionally having ADCC and/or CDC activity. In one embodiment, the constant region is engineered for enhanced ADCC and/or CDC and/or ADCP. In another embodiment, the constant region is engineered for enhanced effector function.

The potency of Fc-mediated effects may be enhanced by engineering the Fc domain by any of the techniques as will be apparent to the skilled person. In another embodiment, the antibodies and fragments disclosed herein may comprise a triple mutation (M252Y/S254T/T256E) which enhances binding to FcRn.

33. The antibody or fragment according to any preceding Clause (eg, a bispecific antibody), further comprising an antigen-binding site that specifically binds another target antigen (optionally human CD5, CD14 or CD19, eg, for treating leukaemia, such as AML).

For example, the other target antigen is human CD5.

In an example, the further binding site is an agonist binding site for said another antigen. In an example, the further binding site is an antagonist binding site for said another antigen.

In an example, the further binding site is an antibody binding site comprising a VH and a VL; a binding site comprised by a constant domain of the antibody (eg, an Fcab binding site) or a non-immunoglobulin binding site (eg, a fibronectin domain). Optionally, the antigen-binding site is any antigen-binding site disclosed herein.

For example, the antibody or fragment is a bispecific antibody or fragment. For example, the antibody or fragment is a dual binding antibody or fragment, or a fusion protein comprising an antibody or fragment thereof as defined in any preceding Clause. A dual binding antibody has the meaning as set out above.

In an example, the antibody, fragment or fusion protein comprises a bispecific format selected from DVD-Ig™, mAb$^2$, FIT-Ig®, mAb-dAb, dock and lock, SEEDbody, scDiabody-Fc, tandem scFv-Fc, Fab-scFv-Fc, Fab-scFv, intrabody, BiTE, diabody, DART, TandAb®, scDiabody, scDiabody-$CH_3$, Diabody-$CH_3$, minibody, knobs-in-holes, knobs-in-holes with common light chain, knobs-in-holes with common light chain and charge pairs, charge pairs, charge pairs with common light chain, in particular mAb$^2$, knob-in-holes, knob-in-holes with common light chain, knobs-in-holes with common light chain and charge pairs and FIT-Ig, e.g. mAb$^2$ and FIT-Ig®.

In one embodiment, the bispecific format is selected from DVD-Ig™, mAb$^2$, FIT-Ig®, mAb-dAb, dock and lock, Fab-arm exchange, SEEDbody, Triomab, LUZ-Y, Fcab, KA-body, orthogonal Fab, scDiabody-Fc, diabody-Fc, tandem scFv-Fc, Fab-scFv-Fc, Fab-scFv, intrabody, BiTE, diabody, DART, TandAb®, scDiabody, scDiabody-$CH_3$, Diabody-$CH_3$, Triple body, Miniantibody, minibody, TriBi minibody, scFv-$CH_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab™, IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig and Zybody™.

In one embodiment, the bispecific format is selected from DVD-Ig™, FIT-Ig®, mAb-dAb, dock and lock, Fab-arm exchange, SEEDbody, Triomab, LUZ-Y, Fcab, KA-body, orthogonal Fab, scDiabody-Fc, diabody-Fc, tandem scFv-Fc, Fab-scFv-Fc, Fab-scFv, intrabody, BiTE, diabody, DART, TandAb®, scDiabody, scDiabody-$CH_3$, Diabody-$CH_3$, Triple body, Miniantibody, minibody, TriBi minibody, scFv-$CH_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab™, IgG(H)-scFv, scFv-(H)IgG, IgG(L)-scFv, scFv-(L)IgG, IgG (L,H)-Fv, IgG(H)-V, V(H)-IgG, IgG(L)-V, V(L)-IgG, KIH IgG-scFab, 2scFv-IgG, IgG-2scFv, scFv4-Ig and Zybody™, for example DVD-Ig™, FIT-Ig®, mAb-dAb dock and lock, SEEDbody, scDiabody-Fc, diabody-Fc, tandem scRv-Fc, Fab-scFv-Fc, Fab-scFv, intrabody, BiTE, diabody, DART, TandAb, scDiabody, scDiabody-$CH_3$, Diabody-$CH_3$, minibody, knobs-in-holes, knobs-in-holes with common light chain, knobs-in-holes with common light chain and charge pairs, charge pairs, charge pairs with common light chain, in particular knob-in-holes, knob-in-holes with common light chain, knobs-in-holes with common light chain and charge pairs and FIT-Ig, e.g. FIT-Ig.

In one embodiment, the bispecific format is selected from DVD-Ig™, mAb$^2$, mAb-dAb, dock and lock, Fab-arm exchange, SEEDbody, Triomab, LUZ-Y, Fcab, KA-body, orthogonal Fab, scDiabody-Fc, diabody-Fc, tandem scFv-Fc, Fab-scFv-Fc, Fab-scFv, intrabody, BiTE, diabody, DART, TandAb®, scDiabody, scDiabody-$CH_3$, Diabody-$CH_3$, Triple body, Miniantibody, minibody, TriBi minibody, scFv-$CH_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab™, IgG(H)-scFv, scFv-(H)IgG, IgG(L)-scFv, scFv-(L)IgG, IgG (L,H)-Fv, IgG(H)-V, V(H)-IgG, IgG(L)-V, V(L)-IgG, KIH IgG-scFab, 2scFv-IgG, IgG-2scFv, scFv4-Ig and Zybody™, for example Zybody™, mAb$^2$, mAb-dAb, dock and lock, SEEDbody, scDiabody-Fc, diabody-Fc, tandem scFv-Fc, Fab-scFv-Fc, Fab-scFv, intrabody, BiTE, diabody, DART, TandAb®, scDiabody, scDiabody-$CH_3$, Diabody-$CH_3$, minibody, knobs-in-holes, knobs-in-holes with common light chain, knobs-in-holes with common light chain and charge pairs, charge pairs, charge pairs with common light chain, in particular mAb$^2$, knob-in-holes, knobs-in-holes with common light chain and charge pairs, and knob-in-holes with common light chain, e.g. mAb$^2$.

In one embodiment, the bispecific format is selected from DVD-Ig™, mAb-dAb, dock and lock, Fab-arm exchange, SEEDbody, Triomab, LUZ-Y, Fcab, κλ-body, orthogonal Fab, scDiabody-Fc, diabody-Fc, tandem scFv-Fc, Fab-scFv-Fc, Fab-scFv, intrabody, BiTE, diabody, DART, TandAb, scDiabody, scDiabody-$CH_3$, Diabody-$CH_3$, Triple body, Miniantibody, minibody, TriBi minibody, scFv-$CH_3$ KIH, scFv-CH-CL-scFv, F(ab')$_2$-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab™, IgG(F)-scFv, scFv-(H)IgG, IgG(L)-scFv, scFv-(L)IgG, IgG(L,H)-Fv, IgG (H)-V, V(H)-IgG, IgG(L)-V, V(L)-IgG, KIH IgG-scFab, 2scFv-IgG, IgG-2scFv, scFv4-Ig and Zybody™, for example DVD-Ig™, mAb-Ab, odk and lock, SEEDbody, scDiabody-Fc, diabody-Fc, tandem scFv-Fc, Fab-scFv-Fc, Fab-scFv, intrabody, BiTE, diabody, DART, TandAb, scDiabody, scDiabody-$CH_3$, Diabody-$CH_3$, minibody, knobs-in-holes, knobs-in-holes with common light chain, knobs-in-holes with common light chain and charge pairs, charge pairs, charge pairs with common light chain, in particular knob-in-holes, knobs-in-holes with common light chain and charge pairs, and knob-in-holes with common light chain.

34. An anti-CD7 antibody or fragment as defined in any preceding Clause for treating or preventing a CD7-mediated disease or condition (optionally a cancer, such as a leukaemia or a lymphoma) in a subject.

35. The anti-CD7 antibody or fragment of Clause 34, wherein the disease or condition is selected from a leukaemia, a lymphoma, a blood cancer and a myelodysplastic syndrome (MDS).

In an example, the subject is a human. In an alternative, the subject is a non-human animal. In an example, the subject is an adult human. In an example, the subject is a paediatric human.

In an example, the antibody or fragment herein is for treating or preventing a disease or condition in a subject (eg, a human) selected from T-cell acute lymphoblastic leukaemia;
Acute Myeloid Leukemia with CD7 expression;
Precursor T-Cell Lymphoblastic Lymphoma;
T-cell Prolymphocytic Leukemia;
T-cell Large Granular Lymphocytic Leukemia;
Peripheral T-cell Lymphoma;
Angioimmunoblastic T-cell Lymphoma;
Extranodal NK/T-cell Lymphoma, Nasal Type;
Enteropathy-type Intestinal T-cell Lymphoma; and
Hepatosplenic T-cell Lymphoma.

In an example, the disease or condition is in a human. In an example, the disease or condition is in an animal.

In an example, the antibody or fragment of the invention is for treating or preventing a CD7-mediated disease or condition in a human, e.g. selected from neoplastic or non-neoplastic disease, chronic viral infections, and malignant tumours, such as melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma.

In an example, the CD7-mediated disease or condition is a neurodegenerative disease, disorder or condition, e.g. selected from Alzheimer's disease, amyotrophic lateral sclerosis, Parkinson's disease, Huntington's disease, primary progressive multiple sclerosis, secondary progressive multiple sclerosis, corticobasal degeneration, Rett syndrome, a retinal degeneration disorder selected from age-related macular degeneration and retinitis pigmentosa; anterior ischemic optic neuropathy, glaucoma, uveitis, depression, trauma-associated stress or post-traumatic stress disorder, frontotemporal dementia, Lewy body dementias, mild cognitive impairments, posterior cortical atrophy, primary progressive aphasia and progressive supranuclear palsy or aged-related dementia, in particular, the neurodegenerative disease, disorder or condition is selected from Alzheimer's disease, amyotrophic lateral sclerosis, Parkinson's disease and Huntington's disease, for example, Alzheimer's disease.

In an example, the antibody, fragment, combination of the invention is administered intravenously to the subject; or is for administration intravenously to the subject. In an example, the antibody, fragment, combination of the invention is administered subcutaneously to the subject; or is for administration subcutaneously to the subject.

36. The antibody or fragment of Clause 33, wherein the antibody or fragment is administered to the subject simultaneously or sequentially with chemotherapy, radiotherapy or an immune checkpoint inhibitor.

Optionally, the chemotherapy is selected from nelarabine; cyclophosphamide; vincristine; adriamycin; and dexamethasone alternating with methotrexate and cytarabine.

37. A combination of an amount of an anti-CD7 antibody or fragment and an amount of a chemotherapeutic agent (optionally comprising multiple doses of said antibody and/or agent), wherein the antibody or fragment is according to any one of Clauses 1 to 36.

There is also provided: A medical kit comprising the combination, a first sterile container comprising said amount of antibody or fragment, and a second sterile container comprising said amount of a chemotherapeutic agent, and optionally instructions for using the combination to treat cancer in a subject.

38. The antibody, fragment or combination according to any one of Clauses 1 to 37 for use in a method of treating leukaemia in a human, wherein the antibody, fragment or combination is administered to the human optionally together with an antagonist of human CD5, CD14 or CD19.

39. The antibody, fragment or combination of Clause 38, wherein the leukaemia is acute myeloid leukaemia or T-ALL, or is a relapsed leukaemia (eg, relapsed AML or T-ALL).

40. The antibody, fragment or combination according to any one of Clauses 1 to 37 for use in a method of treating a disease or condition in a human or animal subject mediated by $CD7^+$ cells in the subject, wherein the method comprises administering the antibody, fragment of combination to the subject wherein CD7 cells are targeted and killed, optionally by ADCP and/or CDC.

41. Use of the antibody, fragment or combination as defined in any preceding Clause in the manufacture of a medicament for administration to a subject for treating or preventing a CD7-mediated disease or condition, optionally a cancer.

42. A method of treating or preventing a CD7-mediated disease or condition in a subject (optionally a cancer), the method comprising administering to said subject a therapeutically effective amount of an antibody, fragment or combination as defined in any one of Clauses 1 to 40, wherein the CD7-mediated disease or condition is thereby treated or prevented.

43. The use according to Clause 41 or the method according to Clause 42, wherein the CD7-mediated disease or condition is a leukaemia (optionally T-ALL).

44. The antibody, fragment, combination, use or the method according to any one of Clauses 34 to 43, further comprising administering to the subject a further therapy, for example a further therapeutic agent, optionally wherein the further therapeutic agent is selected from the group consisting of:

a. Cyclophosphamide;
b. Vincristine;
c. Adriamycin;
d. Dexamethasone;
e. Methotrexate;
f. Cytarabine; and
g. Nelarabine.

45. A pharmaceutical composition comprising an antibody, fragment or combination as defined in any one of Clauses 1 to 40 and 44 and a pharmaceutically acceptable excipient, diluent or carrier and optionally in combination with a further therapeutic agent selected from an agent recited in Clause 44.

46. The pharmaceutical composition according to Clause 45 for treating and/or preventing a CD7-mediated condition or disease, optionally a cancer.

47. The pharmaceutical composition according to Clause 45 or 46 in combination with a label or instructions for use to treat and/or prevent said disease or condition in a human; optionally wherein the label or instructions comprise a marketing authorisation number (optionally an FDA or EMA authorisation number); optionally wherein the kit comprises an IV or injection device that comprises the antibody or fragment.

48. A nucleic acid that encodes a VH domain and/or a VL domain of an antibody or fragment as defined in any one of Clauses 1 to 33.
49. A nucleic acid that encodes a VH domain comprising the amino acid sequence of a VH domain of an antibody selected from G09, F05, C02 and E04; or an amino acid that is at least 70, 80, 85, 90, 95, 96, 97, 98 or 99% identical thereto.

For example, the identity is at least 85%. For example, the identity is at least 90%. For example, the identity is at least 95%, 50. A nucleic acid that encodes a VL domain comprising the amino acid sequence of a VL domain of an antibody selected from G09, F05, C02 and E04; or an amino acid that is at least 70, 80, 85, 90, 95, 96, 97, 98 or 99% identical thereto.

Optionally, the nucleic acid also encodes a VH domain comprising the amino acid sequence of a VH domain of the selected antibody; or an amino acid that is at least 70, 80, 85, 90, 95, 96, 97, 98 or 99% identical thereto. For example, the identity is at least 85%. For example, the identity is at least 90%. For example, the identity is at least 95%.

51. A nucleic acid comprising
    (a) a nucleotide sequence that is at least 70% identical to the sequence of SEQ ID NO: 10; and/or
    (b) a nucleotide sequence that is at least 70% identical to the sequence of SEQ ID NO: 20.
52. A nucleic acid that encodes a heavy chain and/or a light chain of an antibody or fragment as defined in any one of Clauses 1 to 33.
53. A nucleic acid that encodes a heavy chain comprising an amino acid sequence that is at least 70% identical to SEQ ID NO: 8.
54. A nucleic acid that encodes a light chain comprising an amino acid sequence that is at least 70% identical to SEQ ID NO: 18.
55. A nucleic acid (eg, in a host cell, eg, a CHO or HEK293 or Cos cell) comprising
    (a) a nucleotide sequence that is at least 70% identical to a heavy chain sequence selected of an antibody selected from G09, F05, C02 and E04; and/or
    (b) a nucleotide sequence that is at least 70% identical to a sequence selected of an antibody selected from G09, F05, C02 and E04.

Herein in any instance where % identity is mentioned, in an example there is 100% identity.

56. A nucleic acid that encodes a heavy chain and/or a light chain of an antibody or fragment as defined in any one of Clauses 1 to 32.

All of the nucleic acids of the invention herein are expressible in a host cell, eg, a CHO or HEK293 or Cos cell, such as for expressing a variable domain or chain of an antibody or fragment of the invention.

57. A vector comprising the nucleic acid(s) (eg, the nucleic acid(s) of any one of Clauses 48 to 55); optionally wherein the vector is a CHO or HEK293 vector.
58. A host cell comprising the nucleic acid(s) (eg, the nucleic acid(s) of any one of Clauses 48 to 55) or the vector of Clause 57.
59. An antibody, fragment, combination, vector, host cell, composition, use or method according to any preceding Clause, wherein the antibody or fragment comprise an IgG1 (eg, a human IgG1 or IgG1*01) constant region.
60. An antibody, fragment, combination, vector, host cell, composition, use or method according to Clause 59, wherein the constant region comprises a glycine at position 430, an arginine at position 356 and/or an arginine at position 357 (according to EU numbering) in the IgG1 CH3 region.
61. An antibody, fragment, combination, vector, host cell, composition, use or method according to Clause 59, wherein the constant region comprises a glycine at position 430.
62. An antibody, fragment, combination, vector, host cell, composition, use or method as herein described.

the invention provides:

A method of diagnosing a CD7-mediated disease or condition in a subject (optionally a cancer), the method comprising combining an antibody or fragment of the invention with an isolated cell sample (eg, a blood or serum sample) and determining that cells comprised by the sample are specifically bound by the antibody or fragment.

Also provided is:

An in vitro assay for detecting CD7-positive cells in a sample, the assay comprising combining an antibody or fragment of the invention with an isolated cell sample (eg, a blood or serum sample) and determining that cells comprised by the sample are specifically bound by the antibody or fragment.

The disease or condition may be any disease or condition disclosed herein. Detection may be by any conventional means, eg, using a label such as a fluorescence label, ELISA or a RIA.

In an example, the antibody or fragment comprises a HCDR3 length of 9, 10, 11 or 12 residues, eg, 10, eg, 11. In an example, the antibody or fragment comprises a LCDR3 length of 7, 8 or 9 residues, eg, 8, eg, 9. In an example, each VH domain of the antibody or fragment comprises from 1-11 non-germline residues, eg, 1, 2, 3, 4, 5, 6, 7, 8, 9, 10 or 11 non-germline residues. In an example, each VL domain of the antibody or fragment comprises from 3-8 non-germline residues, eg, 3, 4, 5, 6, 7 or 8 non-germline residues.

In an embodiment, a CDR sequence herein is determined according to Kabat. In an alternative, the CDR sequence is determined according to IMGT.

In an example, the selected antibody is G09.

In an example, the selected antibody comprises the heavy chain of G09, F05, C02 or E04. In an example, the selected antibody comprises the heavy chain of G09.

In an example, the heavy chain of the antibody or fragment of the invention is a human gamma-1, gamma-2, gamma-3, gamma-4, mu, delta, epsilon or alpha isotype, preferably a gamma isotype (eg, an IgG4 isotype). In an example, the light chain of the antibody or fragment of the invention comprises a human kappa constant region. Alternatively, in an example, the light chain of the antibody or fragment of the invention comprises a human lambda constant region.

Optionally, the antibody is a 4-chain antibody comprising a dimer of a heavy chain associated with a dimer of a light chain. In an example, the heavy chain comprises one or heavy chain CDRs or a CDR combination as disclosed herein and/or the light chain comprises one or heavy chain CDRs or a CDR combinations as disclosed herein, such as from the same selected antibody. In an example, the heavy chain comprises a VH domain as disclosed herein and/or the light chain comprises a VL as disclosed herein, such as from the same selected antibody. In an example, the heavy chain and the light chain are from the same selected antibody, eg, any antibody disclosed in the sequence table herein or the tables in the Examples herein.

In an example, the selected antibody comprises the light chain of G09, F05, C02 or E04. In an example, the selected antibody comprises the light chain of G09.

In an example, the selected antibody comprises the variable domains of G09, F05, C02 or E04. In an example, the selected antibody comprises the variable domains of G09.

In an example, the selected antibody comprises the VH domains of G09, F05, C02 or E04. In an example, the selected antibody comprises the VH domains of G09.

In an example, the selected antibody comprises the VH and VL domains of G09, F05, C02 or E04. In an example, the selected antibody comprises the VH and VL domains of G09.

In an example, the binding site of the antibody or fragment comprises a VH/VL pair that specifically binds to human CD7.

Optionally, the antibody or fragment competes with G09 (eg, G09 in IgG format, eg, human IgG1) for binding to CD7 as determined by SPR.

Optionally, the amino acid substitutions are conservative amino acid substitutions, optionally wherein each conservative substitution is from group (1) to (6):

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Any SPR herein is, for example, surface plasmon resonance (SPR) at 37° C. and pH 7.6.

Optionally, any CD7 herein is (for example, in in vitro testing) human CD7, eg, comprising the amino acid sequence of human CD7 disclosed herein.

In an example, the antibody or fragment of the invention binds to human CD7 with a Ka of eg, $5\times10^{6}$ $M^{-1}xs^{-1}$; or about $5\times10^{6}$ $M^{-1}xs^{-1}$. In an example, the antibody or fragment of the invention binds to human CD7 with a Kd of eg, 4 or 5 $s^{-1}$; or about 4 or 5 s−1. In an example, the antibody or fragment of the invention binds to human CD7 with a KD of eg, 0.07 or 0.14 nM; or about 0.07 or 0.14 nM. In an embodiment, the fragment is a Fab fragment. In an embodiment, the fragment is a scFv.

Optionally, the antibody of the invention has an affinity (KD) for binding CD7 of from 1 pM to 5 nM, optionally wherein binding is determined by SPR using a Fab of said antibody at 37° C. at pH 7.6.

Optionally, the antibody has off-rate ($K_{off}$) for binding CD7 of from $1\times10^{-5}$ to 1x10−3$S^{-1}$, optionally wherein binding is determined by SPR using a Fab of said antibody at 37° C. at pH 7.6.

Optionally, the antibody has on-rate ($K_{on}$) for binding CD7 of from $1\times10^{5}$ to $1\times10^{7}$ $M^{-1}S^{-1}$, optionally wherein binding is determined by SPR using a Fab of said antibody at 37° C. at pH 7.6.

In an example, the antibody (eg, as a Fab) or fragment has an affinity (KD) for binding CD7 (eg, human CD7) of (a) from 2, 3, 4, 5 or 10 pM to 3, 4 or 5 nM;
(b) from 1-10 pM to 5 nM;
(c) from 10 pM to 3, 4 or 5 nM;
(d) from 50 or 80 pM to 200 nM;
(e) from 50 or 80 pM to 150 nM; or
(f) from 50 or 80 pM to 100 nM.

In an example, the KD is (or is about) 5-15 pM (eg, 10 pM). In an example, the KD is (or is about) 2-5 nM (eg, 3 nM). In an example, the KD is (or is about) 100-400 pM (eg, 140 or 390 pM).

In an example, the antibody (eg, as a Fab) or fragment has an off-rate ($K_{off}$) for binding CD7 (eg, human CD7) of (a) from $1\times10^{-5}$ to $5\times10^{-4}$ $S^{-1}$;
(b) from $1\times10^{-5}$ to $6\times10^{-4}$ $S^{-1}$;
(c) from $1\times10^{-5}$ to $7\times10^{-4}$ $S^{-1}$;
(d) from $1\times10^{-5}$ to $8\times10^{-4}$ $S^{-1}$;
(e) from $2\times10^{-1}$ to $1\times10^{-3}$ $S^{-1}$;
(f) from $2\times10^{-5}$ to $5\times10^{-4}$ $S^{-1}$;
(g) from $2\times10^{-5}$ to $6\times10^{-4}$ $S^{-1}$;
(h) from $2\times10^{-5}$ to $7\times10^{-4}$ $S^{-1}$; or
(i) from $2\times10^{-5}$ to $8\times10^{-4}$ $S^{-1}$.

In an example, the $K_{off}$ is (or is about) $5\times10^{-4}S^{-1}$ (eg, when the KD is (or is about) from 2 nM to 400 pM; when the KD is (or is about) 2-5 nM (eg, 3 nM); or when the KD is (or is about) 100-400 pM (eg, 140 or 390 pM)). In an example, the $K_{off}$ is (or is about) $3\times10^{-5}$ $S^{-1}$ (eg, when the KD is (or is about) from 5-15 pM (eg, 10 pM)).

In an example, the antibody (eg, as a Fab) or fragment has an on-rate ($K_{on}$) for binding CD7 (eg, human CD7) of (a) from $1\times10^{5}$ to $1\times10^{6}$ $M^{-1}S^{-1}$;
(b) from $1\times10^{5}$ to $2\times10^{6}$ $M^{-1}S^{-1}$;
(c) from $1\times10^{5}$ to $3\times10^{6}$ $M^{-1}S^{-1}$;
(d) from $1\times10^{5}$ to $4\times10^{6}$ $M^{-1}S^{-1}$;
(e) from $1\times10^{5}$ to $5\times10^{6}$ $M^{-1}S^{-1}$;
(f) from $2\times10^{5}$ to $5\times10^{6}$ $M^{-1}S^{-1}$;
(g) from $3\times10^{5}$ to $5\times10^{6}$ $M^{-1}S^{-1}$;
(h) from $4\times10^{5}$ to $5\times10^{6}$ $M^{-1}S^{-1}$;
(i) from $5\times10^{5}$ to $5\times10^{6}$ $M^{-1}S^{-1}$; or
(j) from $6\times10^{5}$ to $5\times10^{6}$ $M^{-1}S^{-1}$.

In an example, the $K_{on}$ is (or is about) 1 or $2\times10^{-5}$ $M^{-1}S^{-1}$ (eg, when the KD is 2-5 nM (eg, 3 nM)). In an example, the $K_{on}$ is (or is about) 1-4, 1, 2, 3 or $4\times10^{-6}$ $M^{-1}S^{-1}$ (eg, when the KD is (or is about) from 5-400 pM (eg, 140 or 390 pM) or 5-15 pM (eg, 10 pM)).

As provided in the Clauses or other aspects herein, an anti-CD7 antibody or fragment may bind to CD7, e.g. human CD7 with a $K_D$ of less than 50 nM, less than 40 nM, less than 30 nM as determined by surface plasmon resonance. Another embodiment, anti-CD7 antibody or fragment may bind to CD7, e.g. human CD7 with a $K_D$ of less than 20 nM, less than 15 nM, less than 10 nM as determined by surface plasmon resonance. The anti-CD7 antibody or fragment may bind to CD7, e.g. human CD7 with a $K_D$ of less than 8 nM, less than 5 nM, less than 4 nM, less than 3 nM, less than 2 nM or less than 1 nM as determined by surface plasmon resonance. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less.

In another embodiment, the $K_D$ is within a range of 0.01 to 1 nM, or a range of 0.05 to 2 nM, or a range of 0.05 to 1 nM. The $K_D$ may be with regard to hCD7, cynomolugus monkey (ie, "cyno") CD7 and/or mouse CD7.

In another embodiment, the anti-CD7 antibodies described herein have a $KO_N$ rate (e.g. as measured by SPR, e.g. at 25° C. or at 37° C.) of approximately 0.5 to 10 pM, for example approximately 1 to 8 pM or approximately 1 to 7 μM. In another embodiment, the $KO_N$ rate is approximately 1 to 5 pM, e.g. approximately 1 pM, approximately 1.5 pM, approximately 2 pM, approximately 2.5 pM or approximately 3 μM. In another embodiment, the $K_{ON}$ rate is approximately 3.5 pM, approximately 4 pM, approximately 4.5 pM, approximately 5 pM or approximately 5.5 pM.

In another embodiment, the anti-CD7 antibodies described herein have a $K_{OFF}$ rate (e.g. as measured by SPR, e.g. at 25° C. or at 37° C.) of approximately 0.01 to 100 mM, for example approximately 0.1 to 50 mM or approximately 0.5 to 50 mM. In another embodiment, the KOFF rate is approximately 0.5 to 10 mM, or approximately 0.5 to 10 mM, e.g. approximately 1 mM, approximately 2 mM, approximately 3 mM, approximately 4 mM or approximately 5 mM. In another embodiment, the $K_{OFF}$ rate is approximately 0.6 mM, approximately 0.7 mM, approximately 0.8 mM or approximately 0.9 mM.

In an example, the invention antibody or fragment comprises the VH and VL domains of G09, F05, C02 and E04.

In an example, the invention antibody or fragment comprises the VH and VL domains of G09. In an example, the invention antibody or fragment comprises the VH and VL domains of F05. In an example, the invention antibody or fragment comprises the VH and VL domains of G09. In an example, the invention antibody or fragment comprises the VH and VL domains of C02. In an example, the invention antibody or fragment comprises the VH and VL domains of E04.

In an example, the selected antibody is G09.

In an example, the selected antibody comprises the variable domains of an antibody selected from G09, F05, C02 and E04.

In an example, the selected antibody comprises the VH domains of an antibody selected from G09, F05, C02 and E04. In an example, the selected antibody comprises the VH domains of G09.

In an example, the selected antibody comprises the VH and VL domains of an antibody selected from G09, F05, C02 and E04. In an example, the selected antibody comprises the VH and VL domains of G09.

Optionally, the antibody or fragment of the invention comprises the HCDR3 of an antibody selected from G09, F05, C02 and E04. Optionally, the antibody or fragment of the invention comprises the HCDR1 and/or HCDR2 of said selected antibody.

Optionally the antibody or fragment of the invention comprises the HCDR1 of an antibody selected from G09, F05, C02 and E04. Optionally, the antibody or fragment of the invention comprises the HCDR2 and/or HCDR3 of said selected antibody.

Optionally the antibody or fragment of the invention comprises the HCDR2 of an antibody selected from G09, F05, C02 and E04. Optionally, the antibody or fragment of the invention comprises the HCDR1 and/or HCDR3 of said selected antibody.

Optionally, the antibody or fragment of the invention comprises the VH of an antibody selected from G09, F05, C02 and E04. Optionally, the antibody or fragment of the invention comprises the VL of said selected antibody.

Optionally, the antibody or fragment of the invention comprises the VL of an antibody selected from G09, F05, C02 and E04. Optionally, the antibody or fragment of the invention comprises the VH of said selected antibody.

Optionally, the antibody or fragment of the invention comprises the heavy chain of an antibody selected from G09, F05, C02 and E04. Optionally, the antibody or fragment of the invention comprises the light chain of said selected antibody.

Optionally, the antibody or fragment of the invention comprises the light chain of an antibody selected from G09, F05, C02 and E04. Optionally, the antibody or fragment of the invention comprises the heavy chain of said selected antibody. In an example, the selected antibody is G09.

Optionally, the antibody of the invention comprises a human IgG1*01 constant region. Optionally, the antibody of the invention comprises a human IgG1 E430G constant region, eg, an IgG1*01 E430G constant region. Optionally, the antibody of the invention comprises a human IgG1 E345R constant region, eg, an IgG1*01 E345R constant region.

Preferably, an antibody or a fragment thereof that specifically binds to a hCD7 does not cross-react with other antigens (but may optionally cross-react with different CD7 species, e.g., rhesus, cynomolgus, or murine). An antibody or a fragment thereof that specifically binds to a CD7 antigen can be identified, for example, by immunoassays, BIAcore™, or other techniques known to those of skill in the art. An antibody or a fragment thereof binds specifically to a hCD7 antigen when it binds to a hCD7 antigen with higher affinity than to any cross-reactive antigen as determined using experimental techniques, such as radioimmunoassays (RIA) and enzyme-linked immunosorbent assays (ELISAs). Typically, a specific or selective reaction will be at least twice background signal or noise and more typically more than 10 times background. See, e.g. Paul, ed., 1989, Fundamental Immunology Second Edition, Raven Press, New York at pages 332-336 for a discussion regarding antibody specificity.

Contact amino acid residues involved in the interaction of antibody and antigen, such as CD7, may be determined by various known methods to those skilled in the art.

In one embodiment, if the antibody recognises a linear epitope, short peptides based on the antigen sequence can be produced and binding of the antibody to these peptides can be assessed using standard techniques.

In one embodiment, limited proteolytic digestion and mass spectrophotometry can be used to identify binding epitopes.

In one embodiment, the contact residues of the epitope are identified by X-ray crystallography. In one embodiment, the contact residues of the epitope are identified by cryo-electro microscopy. In one embodiment, the contact residues of the epitope are identified by a combination of limited proteolytic digestion and mass spectrometry.

In another embodiment, the anti-CD7 antibodies (and fragments) described in herein provide improved transient expression levels over other anti-CD7 antibodies and fragments. Thus, in one embodiment, the anti-CD7 antibody (or fragment) is expressed in a HEK293 cell, e.g. a HEK293T cell, at an expression level of approximately 100 μg/mL, or in a range of approximately 100 to 350 μg/mL. In another embodiment, the expression level is above approximately 350 μg/mL.

In another embodiment, the anti-CD7 antibody (or fragment) is expressed in a CHO cell, e.g. an Expi-CHO cell, at an expression level of approximately 100 μg/mL, or in a range of approximately 100 to 350 μg/mL. In another embodiment, the expression level is above approximately 350 μg/mL.

In another embodiment, the anti-CD7 antibody (or fragment) is expressed in a CHO cell, e.g. an Expi-CHO cell or a CHO-E7 EBNA cell, at an expression level of approximately 100 μg/mL, or in a range of approximately 100 to 350 μg/mL. In another embodiment, the expression level is above approximately 350 μg/mL. The antibody for example, comprises the VH and VL domains of any one of G09, formatted as a human IgG1 or human IgG4 (eg, IgG4-PE).

In any of these expression systems, the expression is carried out of a scale of between approximately 0.5 mL and 3 mL, for example between approximately 0.5 mL and 2 mL.

In any of these expression systems, the anti-CD7 antibody (or fragment) may be expressed from a pTT5 vector. In any of these expression systems, the anti-CD7 antibody (or fragment) may be expressed in conjunction with a lipid transfection reagent, and may optionally be expressed in a CHO cell, e.g. an Expi-CHO cell. In any of these expression systems, the anti-CD7 antibody (or fragment) may be expressed in conjunction with a PEI transfection reagent, and may optionally be expressed in a CHO cell, e.g. an CHO-E7 EBNA cell. In any of these expression systems, the anti-CD7 antibody (or fragment) may be expressed in conjunction with a helper plasmid (e.g. an AKT helper plasmid), and may optionally be expressed in a CHO cell, e.g. an CHO-E7 EBNA cell.

In any of these expression systems, the expression level is between approximately 100 μg/mL and approximately 1500 μg/mL, for example between approximately 100 μg/mL and approximately 1000 μg/mL, or between approximately 200 μg/mL and approximately 1000 μg/mL, or between approximately 350 μg/mL and approximately 1000 μg/mL. In any of these expression systems, the lower limit of expression may be approximately 100 μg/mL, approximately 200 μg/mL, approximately 300 μg/mL, or approximately 400 μg/mL. In another embodiment, the lower limit of expression may be approximately 500 μg/mL, approximately 600 μg/mL, approximately 700 μg/mL, or approximately 800 μg/mL. In any of these expression systems, the upper limit of expression may be approximately 2000 μg/mL, approximately 1800 μg/mL, approximately 1600 μg/mL, or approximately 1500 μg/mL. In another embodiment, the upper limit of expression may be approximately 1250 μg/mL, approximately 1000 μg/mL, approximately 900 μg/mL, or approximately 800 μg/mL.

In another embodiment, the expression system is a Lonza expression system, e.g. Lonza X-Ceed" system. In the Lonza expression system, the expression may be carried out at a scale of approximately 30 mL to 2 L, for example 50 mL to 1 L, or 1 L tp 2 L. In the Lonza expression system, the anti-CD7 antibody (or fragment) may be expressed in conjunction with electroporation, and optionally without any helper plasmids. In the Lonza expression system, the anti-CD7 antibody (or fragment) may be expressed at a level of approximately 1 g/L, or approximately 900 mg/L, or approximately 800 mg/L, or approximately 700 mg/L. In another embodiment, In the Lonza expression system, the anti-CD7 antibody (or fragment) may be expressed at a level of approximately 600 mg/L or approximately 500 mg/L or approximately 400 mg/L. In the Lonza expression system, the anti-CD7 antibody (or fragment) may be expressed at a level of between approximately 400 mg/L and approximately 2 g/L, for example between approximately 500 mg/L and approximately 1.5 g/L, or between approximately 500 mg/L and approximately 1 g/L. In another embodiment, the expression level is above 1 g/L. In another embodiment, the anti-CD7 antibodies provide improved half-life over other anti-CD7 antibodies.

In one embodiment, the antibody or fragment is a human antibody or fragment. In one embodiment, the antibody or fragment is a fully human antibody or fragment. In one embodiment, the antibody or fragment is a fully human monoclonal antibody or fragment.

in one embodiment, the antibody or fragment is a humanised antibody or fragment. In one embodiment, the antibody or fragment is a humanised monoclonal antibody or fragment.

Contact amino acid residues involved in the interaction of antibody and antigen may be determined by various known methods to those skilled in the art, such as alanine scanning, protein crystallography, mass spectrophotometry or any other technique as will be apparent to the skilled addressee.

In one embodiment, the recited CDR comprises one amino acid substitution, which may be a conservative amino acid substitution. In one embodiment, the recited CDR comprises two amino acid substitutions, which may be conservative amino acid substitutions. In one embodiment, the recited CDR comprises comprises three amino acid substitutions, which may be conservative amino acid substitutions. In one embodiment, the recited CDR comprises four amino acid substitutions, which may be conservative amino acid substitutions. In one embodiment, the recited CDR comprises five amino acid substitutions, which may be conservative amino acid substitutions. In one embodiment, the recited CDR comprises six amino acid substitutions, which may be conservative amino acid substitutions.

Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g. substituting a charged or hydrophobic amino; acid with alanine), or alternatively, in which a naturally-occurring amino acid is substituted with a non-conventional amino acid.

In one embodiment, the conservative amino acid substitutions are as described herein. For example, the substitution may be of Y with F, T with S or K, P with A, E with D or Q, N with D or G, R with K, G with N or A, T with S or K, D with N or E, I with L or V, F with Y, S with T or A, R with K, G with N or A, K with R, A with S, K or P. In another embodiment, the conservative amino acid substitutions may be wherein Y is substituted with F, T with A or S, I with L or V, W with Y, M with L, N with D, G with A, T with A or S, D with N, I with L or V, F with Y or L, S with A or T and A with S, G, T or V.

Aspects

Any of the following Aspects may be combined with any of the features disclosed herein (eg, with any of the claimed embodiments herein or any of the Clauses herein). For example, the ligand in any of these Aspects may be an antibody or fragment of the invention.

1. An anti-CD7 ligand for administration to a human patient for the treatment of a cancer by complement-dependent cytotoxicity (CDC) of $CD7^+$ cells (eg, cancer cells) in the patient, the ligand comprising an antibody Fc region and a binding site for specifically binding to human CD7.

In an example, the CD7 is human CD7 and the patient is a human.

In an alternative in any Aspect, instead of cancer, the ligand herein is for treating a disease or condition mediated by CD7+ cells, eg, CD7+ T-cells or NK cells. For example, the disease or condition is an autoimmune disease or condition. For example, the disease is graft-versus-host disease (GvHD). For example, the disease or condition is an inflammatory disease or condition.

Optionally, in an alternative in any Aspect the ligand is administered prophylactically to the subject to reduce the risk of cancer or the disease or condition.

Optionally, in any Aspect the cells are cells of the patient's immune system. Optionally, in any Aspect the cells are T- and/or NK-cells. Optionally, in any Aspect the cells are cells of a tissue, cell or organ transplant comprised by the human.

2. An anti-CD7 ligand for administration to a human patient for the treatment of a cancer by ligand-dependent phagocytosis of $CD7^+$ cells (eg, cancer cells) in the patient, the ligand comprising an antibody Fc region and a binding site for specifically binding to human CD7.
3. Wherein the phagocytosis is antibody-dependent cellular phagocytosis (ADCP), wherein the antibody is said ligand.

In vivo, ADCP can be mediated by monocytes, macrophages, neutrophils and dendritic cells via FcγRlia, FcγRI and FcγRlila. While all three receptors can participate in ADCP, FcγRlia is believed to be the predominant Fcγ receptor involved in this process. In an example, the ADCP comprises phagocytosis of $CD7^+$ cancer cells by macrophages and/or monocytes comprised by the patient.

4. An anti-CD7 ligand for administration to a human patient for the treatment of a cancer by ligand-dependent cell-mediated cytotoxicity of $CD7^+$ cancer cells in the patient, the ligand comprising an antibody Fc region and a binding site for specifically binding to human CD7.

In ADCC, cytotoxicity may be mediated by natural killer (NK) cells; but macrophages, neutrophils and eosinophils can also mediate it. In an embodiment of the invention, ADCC may comprise ADCC by CD16+ immune cells of the patient. In an embodiment of the invention, ADCC may comprise ADCC by cells selected from natural killer (NK) cells; but macrophages, neutrophils and eosinophils.

5. The ligand of any preceding Aspect, wherein the cytotoxicity is antibody dependent cell-mediated cytotoxicity (ADCC), wherein the antibody is said ligand.
6. The ligand of any preceding Aspect, wherein the ligand comprises an anti-CD7 antibody, antibody fragment or trap.

In an example, the ligand comprises a paired VH/VL anti-CD7 binding site wherein the VH and VL are human antibody variable domains. Additionally or alternatively, the antibody or fragment comprises a human Fc.

In an example, the ligand is a human ligand, eg, a human antibody or fragment.

In an example, the ligand is capable of being internalised by CD7+ cells. In an example, the ligand is capable of being internalised by the cancer cells. In an example, the ligand is capable of being internalised by CEM cells in vitro.

7. The ligand of any preceding Aspect, wherein the patient has previously received a cancer chemotherapy agent.

In an example, the patient has previously received an immune checkpoint inhibitor, eg, an antibody against an immune checkpoint inhibitor. In an example, the inhibitor is ipilimumab, nivolumab, pembrolizumab or tremelimumab.

In an example, the patient has previously received anti-cancer radiation treatment.

8. The ligand of any preceding Aspect, wherein the patient has previously received GCSF. Chemotherapy can cause myelosuppression and unacceptably low levels of white blood cells (neutropenia), making patients susceptible to infections and sepsis. GCSF stimulates the production of granulocytes, a type of white blood cell. In oncology and hematology, a recombinant form of GCSF is used with certain cancer patients to accelerate recovery from neutropenia after chemotherapy, allowing higher-intensity treatment regimens. It may be administered to oncology patients via subcutaneous or intravenous routes. In the context of the present invention, administration of GCSF simultaneously or sequentially (eg, before) administering the anti-CD7 ligand to the patient may be beneficial for up-regulating cell types involved in the CDC, ADCC and ADCP-mediated $CD7^+$ cell killing of the invention
9. The ligand of any preceding Aspect, wherein the patient has previously undergone chemotherapy and wherein immediately before administration of the ligand to the patient, the patient has received a treatment to enhance complement (eg, Clq) activity.
10. The ligand of any preceding Aspect, wherein the patient has received an administration of one or more complement components (eg, a composition comprising Clq).

For example, the components are comprised by blood or plasma which is administered to the patient.

11. Comprising determining the level or activity of complement (eg, Clq) in the patient before administration of said ligand For example, C1q level is serum concentration in the patient in the range from 70 to 160 micrograms/ml, eg, as determined by quantitative ELISA, such as a sandwich ELISA. An example of a suitable technique for determination is set out in Biotechnol J. 2009 August; 4(8):1210-4. doi: 10.1002/biot.200800273, "Systemic lupus erythematosus and Clq: A quantitative ELISA for determining Clq levels in serum", Dillon S P et al. In an embodiment, said range is 100 to 160 micrograms/ml.

The range of complement level for a normal healthy person:

1. The total complement levels: 41-90 haemolytic units
2. The C1 levels: 16-33 mg/dL
3. The C3 levels: 88-252 mg/dL for males; 88-206 mg/dL for female
4. The C4 levels: 12-72 mg/dL for males; 13-75 mg/dL for females In an example, the invention comprises the administration of an anti-CD7 ligand with anti-CD46, anti-CD55 or anti-CD59 therapy in the patient to neutralize complement regulatory protein (CRP) function.

12. Comprising administering said ligand to the patient, whereby said $CD7^+$ cancer cells are killed, and thereafter carrying out chemotherapy of the patient.
13. The ligand of any preceding Aspect, wherein the cancer cells are immune cells of the patient.
14. The ligand of any preceding Aspect, wherein the cancer cells are T-cells, NK cells, thymocytes or bone marrow $CD34^+CD38^-$ cells.

The cancer cells are, eg, $CD7^+$ $CD34^+$ CD2 T-cells. The cancer cells are, eg, $CD34^+CD38^-$ immune cells (eg, T-cells). The cancer cells are, eg, $CD34^+CD38^+$ immune cells (eg, T-cells).

15. The ligand of any preceding Aspect, wherein the T-cells are immature T-cells.

Optionally, the immature T-cells comprise one, two or more of the following types: DN1, DN2, DN3, DN4 and DP. DN1 cells are positive for the following markers: CD34, CD44, CD117, TdT, HLA-DR. DN2 cells are positive for the following markers: CD2, CD5, CD7, CD25, CD38, CD44, CD117, CD127, TdT, HLA-DR. DN3 cells are positive for the following markers: CD2, CD5, CD7, CD25, CD38, CD44, CD71, CD117, TdT. DN4 cells are positive for the following markers: CD1, CD2, CD5, CD7, CD38, TdT. DP cells are positive for the following markers: CD2, CD3, CD4 or CD8, CD7.

In an embodiment, the cancer cells comprise early thymic precursor (ETP) cells. The presence of such cells has been associated with high leukaemia risk and low or no response to Nelarabine. Thus, in an embodiment, the patient is Nelarabine refractory, eg, wherein the cancer cells comprise ETP cells.

In an example the cancer cells are CD52+.

Optionally, the immature T-cells are $CD2^+$, $CD5^{30}$, $CD7^+$.

16. The ligand of any preceding Aspect, wherein the T-cells are $CD7^+$ $CD34^+$ $CD38^-$ T-cells.

Optionally, the cells are, eg, $CD7^+$ $CD34^+$ $CD38^-$ $Lin^-$ T-cells, such as wherein the cancer is AML.

Optionally, the T-cells are CD8+ T-cells. Wherein the T-cells are CD4+ T-cells.

Optionally, the cells comprise a plurality of cells, each cell of said plurality comprising at least 100, 500 or 1000 copies of cell-surface CD7 (see, eg, Figla, Aandahl, E M et al. J Immunol. 2003. 170: 2349-2355 for guidance on such determination).

17. The ligand of any preceding Aspect, wherein the cells are leukaemia-initiating cells (LICs).

18. The ligand of any preceding Aspect, wherein the cells are leukaemia cells, eg, AML or T-ALL cells.

19. The ligand of any preceding Aspect, wherein the cancer cells are T-cells and NK cells are spared killing in the patient.

20. The ligand of any preceding Aspect, wherein the ligand kills no more than 70% (eg, no more than 80, 90 or 95%) of NK cells in an in a standard vitro cell killing test.

21. The ligand of any preceding Aspect, wherein the Fc region is a human Fc.

22. The ligand of any preceding Aspect, wherein the Fc region is a wild-type Fc.

23. The ligand of any preceding Aspect, wherein the Fc region is a human IGHG1*01 or IGHG1*02 nucleotide sequence.

24. The ligand of any preceding Aspect, wherein the cancer is acute myeloid leukaemia (AML), T-ALL (eg, patient-derived T-ALL), peripheral T cell lymphoma (PTCL) or T-cell prolymphocytic leukaemia (TPLL).

Optionally, the AML is M1/M2 AML. Optionally, the cancer is Mixed lineage leukaemia (MLL)-rearranged human acute lymphoblastic leukemia.

Optionally, the cancer is a cancer mediated by $CD7^+$ immune cells (eg, T-cells).

Optionally, the cancer is lymphoblastic leukemia (LL) (eg, ALL or acute lymphocytic leukemia), Cutaneous T-cell lymphoma (CTCL) or melanoma. Optionally, the cancer is relapsed T-ALL or AML.

Optionally, the cancer is a liver cancer. Optionally, the cancer is selected from melanoma, Merkel cell carcinoma, non-small cell lung cancer (squamous and non-squamous), renal cell cancer, bladder cancer, head and neck squamous cell carcinoma, mesothelioma, virally induced cancers (such as cervical cancer and nasopharyngeal cancer), soft tissue sarcomas, haematological malignancies such as Hodgkin's and non-Hodgkin's disease and diffuse large B-cell lymphoma.

25. The ligand of any preceding Aspect, wherein the AML is CCAAT/enhancer binding protein a (CEBPA) mutated AML.

Optionally, the patient is homozygous for CEBPA mutation.

26. The ligand of any preceding Aspect, wherein the patient has an immunophenotype of $HLA\text{-}DR^+$ $CD7^+$ $CD13^+$ $CD14^-$ $CD15^+$ $CD33^+$ $CD34^+$, eg, wherein the cancer is AML, eg, CEBPA AML.

27. The ligand of any preceding Aspect, wherein the human is an adult.

For example, the adult is at least 18, 20, 30, 40, 50, 60, 70, 80 or 90 years' of age.

28. The ligand of any preceding Aspect, wherein the human is an infant.

For example, the human is a child, eg, a human under 18 years' of aged, eg, less than 17, 16, 15, 14, 13, 12, 11, 10, 9, 8, 7, 6, 5, 4, 3, 2 or 1 year of age.

29. The ligand of any preceding Aspect, wherein the patient is suffering from 1st or 2nd relapse of said cancer following previous treatment, eg, with a chemotherapy agent.

In an example, the agent comprises an immune checkpoint inhibitor, such as an inhibitor described herein.

30. The ligand of any preceding Aspect, wherein the patient has previously received Nelarabine.

31. The ligand of any preceding Aspect, wherein the ligand and Nelarabine are simultaneously or sequentially administered to the patient.

The invention may, for example, enable the administration of a lower dose than standard of care with Nelarabine.

32. The ligand of any preceding Aspect, wherein the ligand is administered to the patient simultaneously or sequentially with a haematopoietic stem cell transplant.

In an example, the transplant is an allogeneic transplant.

In an example, the ligand is administered no more often than once every 2 or 4 weeks. In an example, the ligand is administered fortnightly, monthly or weekly.

33. The ligand of any preceding Aspect, wherein the treatment reduces cancer progression in the patient.

34. The ligand of any preceding Aspect, wherein the treatment enhances cancer survival in human patients.

35. The ligand of any preceding Aspect, wherein the treatment causes cancer remission in the patient.

36. The ligand of any preceding Aspect, wherein said ligand mediates ADCP in a standard ADCP test.

37. The ligand of any preceding Aspect, wherein said ligand mediates CDC killing of CEM cells in an in vitro CEM cell killing assay with an $EC_{50}$ in the range from 10 to 500 pM (eg, from 10 to 500 or 100 pM).

CEM cells are a well-known human T-ALL cell line. In an example, the CEM cells in the assay are in the presence of human complement (eg, the CEM cells are mixed with human serum comprising complement proteins). When assessed against a control using non-cancerous human cells ("normal cells") instead of CEM cells, in an example, the Hand preferentially mediates killing of said cancer cells over normal cells. The normal cells may be cancer patient cells.

Optionally, in the assay the ligand mediates the CEM cell killing with said $EC_{50}$ and killing of 90-100% of CEM cells.

38. The ligand of any preceding Aspect, wherein said ligand mediates ADCP killing of CEM cells in an in vitro CEM cell killing assay with an $EC_{50}$ in the range from 10 to 500 pM (eg, from 10 to 500 or 100 pM).

CEM cells are a well-known human T-ALL cell line. In an example, the CEM cells in the assay are in the presence of human complement (eg, the CEM cells are mixed with human serum comprising complement proteins). When assessed against a control using non-cancerous human cells ("normal cells") instead of CEM cells, in an example, the Hand preferentially mediates killing of said cancer cells over normal cells. The normal cells may be cancer patient cells.

Optionally, in the assay the ligand mediates the CEM cell killing with said $EC_{50}$ and killing of 90-100% of CEM cells.

In an embodiment, said ligand mediates ADCC killing of CEM cells in an in vitro CEM cell killing assay with an $EC_{50}$ in the range from 10 to 500 pM (eg, from 10 to 500 or 100 pM).

CEM cells are a well-known human T-ALL cell line. In an example, the CEM cells in the assay are in the presence of human complement (eg, the CEM cells are mixed with human serum comprising complement proteins). When assessed against a control using non-cancerous human cells ("normal cells") instead of CEM cells, in an example, the Hand preferentially mediates killing of said cancer cells over normal cells. The normal cells may be cancer patient cells.

Optionally, in the assay the ligand mediates the CEM cell killing with said $EC_{50}$ and killing of 90-100% of CEM cells.

In an embodiment, said ligand mediates trogocytosis killing of CEM cells in an in vitro CEM cell killing assay with an $EC_{50}$ in the range from 10 to 500 pM (eg, from 10 to 500 or 100 pM).

CEM cells are a well-known human T-ALL cell line. In an example, the CEM cells in the assay are in the presence of human complement (eg, the CEM cells are mixed with human serum comprising complement proteins). When assessed against a control using non-cancerous human cells ("normal cells") instead of CEM cells, in an example, the Hand preferentially mediates killing of said cancer cells over normal cells. The normal cells may be cancer patient cells.

Optionally, in the assay the ligand mediates the CEM cell killing with said $EC_{50}$ and killing of 90-100% of CEM cells.

39. The ligand of any preceding Aspect, wherein the ligand specifically binds to human CD7 and Cynomolgus monkey CD7.
40. The ligand of any preceding Aspect, wherein said treatment does not produce cytokine storm syndrome in the patient.
41. The ligand of any preceding Aspect, wherein the cancer cells are $CD7^{High}$ cells.
42. A regimen for treating or preventing a cancer in a human patient, wherein the regimen comprises performing the treatment recited in any preceding Aspect, wherein the ligand is an antibody and a first, second and third doses of the antibody are administered to the patient, wherein the doses are administered between 1 and 7 days apart, and wherein the total of said doses is from 0.1 to 100 mg/Kg of the antibody.

The invention also provides a method of treating or preventing a cancer in a human patient comprising administering to the patient a ligand of any of the Aspects.

The invention also provides a method of detecting $CD7^+$ cells in a cell sample (eg, in a blood or serum sample), wherein the method comprises mixing the sample with the ligand of the invention whereby the ligand binds to $CD7^+$ cells in the cell sample, and detecting or quantifying the ligand-bound cells.

Instead of, or as an example of, a "standard test", a test may be a method used in an Example herein.

EXAMPLES

We identified antibodies that usefully target human CD7 and would be useful to treat cancer such as T-ALL.

A particularly desirable antibody, G09, when formatted as an IgG1 comprising an E430G mutation (also referred to as "G09 E430G") displayed human/cynomolgus CD7-cross reactivity and provided highly potent complement dependent cytotoxicity (CDC) dependent killing and potent macrophage-dependent phagocytosis activities in vitro, and robust tumour cell depletion in whole blood assays. This data set demonstrated for an antibody comprising the G09 variable domains:

- Showed potent CDC activity ($EC_{50}$=50-500 pM; ~100% killing) on most non-relapsed or relapsed T-ALL cells tested in vitro
- Showed potent ADCP activity on relapsed T-ALL cells in vitro
- Killed T-ALL cells (~100%) in human whole blood assay
- Killed tumours in most severely immuno-compromised mice (NSG)
- Reduced potency in killing of human peripheral T cells (50-75%) and NK cells (70-90%) in ex vivo assays.

Example 1

Figure 16:
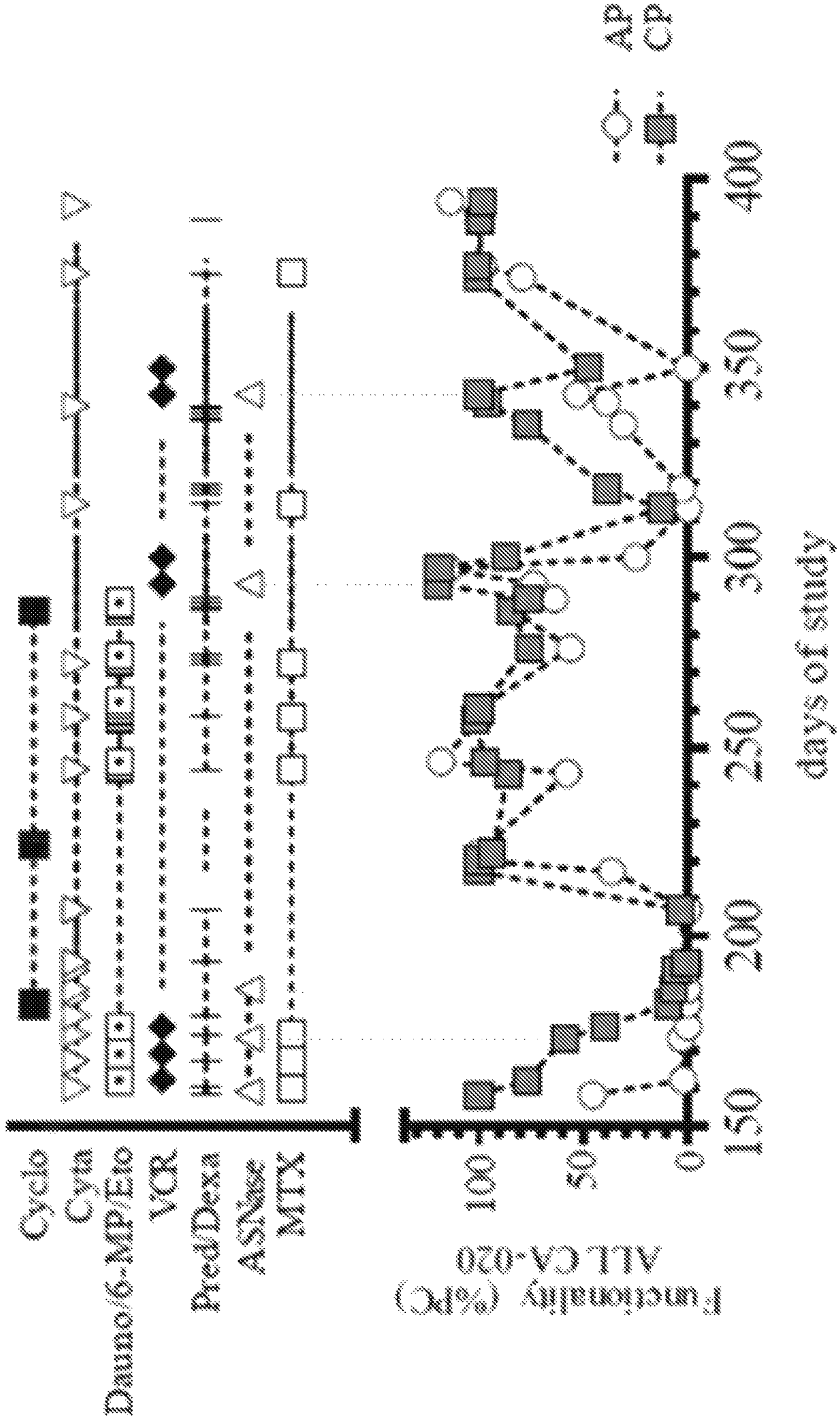
FIG. 16: Complement activity during chemotherapy (see ref 15).

CD7 is expressed throughout the development of the T-cell lineage and is therefore expected to be expressed on all T-ALL blasts. We realised that the binding of an immunocompetent CD7-IgG1 mAb is expected to lead to a depletion of these cells based on CDC, antibody-dependent cell-mediated cytotoxicity (ADCC) and antibody-dependent cell-mediated phagocytosis (ADCP). Considering the importance to kill blasts, we wanted to have a strong depleting effect. We realised that a complicating factor is that CD7 is expressed just not on T cells but also NK cells, so there is the potential to deplete the effector cells of the ADCC response. In addition, patients with T-ALL malignancies receiving intensive chemotherapy may result in low levels of the effector cells to mediate cytotoxicity. Therefore, we realised that efficient depletion of T-ALL cells could not be achieved only by ADCC during anti-CD7 treatment. Although reductions of complement activity following chemotherapy are transient in nature, the complement activities seem effective in ALL patients in certain periods during therapy (15) (FIG. 16).

We hypothesized that by enhancing the potency of CD7-directed cytotoxicity by utilising a strategy that increases CDC activity, we could augment the efficacy of CD7-targeted therapy in patients with T-ALL malignancies.

The classical pathway of CDC relies on C1q binding to cell surface antigen-bound antibodies. The ability of human antibodies to induce CDC is isotype dependent with the order of potency IgM>>IgG3>IgG1>>IgG2=lgG4. IgM and IgG3 are difficult to manufacture making IgG1 the Fc isotype of choice for a therapeutic antibody mediating actions through CDC. Recently several point mutations, E345R, E430G and other variants in the IgG1 CH3 domain have been identified that cause immunoglobulins to form hexamer structures when bound to antigen (16). These hexamer structures can strongly enhance CDC activity by 2 to 3 orders of magnitude, inducing CDC at a level comparable to native IgM.

To evaluate these IgG1 variants, we introduced mutations into the CD7-specific benchmark antibody RFT2 (10,17) and assessed them in the CDC assay on CCRF-CEM cells (herein referred to as CEM cells, available from ATCC as ATCC® CCL-119$^{TT}$), a T-ALL cell line expressing CD7 using human serum as a source of complement. We found that the wild-type IgG1 version of RFT2 antibody has very limited or no killing activity on CEM cells whilst three tested IgG1 variants of the RFT2 antibody mediated potent killing of CEM cells (FIG. 1). Among them, RFT2 E345R antibody had the most potent killing activity with almost 100% maximum killing and $EC_{50}$ below 1 nM.

The classical pathway of CDC would be expected to be the main MOA for our lead antibody. In addition, ADCP mediated by macrophages and trogocytosis mediated by neutrophils would be evaluated. We decided that the anti-CD7 antibodies should bind to CD7 to initiate cell depletion, but they should not activate the cells. Cytokine release using human whole blood was also assessed for the lead antibody.

Methods and Materials a) CDC Assay

CCRF-CEM cells (referred to as CEM cells, ATCC' CCL-119) or other T-ALL cells were suspended to $8.75\times10^4$ cells/ml in the assay media (RPM11640, 10% hiFBS). Cell suspension was plated out at 20 µl/well according to the plate map. Serial dilutions of antibodies were added at 10 pfl/well according to the plate map. The human complement serum (Sigma, S1764) was reconstituted in 1 ml of ice cold water. The reconstituted serum was diluted to 1 to 3 in media and the 10 µl of diluted serum was added to each well of the plate. The plate was incubated at 37° C. and 5% C02 for 2 hours, equilibrated to room temperature for 15 mins, and then added with 40 µl of reconstituted CellTiter-Glo® (Promega) per well. The plate was covered with an optical plate seal, agitated for 2 mins at 300 rpm on a plate shaker to ensure all the cells were lysed, and then read on the Envision plate reader using the CellTiter-Glo® 384 protocol. The luminescent signal generated from the mixtures is proportional to the amount of ATP present. The percentage of maximum killing was calculated from triplicate quadruplicate samples using the following equation:

$$\%\text{ of maximum killing} = 100 - \left(\frac{\text{Assay signal value} - \text{Assay } signal_{mediua+complement}}{\text{Assay } signal_{cells+complement} - \text{Assay } signal_{mediua+complement}}\right)\times 100$$

b) ADCP Assay

Primary human macrophages were differentiated from monocytes seeded at 2×10' cells/well on 12-well plates by culturing for 7-10 days in RPMI+10% FBS supplemented with 100 ng/mL M-CSF (Peprotech) to generate monocyte-derived macrophages (MDMs). The macrophages were labelled with 2 µM CellTrace™ Violet (CTV; ThermoFisher Scientific) the day before the assay and rested overnight in RPMI supplemented with 10% Ultra-Low IgG FBS (Life Technologies) and 50 ng/mL M-CSF. The CEM cell line was maintained in culture in RPMI+10% FBS. For experiments using patient-derived T-ALL xenograft cells (PDTALL-39, -46, -47 and -Ad2R), stocks were recovered from frozen on the day of the assay. Normal primary T cells were freshly isolated from macrophage donor-matched peripheral blood mononuclear cells (PBMCs) by negative selection (using the Stemcell Technologies Human T cell Isolation Kit) immediately prior to the assay. Target cells (CEM, T-ALL or normal T cells) were labelled with 2 M CellTrace™ CFSE (ThermoFisher Scientific) and resuspended in PBS.

Serial dilutions of anti-CD7 or control antibodies were prepared at 2× final concentration in 25 µL PBS. 25 µL of CFSE-labelled target cells at $4\times10^6$ cells/mL (i.e. $1\times10^5$ cells) were pre-opsonised with the different dilutions of anti-CD7 antibodies in PBS by incubating on ice for 0.5-1 hour. As controls, cells were mock-opsonised (no antibody) or opsonised with dilutions of appropriate human IgG1 isotype control antibody. The cells were then washed once with excess assay medium comprising RPMI+10% Ultra-Low IgG FBS (to eliminate unbound antibody) and resuspended to $5\times10^4$ cells/mL in the assay medium. The medium was aspirated from the 12-well plates of CTV-labelled macrophages and 800 µL of the target cell suspension added to duplicate wells (to give $4\times10^4$ target cells/well and an effector: target ratio of 5:1) and incubated for 2.5 hours at 37° C. 5% $CO_2$ to enable target cell phagocytosis.

Non-adherent cells were collected and combined with the adherent macrophages, which were detached using Accutase (Life Technologies) and gentle cell scraping. The cells were then washed with PBS and stained with LIVE/DEAD fixable near infra-red (IR) dead cell stain (30 min at 4° C.; ThermoFisher Scientific) before washing again with PBS and fixing for 20 min at room temp in 4% paraformaldehyde (PFA; Affymetrix). Cells were resuspended in PBS containing 2 mM EDTA for analysis. Compensation was performed using single-labelled cells and live/dead near-IR labelled ArC™ amine-reactive beads (Molecular Probes). Flow cytometry acquisition was performed on the Attune NXT Flow Cytometer using 405, 488 and 637 lasers (ThermoFisher Scientific) and the data analysed with FlowJo v10.0.8r1 (FlowJo LLC). Percent phagocytosis was calculated from duplicate samples using the following equation:

$$\%\text{ of phagocytosis} = \frac{\%\text{ of cells co-labelled with } CTV \text{ and } CFSE}{\%\text{ of cells labelled with CFSE}}$$

c) Human Whole Blood Assay

With respect to the use of an anti-coagulant, it was decided not to use standard heparin but hirudin at a low concentration that led to successful results in the Cynomolgus study. Plasma extracted from hirudin-treated blood mediated CDC of CEM cells in vitro, whereas plasma from heparinised blood did not (data not shown). The final concentrations of 1741G09 E430G, the isotype controls, Rituximab and Ofatumumab were used as in the study.

Whole-blood cultures of three blood donors were set up in TruCulture® tubes (Myriad RBM, USA) and performed. TruCulture® (TC) tubes were filled with freshly produced media±antibodies/controls. Tubes were stored at −20° C. (<7 days) and used after thawing and thorough mixing (adjusted to room temperature). Within 60 min after phlebotomy the freshly drawn blood containing hirudin as anti-coagulants was transferred to the TruCulture® tubes and incubated for 20 h at 37° C. in a block thermostat.

At the end of the culture period, immune cells were analysed by flow cytometry. For an exact enumeration of cell counts, a defined volume of cultured whole blood was added to BD TruCount® tubes (CE, IDV). To determine the immune status 7-colour immunophenotyping panel were used (T cells $CD45^+CD3^+$; NK cells $CD45^+CD3^-CD16^+$ $CD56^+$; B cells $CD45^+CD3^-CD19^+$; monocytes $CD14^+$). The cells were stained with an applied no wash protocol from the antibody manufacturer (Miltenyi Biotec; 7-Colour Immunophenotyping Kit; #130-098-456). Briefly, at the end of the incubation period, TruCulture®-tubes were centrifuged, 2 ml of the supernatant consisting of TruCulture® medium and plasma were removed, and blood cells were thoroughly resuspended. 50 µl of the resuspended immune cells were transferred into TruCount® tubes (containing a defined number of beads), detector antibodies were added and incubated for 10 min at 2-8° C. Haemolysis solution was added to eliminate erythrocytes (20 min at RT). The cells were stored at 2-8° C. before until analysis by flow cytometry. Samples were acquired on a FACSMelody™ flow cytometer (BD Bioscience).

Data were analysed by FlowJo (version 10.4.1; FlowJo, LLC). Cells per volume have been calculated according to the following equation:

$$c(\text{cells}) = \frac{\text{cell count}}{V(\text{cells})} = \frac{\text{cell count}}{\text{bead count}} \cdot c(\text{beads}) = \frac{\text{cell count}}{\text{bead count}} \cdot \frac{\text{beads per tube}}{V(\text{blood})}$$

d) Antigen Capture ELISA for Quantitation of Serum 1741G09

The 96-well high-binding plate was coated overnight at 4° C. with 50 µl recombinant soluble human CD7 protein (Sino Biologicals, 11028-H08H) at 2 µg/ml diluted in PBS. The plate was washed 3×300 µl/well with PBS+0.1% Tween using the plate (washing buffer) washer, blocked with 200 µl PBS+1% BSA per well for at least 1 hr at room temperature, and then washed again. Serially diluted standards, samples and controls were added to the plate at 50 pfl/well. After incubation for 1 hr at room temperature shaking at 300 rpm, the plate was washed 5×300 µl/well with washing buffer. The HRP conjugated anti-human IgG diluted at 1 in 30,000 in PBS+1% BSA was added at 50 µl/well. After incubation for 1 hr at room temperature, shaking at 300 rpm, the plate was washed 5×300 µl/well with washing buffer. The plate was added with TMB substrate at 50 µl/well, incubated for 30 min at room temperature protected from light, and then 50 µl/well of stop solution added. The optical density was determined within 5 min using a microplate reader set to 450 nm and correct at 640 nm. The data was imported to Softmax Pro and regressed using a 4PL curve fit with a weighting factor 1/y.

e) Cytokine Release Assay

High binding plates were coated with 1741G09 E430G and other control antibodies at serial concentrations, and incubated at room temperature overnight, with lids off to air-dry. Plates were washed with PBS, blocked with cell culture medium by standing for 30 mins, then aspirated just before the addition of cells.

Warm medium added drop-wise to vials with cryopreserved human PBMCs and then cells were pre-incubated at high density (0.5-1×10' cells/ml) at 37° C. 5% $CO_2$ for 24 hours. Following pre-incubation, PBMCs were seeded into 96-well polypropylene plates with 240 µl/well of culture medium (RPMI 1640, 10% FBS, 1% penicillin/streptomycin, 2 mM L-glutamine) and then incubated at 37° C. 5% $CO_2$ for 1 hour. PBMC cell cultures (200 µl/well, 2×10' cells/well) were transferred to the immobilized test agents in the pre-prepared plates and incubated at 37° C. 5% $CO_2$ for 48 hours. Plates were centrifuged at 200 g for 10 mins, after which cell culture supernatants were collected and stored at −80° C. until needed for analysis.

Luminex assessment of cytokine levels in the cell culture supernatants was performed per the manufacture's protocol. Levels of induction of each cytokine were interpolated from a standard curve, using a 5-point non-linear regression analysis. The interpolated data were then normalized to the unstimulated control.

f) Transient Protein Expression

Transient protein expression was carried out. Cultures were harvested day 12 post transfection and clarified harvests transferred to the purification team.

g) Stable Pool Protein Expression

Stable pool protein expression was carried out.

Discovery a) Lead Generation

Figure 2:
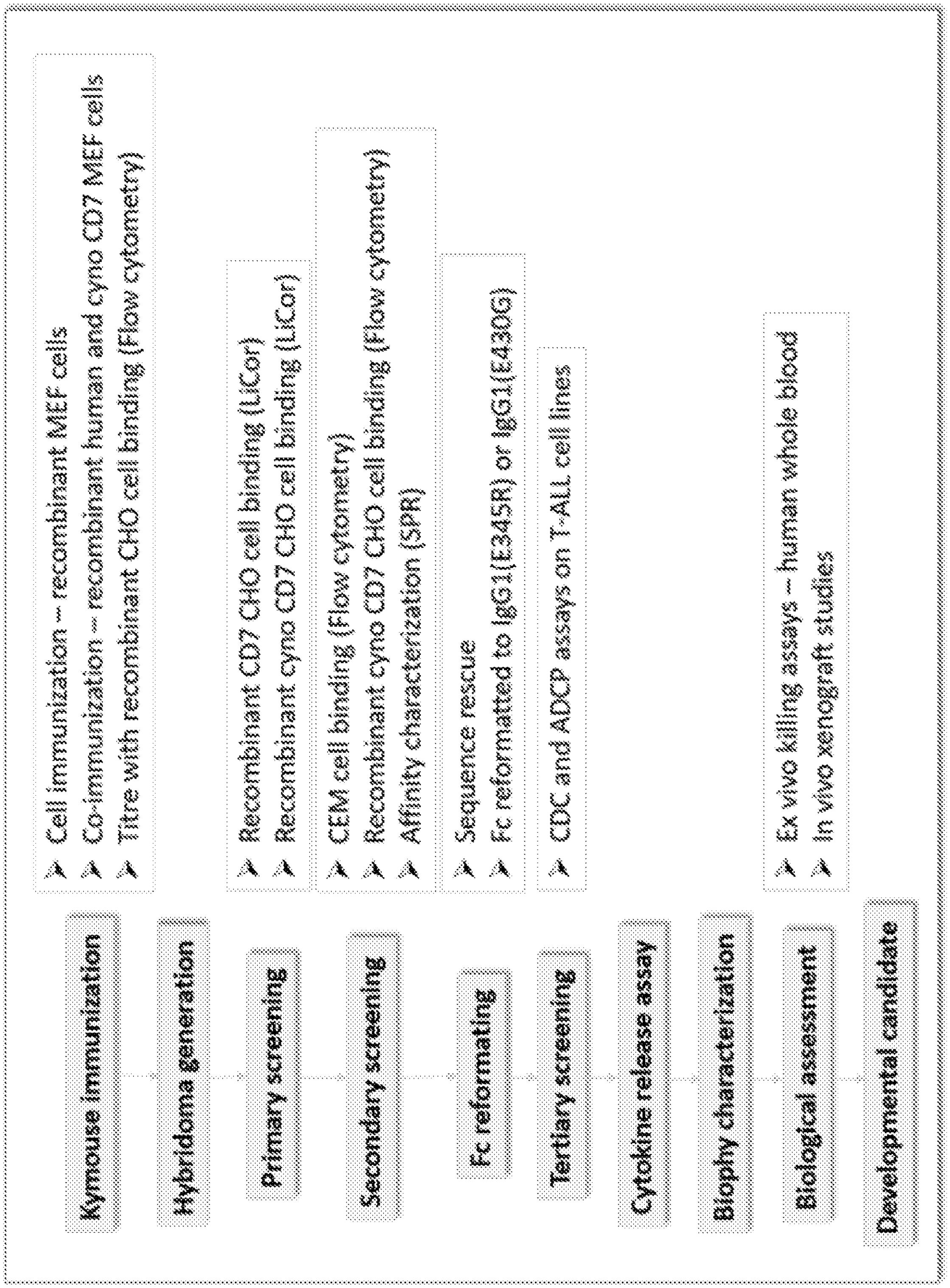
FIG. 2: Flow chart of antibody discovery

The Discovery effort for the anti-CD7 program consisted of immunizations, hybridoma generation, antibody screening, biological assessment of antibody potency, and biophysical characterization as shown in FIG. 2.

Antibodies with cross-reactivity to human and cynomolgus monkey CD7 antigens are required for assessment of the drug toxicology. Human and cynomolgus CD7 proteins only share 86% identity. To ensure this cross-reactivity, Kymice (26) were co-immunized with human and cynomolgus antigens. Titres were examined by flow cytometry analysis in which the extent of binding of polyclonal sera to human and cynomolgus CD7-expressing CHO cells was quantitated. Mice with binding titres detectable when serum was diluted by more than $10^4$ dilutions were used for hybridoma generation. There were four selection criteria for the hits from primary, secondary and tertiary in vitro screening: (i) high levels of binding to human CD7, (ii) specificity for both human and cynomolgus CD7, (iii) potent T-ALL cell depletion and (iv) an inability to cause cytokine release from T-cells.

Figure 3:
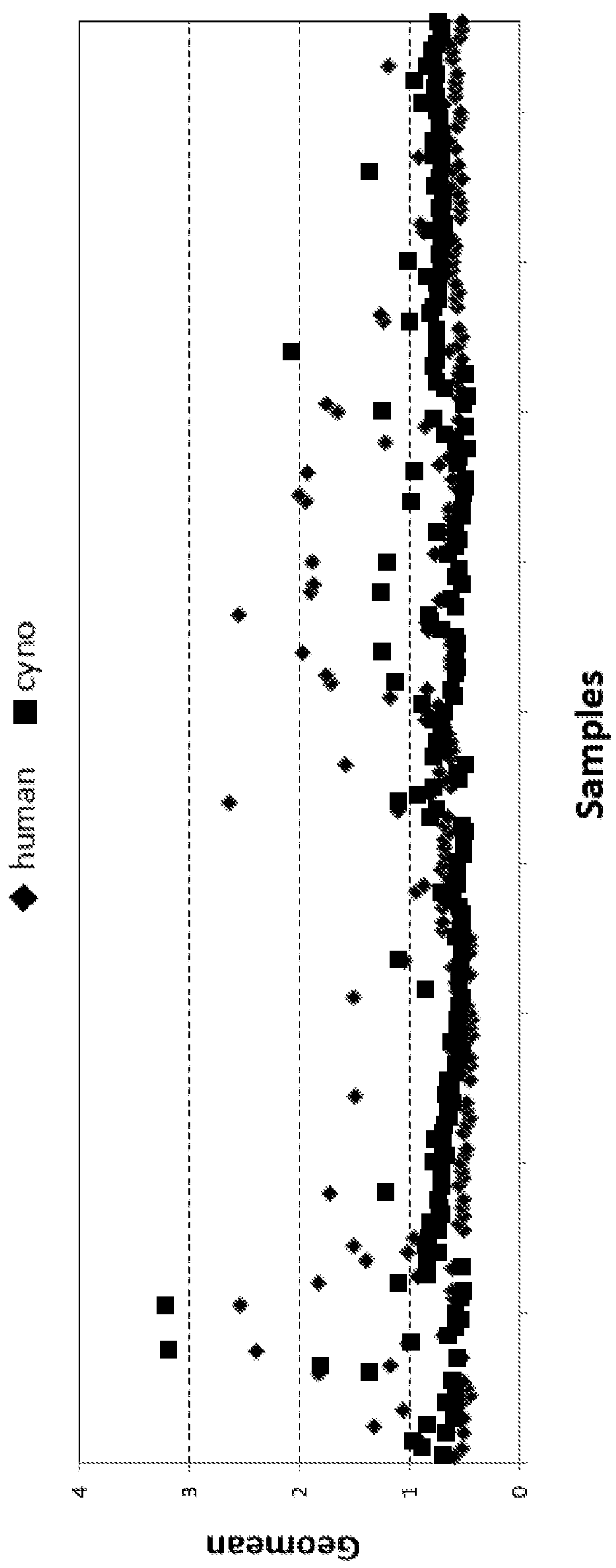
FIG. 3: Secondary screening of antibodies binding to CEM cells and recombinant cynomolgus CD7 CHO cells. Supernatant from hybridoma clones was collected for screening using flow cytometry for detecting the binding to CD7 expressed in CEM cells or recombinant CHO cells. The binding was represented by geomean.

The hybridoma supernatant was used for primary and secondary screenings to identify the binders. The primary screening consisted of high throughput LiCOR-based cell binding assays to include all the potential cross-reactive binders. The secondary screening using flow cytometry was used to confirm the cross-reactivity. The outcomes are shown in FIG. 3. The human and cynomolgus CD7 binding to the CEM cells and recombinant cynomolgus CD7 CHO cells was quantitated by geometric mean fluorescence intensity (geomean) using flow cytometry. CEM cells are a human T-ALL cell line expressing endogenous CD7.

Figure 4:
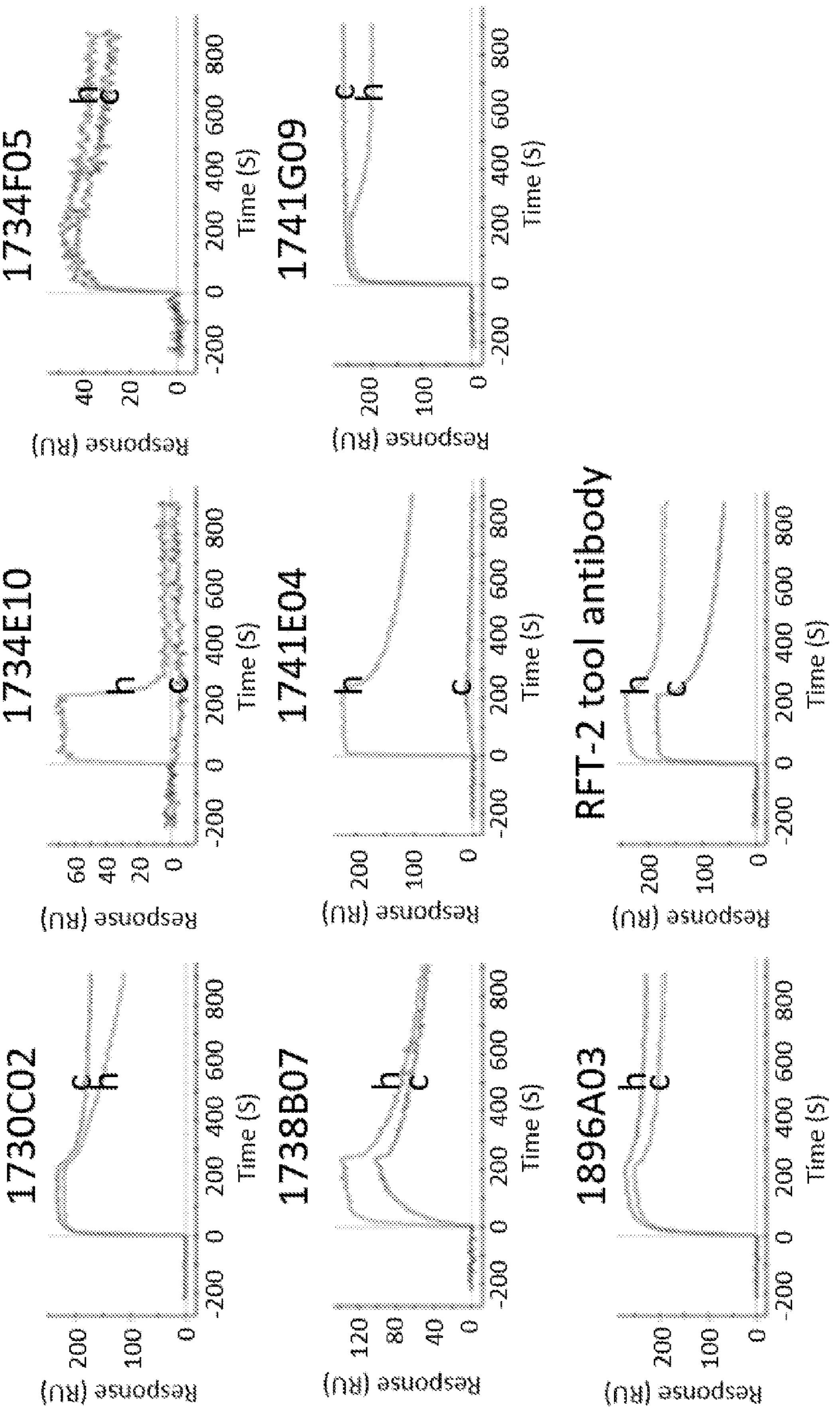
FIG. 4: Characterization of mAb binding to human and cynomolgus CD7 proteins. The binding was measured by SPR. Single concentration sensorgrams of the captured mAbs interacting with Human (h) or Cynomolgus (c) CD7 proteins as indicated.

Seven hits showing strong and cross-reactive binding to human and cynomolgus CD7 were further examined for their relative binding to both antigens by measurement of SPR. Five leads (1730C2, 1734F05, 1738B07, 1741G09, 1896A03) were confirmed to show similar binding to CD7 from both species as shown in FIG. 4 and Table 1. The data were compared to the benchmark RFT2 IgG1, a chimeric antibody with mouse variable region and human constant region.

Figure 5:
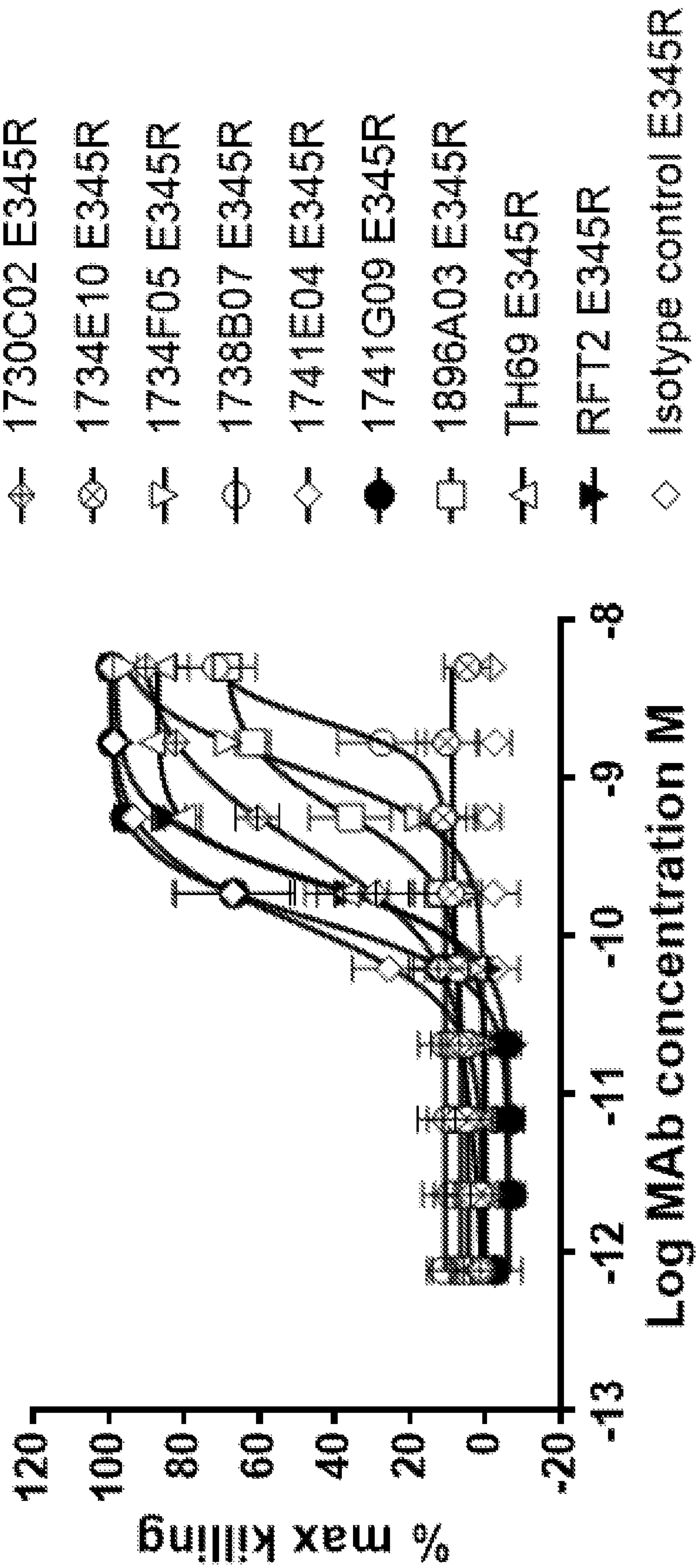
FIG. 5: Tertiary screening of mAbs in the CDC assay. The antibodies were run in duplicate for each concentration point and in 3 independent assays. The areas under the curves were used to compare the antibody potencies. 1741E04 E345R and 1741G09 E345R showed the highest potency for CEM cell killing, followed by RFT2 E345R, TH69 E345R, 1730C02 E345R, 1896A03 E345R, 1734F05 E345R, 1738B07 E345R, whereas the isotype control (IgG1 E345R) and 1734E10 E345R did not show significant efficacy in this assay. Data was analyzed using GraphPad Prism v7.02, where log antibody concentration (M) was plotted against % killing (mean±standard deviation) and a 4-parameter logistic curve fit was applied to data, allowing calculation of $EC_{50}$ values. The statistical comparison of the antibodies is shown in Table 6. TH69 is discussed in Br J Haematol. 1996 November; 95(2):327-38, "Therapy with CD7 monoclonal antibody TH-69 is highly effective for xenografted human T-cell ALL", Baum W et al.

The DNA sequences of hits were retrieved from hybridoma clones and the constant region was reformatted to human IgG1 with the E345R variant. The E345R variant in the IgG1 CH3 region has been shown to enhance complement-dependent cytotoxicity (CDC) activity. As shown in FIG. 1, RFT2 IgG1 E345R but not RFT2 IgG1 could potently kills CEM cells in the CDC assays (FIG. 1). The IgG1 E345R-reformatted antibodies were expressed and tested on the CDC assay using human serum as a source of complement and CEM cells as target cells. Two leads, 1741E04 E345R and 1741G09 E345R were shown to have 100% maximum killing and potency below 200 pM in FIG. 5 and Table 2. The former only binds to human antigen, but the latter binds to both human and cynomolgus antigens. These leads were also generated with wild-type IgG1 and tested in the CDC assay. No significant killing was observed even at a concentration above 10 nM (data not shown).

Figure 6:
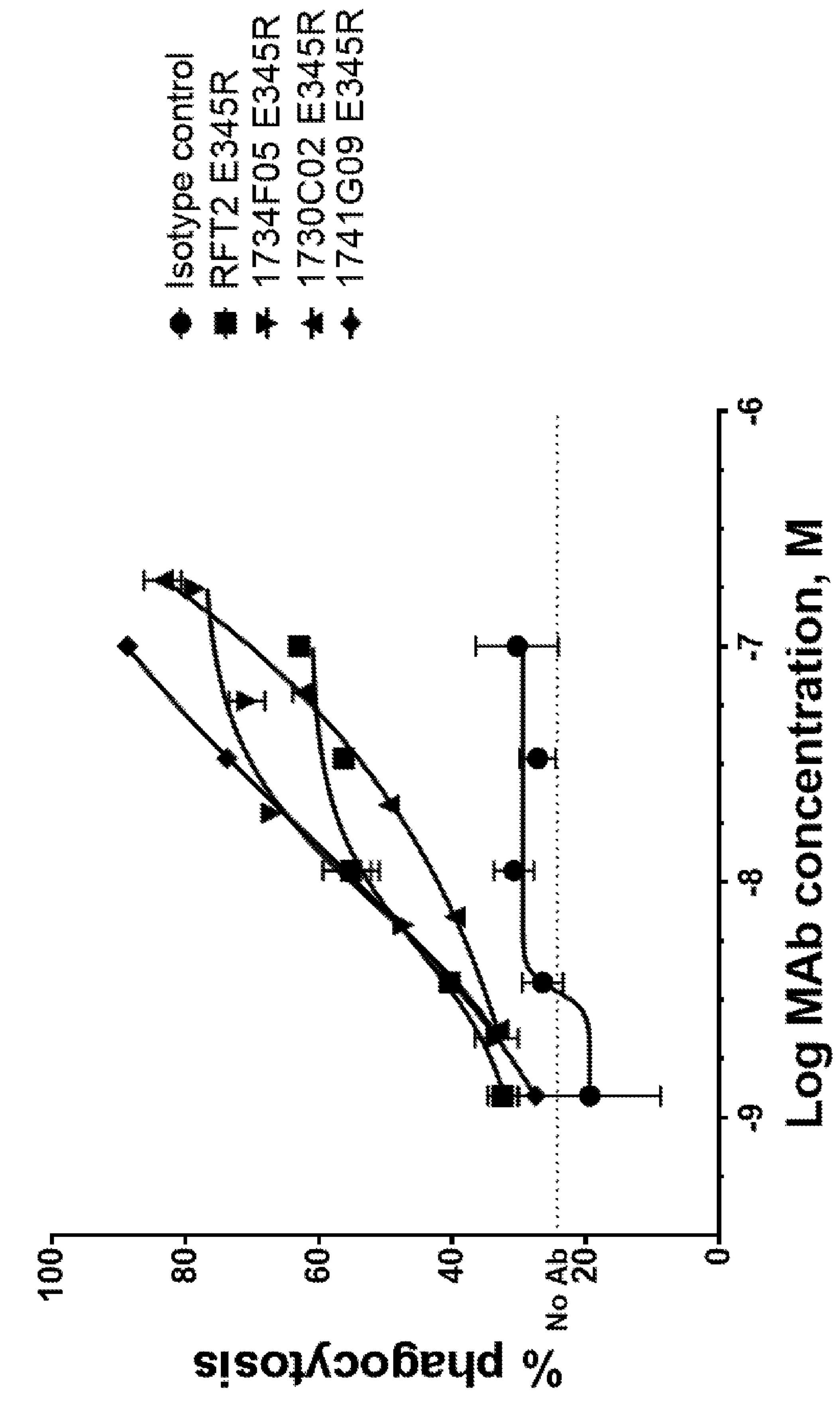
FIG. 6: Tertiary screening of mAbs in the ADCP assay. ADCP by CellTrace™ Violet (CTV)-labelled monocyte-derived macrophages of CFSE-labelled CEM cells pre-opsonised on ice with different concentrations of E345R lead antibodies (1730C02, 1734F05, 1741G09) or benchmark anti-CD7 antibody (RFT2), compared with an IgG1 isotype control. CTV-labelled macrophages were co-cultured with CFSE-labelled CEM cells for 2.5 hrs. Cells were collected, assessed for viability using a fixable amine-reactive near-infra red and analysed by flow cytometry. Tumour cell phagocytosis was detected by flow cytometry and is expressed as % phagocytosis (% phagocytosis=100 x (% CFSE+/CTV+)/(% CFSE+)). The data shown are the mean±SD of duplicate samples from a representative experiment of two independent repeats.

To assess whether the three leads could mediate phagocytosis by macrophages, they were tested in an ADCP assay using macrophages derived from peripheral blood monocytes as a source of phagocytes and CEM cells as target cells. 1741G09 E345R, the lead showing the best activity in the CDC assay, also showed best activity among these three leads in this assay as shown in FIG. 6.

It is generally believed that the dual staining correlates with the internalisation of target cells into the effector cells (or at least sitting inside a phagocytic cup). In the experiment, images were captured for cells at the end-point of the phagocytosis assay using the Amnis Imagestream (Merck Millipore), and were analysed using software tools that allow the discrimination of internalized from extracellular-bound particles to demonstrate phagocytosis of target cells. Similar techniques have been described elsewhere for this purpose (27). Furthermore, the use of Accutase for cell harvesting by enzymatic detachment at the end-point of the assay would likely disrupt inter-cellular contacts that could be mis-interpreted as phagocytosis (internalization) events.

Figure 7A:
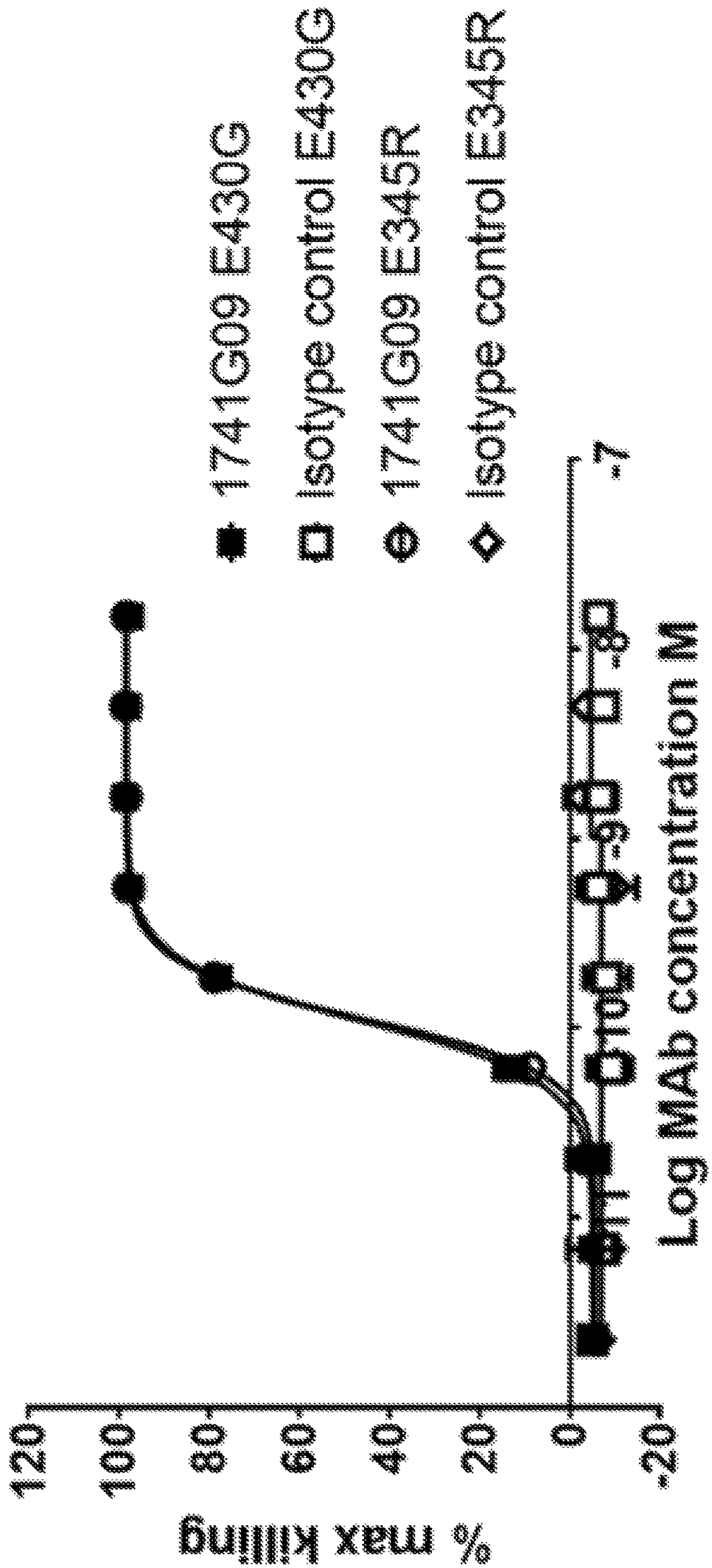
FIG. 7: CDC activity and in vivo pharmacokinetics of 1741G09 E345R and 1741G09 E430G. (A) Two antibodies, 1741G09 E345R and 1741G09 E430G, and their isotype controls were tested in the CDC assay described in the FIG. 6. Both molecules showed similar potent depleting activity (maximum killing and $EC_{50}$) on depletion of CEM cells. Error bars represent standard deviation of 3 replicates for each point. (B) Both antibodies were administrated as a single intravenous dose at 10 mg/kg into NOD SCID gamma (NSG) mice. Serum samples were taken at eight timepoints, with three mice per time point and two timepoints per mouse. The method used to quantify the concentration of antibodies was an antigen capture ELISA. Each experimental run consisted of an antibody calibration curve and two sets of QC samples run in duplicate and placed at the front and back of the plate. Antibody concentrations were calculated using SoftMax Pro7 with the standard curve using a four-parameter logistic and a 1/Y weighting. Pharmacokinetic parameters were calculated using the PKSolver Excel add-in. P value for the difference in half-life is equal to 0.0118 based on the unpaired t test. Data shown are timepoints in triplicate (from three separate mice). Data shown as the mean concentration with the standard deviation. The $t_{1/2}$ for 1741 G09 430G is approximately 7× longer than 1741G09 345R (20.9 hrs vs 136.7 hrs) and the $C_{max}$ is approximately 3× higher for G09 430G than G09 345R (216811 ng/mL vs 75001 ng/mL).
Figure 7B:
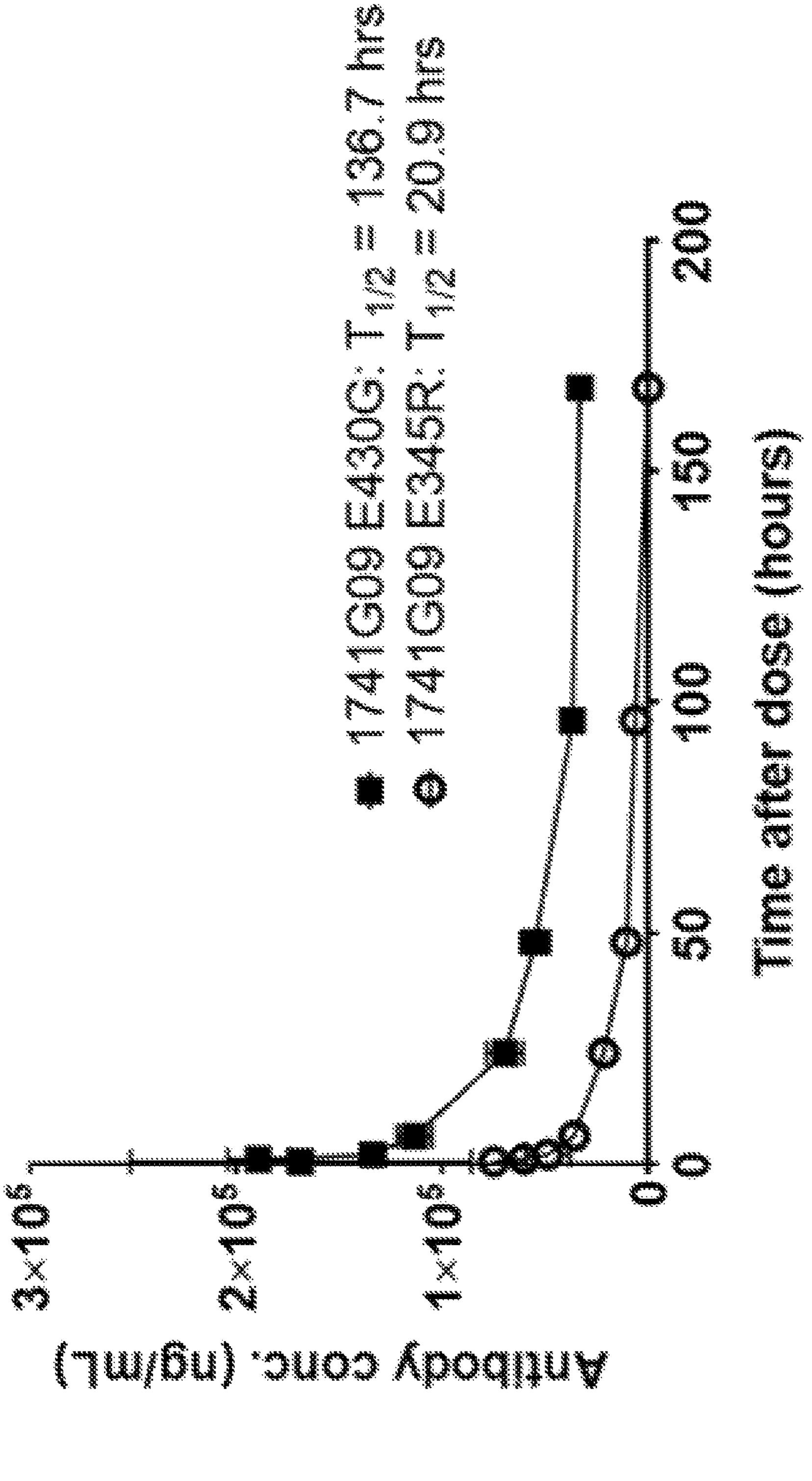
Figure 8A:
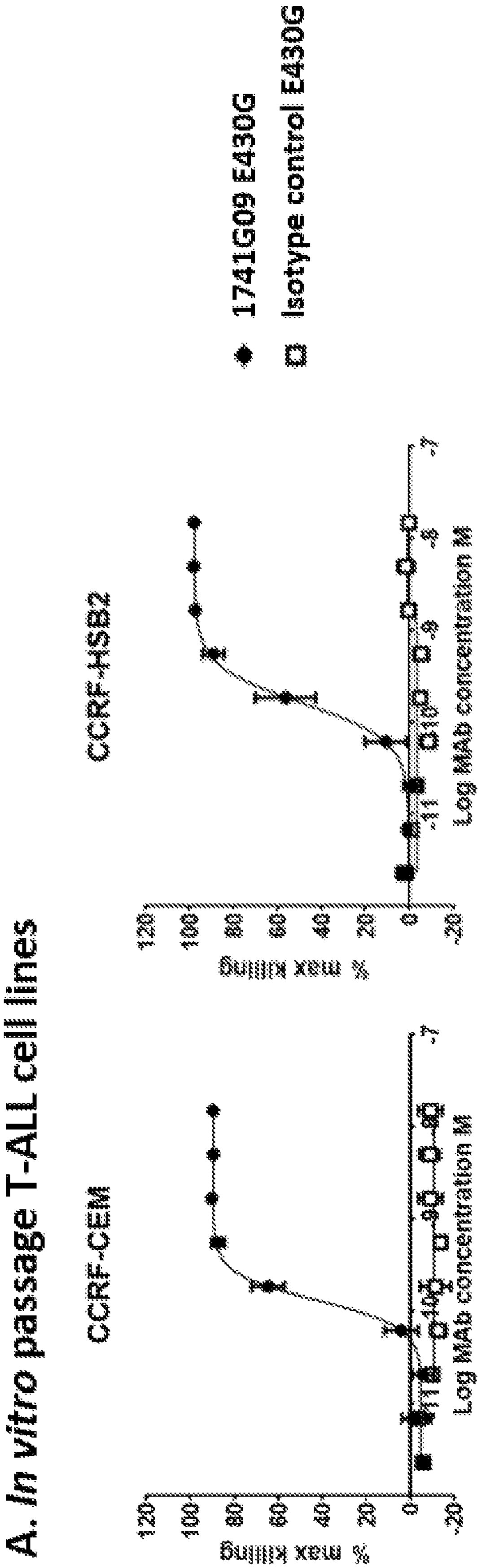
FIG. 8: Potent CDC activity of 1741G09 E430G on non-relapsed and relapsed T-ALL cell lines. T-ALL cells including cell lines (FIG. 8A), patient-derived non-relapsed (FIG. 8B) and patient-derived relapsed (FIG. 8C) were used as target cells and human serum as a complement source. Titrations of 1741G09 E430G as well as an isotype control were added and incubated for 2 hours at 37° C. CellTiter-Glo® was added and luminescence read on an Envision plate reader. Percentage killing is calculated for each antibody based on signal from wells without antibody and with/without cells. Error bars represent standard deviation of 4 replicates for each point. Data was analyzed using GraphPad Prism v7.02, where log antibody concentration (M) was plotted against % killing (mean±standard deviation) and a 4-parameter logistic curve fit was applied to data, allowing calculation of $EC_{50}$ values.
Figure 8B:
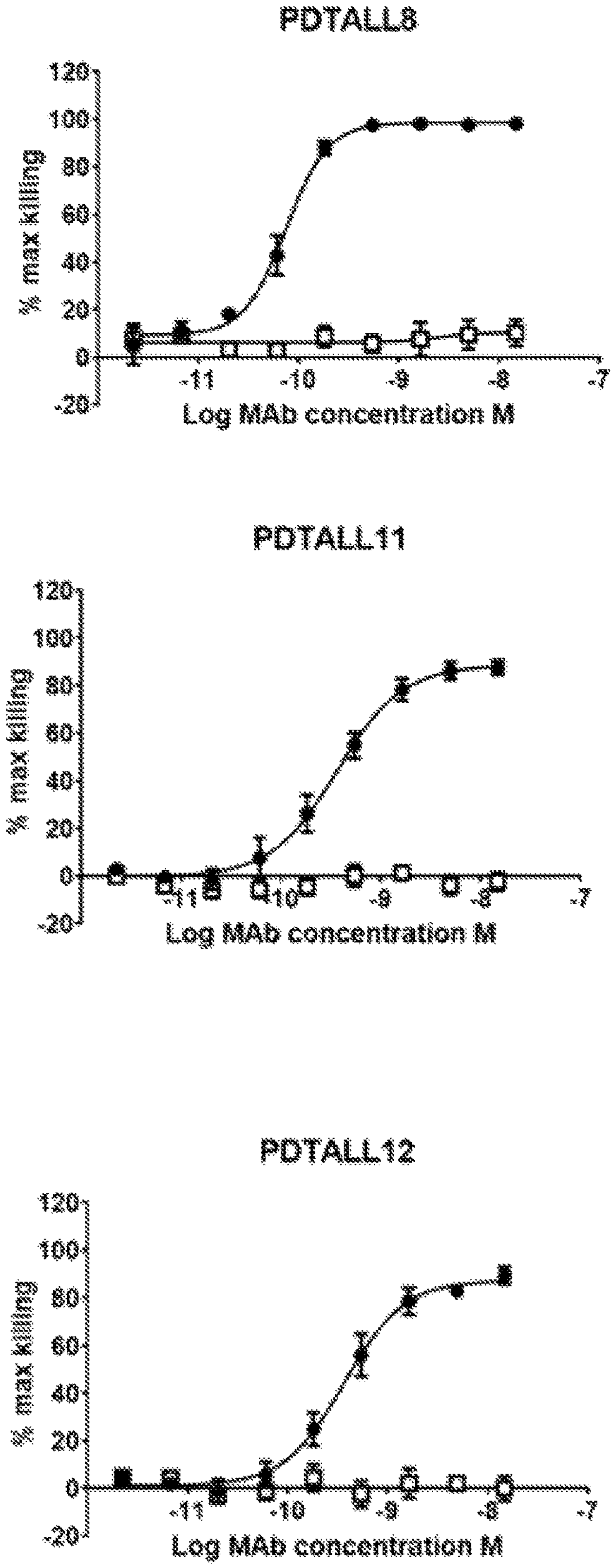
Figure 8B:
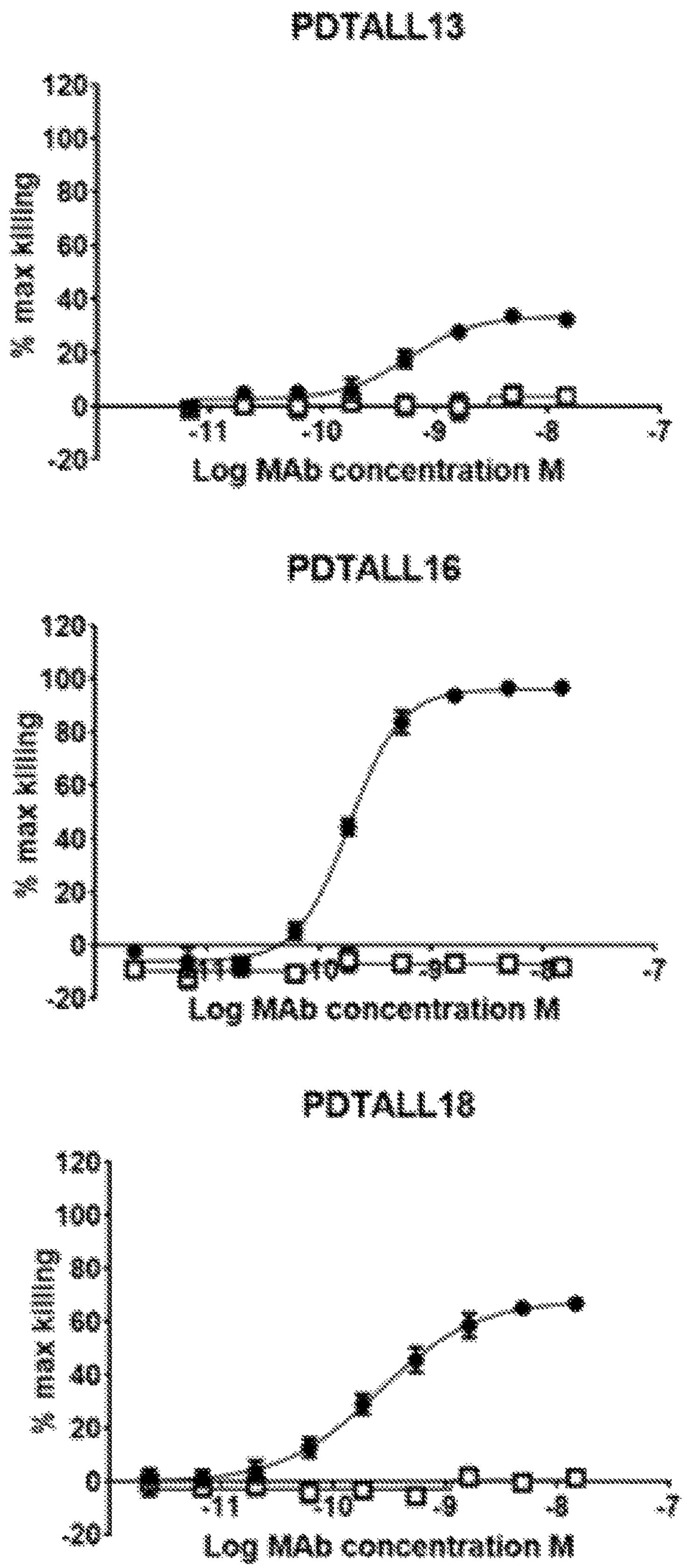
Figure 8C:
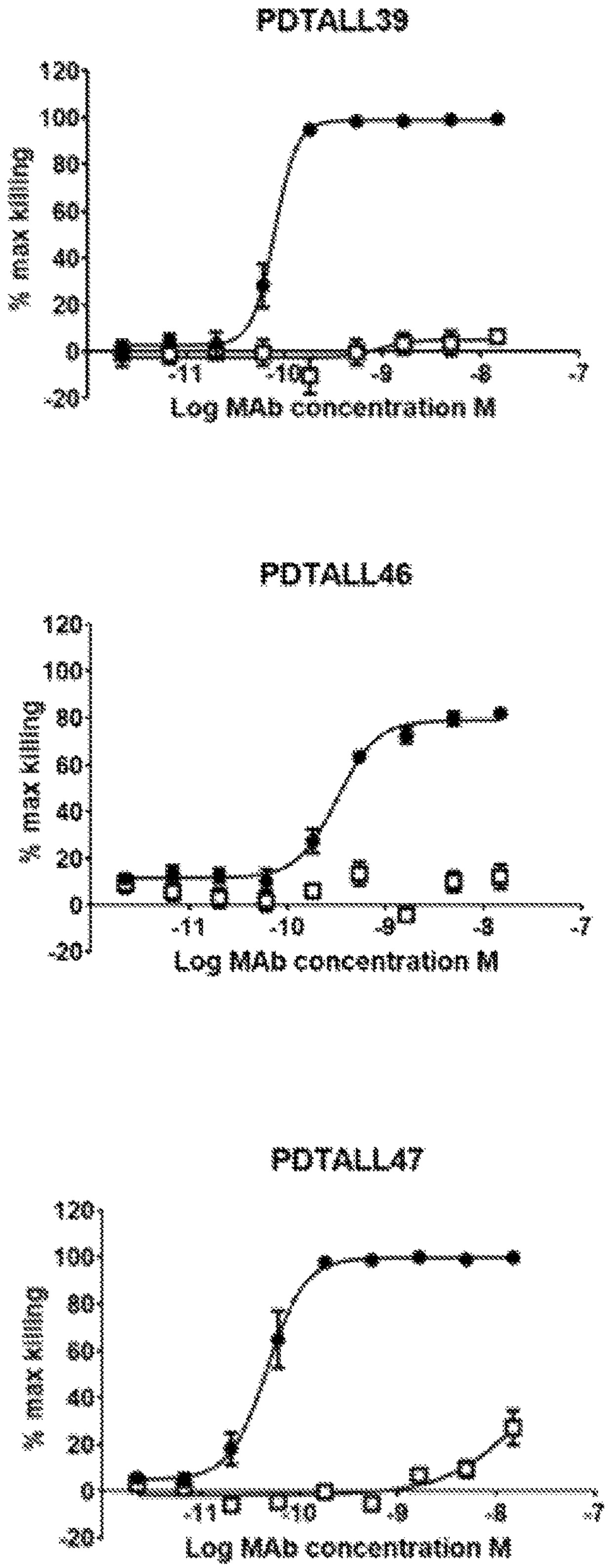
Figure 8C:
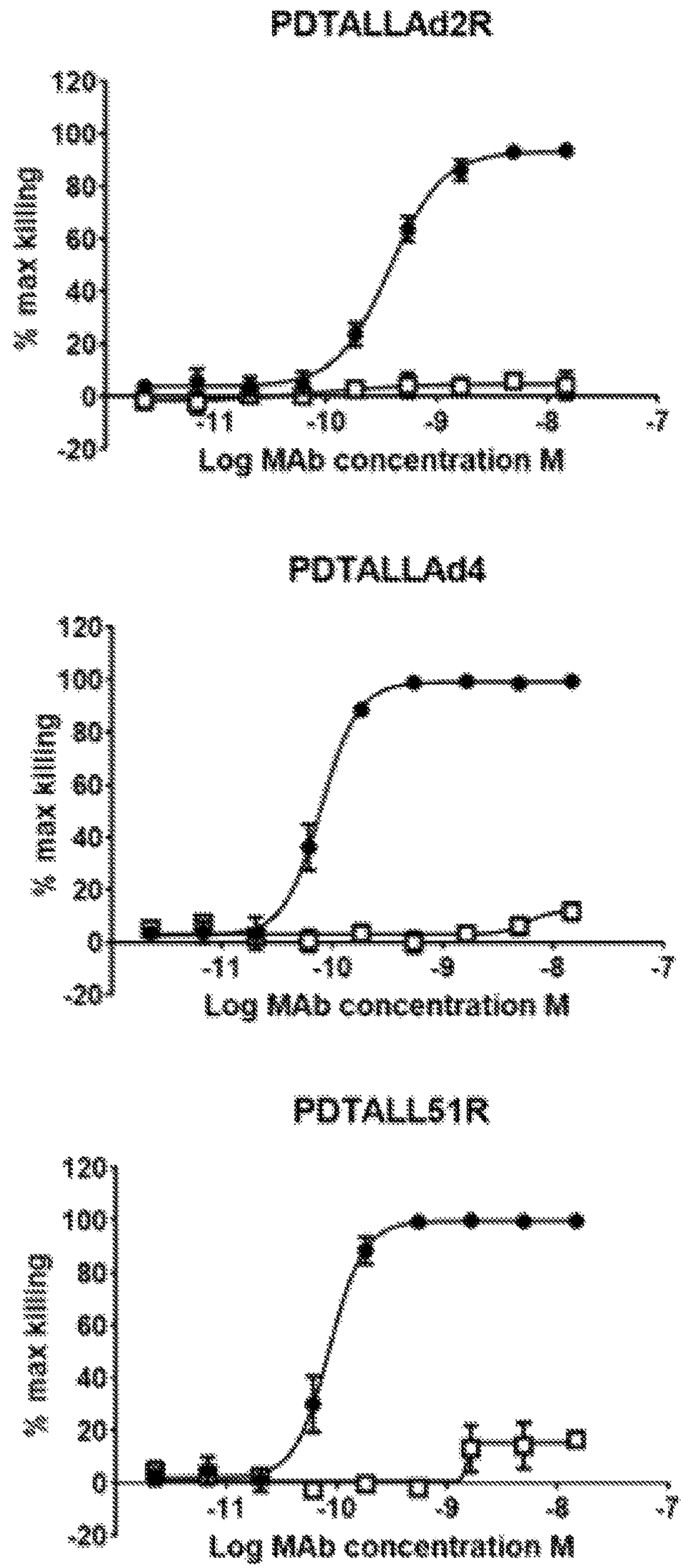

During the progress of our screening, there was another variant, IgG1 E430G that was also reported to enhance the CDC activity (28). The 1741G09 E430G variant has similar killing potency to the 1741G09 E345R variant in our test (FIG. 7. A.). The 1741G09 E430 has a half-life 136.7 hours in NSG mice (FIG. 7. B.), which is within in the normal range of human IgG1 in such mice. However, 1741G09 E345R had a much shorter half-life of only 20.9 hours, potentially because this variant has a higher tendency to aggregate. Based on this observation, we replaced 1741G09 E345R with 1741G09 E430G as a lead molecule and further assessed the CDC and ADCP activities of this molecule.

b) Lead In Vitro Profile

The antibody discovery campaign was based on binding, cell-depletion assays and half-life of molecules identified a lead antibody, 1741G09 E430G. To assess its killing activity on different T-ALL cells, the lead was tested in the CDC assays on 14 different T-ALL cell lines including two commercial in vitro passage cell lines (CEM and HSB2), six in vivo passage non-relapsed cell lines (PDTALL8, PDTALL11, PDTALL12, PDTALL13, PDTALL16 and PDTALL18), and six in vivo passage relapsed cell lines (PDTALL39, PDTALL46, PDTALL47, PDTALL51R, PDTALLAd2R and PDTALLAd4)(29). The clinical and genetic profiles of these cell lines are shown in Table 7. 1741G09 E430G was demonstrated to effectively kill the majority of cell lines (11 cell lines out of 14) (FIG. 8), with a potency around 50-500 pM (Table 3).

Figure 19:
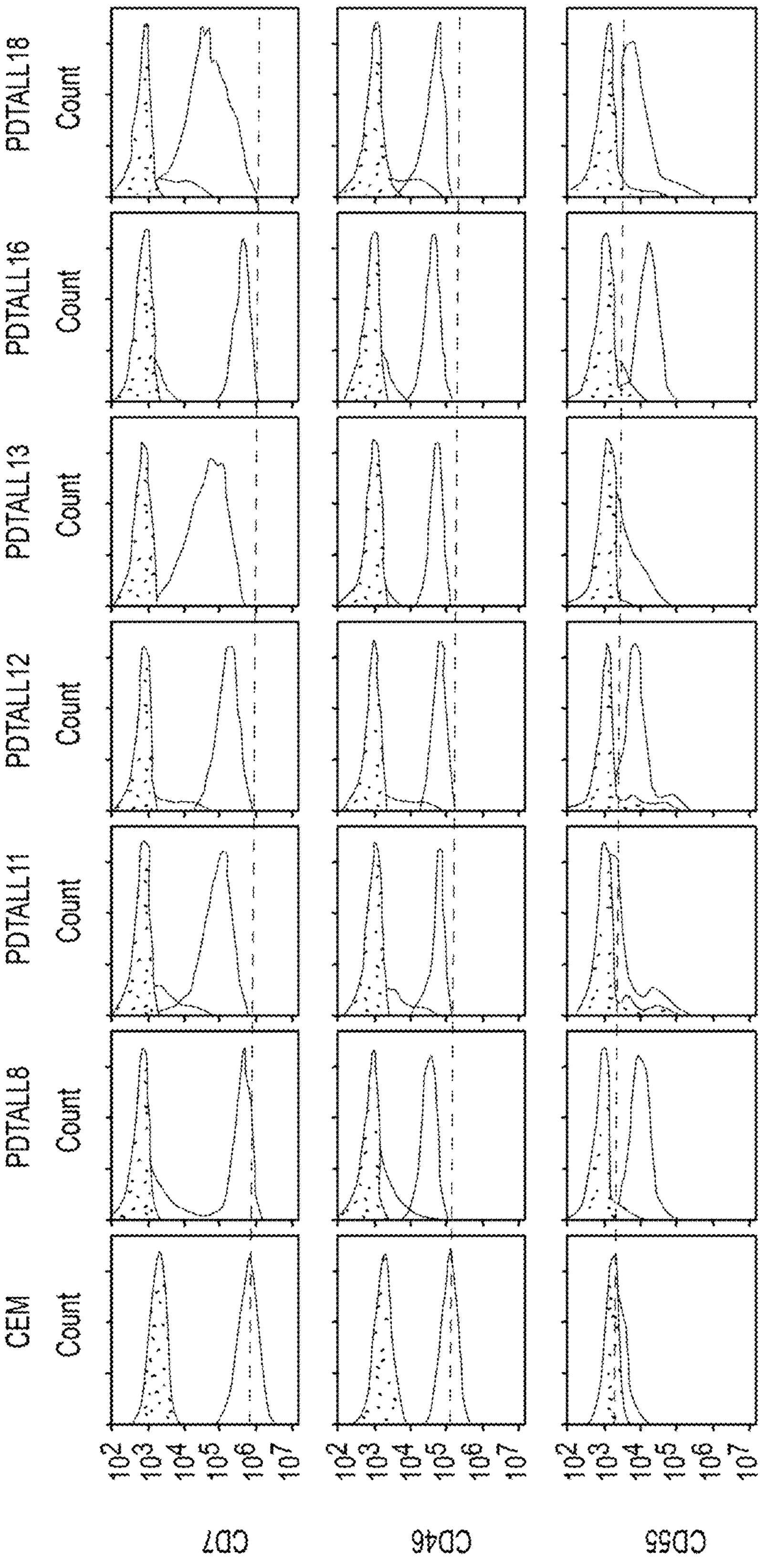
FIG. 19: CD7 and CRP expression profiles of non-relapsed T-ALL cell lines
Figure 19:
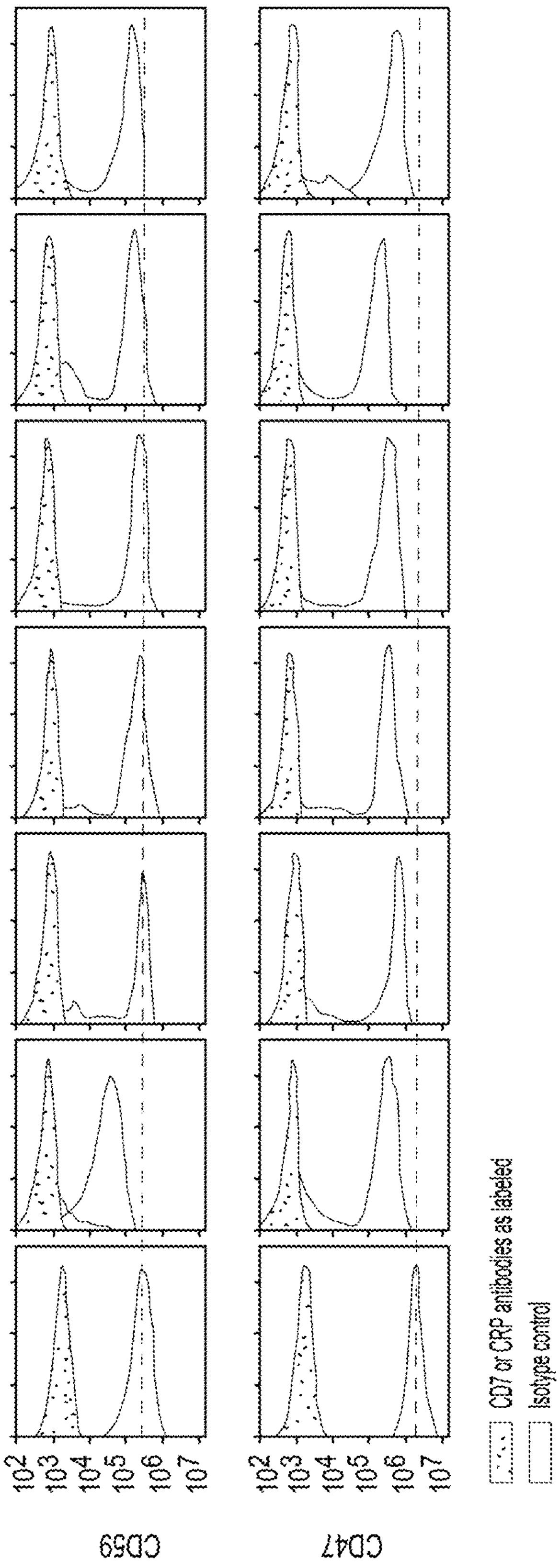
Figure 20:
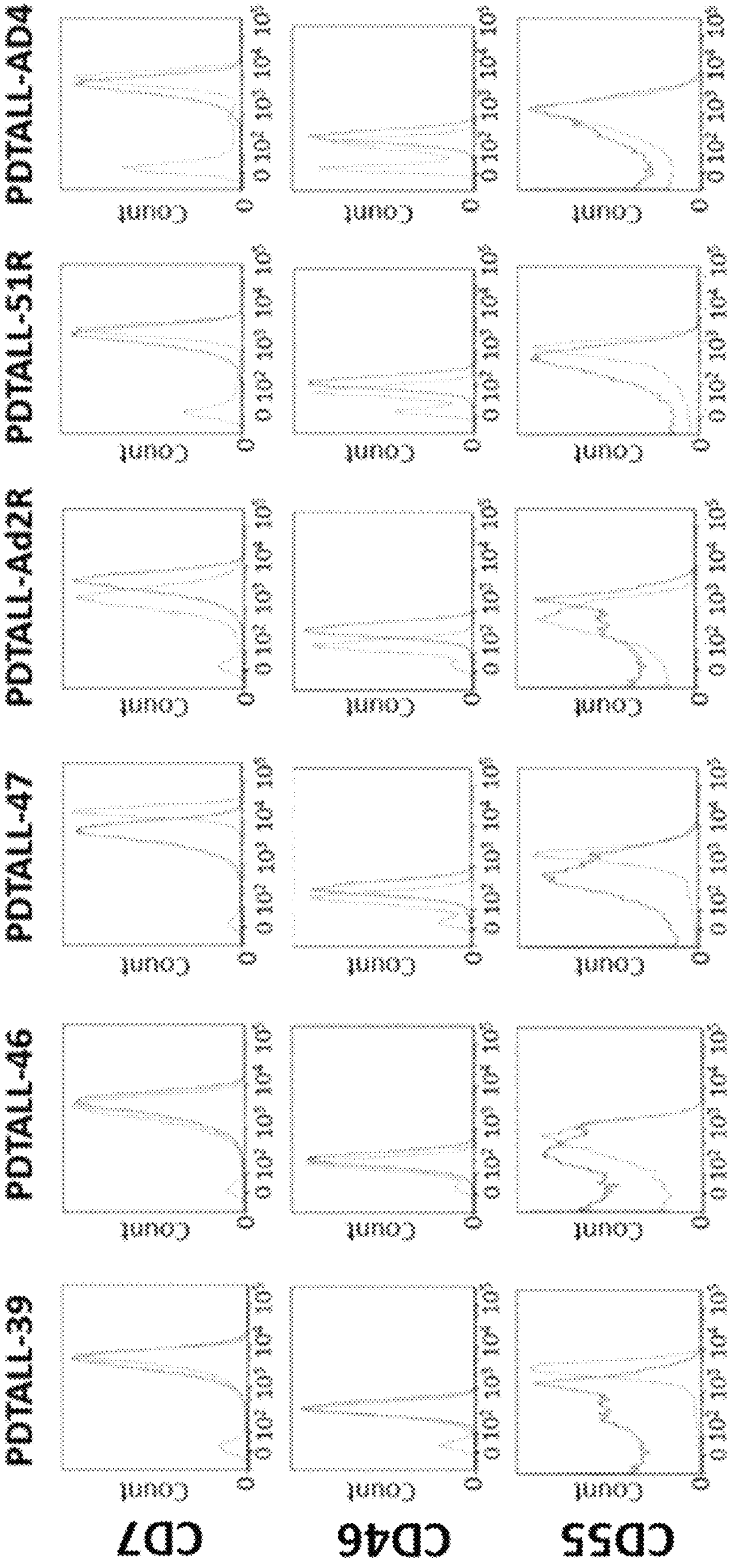
FIG. 20: CD7 and CRP expression profiles of relapsed T-ALL cell lines
Figure 20:
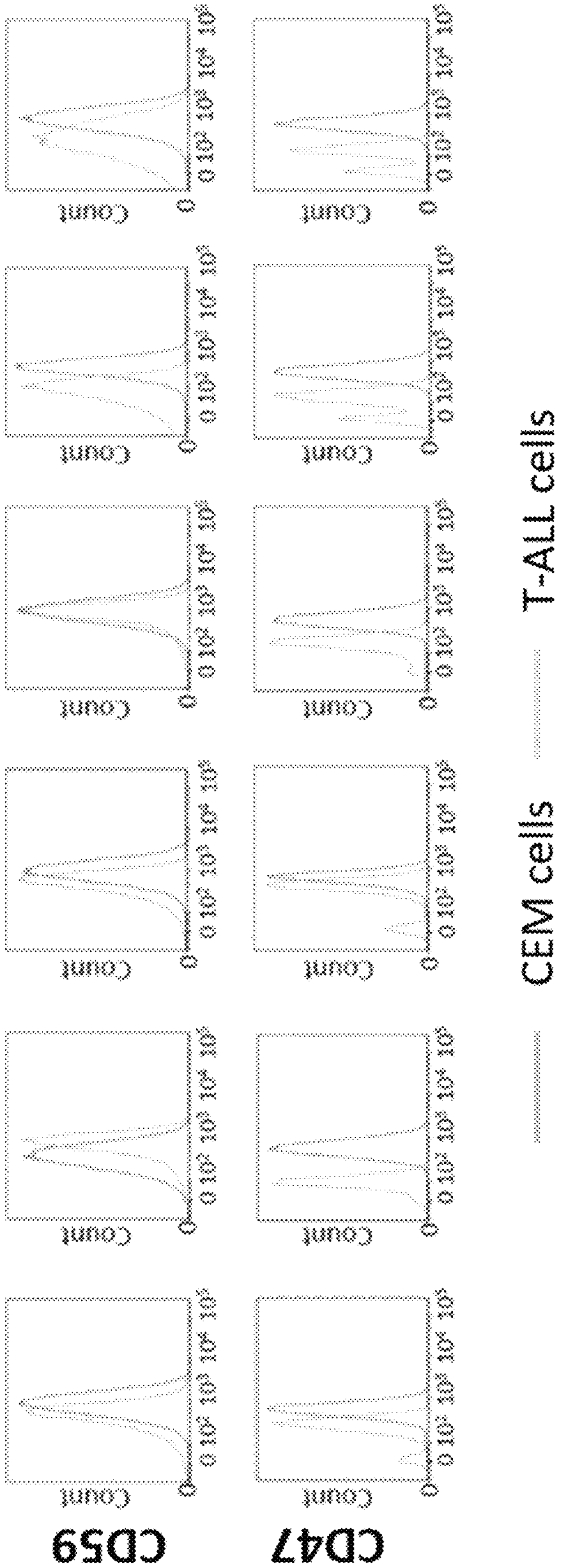

In the assays conducted, the potency and maximum killing were correlated to cell surface CD7 expression (FIGS. 19 and 20). The cell lines could be ranked based on the CD7 expression level on the cell surface as shown in Table 3. Reflecting the expression level, PDTALL47, HSB, PDTALLAd4, PDTALL51R, PDTALL39, PDTALL8, CEM and PDTALL16 with the high or intermediate CD7 expression levels (relatively to CEM cells) had highest maximum killing, close to 100%, and $EC_{50}$ values from 50 pM to 200 pM; PDATLLAd2R, PDATALL12 and PDTALL11 with the intermediate to low expression levels had maximum killing close to 90% and $EC_{50}$ below 400 pM; PDTALL13 and PDTALL18 with much low expression levels had maximum killing below 70% and $EC_{50}$ below 600 pM (Table 3). In consideration of the CD7 expression level, PDTALL46 has a higher level than PDTALLAd2R. Both cell lines had similar $EC_{50}$ close to 350 pM, but PDTALL46 had lower maximum killing than PDTALLAd2R (78% vs 93%) possibly because the former had higher expression levels of complement-regulatory proteins (CRPs: CD46, CD52 and CD59) than the latter (FIG. 20). CRPs have been reported to function as antagonists against complement activity on cell surface. In summary, these results suggest that the antibody potency of CDC activity is majorly dependent on the target antigen expression on the cell surface and can be regulated by CRPs.

Figure 9:
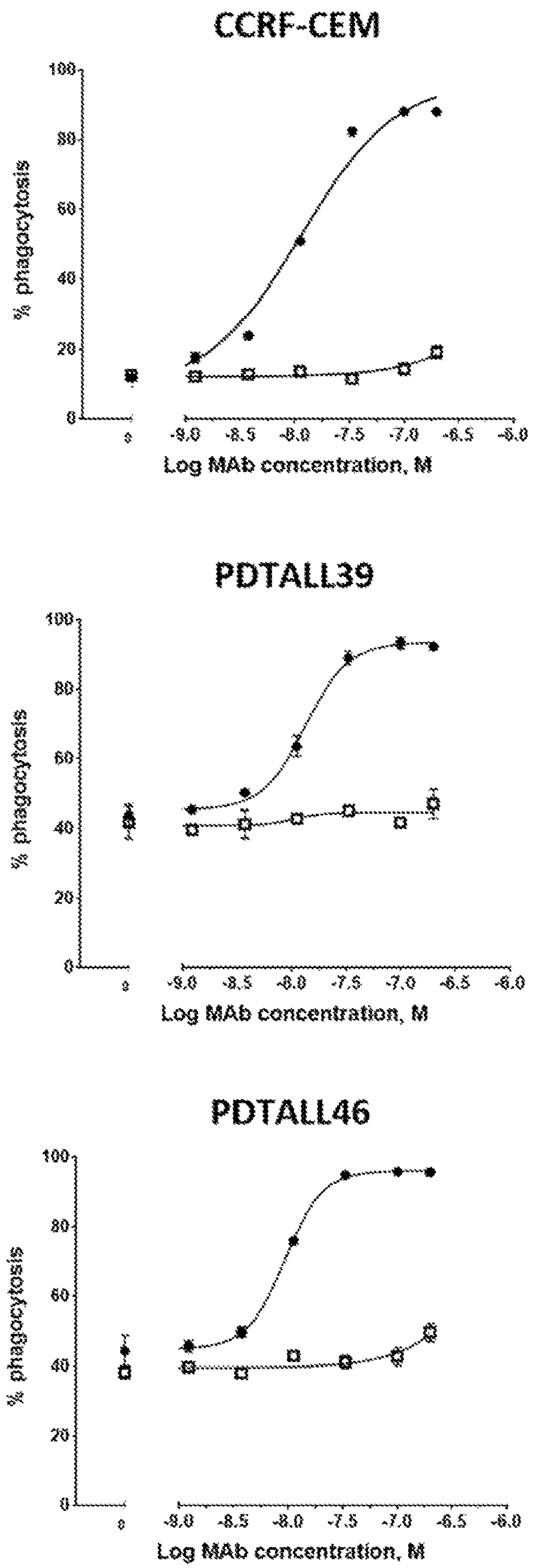
FIG. 9: Potent ADCP activity of 1741G09 on relapsed T-ALL cell lines. Phagocytosis by CellTrace® Violet (CTV)-labelled monocyte-derived macrophages of CellTrace® CFSE-labelled CEM or patient T-ALL cells preopsonised with anti-CD7 antibody 1741G09 E430G or appropriate IgG1 isotype control antibody. The 1741G09 E430G anti-CD7 antibody induces concentration-dependent enhancement of CEM and paediatric patient T-ALL (PDTALL-39, -46, -47) and, to a lesser extent, adult relapsing T-ALL (PDTALL-Ad2R) phagocytosis. Cell phagocytosis of paediatric patient T-ALL using the 1714G09 E340G antibody is statistically significant (p=0.015 using paired t-test), compared to the isotype control, and achieves maximal phagocytosis of 90-95%, compared to ~70% maximal phagocytosis for the PDTALL-Ad2R cells. Data shown are the mean±SD of samples analysed in duplicate.
Figure 9:
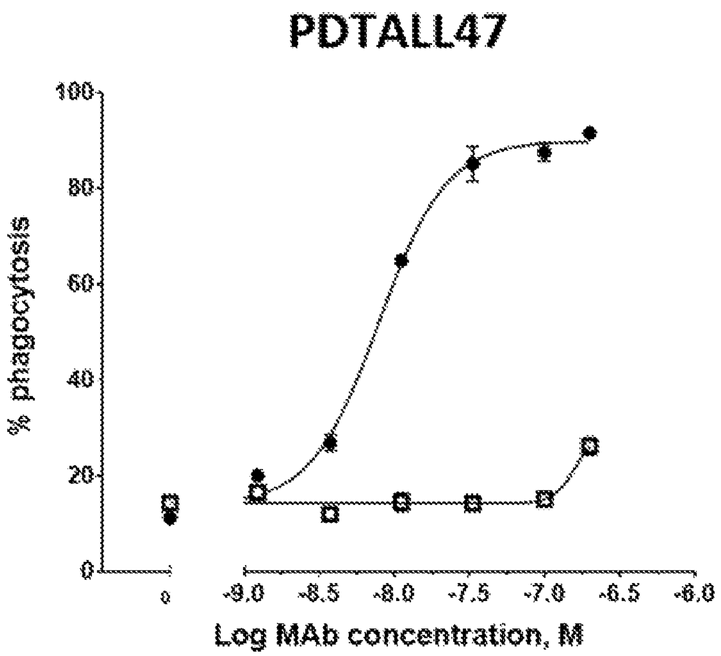
Figure 9:
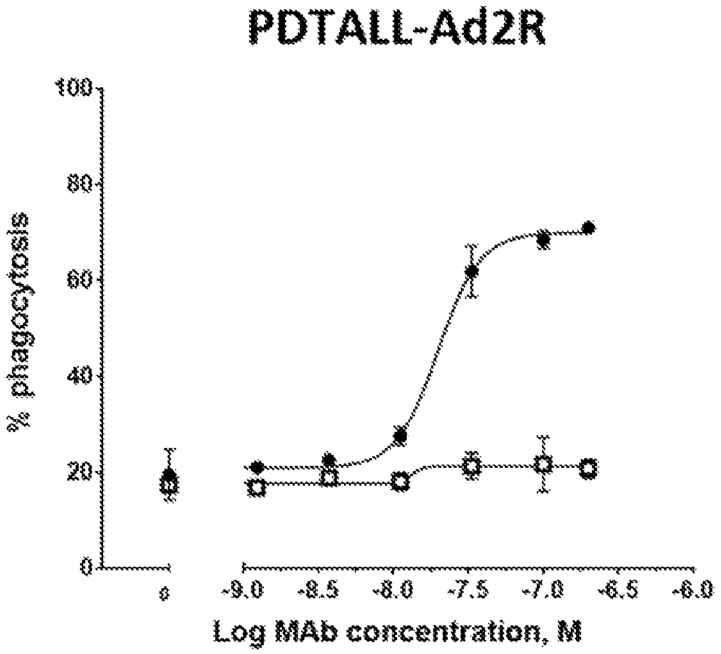

The lead was also tested in the ADCP assay using different T-ALL cells as shown in FIG. 9. Human peripheral monocyte-derived macrophages were differentiated and used to assess the ADCP activity of the 1741G09 E430G molecule on T-ALL cell lines. Among five cell lines tested, four showed close to 100% phagocytosis by macrophages. 1741G09 E430G only depleted 80% of the relapsed cell line PDTALL46 cells in the CDC assay. However, it mediated almost 100% phagocytosis of the same cells in the ADCP assay. On the other hand, 1741G09 E430G only mediated 75% of the other relapsed cell line PDTALLAd2R cells in the ADCP assay. However, 1741G09 E430G depleted close to 95% of the same cells in the CDC assay. These data support the theory that multiple MOAs could complement each other and mediate effective killing of T-ALL cells.

c) Cytokine Release Profile

As CD7 is expressed on peripheral T and NK cells, antibody ligation may lead to activation of these cells. It has been reported that anti-CD7 mAbs could be mitogenic, increasing calcium flux and augmenting IL-2 production (30). However, anti-CD7 mAb, RFT-2 did not raise any significant concerns of cytokine storm in a previous clinical trial for the treatment of renal transplantation (10). To evaluate the ability of the 1741G09 E430G antibody to stimulate human peripheral blood mononuclear cells (PBMCs), we tested the molecule for its effect on cytokine release from PBMC, following immobilization by air-drying.

The 1741G09 E430G was evaluated in PBMCs from five individual donors, as measured by the release of specific cytokines and chemokines. Corresponding isotype controls were used to monitor non-specific activation of the PBMC cultures. Super-agonistic anti-CD28 and anti-CD3 (OKT3) antibodies were used as positive controls.

Figure 10:
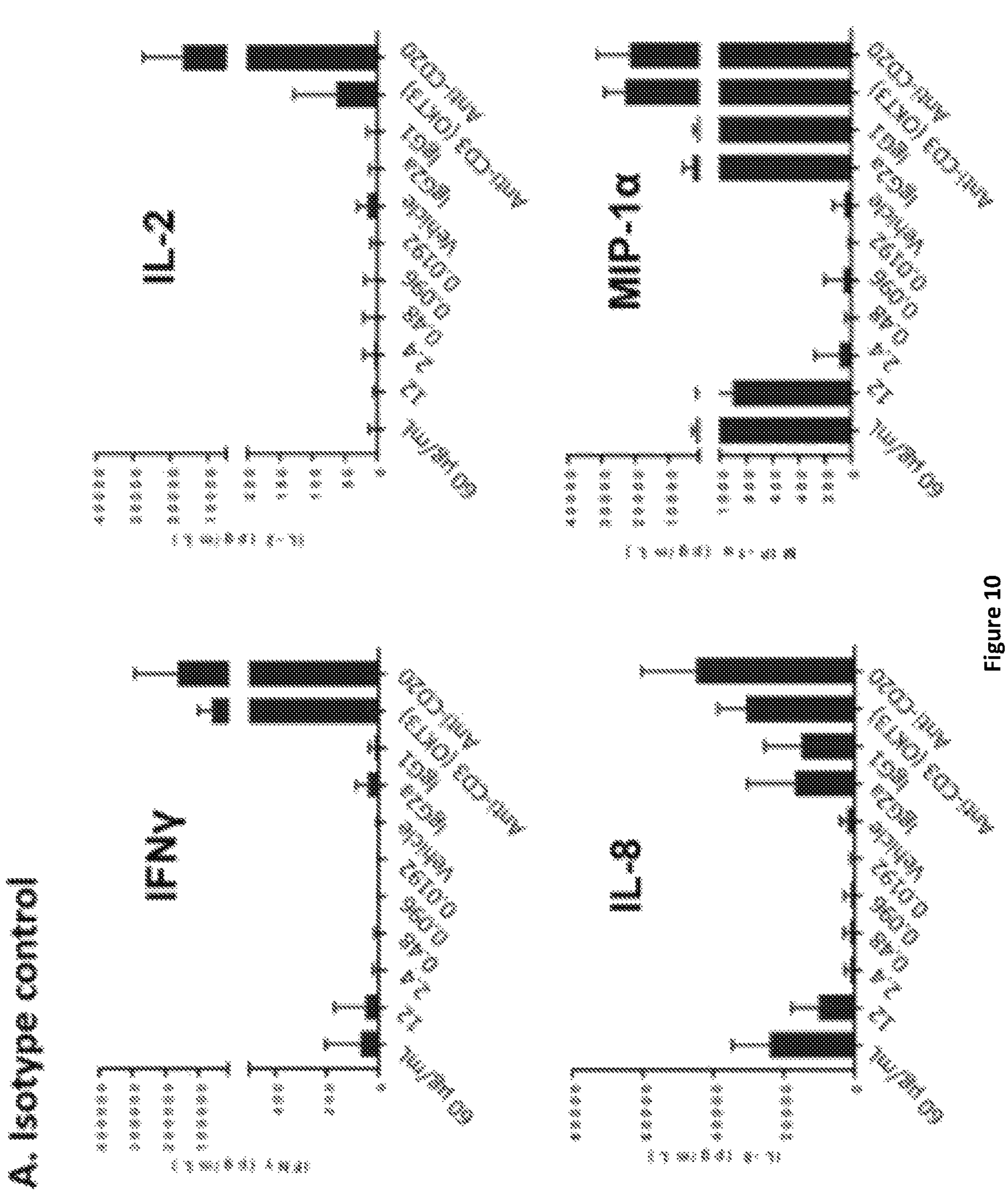
FIG. 10: Cytokine release profile. The 1741G09 E430G antibody was evaluated for the ability to stimulate human PBMC's from five individual donors, as measured by the release of specific cytokines and chemokines. Corresponding isotype control (IgG1 E430G) (A) were used to monitor non-specific activation of the PBMC cultures. Super-agonistic anti-CD28 and anti-CD3 (clone OKT3) antibodies were used as positive controls, following immobilization by air-drying on tissue culture plates. Human PBMCs were seeded into the immobilized test agents in the pre-prepared plates and incubated at 37° C. for 48 hours. Following incubation, the cytokine levels from the cultures were measured by Luminex. Levels of induction of each cytokine were interpolated from a standard curve, using a 5-point non-linear regression analysis. The interpolated data were then normalized to the unstimulated control.
Figure 10:
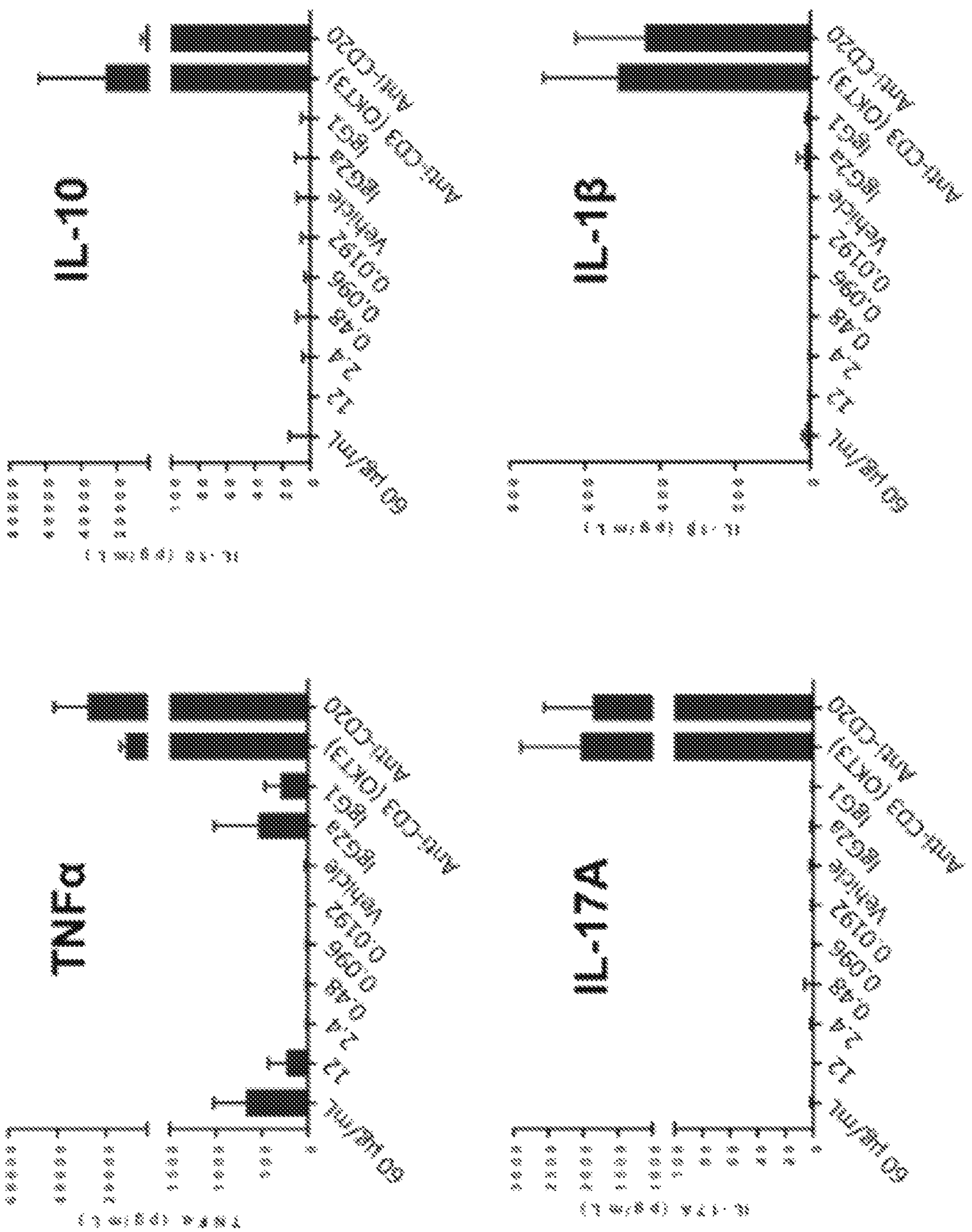
Figure 10:
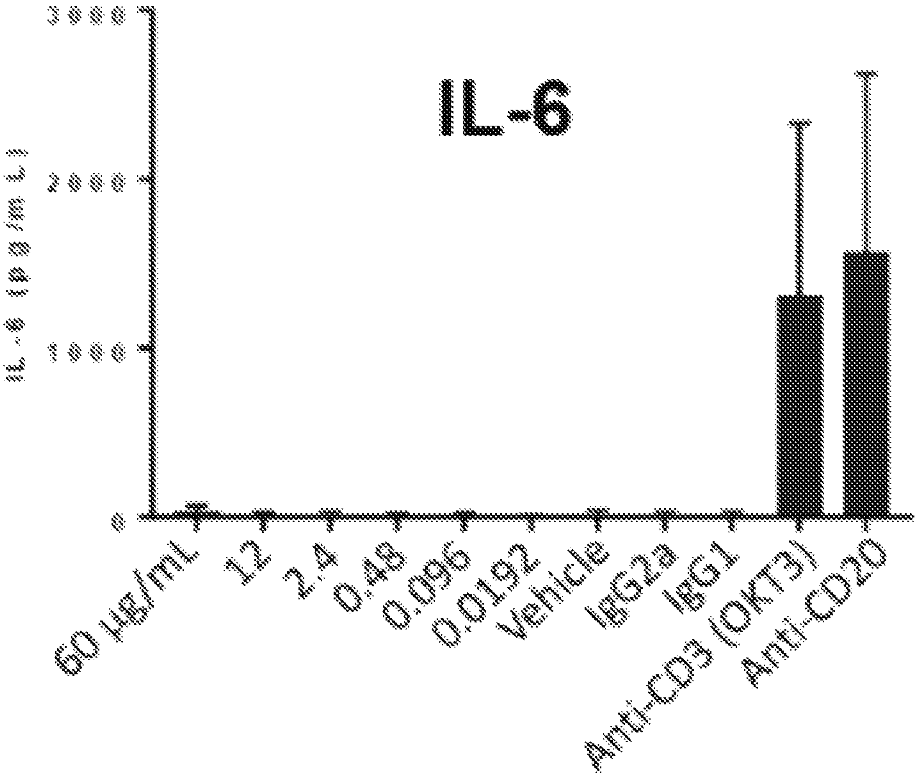
Figure 10:
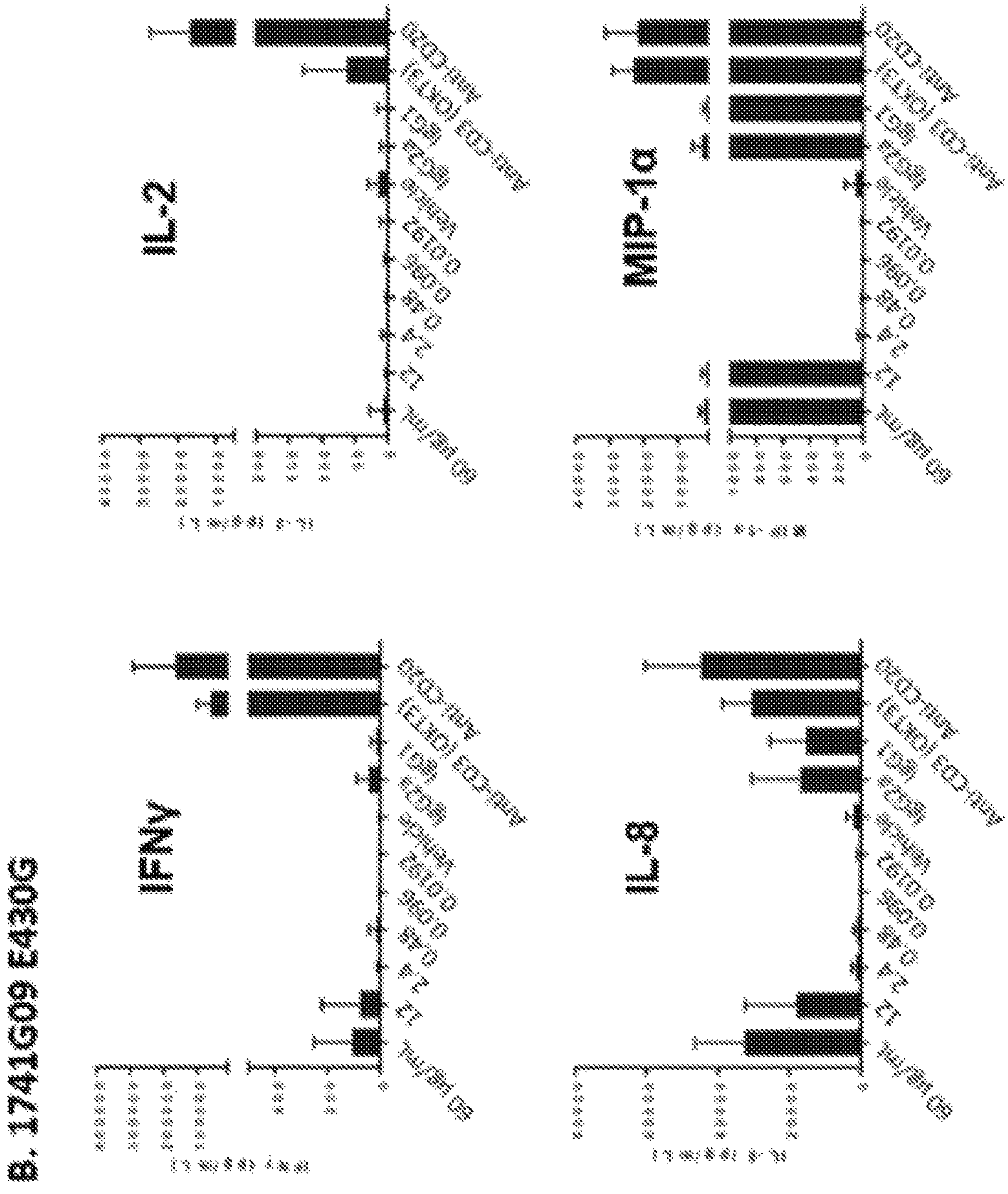
Figure 10:
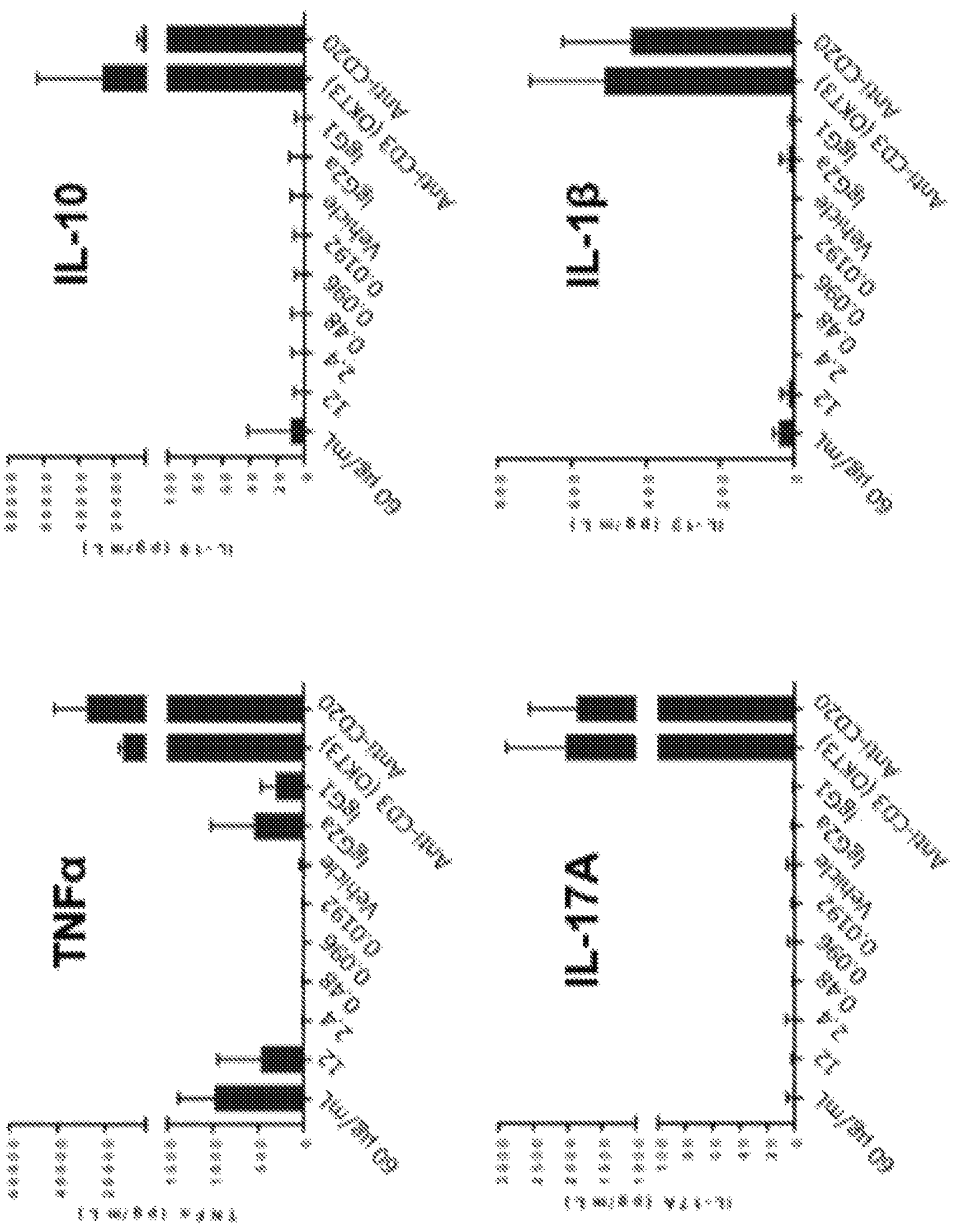

Among the cytokine panels, six cytokines were slightly increased in the samples treated with 1741G09 E430G when compared to ones treated with IgG1 at the top test concentration (60 pg/ml) (IL8, 2.8×; MIP-1α, 2.9×; TNFα, 4.2×; IL1β, 4.6×; IL6, 1.7×). The IgG1 E430G isotype control also slightly increased these cytokine release, suggesting that the increases may not be CD7-specific. The positive controls, anti-CD3 (clone OKT3) and super agonistic anti-CD28, induced characteristic cytokine profiles from all donors, confirming that the assay had performed as expected, with much higher general induction than any test article or isotype control (FIG. 10 & Table 4).

Discovery Campaign Summary

Seven leads were selected from primary and secondary cell binding screening. Five were confirmed with cross-reactivity to human and cynomolgus CD7 proteins via measurement of binding to soluble CD7 by SPR. These five leads were reformatted to human IgG1 E345R Fc and tested in the CDC and ADCP assays on CEM cells. The 1741G09 E345R antibody was selected as the lead molecule as it was with the most potent CDC and ADCP activities. The lead antibody was further reformatted to IgG1 E430G Fc in consideration of better half-life of this variant in vivo. The potent CDC activities of the 1741G9 E430G antibody were also demonstrated in different T-ALL cell lines with maximum killing of 100% for the majority of cell lines and strong potency (ECso=50-500 pM). The 1741G09 E430G mAb did not significantly increase the cytokine release from PBMC, when it was compared to super agonists, anti-CD3 or anti-CD28.

c) Biological Assessment

In Vitro CDC Assay on PBMC T and NK Cells

Figure 17:
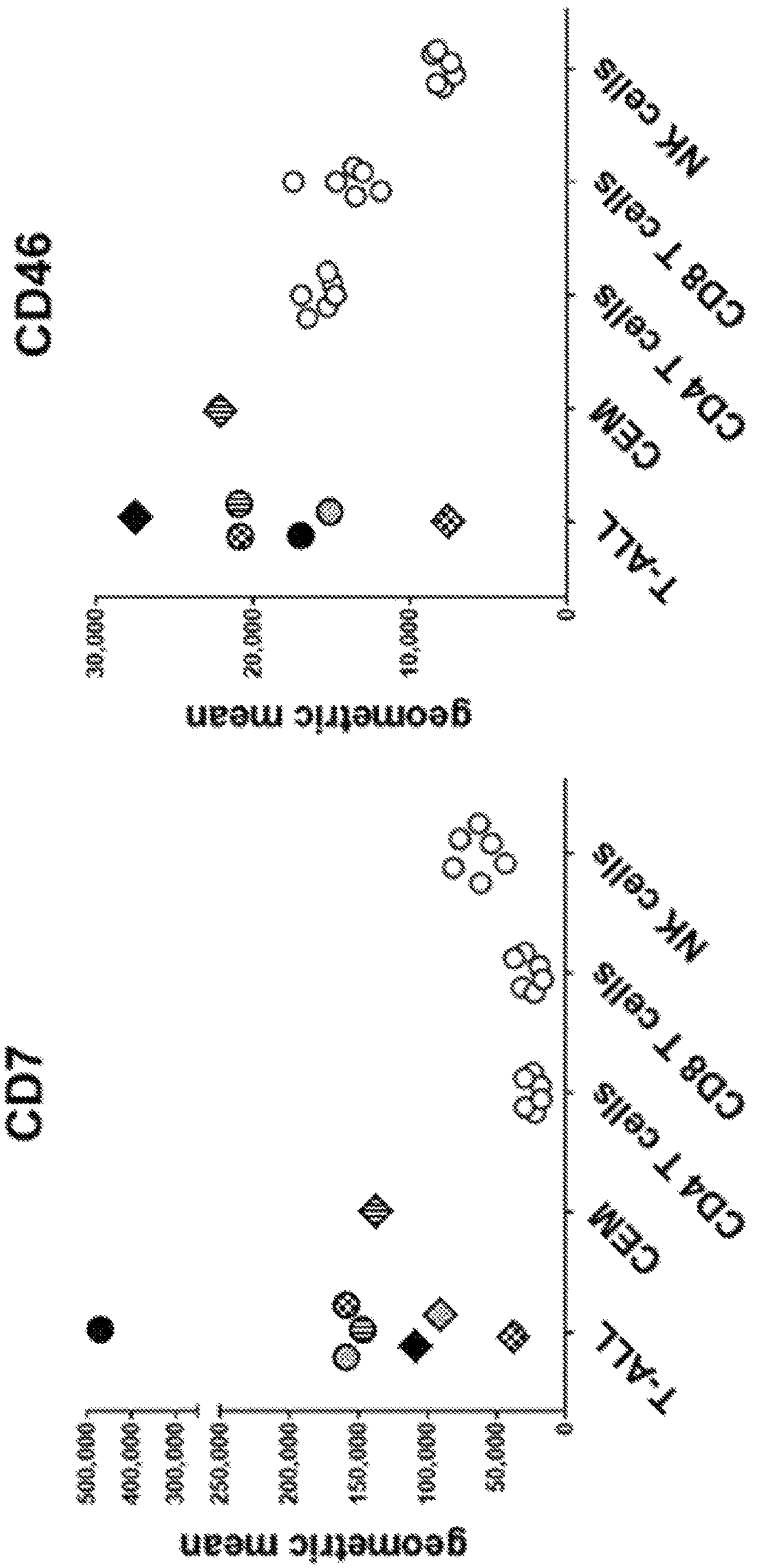
FIG. 17: CD7 and CRP expression profiles of relapsed T-ALL cell lines, CEM and peripheral T and NK cells
Figure 17:
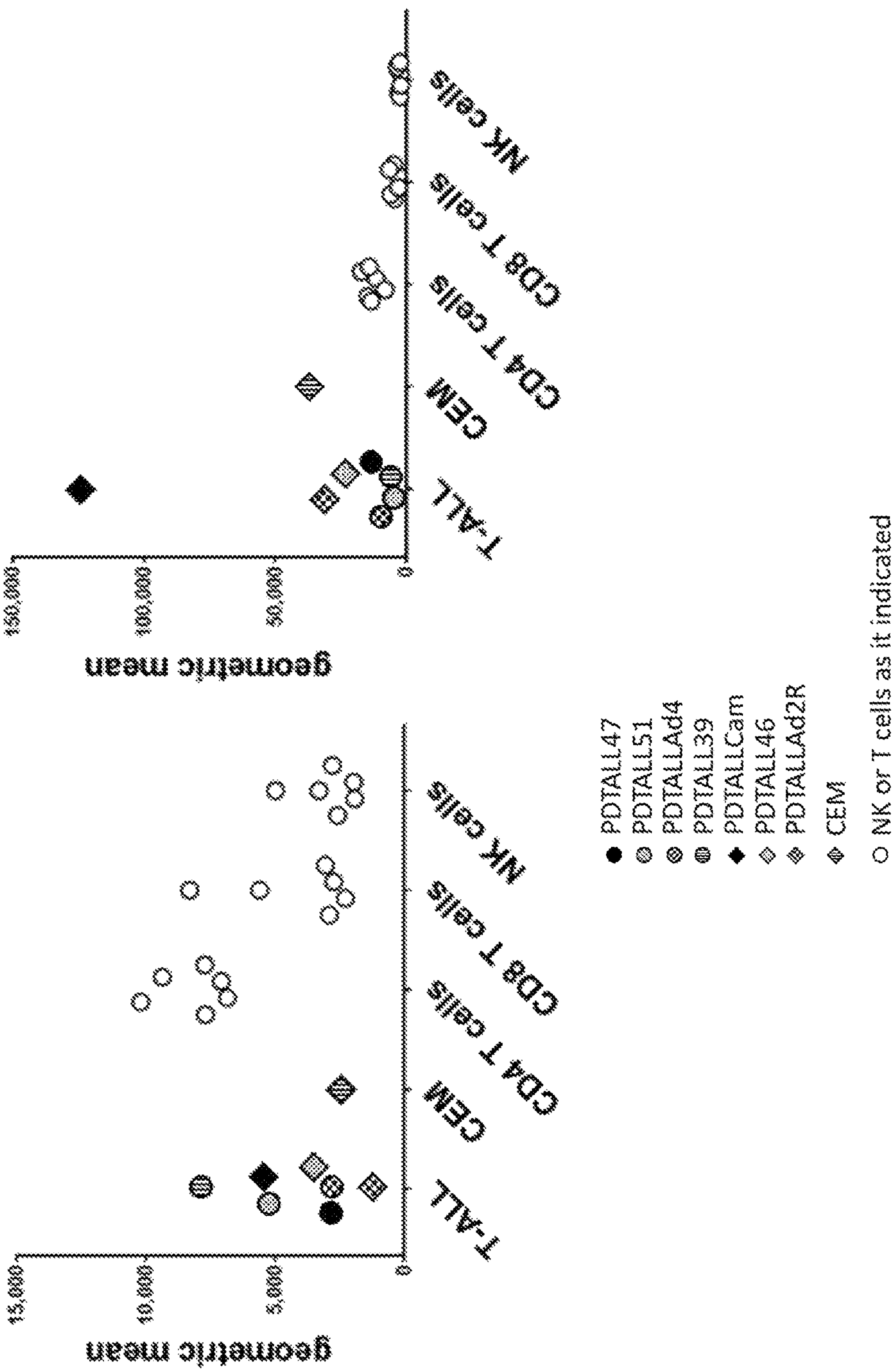

As peripheral T and NK cells express CD7, they are susceptible to depletion mediated by the lead molecule. Peripheral T and NK cells were isolated respectively from two different donors and used to assess the CDC activity of 1741G09 E430G. While no significant T cell depletion was detected (FIG. 11.A.), a maximum of 65% of NK cells were depleted with $EC_{50}$ close to 300 pM (FIG. 11.B.) within the range of $EC_{50}$ values observed for the T-ALL cell depletion (Table 2). Notably, NK cells have a higher expression of CD7 and lower expression of CRPs than T cells (FIG. 17).

Ex Vivo Human Whole Blood Assay

Figure 12:
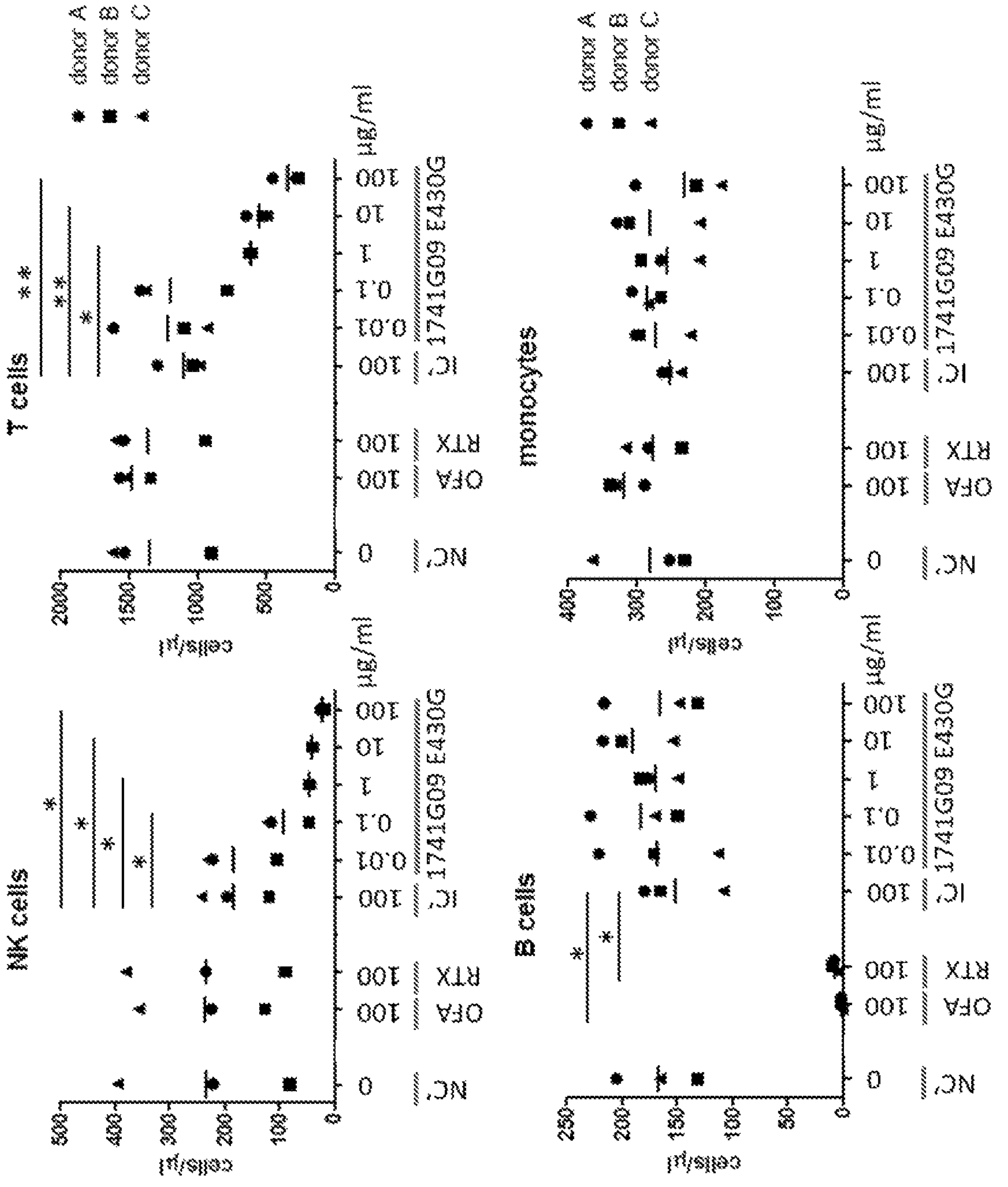
FIG. 12: B cell, monocyte, NK cell and T cell survival in the human whole blood assay. Whole blood from three healthy donors (A, B, C) collected in S-Monovette® Hirudin tubes was treated with different antibodies in three independent experiments and then incubated for 20 hours at 37° C. Hirudin was used as anti-coagulant to preserve the complement activity. After incubation, immunophenotyping were analysed by flow cytometry based on the cell surface markers (T: $CD45^+CD3^+CD19^-$; B: $CD45^+CD3^-CD19^+$; NK: $CD45^+CD3^-CD16^+CD56^{30}$; monocyte: $CD14^{30}$). Data sets of each donor with mean (-) are shown. NC': negative control; IC': isotype control; OFA: Ofatumumab; RTX: Rituximab. Means were compared by paired t-test. * refers to p-value below 0.05; ** refers to p-value below 0.01.

To assess if 1741G09 could deplete normal peripheral T and NK cells in a more physiological context, we used a TruCulture®-based assay to evaluate the effects of the antibody on the human whole blood status. The 1741G09 E430G antibody was used in concentrations ranging from 0.01 to 100 μg/ml and compared to isotype control (100 μg/ml). Two positive controls, rituximab and ofatumumab (100 μg/ml) were also included. Whole blood and antibodies were incubated for 20 hours prior to assessment of cell depletion. Three human donors were used in the assays, referred to as A, B and C. Numbers of cell subset per μl of sample were determined by flow cytometry. Results are shown in FIG. 12. Assay were performed by Hotscreen.

The isotype control treated cultures showed very similar cell counts compared to the negative control across the four cell types measured; B, T, NK cells and monocytes. Ofatumumab and Rituximab are therapeutic antibodies targeting B cells, and were included as positive controls for specific cell depletion. Indeed, B cells were almost completely eliminated throughout the culture. A concentration-dependent depletion of T cells and NK cells by 1741G09 E430G were observed in all three donors. The numbers of T and NK cells were reduced as compared to the negative (no antibody) or isotype control. The 1741G09 E430G antibody depleted NK cells up to 90% and T cells up to 75%. The antibody was more potent for NK depletion than T cell depletion. At the concentration of 0.1 pg/ml (~0.67 nM) of 1741G09 E430G, NK but not T cells were significantly depleted.

The reduction of T cells appeared to have no effect on the ratio between $CD4^+$ and $CD8^+$ T cells (data not shown). There was no significant change of B cell and monocyte counts, indicating the specificity of 1741G09 E430G for its cell depletion activity.

Figure 11:
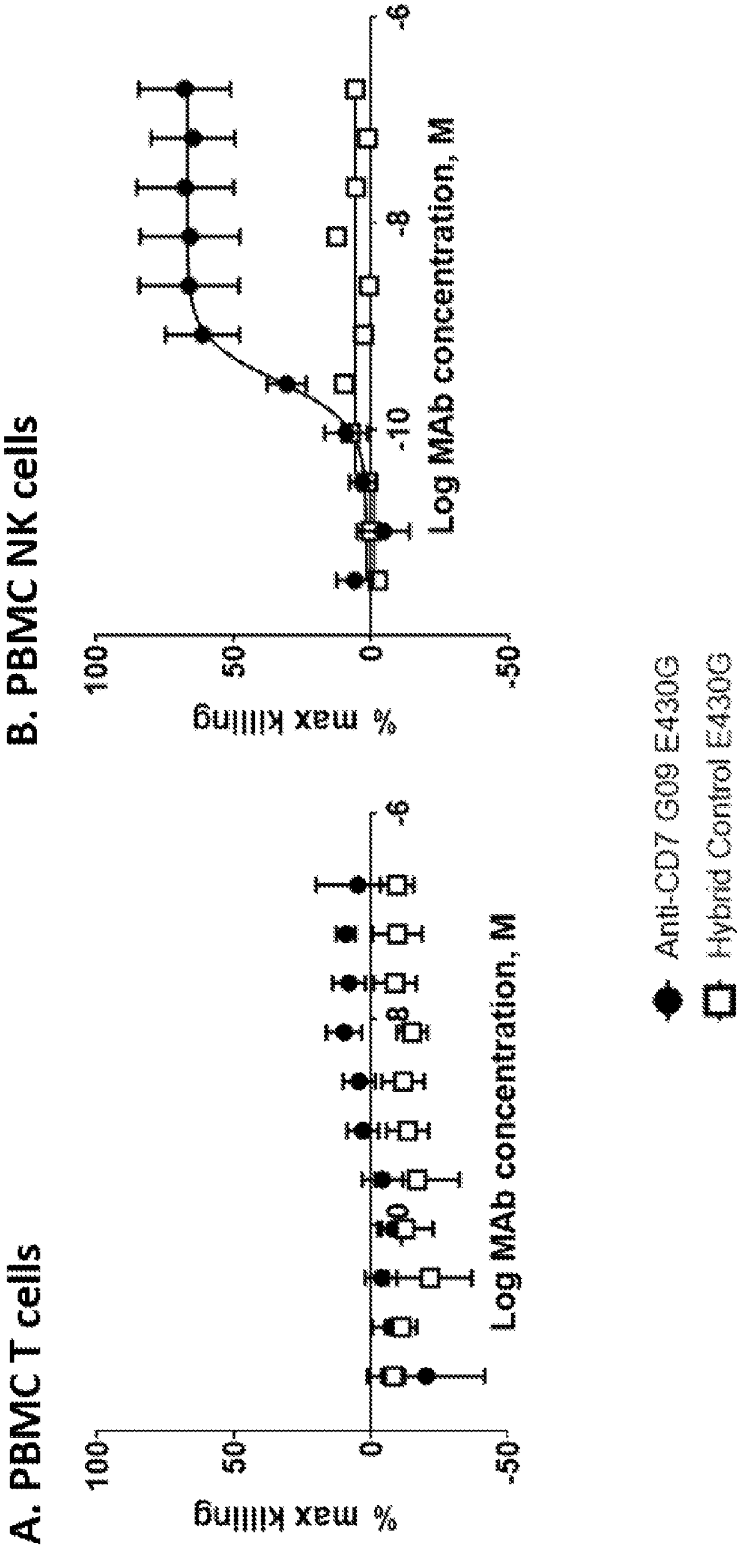
FIG. 11: PBMC T and NK cell depletion profile by 1741G09 E430G in the CDC assay. Human T (A) or NK (B) cells from two healthy donors were isolated from cryopreserved PBMCs using Pan Human T or NK cell isolation kits respectively (Miltenyi Biotech) and plated at 1,750 cells/well. Titrations of 1741G09 E430G as well as matched isotype control were added and incubated at 4° C. for 30 minutes to allow for antibody opsonization. Human complement serum was then added at a 1/16 final concentration and plates were incubated for 2 hours at 37° C. After incubation, CellTiter-Glo® was added to all wells and luminescence output read on an Envision plate reader. Luminescence signal correlated with the number of viable cells per well and % killing was calculated for each antibody concentration based on luminescence signal from wells without antibody (0% killing) and without cells (100% killing). Data was analyzed using GraphPad Prism v7.02, where log antibody concentration (M) was plotted against % killing (mean±standard deviation) and a 4-parameter logistic curve fit was applied to data, allowing calculation of $EC_{50}$ values.

We observed up to 65% depletion of NK cells but no significant T cell depletion in the CDC assay using human serum and isolated NK or T cells (FIG. 11). The higher maximum depletion rates (90% of NK cells and 75% of T cells) obtained from the human whole blood assays (FIG. 12) suggest that there are other effector cell components involved in the cell depletion in this assay.

Ex Vivo Human Whole Blood Assay Spiked with T-ALL Cells

Figure 13:
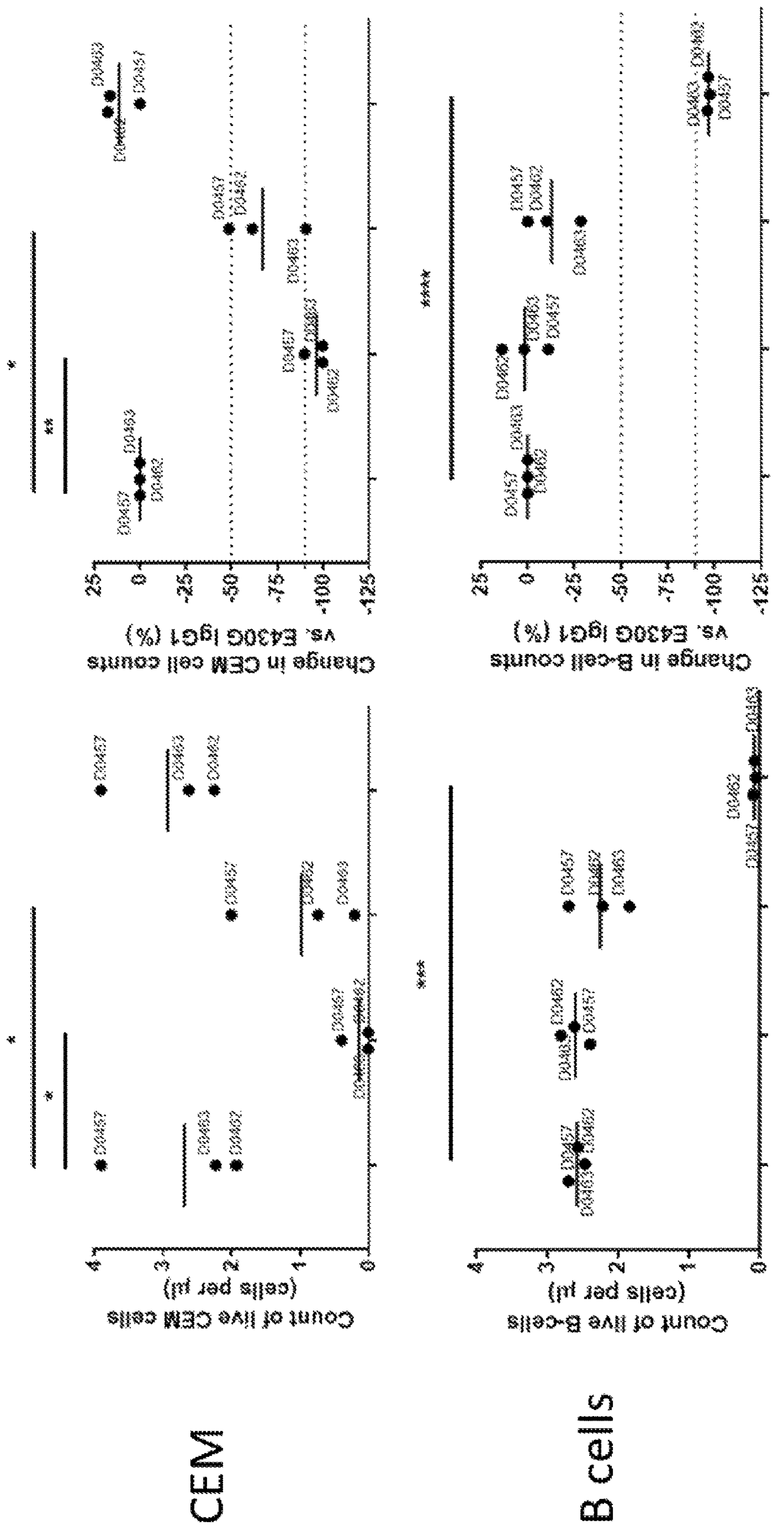
FIG. 13: CEM cell survival in healthy donor blood. Whole blood from three healthy donors (D0457, D0462, D0463) collected in S-Monovette® Hirudin tubes was spiked in with CellTrace® Violet (CTV)-labelled CEM cells and treated with 10 μg/mL of antibodies as indicated in three independent experiments. Hirudin was used as anti-coagulant to preserve the complement activity. After incubation for 20 hours at 37° C., immunophenotyping were analysed by flow cytometry based on the cell surface markers (T: $CD45^+CD3^+CD19^-$; B: $CD45^+CD3^-CD19^+$; NK: $CD45^+CD3^-CD16^+CD56^+$; monocyte: $CD14^+$). Data sets of each donor with mean (-) are shown. IC': isotype control; OFA: Ofatumumab. Change in cell counts, compared to the isotype control, were also determined and plotted in the right panels. Each dot represents a single donor and the mean of the 3 donors is indicated by a plain line for each condition. 50% and 90% thresholds are indicated by discontinued lines. Means were compared by paired t-test. * refers to p-value below 0.05;  refers to p-value below 0.01; * refers to p-value below 0.001; **** refers to p-value below 0.0001.
Figure 13:
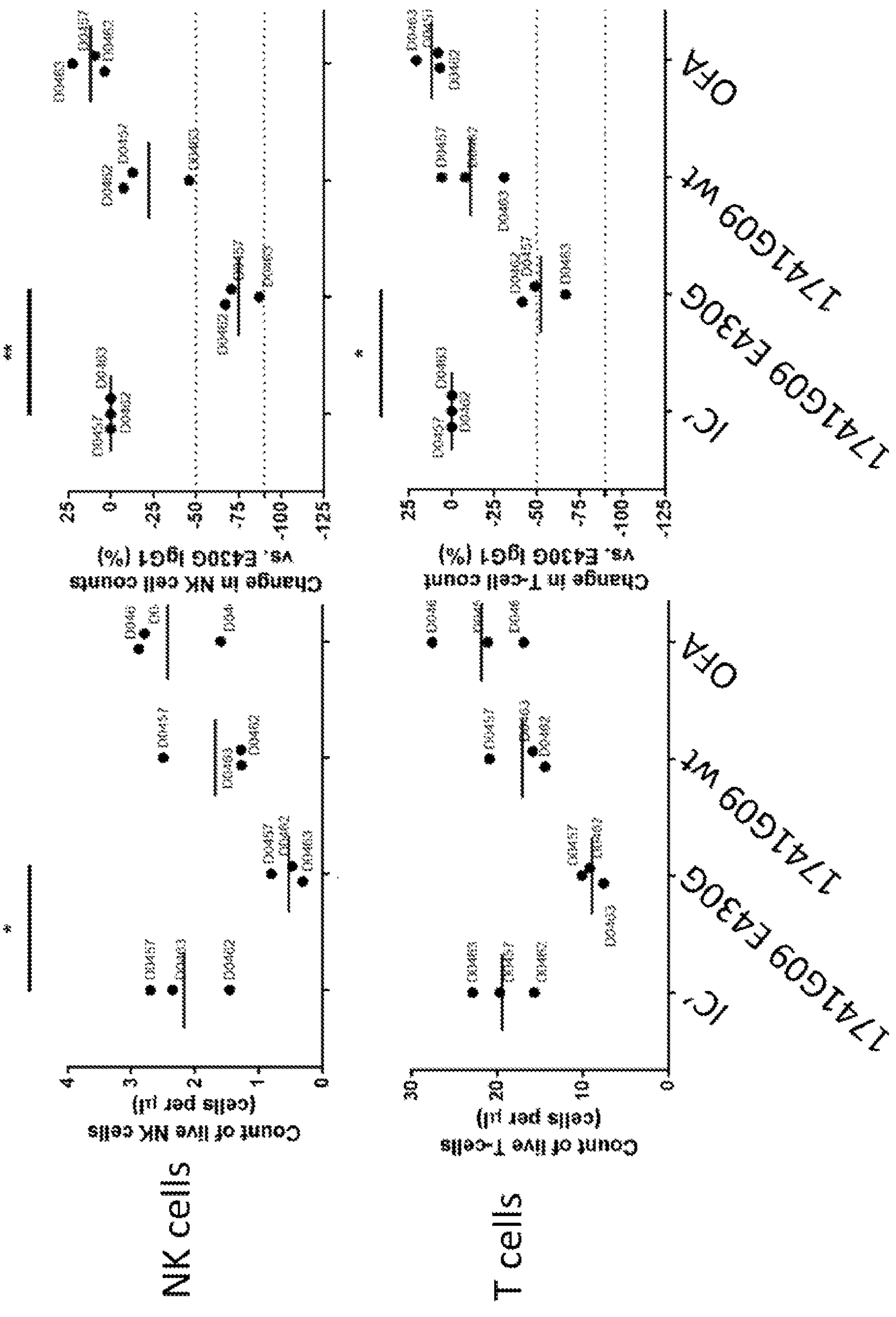

Tumour cell depletion should ideally be assessed in the blood samples from T-ALL. However, it is difficult to obtain such samples as patients are rare and primary T-ALL cells are difficult to keep in culture. To circumvent this issue, we spiked the blood samples from the healthy donor with the T-ALL cell-line, CEM cells. The survival of CEM cells as well as the survival of the NK, T- and B-cells from the healthy donor were assessed in presence of 10 μg/ml (~67 nM) of 1741G09 IgG1 E430G, 1741G09 IgG1 wild type, E430G IgG1 isotype control or Ofatumumab. The high concentration of antibodies was used to ensure maximum killing was achieved. Results are shown in FIG. 13.

1741G09 E430G significantly decreased CEM cell counts in spiked whole blood samples. The 1741G09 wt antibody was included as a comparison to the CDC-enhanced version. Unlike the 1741G09 E430G antibody, the wt Fc version of 1741G09 has been shown not to significantly deplete CEM cells in the CDC assays (data not shown). In the whole blood assay, both wt and E430G versions of 1741G09 significantly decreased the counts of CEM cells but the efficacy of the E430G version was much greater (mean depletion percentage 96.2% vs 66.8%). The depletion of CEM cells by the 1741G09 wt antibody suggests that other effector components except CDC are involved in the process. As expected, ofatumumab strongly decreased B-cell counts without impacting CEM, NK or T-cell counts.

The NK and T cell counts were also significantly decreased by 1741G09 E430G but not 1741G09 wild type. The depletion of NK cells (75%) and T cells (52%) was not as high as the depletion of CEM cells (96%). This data confirmed that the 1741G09 E430G antibody impact is linked to the CD7 expression level of the target cells (CEM cell>NK cell>T cell, FIG. 21), and its impact on cell depletion is greater than the wild type Fc version.

Impact of Anti-C5a Antibody on Lead-Induced Cell Depletion

To better understand the lead's mode of action, we assessed the effect of an anti-complement 5a (C5a) antibody on the cell depletion induced by 1741G09 E430G, 1741G09 wild type and Ofatumumab. The complement pathways can be divided into the activation pathway and the lytic pathway (FIG. 18) (31). C5, via C3, can be cleaved into C5a (activation pathway) and C5b (lytic pathway). C5a has chemotactic and anaphylatoxic properties and plays an essential part of the innate immune response (smooth muscle contraction, vascular permeability, degranulation of mast cells and basophils, directed migration of neutrophils, eosinophils, basophils and monocytes). The antibody used in the present assay is capable of inhibiting the binding of C5a to the C5a receptor, without blocking the cleavage of C5 (32).

Figure 14:
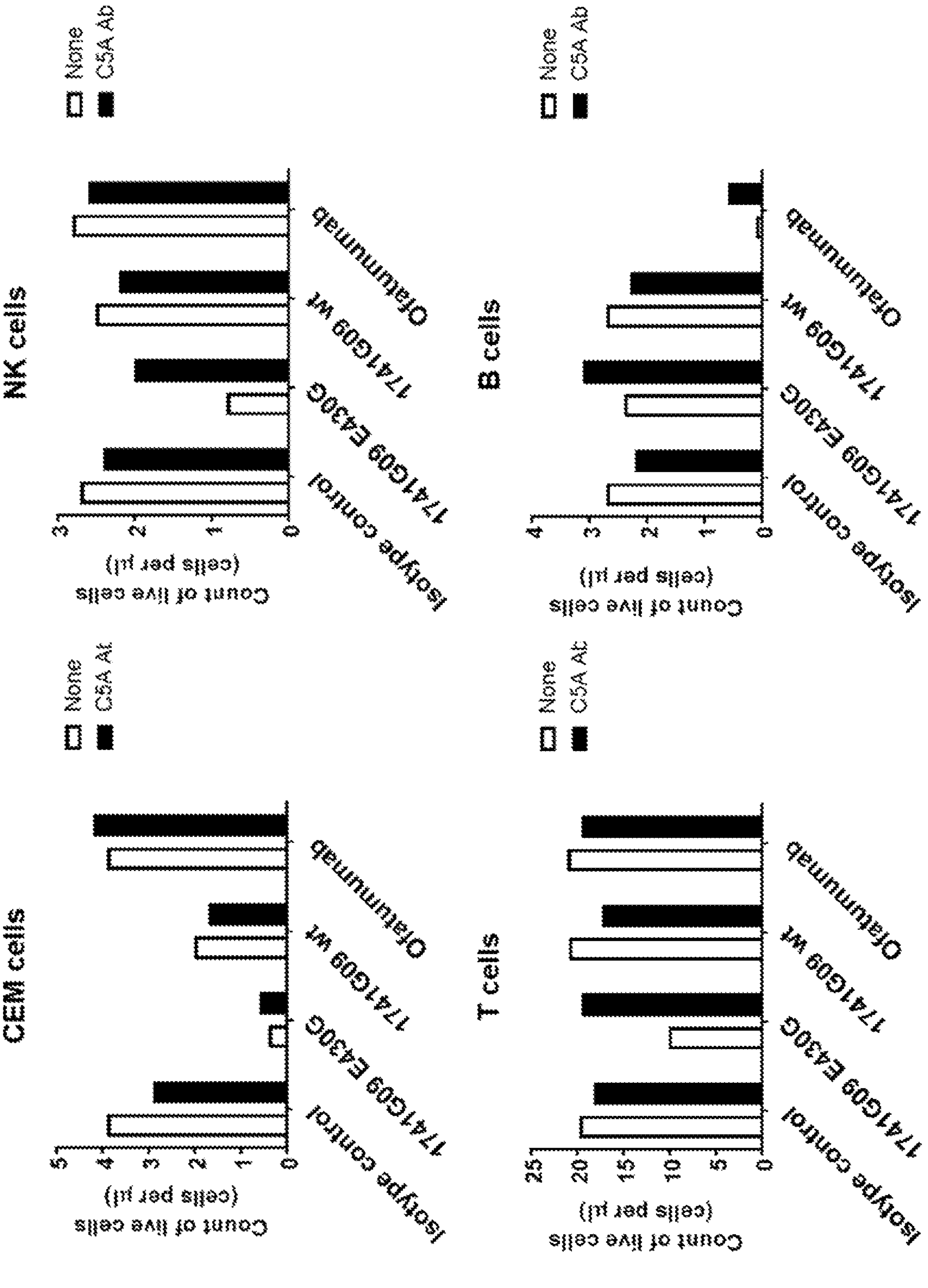
FIG. 14: Impact of anti-C5a Ab on 1741G09 E430G-induced cell death (n=1). CTV-labelled CEM cells were spiked in healthy donor blood with 10 μg/mL of either E430G KY1007, E430G IgG1, WT KY1007 or Ofatumumab±10 μg/mL of anti-C5a Ab and incubated for 20 hours at 37° C. Similar methods to the previous section were used in this assay.

Both wt and E430G versions of 1741G09 decreased the counts of CEM cells (by 49% and 90% respectively) (FIG. 14). Addition of anti-C5a antibody did not impact CEM cell depletion induced by either version. Although CEM cell depletion was not blocked by anti-C5a, the MOAs behind these two versions of 1741G09 are expected to be quite different. The lack of inhibition of CEM depletion by 1741G09 E430G supports the hypothesis that this antibody acts via the lytic pathway. It is unlikely that E430G-driven depletion is attributed to NK cell-mediated ADCC because the NK cells would quickly get depleted through CDC once 1741G09 E430G is added. In contrast, the wt version does not deplete either NK or CEM cells via CDC (data not shown). Thus, depletion of CEM cells by the wt version is likely via NK cells-mediated ADCC, macrophage-mediated phagocytosis or neutrophil-mediated trogocytosis, none of which appear to be inhibited by the anti-C5a antibody in this experimental set-up.

The 1741G09 E430G antibody decreased the counts of NK and T-cells (by 70 and 49% respectively). In contrast to CEM cells, addition of anti-C5a reverted 1741G09 E430G-induced T-cell decrease into the similar cell counts to isotype control (FIG. 14), suggesting that the depletion ofT cells by 1741G09 E430G is not attributed to the classical or lytic pathway but to the inflammatory pathway of the complement activation. This is consistent to the result that 1741G09

E430G did not significantly deplete PBMC T cells in the CDC assay. Addition of anti-C5a also partially reverted 1741G09 E430G-induced NK-cell decrease, suggesting that this molecule depletes NK cells via both activation and lytic pathways. Ofatumumab effects may be partially reversed by anti-C5a; however, it should be noted that this experiment was performed in one donor only. Incubation of whole blood with 1741G09 in the presence of a lytic pathway inhibitor, such as eculizumab, would confirm the requirement for this pathway.

In Vivo Xenograft Study

Anti-CD7 antibodies have previously demonstrated efficacy in the xenograft model (33). To assess the efficacy of the 1741G09 E430G antibody, we tested the antibody in a paediatric relapsed PDX T-ALL xenograft model.

Figure 15:
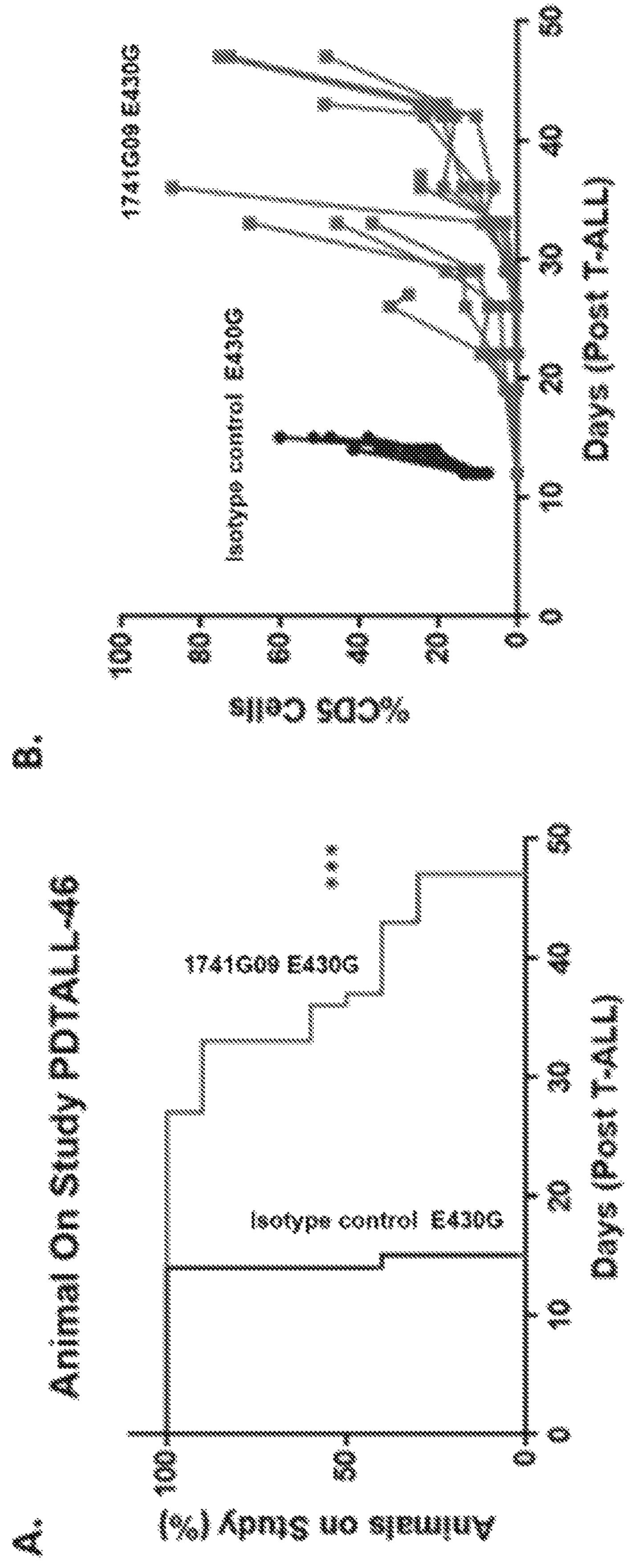
FIG. 15: 1741G09 E430G prolonged the survival of xenograft mice. The NSG mice were injected with $5\times10^6$T-ALL cells, PDTALL46 at day 0 and then dosed at 10 mg/Kg three times a week from day 3 until the end of the study. Two groups (10 mice/group) were treated with 1741G09 E430G and the corresponding isotype control respectively. (A) Kaplan Meier plot showing animals left on study in these two groups. ***: p<0.0001 Log-Rank (Mantel-Cox) Test compared to isotype control. (B) Individual animal flow cytometry data showing the percentage of cells expressing human CD5 on the cell surface present in the blood of the mice on study.

The NSG mice were dosed at 10 mg/Kg three times a week from day 3 until the end of the study following injection with $5\times10^6$ PDTALL46 cells at day 0. Blood draws were taken at serial time points to assess human CD5 expression levels in the blood by flow cytometry, as an antibody to anti-CD7 that does not compete with 1741G09 was not identified. The Kaplan-Meier plot demonstrated a significant increase in survival time in the group treated with 1741G09 E345R compared to the group with isotype control (FIG. 15). As NSG mice are severely immunodeficient they lack T, B and NK cells, and complement activity and macrophages are also defective. Neutrophil-mediated trogocytosis (34) in the presence of 1741G09 E430G is likely to have mediated the observed depletion in this mouse model.

Developability

As part of the developability assessment of the candidate 1741G09 E430G three pre-CMC studies have been performed: early formulation screening, accelerated/real time studies and forced degradation studies.

In early formulation screening the candidate was dissolved into 12+ different platform formulation buffers followed by colloidal and conformation stability assessment ($T_m$ and $T_{agg}$ determination, by intrinsic fluorescence and SLS respectively). Two platform buffers demonstrated suitable stability and were short-listed for the accelerated and real time studies: the candidate was prepared at 1 mg/ml in each of the two formulation buffers, or PBS as additional control and incubated at 5° C., 25° C. and 37° C. for two weeks. The experiment was performed in triplicate for each condition. The following quality attributes were measured: aggregates by SEC-HPLC and DLS, fragments by SDS-PAGE, activity by CDC functional assay. No significant changes were observed in any of the quality attributes or activity after a two-week incubation at any tested condition. Additionally, the candidate was subjected to freeze/thaw stress and no changes in the same quality attributes were observed after 3 cycles of storage at −70° C. for at least 18 hours followed by thawing at room temperature for 3 hours.

Finally, forced degradation studies were performed on the candidate at 1 mg/ml in PBS: forced deamidation (72-hour incubation at 37° C. in 1% ammonium bicarbonate), forced oxidation (24 hour incubation at 25° C. in 0.03%, 0.003% and 0.0003% $H_2 0_2$) and acidic hold (3-hour incubation at 25° C. and pH 2.8). Activity by CDC functional assay was tested in duplicate before and after the stress conditions. No significant changes were observed after forced deamidation, acid hold and forced oxidation at the lower and intermediate level of $H_2 0_2$, while the oxidation at the higher $H_2 0_2$ concentration showed a reduction in activity by 87% and 4-fold increase in $EC_{50}$.

In line with in-silico predictions, experimental data indicated low risk from a developability perspective: the candidate can be purified through platform protein A process with suitable product quality (aggregates lower than 1%, nominal concentration 10 mg/ml into PBS pH 7.4 as platform buffer). The early formulation screening demonstrated platform formulation buffers can further improve colloidal and conformation stability, while accelerated and real time conditions after two weeks do not affect product quality or activity. The force degradation tests highlighted overall a low risk with no effect due to freeze/thaw, acidic hold, deamidation; the risk is considered low/medium for oxidation and may be managed through formulation by addition of sacrificial antioxidant excipients.

Overall, the candidate presents low risks from a pre-CMC standpoint based on the computational and experimental dataset presented here.

Lead Molecule Expression

The lead molecule in the CD7 project, 1741G09 HuIgG1 E430G C-term Lysine clipped, Phe variant of light chain (1741G09 E430G), has been expressed in both a transient and stable pool expression system.

1741G09 E430G was expressed at three different scales in the transient system, 30 ml, 200 ml and 2 L. There was no significant difference in cell growth or viability compared to cultures expressing a control antibody. The expression levels were the same in all scales at day 5 post transfection, whilst expression at day 12 diverged, with expression levels of >600 mg/L at the 30 ml and 2 L scale. Expression plateaued at the 200 ml scale. This difference in expression yield at different scales is not uncommon.

Figure 18:
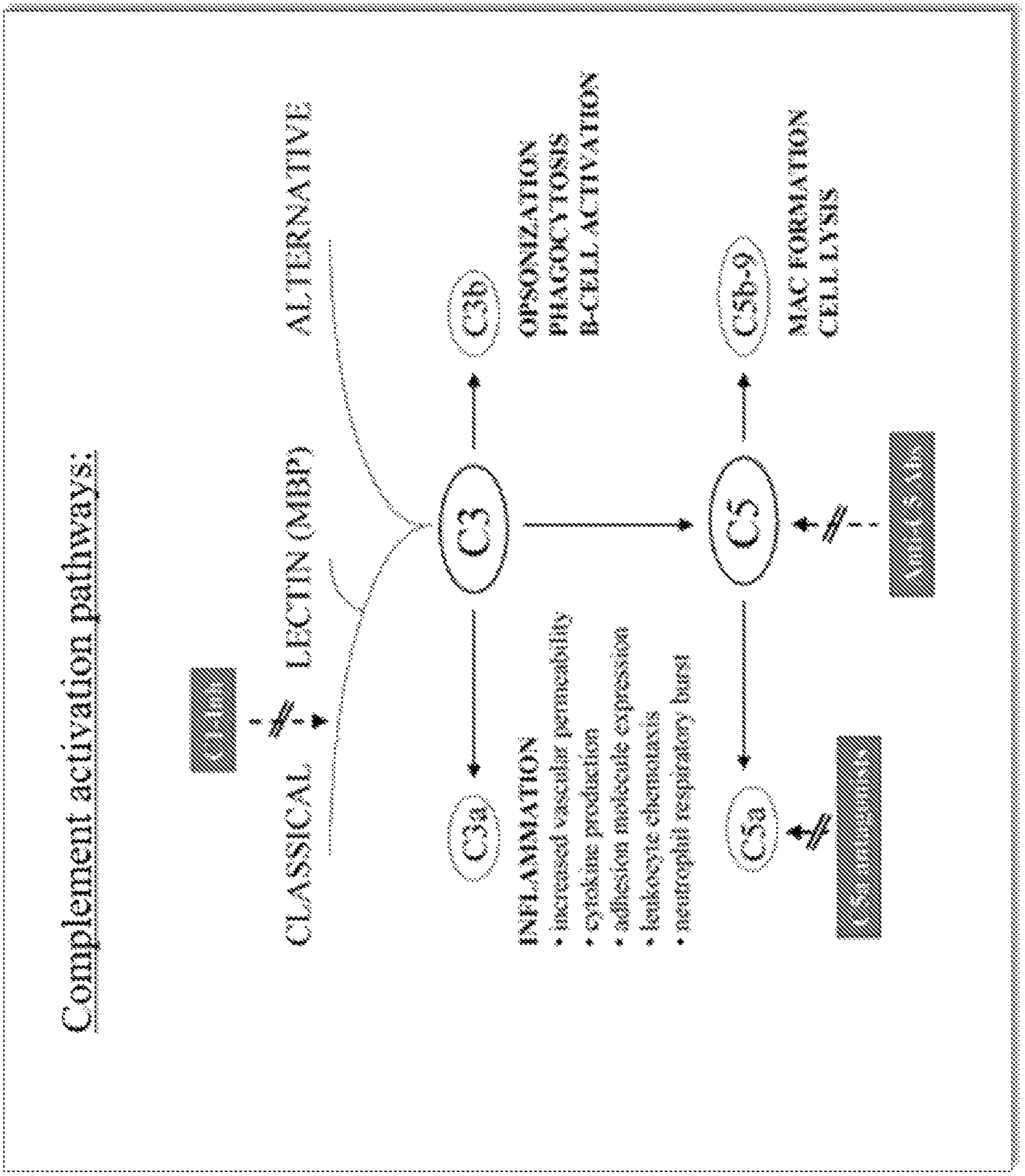
FIG. 18: Pathways of complement activation

1741G09 E430G expression yield at the 30 ml and 2 L scale is greater than the standard, high expressing control antibody expressed alongside all molecules (FIG. 18). This is a good initial indicator that 1741G09 E430G can be expressed at appropriate levels. However, it is important to note that, although anecdotal evidence suggests that if a molecule is high expressing in the transient system then it is likely to yield a high expressing stable cell line, the predictability of stable outcomes from the transient system has not been fully evaluated.

Three cell pools stably expressing 1741G09 E430G have been generated. The average expression of these pools on day 13 of a fed batch overgrow was 385 mg/L. 1741G09 E430G stable pool expression was 43% of that observed with high expressing control antibody pools generated in parallel. Pools likely contain a mixture of high- and low-expressing clones, and so selection of an appropriate clone would probably give us a good yield. Indeed, for an unrelated molecule minipools were generated from a pool that expressed ~50% of control, and >5× improvement in expression achieved.

REFERENCES

1. Ware R E, Haynes B F. T cell CD7 mRNA expression is regulated by both transcriptional and post-transcriptional mechanisms. Int Immunol. 1993 February; 5(2):179-87.
2. Barcena A, Muench M O, Galy A H, Cupp J, Roncarolo M G, Phillips J H, et al. Phenotypic and functional analysis of T-cell precursors in the human fetal liver and thymus: CD7 expression in the early stages of T- and myeloid-cell development. Blood. 1993 Dec. 1; 82(11): 3401-14.
3. Hao Q-L, George A A, Zhu J, Barsky L, Zielinska E, Wang X, et al. Human intrathymic lineage commitment is marked by differential CD7 expression: identification of CD7− lympho-myeloid thymic progenitors. Blood. 2008 Feb. 1; 111(3):1318-26.

4. Reinhold U, Abken H. CD4+ CD7− T cells: a separate subpopulation of memory T cells?J Clin Immunol. 1997 July; 17(4):265-71.
5. Ware R E, Hart M K, Haynes B F. Induction of T cell CD7 gene transcription by nonmitogenic ionomycin-induced transmembrane calcium flux. J Immunol Baltim Md 1950. 1991 Oct. 15; 147(8):2787-94.
6. Rabinowich H, Lin W C, Herberman R B, Whiteside T L. Signaling via CD7 molecules on human NK cells. Induction of tyrosine phosphorylation and beta 1 integrin-mediated adhesion to fibronectin. J Immunol Baltim Md 1950. 1994 Oct. 15; 153(8):3504-13.
7. Lee D M, Staats H F, SundyJS, Patel D D, Sempowski G D, Scearce R M, et al. Immunologic characterization of CD7-deficient mice. J Immunol Baltim Md 1950. 1998 Jun. 15; 160(12):5749-56.
8. Sempowski G D, Lee D M, Scearce R M, Patel D D, Haynes B F. Resistance of CD7-deficient mice to lipopolysaccharide-induced shock syndromes. J Exp Med. 1999 Mar. 15; 189(6):1011-6.
9. Carriere D, Arcier J M, Derocq J M, Fontaine C, Richer G. Antigenic modulation induced by four monoclonal antibodies adsorbed on gold particles (specificity anti-CD4, anti-CD5, anti-CD7, and anti-150-kDa antigen): Relationship between modulation and cytotoxic activity of immunotoxins. Exp Cell Res. 1989 May; 182(1):114-28.
10. Sharma L C, Muirhead N, Lazarovits A I. Human mouse chimeric CD7 monoclonal antibody (SDZCHH380) for the prophylaxis of kidney transplant rejection: analysis beyond 4 years. Transplant Proc. 1997 March; 29(1-2): 323-4.
11. Rappl G, Abken H, Muche J M, Sterry W, Tilgen W, Andre S, et al. CD4+CD7− leukemic T cells from patients with Sezary syndrome are protected from galectin-1-triggered T cell death. Leukemia. 2002 May; 16(5):840-5.
12. Png Y T, Vinanica N, Kamiya T, Shimasaki N, Coustan-Smith E, Campana D. Blockade of CD7 expression in T cells for effective chimeric antigen receptor targeting ofT-cell malignancies. Blood Adv. 2017 Nov. 28; 1(25): 2348-60.
13. Kita K, Miwa H, Nakase K, Kawakami K, Kobayashi T, Shirakawa S, et al. Clinical importance of CD7 expression in acute myelocytic leukemia. The Japan Cooperative Group of Leukemia/Lymphoma. Blood. 1993 May 1; 81(9):2399-405.
14. Rohrs S, Scherr M, Romani J, Zaborski M, Drexler H G, Quentmeier H. CD7 in acute myeloid leukemia: correlation with loss of wild-type CEBPA, consequence of epigenetic regulation. J Hematol OncolJ Hematol Oncol. 2010 Apr. 14; 3:15.
15. Keizer M P, Kamp A M, Aarts C, Geisler J, Caron H N, van de Wetering M D, et al. The High Prevalence of Functional Complement Defects Induced by Chemotherapy. Front Immunol. 2016; 7:420.
16. Diebolder C A, Beurskens F J, de Jong R N, Koning R I, Strumane K, Lindorfer M A, et al. Complement is activated by IgG hexamers assembled at the cell surface. Science. 2014 Mar. 14; 343(6176):1260-3.
17. Heinrich G, Gram H, Kocher H P, Schreier M H, Ryffel B, Akbar A, et al. Characterization of a human T cell-specific chimeric antibody (CD7) with human constant and mouse variable regions. J Immunol Baltim Md 1950. 1989 Dec. 1; 143(11):3589-97.
18. Ravandi F, Aribi A, O'Brien S, Faderl S, Jones D, Ferrajoli A, et al. Phase I I study of alemtuzumab in combination with pentostatin in patients with. J Clin Oncol Off J Am Soc Clin Oncol. 2009 Nov. 10; 27(32): 5425-30.
19. Cooper M L, Choi J, Staser K, Ritchey J K, Devenport J M, Eckardt K, et al. An "off-the-shelf" fratricide-resistant CAR-T for the treatment of T cell hematologic malignancies. Leukemia. 2018 Feb. 20;
20. Haapaniemi E, Botla S, Persson J, Schmierer B, Taipale J. CRISPR-Cas9 genome editing induces a p53-mediated DNA damage response. Nat Med. 2018 July; 24(7):927-30.
21. Kosicki M, Tomberg K, Bradley A. Repair of double-strand breaks induced by CRISPR-Cas9 leads to large deletions and complex rearrangements. Nat Biotechnol. 2018 September; 36(8):765-71.
22. Van Vlierberghe P, Ferrando A. The molecular basis of T cell acute lymphoblastic leukemia. J Clin Invest. 2012 October; 122(10):3398-406.
23. Coustan-Smith E, Mullighan C G, Onciu M, Behm F G, Raimondi S C, Pei D, et al. Early T-cell precursor leukaemia: a subtype of very high-risk acute lymphoblastic leukaemia. Lancet Oncol. 2009 February; 10(2):147-56.
24. Marks D I, Paietta E M, Moorman A V, Richards S M, Buck G, DeWald G, et al. T-cell acute lymphoblastic leukemia in adults: clinical features, immunophenotype, cytogenetics, and outcome from the large randomized prospective trial (UKALLXII/ECOG 2993). Blood. 2009 Dec. 10; 114(25):5136-45.
25. Aldoss I, Bargou R C, Nagorsen D, Friberg G R, Baeuerle P A, Forman S J. Redirecting T cells to eradicate B-cell acute lymphoblastic leukemia: bispecific. Leukemia. 2017 April; 31(4):777-87.
26. Lee E-C, Liang Q, Ali H, Bayliss L, Beasley A, Bloomfield-Gerdes T, et al. Complete humanization of the mouse immunoglobulin loci enables efficient therapeutic antibody discovery. Nat Biotechnol. 2014 April; 32(4):356-63.
27. Phanse Y, Ramer-Tait A E, Friend S L, Carrillo-Conde B, Lueth P, Oster C J, et al. Analyzing cellular internalization of nanoparticles and bacteria by multi-spectral imaging flow cytometry. United States; 2012.
28. de Jong R N, Beurskens F J, Verploegen S, Strumane K, van Kampen M D, Voorhorst M, et al. A Novel Platform for the Potentiation of Therapeutic Antibodies Based on Antigen-Dependent Formation of IgG Hexamers at the Cell Surface. PLoS Biol. 2016 January; 14(1):e1002344.
29. Agnusdei V, Minuzzo S, Frasson C, Grassi A, Axelrod F, Satyal S, et al. Therapeutic antibody targeting of Notch1 in T-acute lymphoblastic leukemia xenografts. Leukemia. 2014 February; 28(2):278-88.
30. Jung L K, Roy A K, Chakkalath H R. CD7 augments T cell proliferation via the interleukin-2 autocrine pathway. Cell Immunol. 1992 Apr. 15; 141(1):189-99.
31. Markiewski M M, Lambris J D. The role of complement in inflammatory diseases from behind the scenes into the spotlight. Am J Pathol. 2007 September; 171(3):715-27.
32. Kola A, Baensch M, Bautsch W, Hennecke M, Klos A, Casaretto M, et al. Epitope mapping of a C5a neutralizing mAb using a combined approach of phage display, synthetic peptides and site-directed mutagenesis. Immunotechnology Int J Immunol Eng. 1996 June; 2(2):115-26.
33. Baum W, Steininger H, Bair H J, Becker W, Hansen-Hagge T E, Kressel M, et al. Therapy with CD7 monoclonal antibody TH-69 is highly effective for xenografted human T-cell ALL. Br J Haematol. 1996 November; 95(2):327-38.

34. Matlung H L, Babes L, Zhao X W, van Houdt M, Treffers L W, van Rees D J, et al. Neutrophils Kill Antibody-Opsonized Cancer Cells by Trogoptosis. Cell Rep. 2018 Jun. 26; 23(13):3946-3959.e6.

35. Frankel A E, Laver J H, Willingham M C, Burns L J, Kersey J H, Vallera D A. Therapy of patients with T-cell lymphomas and leukemias using an anti-CD7 monoclonal antibody-ricin A chain immunotoxin. Leuk Lymphoma. 1997 July; 26(3-4):287-98.

36. DeAngelo D J, Yu D, Johnson J L, Coutre S E, Stone R M, Stopeck A T, et al. Nelarabine induces complete remissions in adults with relapsed or refractory. Blood. 2007 Jun. 15; 109(12):5136-42.

37. Jain N, Lamb A V, O'Brien S, Ravandi F, Konopleva M, Jabbour E, et al. Early T-cell precursor acute lymphoblastic leukemia/lymphoma (ETP-ALL/LBL) in adolescents and adults: a high-risk subtype. Blood. 2016 Apr. 14; 127(15):1863-9.

Glossary

AML acute myeloid leukaemia
ADCC antibody-dependent cell-mediated cytotoxicity
ADCP antibody-dependent cell-mediated phagocytosis
CAR-T chimeric antigen receptor T cells
CDC complement-dependent cytotoxicity
CEBPA CCAAT/enhancer-binding protein alpha gene
CRP complement regulatory protein
DC Developmental Candidate
HSC haernatopoietic stem cell
mAb monoclonal antibody
MOA mode of action
MRD minimal residual disease
PBMC peripheral blood mononuclear cell
SoC standard of care
Tagg aggregation temperature
T-ALL T-cell acute lymphoblastic leukaemia
Tm melting temperature
T-PLL V-cell prolymphocytic leukemia. Glossary
AML acute myeloid leukaemia
ADCC antibody-dependent cell-mediated cytotoxicity
ADCP antibody-dependent cell-mediated phagocytosis
CAR-T chimeric antigen receptor T cells
CDC complement-dependent cytotoxicity
CEBPA CCAAT/enhancer-binding protein alpha gene
CRP complement regulatory protein
DC Developmental Candidate
HSC haematopoietic stem cell
mAb monoclonal antibody
MOA mode of action
MRD minimal residual disease
PBMC peripheral blood mononuclear cell
SoC standard of care
Tagg aggregation temperature
T-ALL T-cell acute lymphoblastic leukaemia
Tm melting temperature
T-PLL T-cell prolymphocytic leukemia

TABLE 1

Affinity characterization measured by SPR. Kinetic rates and Equilibrium binding constants from SPR of mAbs were obtained by global fitting of sensorgrams using a 1:1 Interaction Model.

| | Human CD7 | | | Cynomolgus CD7 | | |
|---|---|---|---|---|---|---|
| | ka, $M^{-1}s^{-1}$ | kd, $s^{-1}$ | KD, nM | ka, $M^{-1}s^{-1}$ | kd, $s^{-1}$ | KD, nM |
| RFT2 | $6.11 \times 10^5$ | $3.70 \times 10 - 3$ | 6.225 | $5.29 \times 10^5$ | $2.54 \times 10^{-2}$ | 50.765 |
| TH69 | $4.51 \times 10^5$ | $1.25 \times 10 - 4$ | 0.279 | nbs | nbs | nbs |
| 1741G09 | $4.16 \times 10^5$ | $1.92 \times 10 - 3$ | 4.735 | $4.24 \times 10^5$ | $6.11 \times 10^{-4}$ | 0.145 |
| 1734F05 | $3.69 \times 10^5$ | $3.56 \times 10 - 4$ | 0.980 | $1.65 \times 10^5$ | $6.42 \times 10^{-4}$ | 3.895 |

nbs = No binding observed.

TABLE 2

Maximum killing and EC50 values for lead mAbs on CEM cells in the CDC assays. The mean max killing and EC50 values were obtained from the experiments in FIG. 5.

| MAbs | Maximum killing | $EC_{50}$ |
|---|---|---|
| 1730C02 E345R | 93.2% | 0.37 pM |
| 1734E10 E345R | 8.8% | 0.09 nM |
| 1734F05 E345R | 100.1% | 1.16 nM |
| 1738B07 E345R | 75.4% | 2.25 nM |
| 1741E04 E345R | 99.8% | 0.12 nM |
| 1741G09 E345R | 99.5% | 0.12 nM |
| 1896A03 E345R | 69.5% | 0.60 nM |
| TH69 E345R | 87.1% | 0.21 nM |
| RFT2 E345R | 98.5% | 0.22 nM |

TABLE 3

Maximum killing and $EC_{50}$ values for 1741G09 E430G on 14 T-ALL cell lines in the CDC assays. These data were obtained from the experiments from FIG. 8. Their relative expression levels of CD7 are based on the data from FIGS. 19 and 20

| T-ALL cell line | Source | Maximum killing | $EC_{50}$ | CD7 expression |
|---|---|---|---|---|
| PDTALL-47 | Relapsed | 99.8% | 47 pM | |
| HSB | In vitro cell line | 97.7% | 161 pM | |
| PDTALL-AD4 | Relapsed | 99.0% | 79 pM | |
| PDTALL-51R | Relapsed | 99.7% | 86 pM | |
| PDTALL-39 | Relapsed | 98.8% | 80 pM | |
| PDTALL-8 | Non-relapsed | 98.5% | 75 pM | |
| CEM | In vitro cell line | 89.5% | 129 pM | |
| pDTALL-16 | Non-relapsed | 96.1% | 187 pM | |
| pDTALL-46 | Relapsed | 78.9% | 322 pM | |
| PDTALL-Ad2R | Relapsed | 93.3% | 374 pM | |
| PDTALL-12 | Non-relapsed | 87.2% | 368 pM | |
| PDTALL-11 | Non-relapsed | 88.5% | 365 pM | |
| PDTALL-13 | Non-relapsed | 33.6% | 588 pM | |
| PDTALL-18 | Non-relapsed | 67.8% | 253 pM | |

TABLE 4

Cytokine levels from PBMCs treated with 1741G09 E430G and control antibodies. IgG1 and IgG1 E430G antibodies were included as negative controls, and anti-CD3 and anti-CD28 as positive controls. PBMCs from 5 donors were treated with different antibodies at the concentration of 60 μg/ml at 37° C. for 48 hours.
1741G09 E430G

| Cytokines | mAb, 60 μg/ml | Donor 1 | Donor 2 | Donor 3 | Donor 4 | Donor 5 | Mean | SD (pg/mL) | p value to | p value to |
|---|---|---|---|---|---|---|---|---|---|---|
| IFNg | 1731G09 E430G | 379.4 | 33.5 | 44.2 | 119.6 | 37.3 | 122.8 | 379.4 | 0.0688 | 0.0185 |
| | IgG1 E430G | 324.0 | 16.4 | 21.1 | 48.3 | 25.1 | 87.0 | 324.0 | 0.1957 | |
| | IgG1 | 205.5 | 17.0 | 26.2 | 37.5 | 33.2 | 63.9 | 205.5 | | |
| | anti-CD3 | 81768.0 | 15838.5 | 104409.0 | 79869.9 | 16352.7 | 59647.6 | 104409.0 | 0.0156 | |
| | anti-CD28 | 176706.2 | 39510.9 | 332610.1 | 234603.9 | 27971.4 | 162280.5 | 332610.1 | 0.0246 | |
| IL-2 | 1731G09 E430G | 27.2 | 6.3 | — | 39.4 | 48.8 | 30.4 | 48.8 | 0.1885 | 0.1410 |
| | IgG1 E430G | 27.1 | 12.1 | 3.8 | 17.7 | 27.7 | 17.7 | 27.7 | 0.4268 | |
| | IgG1 | 25.4 | 13.1 | 1.5 | 32.1 | 11.5 | 16.7 | 32.1 | | |
| | anti-CD3 | 21.1 | 30.5 | 72.4 | 173.0 | 14.7 | 62.3 | 173.0 | 0.0845 | |
| | anti-CD28 | 19123.8 | 7147.5 | 29754.7 | 23012.6 | 4167.3 | 16641.2 | 29754.7 | 0.0130 | |
| IL-8 | 1731G09 E430G | 47373.5 | 39571.9 | 18384.7 | 55423.0 | 25245.7 | 37199.8 | 55423.0 | 0.0035 | 0.0157 |
| | IgG1 E430G | 41038.1 | 30897.0 | 18371.4 | 40096.4 | 12786.3 | 28637.8 | 41038.1 | 0.0037 | |
| | IgG1 | 17713.0 | 18059.4 | 9150.8 | 17990.1 | 3425.5 | 13267.8 | 18059.4 | | |
| | anti-CD3 | 23594.2 | 40748.8 | 23779.7 | 26202.6 | 38104.2 | 30485.9 | 40748.8 | 0.0153 | |
| | anti-CD28 | 23022.4 | 61283.1 | 38889.5 | 58715.7 | 41168.1 | 44615.8 | 61283.1 | 0.0052 | |
| Mip-1α | 1731G09 E430G | 3818.5 | 1850.7 | 705.4 | 3436.7 | 360.7 | 2034.4 | 3818.5 | 0.0240 | 0.0676 |
| | IgG1 E430G | 3240.0 | 1991.0 | 593.9 | 2650.1 | 147.5 | 1724.5 | 3240.0 | 0.0162 | |
| | IgG1 | 1188.1 | 662.7 | 194.1 | 722.4 | — | 691.8 | 1188.1 | | |
| | anti-CD3 | 28382.7 | 14726.4 | 18475.3 | 29620.4 | 23177.8 | 22876.5 | 29620.4 | 0.0042 | |
| | anti-CD28 | 32584.0 | 9903.4 | 23311.9 | 28880.2 | 13288.8 | 21593.7 | 32584.0 | 0.0091 | |
| TNFα | 1731G09 E430G | 1283.5 | 486.3 | 662.4 | 1427.8 | 1157.8 | 1003.6 | 1427.8 | 0.0047 | 0.0333 |
| | IgG1 E430G | 1190.3 | 319.9 | 590.8 | 936.5 | 493.1 | 706.1 | 1190.3 | 0.0044 | |
| | IgG1 | 496.4 | 137.5 | 211.0 | 247.1 | 92.0 | 236.8 | 496.4 | | |
| | anti-CD3 | 12810.6 | 10502.9 | 10746.7 | 15180.0 | 10199.3 | 11887.9 | 15180.0 | 0.0001 | |
| | anti-CD28 | 34118.4 | 14593.3 | 46209.1 | 28840.4 | 13741.9 | 27500.6 | 46209.1 | 0.0055 | |
| IL-10 | 1731G09 E430G | 31.4 | 20.1 | 35.9 | 33.7 | 83.1 | 40.8 | 83.1 | 0.1318 | 0.0778 |
| | IgG1 E430G | 28.1 | 11.7 | 37.3 | 22.4 | 45.7 | 29.0 | 45.7 | 0.3309 | |
| | IgG1 | 34.3 | 9.5 | 38.2 | 25.0 | 28.7 | 27.1 | 38.2 | | |
| | anti-CD3 | 13934.0 | 5430.3 | 93210.8 | 20.2 | 8704.4 | 24259.9 | 93210.8 | 0.1179 | |
| | anti-CD28 | 5379.4 | 1391.5 | 6882.0 | 23.6 | 1192.3 | 2973.7 | 6882.0 | 0.0453 | |
| IL-12p40 | 1731G09 E430G | 10.1 | — | — | — | — | 10.1 | 10.1 | | |
| | IgG1 E430G | 10.0 | — | — | — | — | 10.0 | 10.0 | | |
| | IgG1 | 12.8 | — | — | — | — | 12.8 | 12.8 | | |
| | anti-CD3 | 29.1 | — | 43.0 | — | 14.7 | 29.0 | 43.0 | | |
| | anti-CD28 | 9.5 | — | 21.7 | — | — | 15.6 | 21.7 | | |
| IL-17A | 1731G09 E430G | 7.0 | 1.0 | 18.1 | 4.9 | 16.8 | 9.6 | 18.1 | 0.1079 | 0.1130 |
| | IgG1 E430G | 8.3 | 0.9 | 14.9 | 2.3 | 4.9 | 6.3 | 14.9 | 0.2687 | |
| | IgG1 | 6.8 | 1.3 | 13.6 | 4.0 | 3.5 | 5.8 | 13.6 | | |
| | anti-CD3 | 2812.6 | 1008.4 | 2468.3 | 6.1 | 2723.2 | 1803.7 | 2812.6 | 0.0158 | |
| | anti-CD28 | 2801.1 | 1136.5 | 2424.8 | 5.6 | 1464.9 | 1566.6 | 2801.1 | 0.0170 | |
| IL-1β | 1731G09 E430G | 66.0 | 55.7 | 9.7 | 64.2 | 37.5 | 46.6 | 66.0 | 0.0043 | 0.0130 |
| | IgG1 E430G | 26.0 | 15.0 | 10.4 | 43.1 | 6.4 | 20.2 | 43.1 | 0.0193 | |
| | IgG1 | 15.9 | 11.0 | 2.4 | 20.7 | 1.1 | 10.2 | 20.7 | | |
| | anti-CD3 | 728.9 | 419.1 | 740.0 | 14.5 | 315.6 | 443.6 | 740.0 | 0.0173 | |
| | anti-CD28 | 687.5 | 341.3 | 454.0 | 15.1 | 198.0 | 339.2 | 687.5 | 0.0226 | |
| IL-6 | 1731G09 E430G | 188.6 | 208.3 | 106.2 | 219.6 | 32.1 | 151.0 | 219.6 | 0.0043 | 0.0579 |
| | IgG1 E430G | 159.4 | 116.7 | 105.0 | 205.9 | 10.3 | 119.5 | 205.9 | 0.0154 | |
| | IgG1 | 115.8 | 105.6 | 60.5 | 157.8 | 5.7 | 89.1 | 157.8 | | |
| | anti-CD3 | 2055.5 | 506.1 | 2890.9 | 114.3 | 533.4 | 1220.0 | 2890.9 | 0.0520 | |
| | anti-CD28 | 2408.0 | 570.3 | 2475.5 | 113.7 | 384.0 | 1190.3 | 2475.5 | 0.0505 | |

TABLE 5

| Immuno-phenotype categorisation of T-ALL/LBL using WHO criteria (37) | | | | | | | | |
|---|---|---|---|---|---|---|---|---|
| | CD1a | CD2 | cCD3 | sCD3 | CD4 | CD8 | CD7 | CD34 |
| Pro-T | − | − | + | − | − | − | + | +/− |
| Pre-T | − | + | + | − | − | − | + | +/− |
| Cortical T (Thymic T) | + | + | + | − | + | + | + | − |
| Medullary T (Mature T) | − | + | + | + | Either $CD4^+$ or $CD8^+$ (but not both) | | + | − |

TABLE 6

The statistical comparison of the antibodies is presented in FIG. 6

| Holm-Sidak's multiple comparisons test | Mean Diff. | Significant | Summary | Adjusted P Value |
|---|---|---|---|---|
| 1730C02 E345R vs. 1734E10 E345R | 95.95 | Yes | **** | <0.0001 |
| 1730C02 E345R vs. 1734F05 E345R | 50.83 | Yes | ** | 0.0062 |
| 1730C02 E345R vs. 1738B07 E345R | 60.17 | Yes | ** | 0.0012 |
| 1730C02 E345R vs. 1741E04 E345R | −40.73 | Yes | * | 0.0368 |
| 1730C02 E345R vs. 1741G09 E345R | −38.27 | Yes | * | 0.0491 |
| 1730C02 E345R vs. 1896A03 E345R | 40.24 | Yes | * | 0.038 |
| 1730C02 E345R vs. TH69 E345R | −2.167 | No | ns | 0.9728 |
| 1730C02 E345R vs. RFT2 E345R | −14.1 | No | ns | 0.8255 |
| 1730C02 E345R vs. Isotype control E345R | 110.7 | Yes | **** | <0.0001 |
| 1734E10 E345R vs. 1734F05 E345R | −45.11 | Yes | * | 0.0175 |
| 1734E10 E345R vs. 1738B07 E345R | −35.77 | No | ns | 0.0675 |
| 1734E10 E345R vs. 1741E04 E345R | −136.7 | Yes | **** | <0.0001 |
| 1734E10 E345R vs. 1741G09 E345R | −134.2 | Yes | **** | <0.0001 |
| 1734E10 E345R vs. 1896A03 E345R | −55.71 | Yes | ** | 0.0027 |
| 1734E10 E345R vs. TH69 E345R | −98.11 | Yes | **** | <0.0001 |
| 1734E10 E345R vs. RFT2 E345R | −110 | Yes | **** | <0.0001 |
| 1734E10 E345R vs. Isotype control E345R | 14.78 | No | ns | 0.8255 |
| 1734F05 E345R vs. 1738B07 E345R | 9.34 | No | ns | 0.8542 |
| 1734F05 E345R vs. 1741E04 E345R | −91.57 | Yes | **** | <0.0001 |
| 1734F05 E345R vs. 1741G09 E345R | −89.1 | Yes | **** | <0.0001 |
| 1734F05 E345R vs. 1896A03 E345R | −10.59 | No | ns | 0.8542 |
| 1734F05 E345R vs. TH69 E345R | −53 | Yes | ** | 0.0042 |
| 1734F05 E345R vs. RFT2 E345R | −64.93 | Yes | *** | 0.0005 |
| 1734F05 E345R vs. Isotype control E345R | 59.89 | Yes | ** | 0.0012 |
| 1738B07 E345R vs. 1741E04 E345R | −100.9 | Yes | **** | <0.0001 |
| 1738B07 E345R vs. 1741G09 E345R | −98.44 | Yes | **** | <0.0001 |
| 1738B07 E345R vs. 1896A03 E345R | −19.93 | No | ns | 0.5836 |

TABLE 6-continued

The statistical comparison of the antibodies is presented in FIG. 6

| Holm-Sidak's multiple comparisons test | Mean Diff. | Significant | Summary | Adjusted P Value |
|---|---|---|---|---|
| 1738B07 E345R vs. TH69 E345R | −62.34 | Yes | *** | 0.0008 |
| 1738B07 E345R vs. RFT2 E345R | −74.27 | Yes | **** | <0.0001 |
| 1738B07 E345R vs. Isotype control E345R | 50.55 | Yes | ** | 0.0063 |
| 1741E04 E345R vs. 1741G09 E345R | 2.467 | No | ns | 0.9728 |
| 1741E04 E345R vs. 1896A03 E345R | 80.97 | Yes | **** | <0.0001 |
| 1741E04 E345R vs. TH69 E345R | 38.57 | Yes | * | 0.0491 |
| 1741E04 E345R vs. RFT2 E345R | 26.63 | No | ns | 0.2915 |
| 1741E04 E345R vs. Isotype control E345R | 151.5 | Yes | **** | <0.0001 |
| 1741G09 E345R vs. 1896A03 E345R | 78.51 | Yes | **** | <0.0001 |
| 1741G09 E345R vs. TH69 E345R | 36.1 | No | ns | 0.0675 |
| 1741G09 E345R vs. RFT2 E345R | 24.17 | No | ns | 0.3812 |
| 1741G09 E345R vs. Isotype control E345R | 149 | Yes | **** | <0.0001 |
| 1896A03 E345R vs. TH69 E345R | −42.41 | Yes | * | 0.0282 |
| 1896A03 E345R vs. RFT2 E345R | −54.34 | Yes | ** | 0.0034 |
| 1896A03 E345R vs. Isotype control E345R | 70.49 | Yes | *** | 0.0002 |
| TH69 E345R vs. RFT2 E345R | −11.93 | No | ns | 0.8542 |
| TH69 E345R vs. Isotype control E345R | 112.9 | Yes | **** | <0.0001 |
| RFT2 E345R vs. Isotype control E345R | 124.8 | Yes | **** | <0.0001 |

TABLE 7

Clinical and genetic profiles of PDTALL cell lines

| PEDIATR. TALL | SAMPLE | 1° TTL | Risk | Pheno-type | PPR/ PGR | N1 | Notch1 status | FB W7 | FBW7 status | PTEN status (WB) | GEP profile | p53 | status p53 | in vitro culture | TCR | STR |
|---|---|---|---|---|---|---|---|---|---|---|---|---|---|---|---|---|
| 1 | PD-TALL 1 | 147 | SR | T int | PGR | | HD mut. | | mut. | nd | | | wt | no | | |
| 2 | PD-TALL 5 | 105 | MR | T int | PGR | | PEST mut. | | wt | nd | | | | yes (>5 days) | | |
| 3 | PD-TALL 8 | 132 | MR | T int | PGR | | wt | | wt | positive | TAL-LMO | | | no | | |
| 4 | PD-TALL 7 | 132 | MR | T int | PGR | | HD mut. | | wt | nd | | | wt | yes (>4 days) | | |
| 5 | PD-TALL 6 | 72 | MR | T int | PPR | | HD + PST mut. | | wt | positive | TLX1 | | wt | no | | |
| 6 | PD-TALL 9 | 70 | HR | Early T | relapse (de-ceased) | | wt | | mut. | positive | TAL-LMO | | wt | no | | |
| 7 | PD-TALL 10 | 41 | MR | Early T | PGR | | HD mut. | | wt | positive | | | wt | no | | |
| 8 | PD-TALL 11 | 83 | MR | Thym | PPR | | HD mut. | | wt | negative | | | wt | yes (>2 days) | | |
| 9 | PD-TALL 12 | 34 | MR | Early T | PGR | | HD + PESY mut. | | wt | positive | | | wt | yes (>4 days) | | |
| 10 | PD-TALL 13 | 35 | HR | T | (de-ceased) | | wt | | wt | negative | TAL-LMO | | | yes (>2 days) | | |
| 11 | PD-TALL 14 | 75 | | int/mat | PPR | | wt | | wt | nd | | | | yes (>4 days) | | |
| 12 | PD-TALL 15 | 48 | MR | T | PPR | | wt | | wt | nd | TALL-LMO | | wt | yes (>5 days) | | |
| 13 | PD-TALL 16 | 116 | HR | T mat | PPR | | wt | | wt | nd | TLX3 (pat./ xeno TAL-LMO) | | wt | yes (>4 days) | | |
| 14 | PD-TALL 18 | 75 | MR | T int | PPR | | mut. (ex28) JME | | wt | positive | | | | nd | | |
| 15 | PD-TALL 19 | 119 | MR | Early T | PGR | | HD + PEST mut. | | wt | nd | | | | no | | |
| 16 | PD-TALL 20 | 63 | MR | T int | PGR | | HD mut. | | wt | nd | | | wt | nd | | |
| 17 | PD-TALL 21 | 190 | HR | T int | PGR | | HD mut. | | wt | nd | | | | yes (>4 days) | | |
| 18 | PD-TALL 22 | 35 | MR | Early T | PGR | | PEST mut. | | wt | nd | | | | no | | |
| 19 | PD-TALL 25 | 35 | MR | T int | PPR | | HD + PSET mut. | | wt | nd | TALL-LMO | | | no | | |
| 20 | PD-TALL 26 | 56 | MR | T int | PGR | | HD + PEST mut. | | wt | negative | | | | no | | |
| 21 | PD-TALL 27 | 36 | SR | Early T | PGR | | HD + TAD MUT. | | wt | negative | | | | yes (>5 days) | | |
| 22 | PD-TALL 28 | 41 | SR | T int | PGR | | wt | | wt | negative | TALL-LMO | | | yes (> 5 days) | | |
| 23 | PD-TALL 29 | 159 | SR | T int | PPR | | wt | | wt | nd | TALL-LMO | | | nd | | |
| 24 | PD-TALL 30 | 61 | HR | Early T | PGR | | wt | | wt | positive | | | | nd | | |
| 25 | PD-TALL 31 | 19 | SR | T int | PGR | | TAD mut. | | wt | nd | TAL-LMO | | | nd | | |
| 26 | PD-TALL 32 | 99 | SR | Early T | PPR | | HD mut. | | wt | nd | | | | no | | |
| 27 | PD-TALL 33 | 17 | SR | T int | PGR | | PEST mut. | | mut. | nd | | | | no | | |
| 28 | PD-TALL 36 | 92 | SR | T int | PGR | | HD mut. | | wt | nd | | | | nd | | |
| 29 | PD-TALL 37 | 93 | SR | T int | PGR | | PEST mut. | | wt | nd | TALL-LMO | | | yes (>5 days) | | |
| 30 | PD-TALL 39 | 89 | SR | Thym | relapse (de-ceased) | | HD mut. | | wt | nd | | | mut. | nd | | |

TABLE 7-continued

Clinical and genetic profiles of PDTALL cell lines

| PEDIATR. TALL | SAMPLE | 1° TTL | Risk | Pheno-type | PPR/PGR | N1 | Notch1 status | FB W7 | FBW7 status | PTEN status (WB) | GEP profile | p53 | status p53 | in vitro culture | TCR | STR |
|---|---|---|---|---|---|---|---|---|---|---|---|---|---|---|---|---|
| 31 | PD-TALL 40 | 91 | SR | T int | PPR | | wt | | wt | nd | | | | yes (>4 days) | | |
| 32 | PD-TALL 41 | 27 | SR | T mat | PPR | | wt | | wt | nd | | | | nd | | |
| 33 | PD-TALL 43 | 41 | SR | T int | PGR | | HD mut. | | mut. | no | TALL-LMO | | | yes (>4 days) | | |
| 34 | PD-TALL 44 | 21 | na | T int | PGR | | HD mut. | | mut. | nd | | | | nd | | |
| 35 | PD-TALL 45 | 33 | na | Thym | PPR | | HD mut. | | wt | nd | | | | nd | | |
| 36 | PD-TALL 46 | 115 | MR | Early T | relapse PPR | | HD mut. | | mut. | nd | TLX3 | | mut. | no | | |
| 37 | PD-TALL 47 | 88 | na | Early T | relapse | | HD mut. | | mut. | positive | | | mut. | yes (>2 days) | | |
| 38 | PD-TALL 48 | 41 | na | | onset | | wt | | wt | negative | | | wt | nd | | |
| 39 | PD-TALL 51D | 33 | na | Early T | onset | | wt | | wt | negative | | | wt | nd | | |
| 40 | PD-TALL 51R | 88 | na | Early T/ETP like | relapse | | wt | | wt | positive | | | wt | yes (>2 days) | | |
| 41 | PD-TALL 38R | | | Mixed Leuk. (AML/TALL) | relapse | | mut. (ex28) JME | | wt | nd | | | | nd | | |
| | ADULT TALL | | | | onset/relapse | | | | | | | | | | | |
| 1 | PD-TALL-Adf | 65 | na | T | onset | | wt | | wt | nd | | | | nd | | |
| 2/E | PD-TALL-Ad2E | 54 | na | T | onset | | PEST mut. Het | | wt | nd | | | wt | nd | | |
| 2/R | PD-TALL-Ad2/R | 27 | na | T | relapse | | PEST mut. Hom. | | wt | nd | | | mut. | nd | | |
| | | | | | | | | | | | | | mut. | nd | | |
| 3 | PD-TALL-AM3 | 98 | na | T | relapse | | wt | | wt | nd | | | | | | |
| 4 | PD-TALL-Ad4 | 28 | | T | relapse | | HD mut. | | wt | nd | | | mut. | nd | | |

KEY TO DESCRIPTORS

| | |
|---|---|
| 1° TTL: | primary time to leukemia assessed in xenografted mouse |
| Risk: | minimal residual disease risk - SR for standard risk and MR for medium risk |
| Phenotype: | indication of stages of TLL cells |
| PPR/PGR: | prednisone poor responder/prednisone good responder |
| N1 | Notch1 information |
| Notch1 status: | genotypes of Notch 1 gene |
| FBW7: | F-box and WD repeat domain-containing protein 7 information |
| FBW7 status: | genotype of FBW7 gene |
| PTEN status: | phosphatase and tensin homolog expression |
| GEP profile | gene expression profile |
| p53: | p53 gene information |
| p53 status: | genotype of p53 gene |
| In vitro culture: | ability of cell lines growing in vitro passage |
| TCR: | T cell receptor re-arrangement exits |
| STR: | short tandem repeats exit |

TABLE 8

Biophysical summary for 1741G09 E430G

| Research code | 1741G09 E430G |
|---|---|
| Immunogen | Recombinant human and cynomolgus CD7 MEFs (mouse embryonic fibroblasts) |
| Affinity to soluble CD7 | Human CD7: 4.75 nM; cynomolgus CD7: 0.15 nM |
| $EC_{50}$ value for CEM cell depletion in the in vitro human CDC assay | 100-150 pM; maximum killing ~100% |

TABLE 8-continued

Biophysical summary for 1741G09 E430G

| Research code | 1741G09 E430G |
|---|---|
| Transient expression/CHOE7 (pTT5) | 345 to 679 mg/L |
| Stable expression pools/ Lonza Xceed CHO | 353 to 445 mg/L |
| Tm | 73.0° C. in 10 mM sodium succinate, 50 mM Arginine-HCl, pH 5.5 |

TABLE 8-continued

| Biophysical summary for 1741G09 E430G | |
|---|---|
| Research code | 1741G09 E430G |
| Impurities | No issue with aggregates, purity >95% of Protein A |
| Biophysical data | No significant change in aggregation, fragmentation and activity after freeze thaw, force deamidation and acidic hold. Following oxidation stress, decrease in activity is H202 concentration dependant |

TABLE 9

Sequences
Sequences for use in the present invention.

| Seq ID No: | | | Description | Sequence |
|---|---|---|---|---|
| 1 | G09 | CDRH1 (IMGT) | Amino acid sequence of CDRH1 using IMGT | GFSFSVAW |
| 2 | G09 | CDRH2 (IMGT) | Amino acid sequence of CDRH2 using IMGT | IKRKTDGGTT |
| 3 | G09 | CDRH3 (IMGT) | Amino acid sequence of CDRH3 using IMGT | TTDPLLRYSDWLSHSLMGDV |
| 4 | G09 | CDRH1 (KABAT) | Amino acid sequence of CDRH1 using Kabat | SVAWMS |
| 5 | G09 | CDRH2 (KABAT) | Amino acid sequence of CDRH2 using Kabat | RIKRKTDGGTTDYAAPVKG |
| 6 | G09 | CDRH3 (KABAT) | Amino acid sequence of CDRH3 using Kabat | DPLLRYSDWLSHSLMGDV |
| 7 | G09 | Heavy chain variable region | Amino acid sequence of VH IGHV3-15*01; IGHD3-9*01; IGHJ6*02 CDRH3 = 20 a.a.s Non-germline residues = 17 a.a.s (including junctional insertion and hypermutation) | EVQLVESGGGLVKPGGSLRLSCAASGFSFSVAWMSWVRQAPGKGLEWVGRIKRKTDGGTTDYAAPVKGRFIISRDDSI KALYLQMNSLKTEDTAVYYCTTDPLLRYSDWLSHSLMGDVWGQGTTVTVSS |
| 8 | G09 | Heavy chain variable region | Nucleotide sequence of $V_H$ | GAGGTGCAGCTGGTGGAGTCTGGGGGAGGCTTGGTAAAGCCTGGGGGGTCCCTTAGACTCTCCTGTGCAGCCTCTGGA TTCAGTTTCAGTGTCGCCTGGATGAGCTGGGTCCGCCAGGCTCCAGGGAAGGGGCTGGAGTGGGTTGGCCGTATTAAG CGCAAAACTGATGGTGGGACAACAGACTACGCTGCACCCGTGAAAGGCAGATTCATCATCTCAAGAGATGATTCAATA AAAGCGCTGTATCTGCAAATGAACAGCCTGAAAACCGAGGACACAGCCGTGTATTACTGTACCACAGATCCCTTATTA CGATATTCTGACTGGTTATCCCACTCCCTTATGGGGACGTCTGGGGCCAAGGGACCACGGTCACCGTCTCCTCAG |
| 9 | G09 | Full heavy chain sequence | Amino acid sequence heavy chain | EVQLVESGGGLVKPGGSLRLSCAASGFSFSVAWMSWVRQAPGKGLEWVGRIKRKTDGGTTDYAAPVKGRFIISRDDSI KALYLQMNSLKTEDTAVYYCTTDPLLRYSDWLSHSLMGDVWGQGTTVTVSSASTKGPSVFPLAPSSKSTSGGTAALGC LVKDYFPEPVTVSWNSGALTSGVHTFPAVLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSVMHGALHNHYTQKSLSLSPG |
| 10 | G09 | Full heavy chain sequence | Nucleic acid sequence heavy chain | GAGGTGCAGCTGGTGGAGTCTGGGGGAGGCTTGGTAAAGCCTGGGGGGTCCCTTAGACTCTCCTGTGCAGCCTCTGGA TTCAGTTTCAGTGTCGCCTGGATGAGCTGGGTCCGCCAGGCTCCAGGGAAGGGGCTGGAGTGGGTTGGCCGTATTAAG CGCAAAACTGATGGTGGGACAACAGACTACGCTGCACCCGTGAAAGGCAGATTCATCATCTCAAGAGATGATTCAATA AAAGCGCTGTATCTGCAAATGAACAGCCTGAAAACCGAGGACACAGCCGTGTATTACTGTACCACAGATCCCTTATTA CGATATTCTGACTGGTTATCCCACTCCCTTATGGGGACGTCTGGGGCCAAGGGACCACGGTCACCGTCTCCTCAGGC |

TABLE 9-continued

Sequences
Sequences for use in the present invention.

| Seq ID No: | | | Description | Sequence |
|---|---|---|---|---|
| | | | | CAGCACCAAGGGCCCCTCTGTGTTCCCTCTGGCCCCTTCCAGCAAGTCCACCTCTGGCGGAACAGCCGCTCTGGGCTG CCTCGTGAAGGACTACTTCCCCGAGCCTGTGACCGTGTCCTGGAACTCTGGCGCTCTGACCAGCGGAGTGCACACCTT CCCTGCTGTGCTGCAGTCCTCCGGCCTGTACTCCCTGTCCTCCGTCGTGACCGTGCCTTCCAGCTCTCTGGGCACCCA GACCTACATCTGCAACGTGAACCACAAGCCCTCCAACACCAAGGTGGACAAGAAGGTGGAACCCAAGTCCTGCGACAA GACCCACACCTGTCCCCCTTGTCCTGCCCCTGAACTGCTGGGCGGACCTTCCGTGTTCCTGTTCCCCCCAAAGCCCAA GGACACCCTGATGATCTCCCGGACCCCCGAAGTGACCTGCGTGGTGGTGGATGTGTCCCACGAGGACCCTGAAGTGAA GTTCAATTGGTACGTGGACGGCGTGGAAGTGCACAACGCCAAGACCAAGCCTAGAGAGGAACAGTACAACTCCACCTA CCGGGTGGTGTCCGTGCTGACCGTGCTGCACCAGGATTGGCTGAACGGCAAAGAGTACAAGTGCAAGGTGTCCAACAA GGCCCTGCCTGCCCCCATCGAAAAGACCATCTCCAAGGCCAAGGGCCAGCCCCGGGAACCCCAGGTGTACACACTGCC CCCTAGCAGGGACGAGCTGACCAAGAACCAGGTGTCCCTGACCTGTCTCGTGAAAGGCTTCTACCCCTCCGATATCGC CGTGGAATGGGAGTCCAACGGCCAGCCTGAGAACAACTACAAGACCACCCCCCCTGTGCTGGACTCCGACGGCTCATT CTTCCTGTACAGCAAGCTGACAGTGGACAAGTCCCGGTGGCAGCAGGGCAACGTGTTCTCCTGCTCCGTGATGCACGG CGCCCTGCACAACCACTACACCCAGAAGTCCCTGTCCCTGAGCCCCGGC |
| 11 | G09 | CDRL1 (IMGT) | Amino acid sequence of CDRL1 using IMGT | QNINNY |
| 12 | G09 | CDRL2 (IMGT) | Amino acid sequence of CDRL2 using IMGT | AAS |
| 13 | G09 | CDRL3 (IMGT) | Amino acid sequence of CDRL3 using IMGT | QQTYSIPLTFGGG |
| 14 | G09 | CDRL1 (KABAT) | Amino acid sequence of CDRL1 using KABAT | NNYLN |
| 15 | G09 | CDRL2 (KABAT) | Amino acid sequence of CDRL2 using KABAT | YAASSLQSGVPS |
| 16 | G09 | CDRL3 (KABAT) | Amino acid sequence of CDRL3 using KABAT | QQTYSIPLTFGGG |
| 17 | G09 | Light chain variable region | Amino acid sequence of $V_L$ IGKV1D-39*01; IGKJ4*01 CDRK3 = 9 a.a.s Non-germline residues = 10 a.a.s F - Serine present at this position in the sequence obgtained from the hybridoma; Serine was back engineered to Phenylalanine to improve the expression | DIQMTQSPSSLSASVGDRVAITCRTSQNINNYLNWYQQKPGKAPKPLIYAASSLQSGVPSRFSGSGSGTDFTLTISTL HPEDFATYYCQQTYSIPLTFGGGTKVEIK |
| 18 | G09 | Light chain variable region | Nucleic acid sequence of $V_L$ | GATATCCAGATGACCCAGTCCCCCTCCAGCCTGTCTGCCTCTGTGGGCGACAGAGTGGCCATCACCTGTCGGACCTCC CAGAACATCAACAACTACCTGAACTGGTATCAGCAGAAGCCCGGCAAGGCCCCCAAGCCCCTGATCTACGCTGCTTCC |

TABLE 9-continued

Sequences
Sequences for use in the present invention.

| Seq ID No: | | | Description | Sequence |
|---|---|---|---|---|
| | | | | AGTCTGCAGTCCGGCGTGCCCTCTAGATTCTCCGGCTCTGGCTCTGGCACCGACTTCACCCTGACCATCTCCACCCTG CACCCCGAGGACTTCGCCACCTACTACTGCCAGCAGACCTACTCCATCCCCCTGACCTTTGGCGGAGGCACCAAGGTG GAAATCAAA |
| 19 | G09 | Full light chain sequence | Amino acid sequence light chain | DIQMTQSPSSLSASVGDRVAITCRTSQNINNYLNWYQQKPGKAPKPLIYAASSLQSGVPSRFSGSGSGTDFTLTISTL HPEDFATYYCQQTYSIPLTFGGGTKVEIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSFNRGEC |
| 20 | G09 | Full light chain sequence | Nucleic acid sequence light chain | GATATCCAGATGACCCAGTCCCCCTCCAGCCTGTCTGCCTCTGTGGGCGACAGAGTGGCCATCACCTGTCGGACCTCC CAGAACATCAACAACTACCTGAACTGGTATCAGCAGAAGCCCGGCAAGGCCCCCAAGCCCCTGATCTACGCTGCTTCC AGTCTGCAGTCCGGCGTGCCCTCTAGATTCTCCGGCTCTGGCTCTGGCACCGACTTCACCCTGACCATCTCCACCCTG CACCCCGAGGACTTCGCCACCTACTACTGCCAGCAGACCTACTCCATCCCCCTGACCTTTGGCGGAGGCACCAAGGTG GAAATCAAACGTACGGTGGCCGCTCCCTCCGTGTTCATCTTCCCACCTTCCGACGAGCAGCTGAAGTCCGGCACCGCT TCTGTCGTGTGCCTGCTGAACAACTTCTACCCCCGCGAGGCCAAGGTGCAGTGGAAGGTGGACAACGCCCTGCAGTCC GGCAACTCCCAGGAATCCGTGACCGAGCAGGACTCCAAGGACAGCACCTACTCCCTGTCCTCCACCCTGACCCTGTCC AAGGCCGACTACGAGAAGCACAAGGTGTACGCCTGCGAAGTGACCCACCAGGGCCTGTCTAGCCCCGTGACCAAGTCT TTCAACCGGGGCGAGTGT |
| 21 | F05 | CDRH1 (IMGT) | Amino acid sequence of CDRH1 using IMGT | QSVSSY |
| 22 | F05 | CDRH2 (IMGT) | Amino acid sequence of CDRH2 using IMGT | DTS |
| 23 | F05 | CDRH3 (IMGT) | Amino acid sequence of CDRH3 using IMGT | QQRRNWPLT |
| 24 | F05 | CDRH1 (KABAT) | Amino acid sequence of CDRH1 using Kabat | RVSQSVSSYLA |
| 25 | F05 | CDRH2 (KABAT) | Amino acid sequence of CDRH2 using Kabat | DTSNRAT |
| 26 | F05 | CDRH3 (KABAT) | Amino acid sequence of CDRH3 using Kabat | QQRRNWPLT |
| 27 | F05 | Heavy chain variable region | Amino acid sequence of $V_H$ | EVQLVESGGGLVQPGGSLRLSCAASGFTFSRYAMSWVRQAPGKGLEWVSSISASGATTFYADPVKGRFTISRDNSKKT LYLQMNSLRAEDTAVYYCAKDQDFDILTGYLNWFDPWGQGTLVTVSS |
| 28 | F05 | Heavy chain variable region | Nucleotide sequence of $V_H$ | GAAGTGCAGCTGGTTGAATCTGGCGGCGGATTGGTTCAGCCTGGCGGATCTCTGAGACTGTCTTGTGCCGCCTCCGG TTCACCTTCTCCAGATACGCTATGTCCTGGGTCCGACAGGCTCCTGGCAAAGGACTGGAATGGGTGTCCTCCATCTC TGCCTCTGGCGCCACCACCTTTTACGCCGATCCTGTGAAGGGCAGATTCACCATCAGCCGGGACAACTCCAAGAAAA CCCTGTACCTGCAGATGAACTCCCTGAGAGCCGAGGACACCGCCGTGTACTACTGTGCCAAGGACCAGGACTTCGAC ATCCTGACCGGCTACCTGAATTGGTTCGACCCTTGGGGCCAGGGCACACTGGTTACAGTGTCTAGC |
| 29 | F05 | Full heavy chain | Amino acid sequence heavy chain | EVQLVESGGGLVQPGGSLRLSCAASGFTFSRYAMSWVRQAPGKGLEWVSSISASGATTFYADPVKGRFTISRDNSKKT LYLQMNSLRAEDTAVYYCAKDQDFDILTGYLNWFDPWGQGTLVTVSSASTKGPSVFPLAPSSKSTSGGTAALGCLVKD |

TABLE 9-continued

Sequences
Sequences for use in the present invention.

| Seq ID No: | | | Description | Sequence |
|---|---|---|---|---|
| | | sequence | | YFPEPVTVSWNSGALTSGVHTFPAVLQSSGLYSLSSVVTVPSSSLGTQTYICNVNHKPSNTKVDKKVEPKSCDKTHTC PPCPAPELLGGPSVFLFPPKPKDTLMISRTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRDELTKNQVSLTCLVKGFYPSDIAVEWE SNGQPENNYKTTPPVLDSDGSFFLYSKLTVDKSRWQQGNVFSCSVMHGALHNHYTQKSLSLSPG |
| 30 | F05 | Full heavy chain sequence | Nucleic acid sequence heavy chain | GAAGTGCAGCTGGTTGAATCTGGCGGCGGATTGGTTCAGCCTGGCGGATCTCTGAGACTGTCTTGTGCCGCCTCCGGC TTCACCTTCTCCAGATACGCTATGTCCTGGGTCCGACAGGCTCCTGGCAAAGGACTGGAATGGGTGTCCTCCATCTCT GCCTCTGGCGCCACCACCTTTTACGCCGATCCTGTGAAGGGCAGATTCACCATCAGCCGGGACAACTCCAAGAAAACC CTGTACCTGCAGATGAACTCCCTGAGAGCCGAGGACACCGCCGTGTACTACTGTGCCAAGGACCAGGACTTCGACATC CTGACCGGCTACCTGAATTGGTTCGACCCTTGGGGCCAGGGCACACTGGTTACAGTGTCTAGCGCCAGCACCAAGGGC CCCTCTGTGTTCCCTCTGGCCCCTTCCAGCAAGTCCACCTCTGGCGGAACAGCCGCTCTGGGCTGCCTCGTGAAGGAC TACTTCCCCGAGCCTGTGACCGTGTCCTGGAACTCTGGCGCTCTGACCAGCGGAGTGCACACCTTCCCTGCTGTGCTG CAGTCCTCCGGCCTGTACTCCCTGTCCTCCGTCGTGACCGTGCCTTCCAGCTCTCTGGGCACCCAGACCTACATCTGC AACGTGAACCACAAGCCCTCCAACACCAAGGTGGACAAGAAGGTGGAACCCAAGTCCTGCGACAAGACCCACACCTGT CCCCCTTGTCCTGCCCCTGAACTGCTGGGCGGACCTTCCGTGTTCCTGTTCCCCCCAAAGCCCAAGGACACCCTGATG ATCTCCCGGACCCCCGAAGTGACCTGCGTGGTGGTGGATGTGTCCCACGAGGACCCTGAAGTGAAGTTCAATTGGTAC GTGGACGGCGTGGAAGTGCACAACGCCAAGACCAAGCCTAGAGAGGAACAGTACAACTCCACCTACCGGGTGGTGTCC GTGCTGACCGTGCTGCACCAGGATTGGCTGAACGGCAAAGAGTACAAGTGCAAGGTGTCCAACAAGGCCCTGCCTGCC CCCATCGAAAAGACCATCTCCAAGGCCAAGGGCCAGCCCCGGGAACCCCAGGTGTACACACTGCCCCCTAGCAGGGAC GAGCTGACCAAGAACCAGGTGTCCCTGACCTGTCTCGTGAAAGGCTTCTACCCCTCCGATATCGCCGTGGAATGGGAG TCCAACGGCCAGCCTGAGAACAACTACAAGACCACCCCCCCTGTGCTGGACTCCGACGGCTCATTCTTCCTGTACAGC AAGCTGACAGTGGACAAGTCCCGGTGGCAGCAGGGCAACGTGTTCTCCTGCTCCGTGATGCACGGCGCCCTGCACAAC CACTACACCCAGAAGTCCCTGTCCCTGAGCCCCGGC |
| 31 | F05 | CDRL1 (IMGT) | Amino acid sequence of CDRL1 using IMGT | QSVSSY |
| 32 | F05 | CDRL2 (IMGT) | Amino acid sequence of CDRL2 using IMGT | DTS |
| 33 | F05 | CDRL3 (IMGT) | Amino acid sequence of CDRL3 using IMGT | QQRRNWPLT |
| 34 | F05 | CDRL1 (KABAT) | Amino acid sequence of CDRL1 using KABAT | RVSQSVSSYLA |
| 35 | F05 | CDRL2 (KABAT) | Amino acid sequence of CDRL2 using KABAT | DTSNRAT |
| 36 | F05 | CDRL3 (KABAT) | Amino acid sequence of CDRL3 using KABAT | QQRRNWPLT |
| 37 | F05 | Light chain variable region | Amino acid sequence of $V_L$ | EIVLTQSPATLSLSPGERVILSCRVSQSVSSYLAWYQQKPGQAPRLLIYDTSNRATGIPARFSGSGSGTDFTLTISSL EPEDFAVYYCQQRRNWPLTFGGGTKVEIK |
| 38 | F05 | Light chain variable region | Nucleic acid sequence of $V_L$ | GAGATCGTGCTGACCCAGTCTCCTGCCACACTGTCACTGTCTCCAGGCGAGAGAGTGATCCTGTCTTGCCGGGTGTCC CAGTCCGTGTCCTCTTACCTGGCTTGGTATCAGCAGAAGCCCGGCCAGGCTCCTAGACTGCTGATCTACGACACCTCC |

TABLE 9-continued

Sequences
Sequences for use in the present invention.

| Seq ID No: | | | Description | Sequence |
|---|---|---|---|---|
| | | | | AACAGAGCCACAGGCATCCCCGCCAGATTTTCCGGCTCTGGCTCTGGCACAGACTTTACCCTGACCATCTCCAGCCTG GAACCTGAGGACTTCGCCGTGTACTACTGCCAGCAGCGGAGAAACTGGCCCCTGACATTTGGCGGCGGAACAAAGGTG GAAATCAAG |
| 39 | F05 | Full light chain sequence | Amino acid sequence light chain | EIVLTQSPATLSLSPGERVILSCRVSQSVSSYLAWYQQKPGQAPRLLIYDTSNRATGIPARFSGSGSGTDFTLTISSL EPEDFAVYYCQQRRNWPLTFGGGTKVEIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSFNRGEC |
| 40 | F05 | Full light chain sequence | Nucleic acid sequence light chain | GAGATCGTGCTGACCCAGTCTCCTGCCACACTGTCACTGTCTCCAGGCGAGAGAGTGATCCTGTCTTGCCGGGTGTCC CAGTCCGTGTCCTCTTACCTGGCTTGGTATCAGCAGAAGCCCGGCCAGGCTCCTAGACTGCTGATCTACGACACCTCC AACAGAGCCACAGGCATCCCCGCCAGATTTTCCGGCTCTGGCTCTGGCACAGACTTTACCCTGACCATCTCCAGCCTG GAACCTGAGGACTTCGCCGTGTACTACTGCCAGCAGCGGAGAAACTGGCCCCTGACATTTGGCGGCGGAACAAAGGTG GAAATCAAGCGTACGGTGGCCGCTCCCTCCGTGTTCATCTTCCCACCTTCCGACGAGCAGCTGAAGTCCGGCACCGCT TCTGTCGTGTGCCTGCTGAACAACTTCTACCCCCGCGAGGCCAAGGTGCAGTGGAAGGTGGACAACGCCCTGCAGTCC GGCAACTCCCAGGAATCCGTGACCGAGCAGGACTCCAAGGACAGCACCTACTCCCTGTCCTCCACCCTGACCCTGTCC AAGGCCGACTACGAGAAGCACAAGGTGTACGCCTGCGAAGTGACCCACCAGGGCCTGTCTAGCCCCGTGACCAAGTCT TTCAACCGGGGCGAGTGT |
| 41 | C02 | CDRH1 (IMGT) | Amino acid sequence of CDRH1 using IMGT | GLTFNNYA |
| 42 | C02 | CDRH2 (IMGT) | Amino acid sequence of CDRH2 using IMGT | ISGSGGST |
| 43 | C02 | CDRH3 (IMGT) | Amino acid sequence of CDRH3 using IMGT | AKGGLLYFGEFHFDY |
| 44 | C02 | CDRH1 (KABAT) | Amino acid sequence of CDRH1 using Kabat | NNYA |
| 45 | C02 | CDRH2 (KABAT) | Amino acid sequence of CDRH2 using Kabat | TISGSGGSTYYADSAKG |
| 46 | C02 | CDRH3 (KABAT) | Amino acid sequence of CDRH3 using Kabat | GGLLYFGEFHFDY |
| 47 | C02 | Heavy chain variable region | Amino acid sequence of $V_H$ | EVQLVESGGGLVQLGGSLRLSCAASGLTFNNYAMSWVRQAPGKGLEWVSTISGSGGSTYYADSAKGRFTISRDNSKNT LYLQMNSLRAEDTAVYYCAKGGLLYFGEFHFDYWGQGTLVTVSS |
| 48 | C02 | Heavy chain variable region | Nucleotide sequence of $V_H$ | GAGGTGCAGCTGGTGGAGTCTGGGGGAGGCTTGGTACAGCTTGGGGGGTCCCTGAGACTCTCCTGTGCAGCCTCTGGA CTCACCTTTAACAACTATGCCATGAGCTGGGTCCGCCAGGCTCCAGGGAAGGGGCTGGAGTGGGTCTCAACTATTAGT GGAAGTGGTGGCAGCACATACTACGCAGACTCCGCGAAGGGCCGGTTCACCATCTCCAGAGACAATTCCAAGAACACG CTGTATCTGCAAATGAACAGCCTGAGAGCCGAGGACACGGCCGTATATTACTGTGCGAAAGGGGGCTTACTATACTTC GGGGAGTTCCACTTTGACTACTGGGGCCAGGGAACCCTGGTCACCGTCTCCTCA |
| 49 | C02 | Full heavy chain | Amino acid sequence heavy chain | EVQLVESGGGLVQLGGSLRLSCAASGLTFNNYAMSWVRQAPGKGLEWVSTISGSGGSTYYADSAKGRFTISRDNSKNT LYLQMNSLRAEDTAVYYCAKGGLLYFGEFHFDYWGQGTLVTVSSASTKGPSVFPLAPSSKSTSGGTAALGCLVKDYFP |

TABLE 9-continued

Sequences
Sequences for use in the present invention.

| Seq ID No: | | | Description | Sequence |
|---|---|---|---|---|
| | | sequence | | EPVTVSWNSGALTSGVHTFPAVLQSSGLYSLSSVVTVPSSSLGTQTYICNVNHKPSNTKVDKKVEPKSCDKTHTCPPC PAPELLGGPSVFLFPPKPKDTLMISRTPEVTCVVVDVSHEDPEVKFNWYVDGVEVHNAKTKPREEQYNSTYRVVSVLI VLHQDWLNGKEYKCKVSNKALPAPIEKTISKAKGQPREPQVYTLPPSRDELTKNQVSLTCLVKGFYPSDIAVEWESNG QPENNYKTTPPVLDSDGSFFLYSKLTVDKSRWQQGNVFSCSVMHGALHNHYTQKSLSLSPG |
| 50 | C02 | Full heavy chain sequence | Nucleic acid sequence heavy chain | GAGGTGCAGCTGGTGGAGTCTGGGGGAGGCTTGGTACAGCTTGGGGGGTCCCTGAGACTCTCCTGTGCAGCCTCTGGA CTCACCTTTAACAACTATGCCATGAGCTGGGTCCGCCAGGCTCCAGGGAAGGGGCTGGAGTGGGTCTCAACTATTAGT GGAAGTGGTGGCAGCACATACTACGCAGACTCCGCGAAGGGCCGGTTCACCATCTCCAGAGACAATTCCAAGAACACG CTGTATCTGCAAATGAACAGCCTGAGAGCCGAGGACACGGCCGTATATTACTGTGCGAAAGGGGGCTTACTATACTTC GGGGAGTTCCACTTTGACTACTGGGGCCAGGGAACCCTGGTCACCGTCTCCTCAGCCAGCACCAAGGGCCCCTCTGTG TTCCCTCTGGCCCCTTCCAGCAAGTCCACCTCTGGCGGAACAGCCGCTCTGGGCTGCCTCGTGAAGGACTACTTCCCC GAGCCTGTGACCGTGTCCTGGAACTCTGGCGCTCTGACCAGCGGAGTGCACACCTTCCCTGCTGTGCTGCAGTCCTCC GGCCTGTACTCCCTGTCCTCCGTCGTGACCGTGCCTTCCAGCTCTCTGGGCACCCAGACCTACATCTGCAACGTGAAC CACAAGCCCTCCAACACCAAGGTGGACAAGAAGGTGGAACCCAAGTCCTGCGACAAGACCCACACCTGTCCCCCTTGT CCTGCCCCTGAACTGCTGGGCGGACCTTCCGTGTTCCTGTTCCCCCCAAAGCCCAAGGACACCCTGATGATCTCCCGG ACCCCCGAAGTGACCTGCGTGGTGGTGGATGTGTCCCACGAGGACCCTGAAGTGAAGTTCAATTGGTACGTGGACGGC GTGGAAGTGCACAACGCCAAGACCAAGCCTAGAGAGGAACAGTACAACTCCACCTACCGGGTGGTGTCCGTGCTGACC GTGCTGCACCAGGATTGGCTGAACGGCAAAGAGTACAAGTGCAAGGTGTCCAACAAGGCCCTGCCTGCCCCCATCGAA AAGACCATCTCCAAGGCCAAGGGCCAGCCCCGGGAACCCCAGGTGTACACACTGCCCCCTAGCAGGGACGAGCTGACC AAGAACCAGGTGTCCCTGACCTGTCTCGTGAAAGGCTTCTACCCCTCCGATATCGCCGTGGAATGGGAGTCCAACGGC CAGCCTGAGAACAACTACAAGACCACCCCCCCTGTGCTGGACTCCGACGGCTCATTCTTCCTGTACAGCAAGCTGACA GTGGACAAGTCCCGGTGGCAGCAGGGCAACGTGTTCTCCTGCTCCGTGATGCACGGCGCCCTGCACAACCACTACACC CAGAAGTCCCTGTCCCTGAGCCCCGGC |
| 51 | C02 | CDRL1 (IMGT) | Amino acid sequence of CDRL1 using IMGT | QGISNY |
| 52 | C02 | CDRL2 (IMGT) | Amino acid sequence of CDRL2 using IMGT | AAS |
| 53 | C02 | CDRL3 (IMGT) | Amino acid sequence of CDRL3 using IMGT | QHYNSYPLT |
| 54 | C02 | CDRL1 (KABAT) | Amino acid sequence of CDRL1 using KABAT | RASQGISNYLA |
| 55 | C02 | CDRL2 (KABAT) | Amino acid sequence of CDRL2 using KABAT | AASSLQS |
| 56 | C02 | CDRL3 (KABAT) | Amino acid sequence of CDRL3 using KABAT | QHYNSYPLT |
| 57 | C02 | Light chain variable region | Amino acid sequence of $V_L$ | DIQMTQSPSSLSASVGDRVTIICRASQGISNYLAWFQQKPGKAPKSLIYAASSLQSGVPSKFSGSGSGTDFTLTISSL QPEDFATYYCQHYNSYPLTFGGGTKVEIK |
| 58 | C02 | Light chain variable region | Nucleic acid sequence of $V_L$ | GACATCCAGATGACCCAGTCTCCATCCTCACTGTCTGCATCTGTAGGAGACAGAGTCACCATCATTTGTCGGGCGAGT CAGGGCATTAGCAATTATTTAGCCTGGTTTCAGCAGAAACCAGGGAAAGCCCCTAAGTCCCTGATCTATGCTGCATCC |

TABLE 9-continued

Sequences
Sequences for use in the present invention.

| Seq ID No: | | | Description | Sequence |
|---|---|---|---|---|
| | | | | AGTTTGCAAAGTGGGGTCCCATCAAAGTTCAGCGGCAGTGGATCTGGGACAGATTTCACTCTCACCATCAGCAGCCTG CAGCCTGAAGATTTTGCAACTTATTACTGCCAACATTATAATAGTTACCCGCTCACTTTCGGCGGAGGGACCAAGGTG GAGATCAAA |
| 59 | C02 | Full light chain sequence | Amino acid sequence light chain | DIQMTQSPSSLSASVGDRVTIICRASQGISNYLAWFQQKPGKAPKSLIYAASSLQSGVPSKFSGSGSGTDFTLTISSL QPEDFATYYCQHYNSYPLTFGGGTKVEIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKSFNRGEC |
| 60 | C02 | Full light chain sequence | Nucleic acid sequence light chain | GACATCCAGATGACCCAGTCTCCATCCTCACTGTCTGCATCTGTAGGAGACAGAGTCACCATCATTTGTCGGGCGAGT CAGGGCATTAGCAATTATTTAGCCTGGTTTCAGCAGAAACCAGGGAAAGCCCCTAAGTCCCTGATCTATGCTGCATCC AGTTTGCAAAGTGGGGTCCCATCAAAGTTCAGCGGCAGTGGATCTGGGACAGATTTCACTCTCACCATCAGCAGCCTG CAGCCTGAAGATTTTGCAACTTATTACTGCCAACATTATAATAGTTACCCGCTCACTTTCGGCGGAGGGACCAAGGTG GAGATCAAACGTACGGTGGCCGCTCCCTCCGTGTTCATCTTCCCACCTTCCGACGAGCAGCTGAAGTCCGGCACCGCT TCTGTCGTGTGCCTGCTGAACAACTTCTACCCCCGCGAGGCCAAGGTGCAGTGGAAGGTGGACAACGCCCTGCAGTCC GGCAACTCCCAGGAATCCGTGACCGAGCAGGACTCCAAGGACAGCACCTACTCCCTGTCCTCCACCCTGACCCTGTCC AAGGCCGACTACGAGAAGCACAAGGTGTACGCCTGCGAAGTGACCCACCAGGGCCTGTCTAGCCCCGTGACCAAGTCT TTCAACCGGGGCGAGTGT |
| 61 | E04 | CDRH1 (IMGT) | Amino acid sequence of CDRH1 using IMGT | GVTFSNAW |
| 62 | E04 | CDRH2 (IMGT) | Amino acid sequence of CDRH2 using IMGT | IKSKTDGGTT |
| 63 | E04 | CDRH3 (IMGT) | Amino acid sequence of CDRH3 using IMGT | TIEAVAGHFDY |
| 64 | E04 | CDRH1 (KABAT) | Amino acid sequence of CDRH1 using Kabat | SNAWMS |
| 65 | E04 | CDRH2 (KABAT) | Amino acid sequence of CDRH2 using Kabat | RIKSKTDGGTTDYAAPVKG |
| 66 | E04 | CDRH3 (KABAT) | Amino acid sequence of CDRH3 using Kabat | EAVAGHFDY |
| 67 | E04 | Heavy chain variable region | Amino acid sequence of $V_H$ | EVQLVESGGGLVKPGGSPRLSCAAYGVTFSNAWMSWVRQAPGKGLEWVGRIKSKTDGGTTDYAAPVKGRFTISRDDSK NTLYLQMNSLKTEDTAVYYCTIEAVAGHFDYWGQGTLVTVSS |
| 68 | E04 | Heavy chain variable region | Nucleotide sequence of $V_H$ | GAGGTGCAGTTGGTGGAGTCTGGGGGAGGCTTGGTAAAGCCTGGGGGGTCCCCTAGACTCTCCTGTGCAGCCTATGGA GTCACTTTCAGTAACGCCTGGATGAGTTGGGTCCGCCAGGCTCCAGGGAAGGGGCTGGAGTGGGTTGGCCGTATTAAA AGCAAAACTGATGGTGGGACAACAGACTATGCTGCACCCGTGAAAGGCAGATTCACCATCTCAAGAGATGATTCAAAA AACACGCTGTATCTGCAAATGAACAGCCTGAAAACCGAGGACACAGCCGTGTATTACTGTACCATAGAAGCAGTGGCT GGTCACTTTGACTACTGGGGCCAGGGAACCCTGGTCACCGTCTCCTCA |

TABLE 9-continued

Sequences
Sequences for use in the present invention.

| Seq ID No: | | | Description | Sequence |
|---|---|---|---|---|
| 69 | E04 | Full heavy chain sequence | Amino acid sequence heavy chain | EVQLVESGGGLVKPGGSPRLSCAAYGVTFSNAWMSWVRQAPGKGLEWVGRIKSKTDGGTTDYAAPVKGRFTISRDDSK<br>NTLYLQMNSLKTEDTAVYYCTIEAVAGHFDYWGQGTLVTVSSASTKGPSVFPLAPSSKSTSGGTAALGCLVKDYFPEP<br>VTVSWNSGALTSGVHTFPAVLCISSGLYSLSSVVTVPSSSLGTQTYICNVNHKPSNTKVDKKVEPKSCDKTHTCPPCP<br>APELLGGPSVFLFPPKPKDTLMISRTPEVTCVVVDVSHEDPEVKFNWYVDGVEVHNAKTKPREEQYNSTYRVVSVLIV<br>LHQDWLNGKEYKCKVSNKALPAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHGALHNHYTQKSLSLSPG |
| 70 | E04 | Full heavy chain sequence | Nucleic acid sequence heavy chain | GAGGTGCAGTTGGTGGAGTCTGGGGGAGGCTTGGTAAAGCCTGGGGGGTCCCCTAGACTCTCCTGTGCAGCCTATGGA<br>GTCACTTTCAGTAACGCCTGGATGAGTTGGGTCCGCCAGGCTCCAGGGAAGGGGCTGGAGTGGGTTGGCCGTATTAAA<br>AGCAAAACTGATGGTGGGACAACAGACTATGCTGCACCCGTGAAAGGCAGATTCACCATCTCAAGAGATGATTCAAAA<br>AACACGCTGTATCTGCAAATGAACAGCCTGAAAACCGAGGACACAGCCGTGTATTACTGTACCATAGAAGCAGTGGCT<br>GGTCACTTTGACTACTGGGGCCAGGGAACCCTGGTCACCGTCTCCTCAGCCAGCACCAAGGGCCCCTCTGTGTTCCCT<br>CTGGCCCCTTCCAGCAAGTCCACCTCTGGCGGAACAGCCGCTCTGGGCTGCCTCGTGAAGGACTACTTCCCCGAGCCT<br>GTGACCGTGTCCTGGAACTCTGGCGCTCTGACCAGCGGAGTGCACACCTTCCCTGCTGTGCTGCAGTCCTCCGGCCTG<br>TACTCCCTGTCCTCCGTCGTGACCGTGCCTTCCAGCTCTCTGGGCACCCAGACCTACATCTGCAACGTGAACCACAAG<br>CCCTCCAACACCAAGGTGGACAAGAAGGTGGAACCCAAGTCCTGCGACAAGACCCACACCTGTCCCCCTTGTCCTGCC<br>CCTGAACTGCTGGGCGGACCTTCCGTGTTCCTGTTCCCCCCAAAGCCCAAGGACACCCTGATGATCTCCCGGACCCCC<br>GAAGTGACCTGCGTGGTGGTGGATGTGTCCCACGAGGACCCTGAAGTGAAGTTCAATTGGTACGTGGACGGCGTGGAA<br>GTGCACAACGCCAAGACCAAGCCTAGAGAGGAACAGTACAACTCCACCTACCGGGTGGTGTCCGTGCTGACCGTGCTG<br>CACCAGGATTGGCTGAACGGCAAAGAGTACAAGTGCAAGGTGTCCAACAAGGCCCTGCCTGCCCCCATCGAAAAGACC<br>ATCTCCAAGGCCAAGGGCCAGCCCCGGGAACCCCAGGTGTACACACTGCCCCCTAGCAGGGACGAGCTGACCAAGAAC<br>CAGGTGTCCCTGACCTGTCTCGTGAAAGGCTTCTACCCCTCCGATATCGCCGTGGAATGGGAGTCCAACGGCCAGCCT<br>GAGAACAACTACAAGACCACCCCCCCTGTGCTGGACTCCGACGGCTCATTCTTCCTGTACAGCAAGCTGACAGTGGAC<br>AAGTCCCGGTGGCAGCAGGGCAACGTGTTCTCCTGCTCCGTGATGCACGGCGCCCTGCACAACCACTACACCCAGAAG<br>TCCCTGTCCCTGAGCCCCGGC |
| 71 | E04 | CDRL1 (IMGT) | Amino acid sequence of CDRL1 using IMGT | QSISSW |
| 72 | E04 | CDRL2 (IMGT) | Amino acid sequence of CDRL2 using IMGT | KAS |
| 73 | E04 | CDRL3 (IMGT) | Amino acid sequence of CDRL3 using IMGT | QQYNNYSPT |
| 74 | E04 | CDRL1 (KABAT) | Amino acid sequence of CDRL1 using KABAT | RASQSISSWLA |
| 75 | E04 | CDRL2 (KABAT) | Amino acid sequence of CDRL2 using KABAT | KASSLES |
| 76 | E04 | CDRL3 (KABAT) | Amino acid sequence of CDRL3 using KABAT | QQYNNYSPT |
| 77 | E04 | Light chain variable region | Amino acid sequence of $V_L$ | DIQMTQSPSTLSASVGDRVTITCRASQSISSWLAWYQQKPGKAPKLLIYKASSLESGVPSRFSGSGSGTEFTLTISSL<br>QPDDFATYYCQQYNNYSPTFGQGTKVEIK |

TABLE 9-continued

Sequences
Sequences for use in the present invention.

| Seq ID No: | | | Description | Sequence |
|---|---|---|---|---|
| 78 | E04 | Light chain variable region | Nucleic acid sequence of $V_L$ | GACATCCAGATGACCCAGTCTCCTTCCACCCTGTCTGCATCTGTAGGAGACAGAGTCACCATCACTTGCCGGGCCAGTCAGAGTATTAGTAGCTGGTTGGCCTGGTATCAGCAGAAACCAGGGAAAGCCCCTAAGCTCCTGATCTATAAGGCGTCTAGTTTAGAAAGTGGGGTCCCATCAAGGTTCAGCGGCAGTGGATCTGGGACAGAATTCACTCTCACCATCAGCAGCCTGCAGCCTGATGATTTTGCAACTTATTACTGCCAACAGTATAATAATTATTCTCCGACGTTCGGCCAGGGGACCAAGGTGGAAATCAAA |
| 79 | E04 | Full light chain sequence | Amino acid sequence light chain | DIQMTQSPSTLSASVGDRVTITCRASQSISSWLAWYQQKPGKAPKLLIYKASSLESGVPSRFSGSGSGTEFTLTISSLQPDDFATYYCQQYNNYSPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 80 | E04 | Full light chain sequence | Nucleic acid sequence light chain | GACATCCAGATGACCCAGTCTCCTTCCACCCTGTCTGCATCTGTAGGAGACAGAGTCACCATCACTTGCCGGGCCAGTCAGAGTATTAGTAGCTGGTTGGCCTGGTATCAGCAGAAACCAGGGAAAGCCCCTAAGCTCCTGATCTATAAGGCGTCTAGTTTAGAAAGTGGGGTCCCATCAAGGTTCAGCGGCAGTGGATCTGGGACAGAATTCACTCTCACCATCAGCAGCCTGCAGCCTGATGATTTTGCAACTTATTACTGCCAACAGTATAATAATTATTCTCCGACGTTCGGCCAGGGGACCAAGGTGGAAATCAAACGTACGGTGGCCGCTCCCTCCGTGTTCATCTTCCCACCTTCCGACGAGCAGCTGAAGTCCGGCACCGCTTCTGTCGTGTGCCTGCTGAACAACTTCTACCCCCGCGAGGCCAAGGTGCAGTGGAAGGTGGACAACGCCCTGCAGTCCGGCAACTCCCAGGAATCCGTGACCGAGCAGGACTCCAAGGACAGCACCTACTCCCTGTCCTCCACCCTGACCCTGTCCAAGGCCGACTACGAGAAGCACAAGGTGTACGCCTGCGAAGTGACCCACCAGGGCCTGTCTAGCCCCGTGACCAAGTCTTTCAACCGGGGCGAGTGT |
| 81 | Human CD7 | | Nucleic acid sequence | ATGGCCGGGCCTCCGAGGCTCCTGCTGCTGCCCCTGCTTCTGGCGCTGGCTCGCGGCCTGCCTGGGGCCCTGGCTGCCCAAGAGGTGCAGCAGTCTCCCCACTGCACGACTGTCCCCGTGGGAGCCTCCGTCAACATCACCTGCTCCACCAGCGGGGGCCTGCGTGGGATCTACCTGAGGCAGCTCGGGCCACAGCCCCAAGACATCATTTACTACGAGGACGGGGTGGTGCCCACTACGGACAGACGGTTCCGGGGCCGCATCGACTTCTCAGGGTCCCAGGACAACCTGACTATCACCATGCACCGCCTGCAGCTGTCGGACACTGGCACCTACACCTGCCAGGCCATCACGGAGGTCAATGTCTACGGCTCCGGCACCCTGGTCCTGGTGACAGAGGAACAGTCCCAAGGATGGCACAGATGCTCGGACGCCCCACCAAGGGCCTCTGCCCTCCCTGCCCCACCGACAGGCTCCGCCCTCCCTGACCCGCAGACAGCCTCTGCCCTCCCTGACCCGCCAGCAGCCTCTGCCCTCCCTGCGGCCCTGGCGGTGATCTCCTTCCTCCTCGGGCTGGGCCTGGGGGTGGCGTGTGTGCTGGCGAGGACACAGATAAAGAAACTGTGCTCGTGGCGGGATAAGAATTCGGCGGCATGTGTGGTGTACGAGGACATGTCGCACAGCCGCTGCAACACGCTGTCCTCCCCCAACCAGTACCAGTGA |
| 82 | Human | CD7 | Amino acid sequence | MAGPPRLLLLPLLLALARGLPGALAAQEVQQSPHCTTVPVGASVNITCSTSGGLRGIYLRQLGPQPQDIIYYEDGVVPTTDRRFRGRIDFSGSQDNLTITMHRLQLSDTGTYTCQAITEVNVYGSGTLVLVTEEQSQGWHRCSDAPPRASALPAPPTGSALPDPQTASALPDPPAASALPAALAVISFLLGLGLGVACVLARTQIKKLCSWRDKNSAACVVYEDMSHSRCNTLSSPNQ |
| 83 | Cynomolgus monkey (*Macaca fascicularis*) CD7 | | Nucleic acid sequence | ATGGCCGGGCTCCCGAGGCTCCTGCTGCTGCCCCTCCTCCTGGCGCTGGCTCGTGGCCTGCCTGGGGCCCTGGCCGCCCAAGAGGTGCAGCAGTCTCCCCACTGCACGATTGCCCCCGTGGGAGGCTCCGTCAACATCACCTGCTCCACCAGCGGGGAACTGCATGGGATCTACCTGAGGCAGCTCGGGCCACAGCCCCAAAACATCATTTACTACGAGGACAGGGTGGTGCCCACTACGGACAAACGGTTCCAGGGCCGCATTGACTTCTCGGGGTCCCAGGACAACCTGACTATTACCATGCACCACCTGCAGCCGTCGGACACTGGCACCTACACCTGCCAGGCCGTCACGGAGATCAATGTCTACGGCTCCGGTACCCTGGTCCTGGTGACAGAGGAACAGTCCCAAGGATTGCACAGATGCTCGGACGCCCCGCCGACAGGCTCTGCCCTCCCTGTCCCGCCGACAACCTCTGCCCTCCCTGCCCTGCCAACAGCCTCTGCCCTCCCTGCCCTGCCGACAGCCTCTGCCCTCCCTGTGGCCCTGGCAGTGGTCTCCTTCCTCCTCGGGCTGGCCCTGGGGGTGGCCTGTGTGCTGGTGAGGACGCAGATGAAGAAACTGTGCTCGTCGCGGGATAAGAATTCGGCAGCGTGTGTGGTGTACGAGGACATGTCCCGCAGCCGCTGCAACACGCTGTCCTCCCCCAACCAGTACCAGTGA |

TABLE 9-continued

Sequences
Sequences for use in the present invention.

| Seq ID No: | | | Description | Sequence |
|---|---|---|---|---|
| 84 | Cynomolgus monkey (*Macaca fascicularis*) CD7 | | Amino acid sequence | MAGLPRLLLLPLLLALARGLPGALAAQEVQQSPHCTIAPVGGSVNITCSTSGELHGIYLRQLGPQPQNIIYYEDRVVP<br>TTDKRFQGRIDFSGSQDNLTITMHHLQPSDTGTYTCQAVTEINVYGSGTLVLVTEEQSQGLHRCSDAPPTGSALPVPP<br>TTSALPALPTASALPALPTASALPVALAVVSFLLGLALGVACVLVRTQMKKLCSSRDKNSAACVVYEDMSRSRCNTLS<br>SPNQYQ |
| 85 | Rat (*Rattus norvegicus*) CD7 | | Nucleic acid sequence | ATGACTCAGGCACTGTTGGCTTTGCTACTTACACTGGCTAGAATCCTGCCTGGCCCCCTGGATGCCCAAGAGGTACAT<br>CAGTCTCCCCGAGTCGTGATCGCCTCCGAGGGAGAGTCCATCAACATCACCTGCTCTACAAGAGGGGATTTGGAAGGG<br>CTCATAATGAAGCGGATCTGGCCACAGGCTTCCAATGTGATTTACTTTGAAGACGAATTGGAGCCCACAGTAGACAGT<br>GCCTTCTCAGGCCGAATTAATTTCTCTGGGTCCCAGAAGAATCTGACCATCATCATGAGCCTTCTCCAGGAGGCAGAC<br>ACTGGAGCCTACACCTGCGAGGCCGTCAGAAAAGTCAGTGTCCATGGCTTGTTCACCACGGTTGTGGTGAAAGAAAAA<br>CTATCCCATGAAGCGTACAGATCCCAGGAACCTCTGCAGACATCAGTTTCCCTCCCAGCTGCCATTGCTGTAAGCTTC<br>TTCCTCACTGGGCTGATCCTTGGGGTGCTGTGCAGCATGCTGAGGAAGACGCAGATCAAGAAACTGTGTGCCTCAGGG<br>AATAAGGACTCTCTGTGCGTCGTGTATGAAGACATGTCCTGCAGCAACCGCAAGATACCATGTACCCCCAACCAGTAC<br>CAATGA |
| 86 | Rat (*Rattus norvegicus*) CD7 | | Amino acid sequence | MTQALLALLLTLARILPGPLDAQEVHQSPRVVIASEGESINITCSTRGDLEGLIMKRIWPQASNVIYFEDELEPTVDS<br>AFSGRINFSGSQKNLTIIMSLLQEADTGAYTCEAVRKVSVHGLFTTVVVKEKLSHEAYRSQEPLQTSVSLPAAIAVSF<br>FLTGLILGVLCSMLRKTQIKKLCASGNKDSLCVVYEDMSCSNRKIPCTPNQYQ |
| 87 | Human IgG1 constant region | IGHG1*01 | Human Heavy Chain Constant Region (IGHG1*01) Nucleotide Sequence | gcctccaccaagggcccatcggtcttccccctggcaccctcctccaagagcacctctgggggcacagcggccctgggc<br>tgcctggtcaaggactacttccccgaaccggtgacggtgtcgtggaactcaggcgccctgaccagcggcgtgcacacc<br>ttcccggctgtcctacagtcctcaggactctactccctcagcagcgtggtgaccgtgccctccagcagcttgggcacc<br>cagacctacatctgcaacgtgaatcacaagcccagcaacaccaaggtggacaagaaagttgagcccaaatcttgtgac<br>aaaactcacacatgcccaccgtgcccagcacctgaactcctggggggaccgtcagtcttcctcttccccccaaaaccc<br>aaggacaccctcatgatctcccggacccctgaggtcacatgcgtggtggtggacgtgagccacgaagaccctgaggtc<br>aagttcaactggtacgtggacggcgtggaggtgcataatgccaagacaaagccgcgggaggagcagtacaacagcacg<br>taccgggtggtcagcgtcctcaccgtcctgcaccaggactggctgaatggcaaggagtacaagtgcaaggtctccaac<br>aaagccctcccagcccccatcgagaaaaccatctccaaagccaaagggcagccccgagaaccacaggtgtacaccctg<br>cccccatcccgggatgagctgaccaagaaccaggtcagcctgacctgcctggtcaaaggcttctatcccagcgacatc<br>gccgtggagtgggagagcaatgggcagccggagaacaactacaagaccacgcctcccgtgctggactccgacggctcc<br>ttcttcctctacagcaagctcaccgtggacaagagcaggtggcagcaggggaacgtcttctcatgctccgtgatgcat<br>gaggctctgcacaaccactacacgcagaagagcctctccctgtctccgggtaaa |
| 88 | | | Human Heavy Chain Constant Region (IGHG1*01) Protein Sequence (P01857) | ASTKGPSVFPLAPSSKSTSGGTAALGCLVKDYFPEPVTVSWNSGALTSGVHTFPAVLQSSGLYSLSSVVTVPSSSLGT<br>QTYICNVNHKPSNTKVDKKVEPKSCDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKALPAPIEKTISKAKGQPREPQVYTL<br>PPSRDELTKNQVSLTCLVKGFYPSDIAVEWESNGQPENNYKTTPPVLDSDGSFFLYSKLTVDKSRWQQGNVFSCSVMH<br>EALHNHYTQKSLSLSPGK |
| 89 | Human IgG1 constant region | IGHG1*02 or IGHG1*05 | Human Heavy Chain Constant Region (IGHG1*02 or IGHG1*05) Nucleotide Sequence | gcctccaccaagggcccatcggtcttccccctggcaccctcctccaagagcacctctgggggcacagcggccctgggc<br>tgcctggtcaaggactacttccccgaaccggtgacggtgtcgtggaactcaggcgccctgaccagcggcgtgcacacc<br>ttcccggctgtcctacagtcctcaggactctactccctcagcagcgtggtgaccgtgccctccagcagcttgggcacc<br>cagacctacatctgcaacgtgaatcacaagcccagcaacaccaaggtggacaagaaagttgagcccaaatcttgtgac<br>aaaactcacacatgcccaccgtgcccagcacctgaactcctggggggaccgtcagtcttcctcttccccccaaaaccc<br>aaggacaccctcatgatctcccggacccctgaggtcacatgcgtggtggtggacgtgagccacgaagaccctgaggtc<br>aagttcaactggtacgtggacggcgtggaggtgcataatgccaagacaaagccgcgggaggagcagtacaacagcacg |

TABLE 9-continued

Sequences
Sequences for use in the present invention.

| Seq ID No: | | | Description | Sequence |
| --- | --- | --- | --- | --- |
| | | | | taccgtgtggtcagcgtcctcaccgtcctgcaccaggactggctgaatggcaaggagtacaagtgcaaggtctccaac<br>aaagccctcccagcccccatcgagaaaaccatctccaaagccaaagggcagccccgagaaccacaggtgtacaccctg<br>cccccatcccgggatgagctgaccaagaaccaggtcagcctgacctgcctggtcaaaggcttctatcccagcgacatc<br>gccgtggagtgggagagcaatgggcagccggagaacaactacaagaccacgcctcccgtgctggactccgacggctcc<br>ttcttcctctacagcaagctcaccgtggacaagagcaggtggcagcaggggaacgtcttctcatgctccgtgatgcat<br>gaggctctgcacaaccactacacgcagaagagcctctccctgtctccgggtaaa |
| 90 | | | Human Heavy Chain Constant Region (IGHG1*02) Protein Sequence | A S T K G P S V F P L A P S S K S T S G G T A A L G C L V K D Y F P E P V T V<br>S W N S G A L T S G V H T F P A V L Q S S G L Y S L S S V V T V P S S S L G T<br>Q T Y I C N V N H K P S N T K V D K K V E P K S C D K T H T C P P C P A P E L<br>L G G P S V F L F P P K P K D T L M I S R T P E V T C V V V D V S H E D P E V<br>K F N W Y V D G V E V H N A K T K P R E E Q Y N S T Y R V V S V L T V L H Q D<br>W L N G K E Y K C K V S N K A L P A P I E K T I S K A K G Q P R E P Q V Y T L<br>P P S R D E L T K N Q V S L T C L V K G F Y P S D I A V E W E S N G Q P E N N<br>Y K T T P P V L D S D G S F F L Y S K L T V D K S R W Q Q G N V F S C S V M H<br>E A L H N H Y T Q K S L S L S P G K |
| 91 | Human IgG1 constant region | IGHG1*03 | Human Heavy Chain Constant Region (IGHG1*03) Nucleotide Sequence (Y14737) | gcctccaccaagggcccatcggtcttccccctggcaccctcctccaagagcacctctgggggcacagcggccctgggc<br>tgcctggtcaaggactacttccccgaaccggtgacggtgtcgtggaactcaggcgccctgaccagcggcgtgcacacc<br>ttcccggctgtcctacagtcctcaggactctactccctcagcagcgtggtgaccgtgccctccagcagcttgggcacc<br>cagacctacatctgcaacgtgaatcacaagcccagcaacaccaaggtggacaagagagttgagcccaaatcttgtgac<br>aaaactcacacatgcccaccgtgcccagcacctgaactcctggggggaccgtcagtcttcctcttccccccaaaaccc<br>aaggacaccctcatgatctcccggacccctgaggtcacatgcgtggtggtggacgtgagccacgaagaccctgaggtc<br>aagttcaactggtacgtggacggcgtggaggtgcataatgccaagacaaagccgcgggaggagcagtacaacagcacg<br>taccgtgtggtcagcgtcctcaccgtcctgcaccaggactggctgaatggcaaggagtacaagtgcaaggtctccaac<br>aaagccctcccagcccccatcgagaaaaccatctccaaagccaaagggcagccccgagaaccacaggtgtacaccctg<br>cccccatcccgggaggagatgaccaagaaccaggtcagcctgacctgcctggtcaaaggcttctatcccagcgacatc<br>gccgtggagtgggagagcaatgggcagccggagaacaactacaagaccacgcctcccgtgctggactccgacggctcc<br>ttcttcctctatagcaagctcaccgtggacaagagcaggtggcagcaggggaacgtcttctcatgctccgtgatgcat<br>gaggctctgcacaaccactacacgcagaagagcctctccctgtccccgggtaaa |
| 92 | | | Human Heavy Chain Constant Region (IGHG1*03) Protein Sequence | A S T K G P S V F P L A P S S K S T S G G T A A L G C L V K D Y F P E P V T V<br>S W N S G A L T S G V H T F P A V L Q S S G L Y S L S S V V T V P S S S L Q T<br>Q T Y I C N V N H K P S N T K V D K R V E P K S C D K T H T C P P C P A P E L<br>L G G P S V F L F P P K P K D T L M I S R T P E V T C V V V D V S H E D P E V<br>K F N W Y V D G V E V H N A K T K P R E E Q Y N S T Y R V V S V L T V L H Q D<br>W L N G K E Y K C K V S N K A L P A P I E K T I S K A K G Q P R E P Q V Y T L<br>P P S R E E M T K N Q V S L T C L V K G F Y P S D I A V E W E S N G Q P E N N<br>Y K T T P P V L D S D G S F F L Y S K L T V D K S R W Q Q G N V F S C S V M H<br>E A L H N H Y T Q K S L S L S P G K |
| 93 | Human IgG1 constant region | IGHG1*04 | Human Heavy Chain Constant Region (IGHG1*04) Nucleotide Sequence | gcctccaccaagggcccatcggtcttccccctggcaccctcctccaagagcacctctgggggcacagcggccctgggc<br>tgcctggtcaaggactacttccccgaaccggtgacggtgtcgtggaactcaggcgccctgaccagcggcgtgcacacc<br>ttcccggctgtcctacagtcctcaggactctactccctcagcagcgtggtgaccgtgccctccagcagcttgggcacc<br>cagacctacatctgcaacgtgaatcacaagcccagcaacaccaaggtggacaagaaagttgagcccaaatcttgtgac<br>aaaactcacacatgcccaccgtgcccagcacctgaactcctggggggaccgtcagtcttcctcttccccccaaaaccc<br>aaggacaccctcatgatctcccggacccctgaggtcacatgcgtggtggtggacgtgagccacgaagaccctgaggtc<br>aagttcaactggtacgtggacggcgtggaggtgcataatgccaagacaaagccgcgggaggagcagtacaacagcacg<br>taccgtgtggtcagcgtcctcaccgtcctgcaccaggactggctgaatggcaaggagtacaagtgcaaggtctccaac |

TABLE 9-continued

Sequences
Sequences for use in the present invention.

| Seq ID No: | | | Description | Sequence |
|---|---|---|---|---|
| | | | | aaagccctcccagcccccatcgagaaaaccatctccaaagccaaagggcagccccgagaaccacaggtgtacaccctg cccccatcccgggatgagctgaccaagaaccaggtcagcctgacctgcctggtcaaaggcttctatcccagcgacatc gccgtggagtgggagagcaatgggcagccggagaacaactacaagaccacgcctcccgtgctggactccgacggctcc ttcttcctctacagcaagctcaccgtggacaagagcaggtggcagcaggggaacatcttctcatgctccgtgatgcat gaggctctgcacaaccactacacgcagaagagcctctccctgtctccgggtaaa |
| 94 | | | Human Heavy Chain Constant Region (IGHG1*04) Protein Sequence | ASTKGPSVFPLAPSSKSTSGGTAALGCLVKDYFPEPVTVSWNSGALTSGVHTFPAVLQSSGLYSLSSVVTVPSSSLGT QTYICNVNHKPSNTKVDKKVEPKSCDKTHTCPPCPAPELLGGPSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKTISKAKGQPREPQVYTL PPSRDELTKNQVSLTCLVKGFYPSDIAVEWESNGQPENNYKTTPPVLDSDGSFFLYSKLTVDKSRWQQGNIFSCSVMH EALHNHYTQKSLSLSPGK |
| 95 | Disabled Human IgG1 heavy chain constant region | Disabled human IGHG1*01 | Disabled Human IGHG1*01 Heavy Chain Constant Region Nucleotide Sequence. | Gcctccaccaagggcccatcggtcttcccctggcaccctcctccaagagcacctctgggggcacagcggccctgggc tgcctggtcaaggactacttccccgaaccggtgacggtgtcgtggaactcaggcgccctgaccagcggcgtgcacacc ttcccggctgtcctacagtcctcaggactctactccctcagcagcgtggtgaccgtgccctccagcagcttgggcacc cagacctacatctgcaacgtgaatcacaagcccagcaacaccaaggtggacaagaaagtggagcccaaatcttgtgac aaaactcacacatgcccaccgtgcccagcacctgaactcgcgggggcaccgtcagtcttcctcttccccccaaaaccc aaggacaccctcatgatctcccggacccctgaggtcacatgcgtggtggtggacgtgagccacgaagaccctgaggtc aagttcaactggtacgtggacggcgtggaggtgcataatgccaagacaaagccgcgggaggagcagtacaacagcacg taccgtgtggtcagcgtcctcaccgtcctgcaccaggactggctgaatggcaaggagtacaagtgcaaggtctccaac aaagccctcccagcccccatcgagaaaaccatctccaaagccaaagggcagccccgagaaccacaggtgtacaccctg cccccatcccgggatgagctgaccaagaaccaggtcagcctgacctgcctggtcaaaggcttctatcccagcgacatc gccgtggagtgggagagcaatgggcagccggagaacaactacaagaccacgcctcccgtgctggactccgacggctcc ttcttcctctacagcaagctcaccgtggacaagagcaggtggcagcaggggaacgtcttctcatgctccgtgatgcat gaggctctgcacaaccactacacgcagaagagcctctccctgtctccgggtaaa |
| 96 | | | Disabled Human IGHG1*01 Heavy Chain Constant Region Amino Acid Sequence. Two residues that differ from the wild-type sequence are identified in bold. | ASTKGPSVFPLAPSSKSTSGGTAALGCLVKDYFPEPVTVSWNSGALTSGVHTFPAVLQSSGLYSLSSVVTVPSSSLGT QTYICNVNHKPSNTKVDKKVEPKSCDKTHTCPPCPAPEL**A**G**A**PSVFLFPPKPKDTLMISRTPEVTCVVVDVSHEDPEV KFNWYVDGVEVHNAKTKPREEQYNSTYRVVSVLTVLHQDWLNGKEYKCKVSNKALPAPIEKTISKAKGQPREPQVYTL PPSRDELTKNQVSLTCLVKGFYPSDIAVEWESNGQPENNYKTTPPVLDSDGSFFLYSKLTVDKSRWQQGNVFSCSVMH EALHNHYTQKSLSLSPGK |
| 97 | Human IgG2 constant region | IGHG2*01 or IGHG2*04 or IGHG2*05 | Human Heavy Chain Constant Region (IGHG2*01 or IGHG2*03 or IGHG2*05) Nucleotide Sequence | gcctccaccaagggcccatcggtcttccccctggcgccctgctccaggagcacctccgagagcacagccgccctgggc tgcctggtcaaggactacttccccgaaccggtgacggtgtcgtggaactcaggcgctctgaccagcggcgtgcacacc ttcccagctgtcctacagtcctcaggactctactccctcagcagcgtggtgaccgtgccctccagcaacttcggcacc cagacctacacctgcaacgtagatcacaagcccagcaacaccaaggtggacaagacagttgagcgcaaatgttgtgtc gagtgcccaccgtgcccagcaccacctgtggcaggaccgtcagtcttcctcttccccccaaaacccaaggacaccctc atgatctcccggacccctgaggtcacgtgcgtggtggtggacgtgagccacgaagaccccgaggtccagttcaactgg tacgtggacggcgtggaggtgcataatgccaagacaaagccacgggaggagcagttcaacagcacgttccgtgtggtc agcgtcctcaccgttgtgcaccaggactggctgaacggcaaggagtacaagtgcaaggtctccaacaaaggcctccca gcccccatcgagaaaaccatctccaaaaccaaagggcagccccgagaaccacaggtgtacaccctgcccccatcccgg gaggagatgaccaagaaccaggtcagcctgacctgcctggtcaaaggcttctaccccagcgacatcgccgtggagtgg gagagcaatgggcagccggagaacaactacaagaccacacctcccatgctggactccgacggctccttcttcctctac agcaagctcaccgtggacaagagcaggtggcagcaggggaacgtcttctcatgctccgtgatgcatgaggctctgcac aaccactacacgcagaagagcctctccctgtctccgggtaaa |
| 98 | | | Human Heavy Chain Constant Region (IGHG2*01) Protein Sequence | ASTKGPSVFPLAPCSRSTSESTAALGCLVKDYFPEPVTVSWNSGALTSGVHTFPAVLQSSGLYSLSSVVTVPSSNFGT QTYTCNVDHKPSNTKVDKTVERKCCVECPPCPAPPVAGPSVFLFPPKPKDTLMISRTPEVTCVVVDVSHEDPEVQFNW YVDGVEVHNAKTKPREEQFNSTFRVVSVLTVVHQDWLNGKEYKCKVSNKGLPAPIEKTISKTKGQPREPQVYTLPPSR |

TABLE 9-continued

Sequences
Sequences for use in the present invention.

| Seq ID No: | | | Description | Sequence |
|---|---|---|---|---|
| | | | | EEMTKNQVSLTCLVKGFYPSDIAVEWESNGQPENNYKTTPPMLDSDGSFFLYSKLTVDKSRWQQGNVFSCSVMHEALH<br>NHYTQKSLSLSPGK |
| 99 | Human IgG2 constant region | IGHG2*02 | Human Heavy Chain Constant Region (IGHG2*02) Nucleotide Sequence | GCCTCCACCAAGGGCCCATCGGTCTTCCCCCTGGCGCCCTGCTCCAGGAGCACCTCCGAGAGCACAGCGGCCCTGGGC<br>TGCCTGGTCAAGGACTACTTCCCCGAACCGGTGACGGTGTCGTGGAACTCAGGCGCTCTGACCAGCGGCGTGCACACC<br>TTCCCGGCTGTCCTACAGTCCTCAGGACTCTACTCCCTCAGCAGCGTGGTGACCGTGACCTCCAGCAACTTCGGCACC<br>CAGACCTACACCTGCAACGTAGATCACAAGCCCAGCAACACCAAGGTGGACAAGACAGTTGAGCGCAAATGTTGTGTC<br>GAGTGCCCACCGTGCCCAGCACCACCTGTGGCAGGACCGTCAGTCTTCCTCTTCCCCCCAAAACCCAAGGACACCCTC<br>ATGATCTCCCGGACCCCTGAGGTCACGTGCGTGGTGGTGGACGTGAGCCACGAAGACCCCGAGGTCCAGTTCAACTGG<br>TACGTGGACGGCATGGAGGTGCATAATGCCAAGACAAAGCCACGGGAGGAGCAGTTCAACAGCACGTTCCGTGTGGTC<br>AGCGTCCTCACCGTCGTGCACCAGGACTGGCTGAACGGCAAGGAGTACAAGTGCAAGGTCTCCAACAAAGGCCTCCCA<br>GCCCCCATCGAGAAAACCATCTCCAAAACCAAAGGGCAGCCCCGAGAACCACAGGTGTACACCCTGCCCCCATCCCGG<br>GAGGAGATGACCAAGAACCAGGTCAGCCTGACCTGCCTGGTCAAAGGCTTCTACCCCAGCGACATCGCCGTGGAGTGG<br>GAGAGCAATGGGCAGCCGGAGAACAACTACAAGACCACACCTCCCATGCTGGACTCCGACGGCTCCTTCTTCCTCTAC<br>AGCAAGCTCACCGTGGACAAGAGCAGGTGGCAGCAGGGGAACGTCTTCTCATGCTCCGTGATGCATGAGGCTCTGCAC<br>AACCACTACACACAGAAGAGCCTCTCCCTGTCTCCGGGTAAA |
| 100 | | | Human Heavy Chain Constant Region (IGHG2*02) Protein Sequence | ASTKGPSVFPLAPCSRSTSESTAALGCLVKDYFPEPVTVSWNSGALTSGVHTFPAVLQSSGLYSLSSVVTVTSSNFGT<br>QTYTCNVDHKPSNTKVDKTVERKCCVECPPCPAPPVAGPSVFLFPPKPKDTLMISRTPEVTCVVVDVSHEDPEVQFNW<br>YVDGMEVHNAKTKPREEQFNSTFRVVSVLTVVHQDWLNGKEYKCKVSNKGLPAPIEKTISKTKGQPREPQVYTLPPSR<br>EEMTKNQVSLTCLVKGFYPSDIAVEWESNGQPENNYKTTPPMLDSDGSFFLYSKLTVDKSRWQQGNVFSCSVMHEALH<br>NHYTQKSLSLSPGK |
| 101 | Human IgG2 constant region | IGHG2*04 | Human Heavy Chain Constant Region (IGHG2*04) Nucleotide Sequence | gcctccaccaagggcccatcggtcttccccctggcgccctgctccaggagcacctccgagagcacagcggccctgggc<br>tgcctggtcaaggactacttccccgaaccggtgacggtgtcgtggaactcaggcgctctgaccagcggcgtgcacacc<br>ttcccagctgtcctacagtcctcaggactctactccctcagcagcgtggtgaccgtgccctccagcagcttgggcacc<br>cagacctacacctgcaacgtagatcacaagcccagcaacaccaaggtggacaagacagttgagcgcaaatgttgtgtc<br>gagtgcccaccgtgcccagcaccacctgtggcaggaccgtcagtcttcctcttccccccaaaacccaaggacaccctc<br>atgatctcccggacccctgaggtcacgtgcgtggtggtggacgtgagccacgaagaccccgaggtccagttcaactgg<br>tacgtggacggcgtggaggtgcataatgccaagacaaagccacgggaggagcagttcaacagcacgttccgtgtggtc<br>agcgtcctcaccgttgtgcaccaggactggctgaacggcaaggagtacaagtgcaaggtctccaacaaaggcctccca<br>gcccccatcgagaaaaccatctccaaaaccaaagggcagccccgagaaccacaggtgtacaccctgcccccatcccgg<br>gaggagatgaccaagaaccaggtcagcctgacctgcctggtcaaaggcttctaccccagcgacatcgccgtggagtgg<br>gagagcaatgggcagccggagaacaactacaagaccacacctcccatgctggactccgacggctccttcttcctctac<br>agcaagctcaccgtggacaagagcaggtggcagcaggggaacgtcttctcatgctccgtgatgcatgaggctctgcac<br>aaccactacacgcagaagagcctctccctgtctccgggtaaa |
| 102 | | | Human Heavy Chain Constant Region (IGHG2*04) Protein Sequence | ASTKGPSVFPLAPCSRSTSESTAALGCLVKDYFPEPVTVSWNSGALTSGVHTFPAVLQSSGLYSLSSVVTVPSSSLGT<br>QTYTCNVDHKPSNTKVDKTVERKCCVECPPCPAPPVAGPSVFLFPPKPKDTLMISRTPEVTCVVVDVSHEDPEVQFNW<br>YVDGVEVHNAKTKPREEQFNSTFRVVSVLTVVHQDWLNGKEYKCKVSNKGLPAPIEKTISKTKGQPREPQVYTLPPSR<br>EEMTKNQVSLTCLVKGFYPSDIAVEWESNGQPENNYKTTPPMLDSDGSFFLYSKLTVDKSRWQQGNVFSCSVMHEALH<br>NHYTQKSLSLSPGK |
| 103 | Human IgG2 constant region | IGHG2*06 | Human Heavy Chain Constant Region (IGHG2*06) Nucleotide Sequence | GCCTCCACCAAGGGCCCATCGGTCTTCCCCCTGGCGCCCTGCTCCAGGAGCACCTCCGAGAGCACAGCGGCCCTGGGC<br>TGCCTGGTCAAGGACTACTTCCCCGAACCGGTGACGGTGTCGTGGAACTCAGGCGCTCTGACCAGCGGCGTGCACACC<br>TTCCCGGCTGTCCTACAGTCCTCAGGACTCTACTCCCTCAGCAGCGTGGTGACCGTGCCCTCCAGCAACTTCGGCACC<br>CAGACCTACACCTGCAACGTAGATCACAAGCCCAGCAACACCAAGGTGGACAAGACAGTTGAGCGCAAATGTTGTGTC<br>GAGTGCCCACCGTGCCCAGCACCACCTGTGGCAGGACCGTCAGTCTTCCTCTTCCCCCCAAAACCCAAGGACACCCTC<br>ATGATCTCCCGGACCCCTGAGGTCACGTGCGTGGTGGTGGACGTGAGCCACGAAGACCCCGAGGTCCAGTTCAACTGG |

TABLE 9-continued

Sequences
Sequences for use in the present invention.

| Seq ID No: | | | Description | Sequence |
|---|---|---|---|---|
| | | | | TACGTGGACGGCGTGGAGGTGCATAATGCCAAGACAAAGCCACGGGAGGAGCAGTTCAACAGCACGTTCCGTGTGGTC<br>AGCGTCCTCACCGTCGTGCACCAGGACTGGCTGAACGGCAAGGAGTACAAGTGCAAGGTCTCCAACAAAGGCCTCCCA<br>GCCCCCATCGAGAAAACCATCTCCAAAACCAAAGGGCAGCCCCGAGAACCACAGGTGTACACCCTGCCCCCATCCCGG<br>GAGGAGATGACCAAGAACCAGGTCAGCCTGACCTGCCTGGTCAAAGGCTTCTACCCCAGCGACATCTCCGTGGAGTGG<br>GAGAGCAATGGGCAGCCGGAGAACAACTACAAGACCACACCTCCCATGCTGGACTCCGACGGCTCCTTCTTCCTCTAC<br>AGCAAGCTCACCGTGGACAAGAGCAGGTGGCAGCAGGGGAACGTCTTCTCATGCTCCGTGATGCATGAGGCTCTGCAC<br>AACCACTACACACAGAAGAGCCTCTCCCTGTCTCCGGGTAAA |
| 104 | | | Human Heavy Chain Constant Region (IGHG2*06) Protein Sequence | ASTKGPSVFPLAPCSRSTSESTAALGCLVKDYFPEPVTVSWNSGALTSGVHTFPAVLQSSGLYSLSSVVTVPSSNFGT<br>QTYTCNVDHKPSNTKVDKTVERKCCVECPPCPAPPVAGPSVFLFPPKPKDTLMISRTPEVTCVVVDVSHEDPEVQFN<br>WYVDGVEVHNAKTKPREEQFNSTFRVVSVLTVVHQDWLNGKEYKCKVSNKGLPAPIEKTISKTKGQPREPQVYTLPPS<br>REEMTKNQVSLTCLVKGFYPSDISVEWESNGQPENNYKTTPPMLDSDGSFFLYSKLTVDKSRWQQGNVFSCSVMHEAL<br>HNHYTQKSLSLSPGK |
| 105 | Human IgG4 constant region | IGHG4*01 or IGHG4*04 | Human Heavy Chain Constant Region (IGHG4*01 or IGHG4*04) Nucleotide Sequence | gcttccaccaagggcccatccgtcttccccctggcgccctgctccaggagcacctccgagagcacagccgccctgggc<br>tgcctggtcaaggactacttccccgaaccggtgacggtgtcgtggaactcaggcgccctgaccagcggcgtgcacacc<br>ttcccggctgtcctacagtcctcaggactctactccctcagcagcgtggtgaccgtgccctccagcagcttgggcacg<br>aagacctacacctgcaacgtagatcacaagcccagcaacaccaaggtggacaagagagttgagtccaaatatggtccc<br>ccatgcccatcatgcccagcacctgagttcctggggggaccatcagtcttcctgttccccccaaaacccaaggacact<br>ctcatgatctcccggacccctgaggtcacgtgcgtggtggtggacgtgagccaggaagaccccgaggtccagttcaac<br>tggtacgtggatggcgtggaggtgcataatgccaagacaaagccgcgggaggagcagttcaacagcacgtaccgtgtg<br>gtcagcgtcctcaccgtcctgcaccaggactggctgaacggcaaggagtacaagtgcaaggtctccaacaaaggcctc<br>ccgtcctccatcgagaaaaccatctccaaagccaaagggcagccccgagagccacaggtgtacaccctgcccccatcc<br>caggaggagatgaccaagaaccaggtcagcctgacctgcctggtcaaaggcttctaccccagcgacatcgccgtggag<br>tgggagagcaatgggcagccggagaacaactacaagaccacgcctcccgtgctggactccgacggctccttcttcctc<br>tacagcaggctaaccgtggacaagagcaggtggcaggaggggaatgtcttctcatgctccgtgatgcatgaggctctg<br>cacaaccactacacacagaagagcctctccctgtctctgggtaaa |
| 106 | | | Human Heavy Chain Constant Region (IGHG4*01) Protein Sequence (P01861) | ASTKGPSVFPLAPCSRSTSESTAALGCLVKDYFPEPVTVSWNSGALTSGVHTFPAVLQSSGLYSLSSVVTVPSSSLGT<br>KTYTCNVDHKPSNTKVDKRVESKYGPPCPSCPAPEFLGGPSVFLFPPKPKDTLMISRTPEVTCVVVDVSQEDPEVQFN<br>WYVDGVEVHNAKTKPREEQFNSTYRVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSRLTVDKSRWQEGNVFSCSVMHEAL<br>HNHYTQKSLSLSLGK |
| 107 | Human IgG4 constant region | IGHG4*02 | Human Heavy Chain Constant Region (IGHG4*02) Nucleotide Sequence | gcttccaccaagggcccatccgtcttccccctggcgccctgctccaggagcacctccgagagcacagccgccctgggc<br>tgcctggtcaaggactacttccccgaaccggtgacggtgtcgtggaactcaggcgccctgaccagcggcgtgcacacc<br>ttcccggctgtcctacagtcctcaggactctactccctcagcagcgtggtgaccgtgccctccagcagcttgggcacg<br>aagacctacacctgcaacgtagatcacaagcccagcaacaccaaggtggacaagagagttgagtccaaatatggtccc<br>ccgtgcccatcatgcccagcacctgagttcctggggggaccatcagtcttcctgttccccccaaaacccaaggacact<br>ctcatgatctcccggacccctgaggtcacgtgcgtggtggtggacgtgagccaggaagaccccgaggtccagttcaac<br>tggtacgtggatggcgtggaggtgcataatgccaagacaaagccgcgggaggagcagttcaacagcacgtaccgtgtg<br>gtcagcgtcctcaccgtcgtgcaccaggactggctgaacggcaaggagtacaagtgcaaggtctccaacaaaggcctc<br>ccgtcctccatcgagaaaaccatctccaaagccaaagggcagccccgagagccacaggtgtacaccctgcccccatcc<br>caggaggagatgaccaagaaccaggtcagcctgacctgcctggtcaaaggcttctaccccagcgacatcgccgtggag<br>tgggagagcaatgggcagccggagaacaactacaagaccacgcctcccgtgctggactccgacggctccttcttcctc<br>tacagcaggctaaccgtggacaagagcaggtggcaggaggggaatgtcttctcatgctccgtgatgcatgaggctctg<br>cacaaccactacacgcagaagagcctctccctgtctctgggtaaa |
| 108 | | | Human Heavy Chain Constant Region (IGHG4*02) Protein | ASTKGPSVFPLAPCSRSTSESTAALGCLVKDYFPEPVTVSWNSGALTSGVHTFPAVLQSSGLYSLSSVVTVPSSSLGT<br>KTYTCNVDHKPSNTKVDKRVESKYGPPCPSCPAPEFLGGPSVFLFPPKPKDTLMISRTPEVTCVVVDVSQEDPEVQFN |

TABLE 9-continued

Sequences
Sequences for use in the present invention.

| Seq ID No: | | | Description | Sequence |
|---|---|---|---|---|
| | | | Sequence | WYVDGVEVHNAKTKPREEQFNSTYRVVSVLTVVHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSRLTVDKSRWQEGNVFSCSVMHEAL<br>HNHYTQKSLSLSLGK |
| 109 | Human IgG4 constant region | IGHG4*03 | Human Heavy Chain Constant Region (IGHG4*03) Nucleotide Sequence | gcttccaccaagggcccatccgtcttccccctggcgccctgctccaggagcacctccgagagcacagccgccctgggc<br>tgcctggtcaaggactacttccccgaaccggtgacggtgtcgtggaactcaggcgccctgaccagcggcgtgcacacc<br>ttcccggctgtcctacagtcctcaggactctactccctcagcagcgtggtgaccgtgccctccagcagcttgggcacg<br>aagacctacacctgcaacgtagatcacaagcccagcaacaccaaggtggacaagagagttgagtccaaatatggtccc<br>ccatgcccatcatgcccagcacctgagttcctggggggaccatcagtcttcctgttccccccaaaacccaaggacact<br>ctcatgatctcccggacccctgaggtcacgtgcgtggtggtggacgtgagccaggaagaccccgaggtccagttcaac<br>tggtacgtggatggcgtggaggtgcataatgccaagacaaagccgcgggaggagcagttcaacagcacgtaccgtgtg<br>gtcagcgtcctcaccgtcctgcaccaggactggctgaacggcaaggagtacaagtgcaaggtctccaacaaaggcctc<br>ccgtcctccatcgagaaaaccatctccaaagccaaagggcagccccgagagccacaggtgtacaccctgcccccatcc<br>caggaggagatgaccaagaaccaggtcagcctgacctgcctggtcaaaggcttctaccccagcgacatcgccgtggag<br>tgggagagcaatgggcagccggagaacaactacaagaccacgcctcccgtgctggactccgacggctccttcttcctc<br>tacagcaagctcaccgtggacaagagcaggtggcaggaggggaacgtcttctcatgctccgtgatgcatgaggctctg<br>cacaaccactacacgcagaagagcctctccctgtctctgggtaaa |
| 110 | | | Human Heavy Chain Constant Region (IGHG4*03) Protein Sequence | ASTKGPSVFPLAPCSRSTSESTAALGCLVKDYFPEPVTVSWNSGALTSGVHTFPAVLQSSGLYSLSSVVTVPSSSLGT<br>KTYTCNVDHKPSNTKVDKRVESKYGPPCPSCPAPEFLGGPSVFLFPPKPKDTLMISRTPEVTCVVVDVSQEDPEVQFN<br>WYVDGVEVHNAKTKPREEQFNSTYRVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSKLTVDKSRWQEGNVFSCSVMHEAL<br>HNHYTQKSLSLSLGK |
| 111 | Human IgG4-PE constant region | IGHG4-PE | Human Heavy Chain Constant Region (IGHG4-PE) Nucleotide Sequence Version A | gcctccaccaagggcccatccgtcttccccctggcgccctgctccaggagcacctccgagagcacggccgccctgggc<br>tgcctggtcaaggactacttccccgaaccagtgacggtgtcgtggaactcaggcgccctgaccagcggcgtgcacacc<br>ttcccggctgtcctacagtcctcaggactctactccctcagcagcgtggtgaccgtgccctccagcagcttgggcacg<br>aagacctacacctgcaacgtagatcacaagcccagcaacaccaaggtggacaagagagttgagtccaaatatggtccc<br>ccatgcccaccatgcccagcgcctgaatttgaggggggaccatcagtcttcctgttccccccaaaacccaaggacact<br>ctcatgatctcccggacccctgaggtcacgtgcgtggtggtggacgtgagccaggaagaccccgaggtccagttcaac<br>tggtacgtggatggcgtggaggtgcataatgccaagacaaagccgcgggaggagcagttcaacagcacgtaccgtgtg<br>gtcagcgtcctcaccgtcctgcaccaggactggctgaacggcaaggagtacaagtgcaaggtctccaacaaaggcctc<br>ccgtcatcgatcgagaaaaccatctccaaagccaaagggcagccccgagagccacaggtgtacaccctgcccccatcc<br>caggaggagatgaccaagaaccaggtcagcctgacctgcctggtcaaaggcttctaccccagcgacatcgccgtggag<br>tgggagagcaatgggcagccggagaacaactacaagaccacgcctcccgtgctggactccgacggatccttcttcctc<br>tacagcaggctaaccgtggacaagagcaggtggcaggaggggaatgtcttctcatgctccgtgatgcatgaggctctg<br>cacaaccactacacacagaagagcctctccctgtctctgggtaaa |
| 112 | | | Human Heavy Chain Constant Region (IGHG4-PE) Nucleotide Sequence Version B | gcctccaccaagggacctagcgtgttccctctcgccccctgttccaggtccacaagcgagtccaccgctgccctcggc<br>tgtctggtgaaagactactttcccgagcccgtgaccgtctcctggaatagcggagccctgacctccggcgtgcacaca<br>tttcccgccgtgctgcagagcagcggactgtatagcctgagcagcgtggtgaccgtgcccagctccagcctcggcacc<br>aaaacctacacctgcaacgtggaccacaagccctccaacaccaaggtggacaagcgggtggagagcaagtacggcccc<br>ccttgccctccttgtcctgcccctgagttcgagggaggaccctccgtgttcctgtttccccccaaacccaaggacacc<br>ctgatgatctcccggacacccgaggtgacctgtgtggtcgtggacgtcagccaggaggaccccgaggtgcagttcaac<br>tggtatgtggacggcgtggaggtgcacaatgccaaaaccaagcccagggaggagcagttcaattccacctacagggtg<br>gtgagcgtgctgaccgtcctgcatcaggattggctgaacggcaaggagtacaagtgcaaggtgtccaacaagggactg<br>cccagctccatcgagaagaccatcagcaaggctaagggccagccgagggagccccaggtgtataccctgcctcctagc<br>caggaagagatgaccaagaaccaagtgtccctgacctgcctggtgaagggattctacccctccgacatcgccgtggag<br>tgggagagcaatggccagcccgagaacaactacaaaacaacccctcccgtgctcgatagcgacggcagcttctttctc |

TABLE 9-continued

Sequences
Sequences for use in the present invention.

| Seq ID No: | | | Description | Sequence |
|---|---|---|---|---|
| | | | | tacagccggctgacagtggacaagagcaggtggcaggagggcaacgtgttctcctgttccgtgatgcacgaggccctg<br>cacaatcactacacccagaagagcctctccctgtccctgggcaag |
| 113 | | | Human Heavy Chain Constant Region (IGHG4-PE) Nucleotide Sequence Version C | gccagcaccaagggcccttccgtgttcccccctggccccttgcagcaggagcacctccgaatccacagctgccctgggc<br>tgtctggtgaaggactactttcccgagcccgtgaccgtgagctggaacagcggcgctctgacatccggcgtccacacc<br>tttcctgccgtcctgcagtcctccggcctctactccctgtcctccgtggtgaccgtgcctagctcctccctcggcacc<br>aagacctacacctgtaacgtggaccacaaaccctccaacaccaaggtggacaaacgggtcgagagcaagtacggccct<br>ccctgccctccttgtcctgcccccgagttcgaaggcggacccagcgtgttcctgttccctcctaagcccaaggacacc<br>ctcatgatcagccggacacccgaggtgacctgcgtggtggtggatgtgagccaggaggaccctgaggtccagttcaac<br>tggtatgtggatggcgtggaggtgcacaacgccaagacaaagccccgggaagagcagttcaactccacctacagggtg<br>gtcagcgtgctgaccgtgctgcatcaggactggctgaacggcaaggagtacaagtgcaaggtcagcaataagggactg<br>cccagcagcatcgagaagaccatctccaaggctaaaggccagccccgggaacctcaggtgtacaccctgcctcccagc<br>caggaggagatgaccaagaaccaggtgagcctgacctgcctggtgaagggattctacccttccgacatcgccgtggag<br>tgggagtccaacggccagcccgagaacaattataagaccacccctcccgtcctcgacagcgacggatccttctttctg<br>tactccaggctgaccgtggataagtccaggtggcaggaaggcaacgtgttcagctgctccgtgatgcacgaggccctg<br>cacaatcactacacccagaagtccctgagcctgtccctgggaaag |
| 114 | | | Human Heavy Chain Constant Region (IGHG4-PE) Protein Sequence (Amino acid substitution shown in BOLD) | ASTKGPSVFPLAPCSRSTSESTAALGCLVKDYFPEPVTVSWNSGALTSGVHTFPAVLQSSGLYSLSSVVTVPSSSLGT<br>KTYTCNVDHKPSNTKVDKRVESKYGPPCP**P**CPAPEF**E**GGPSVFLFPPKPKDTLMISRTPEVTCVVVDVSQEDPEVQFN<br>WYVDGVEVHNAKTKPREEQFNSTYRVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSRLTVDKSRWQEGNVFSCSVMHEAL<br>HNHYTQKSLSLSLGK |
| 115 | Inactivated Human IgG4 constant region | Inactivated IGHG4 | Inactivated Human Heavy Chain Constant Region (IGHG4) Nucleotide Sequence | gcctccaccaagggcccatccgtcttcccccctggcgccctgctccaggagcacctccgagagcacggccgccctgggc<br>tgcctggtcaaggactacttccccgaaccagtgacggtgtcgtggaactcaggcgccctgaccagcggcgtgcacacc<br>ttcccggctgtcctacagtcctcaggactctactccctcagcagcgtggtgaccgtgccctccagcagcttgggcacg<br>aagacctacacctgcaacgtagatcacaagcccagcaacaccaaggtggacaagagagttgagtccaaatatggtccc<br>ccatgcccaccatgcccagcgcctccagttgcgggggggaccatcagtcttcctgttccccccaaaacccaaggacact<br>ctcatgatctcccggacccctgaggtcacgtgcgtggtggtggacgtgagccaggaagaccccgaggtccagttcaac<br>tggtacgtggatggcgtggaggtgcataatgccaagacaaagccgcgggaggagcagttcaacagcacgtaccgtgtg<br>gtcagcgtcctcaccgtcctgcaccaggactggctgaacggcaaggagtacaagtgcaaggtctccaacaaaggcctc<br>ccgtcatcgatcgagaaaaccatctccaaagccaaagggcagccccgagagccacaggtgtacaccctgcccccatcc<br>caggaggagatgaccaagaaccaggtcagcctgacctgcctggtcaaaggcttctaccccagcgacatcgccgtggag<br>tgggagagcaatgggcagccggagaacaactacaagaccacgcctcccgtgctggactccgacggatccttcttcctc<br>tacagcaggctaaccgtggacaagagcaggtggcaggaggggaatgtcttctcatgctccgtgatgcatgaggctctg<br>cacaaccactacacacagaagagcctctccctgtctctgggtaaa |
| 116 | | | Inactivated Human Heavy Chain Constant Region (IGHG4) Protein Sequence (inactivating mutations from human IgG4 shown in bold) | ASTKGPSVFPLAPCSRSTSESTAALGCLVKDYFPEPVTVSWNSGALTSGVHTFPAVLQSSGLYSLSSVVTVPSSSLGT<br>KTYTCNVDHKPSNTKVDKRVESKYGPPCP**P**CPAP**PVA**GGPSVFLFPPKPKDTLMISRTPEVTCVVVDVSQEDPEVQFN<br>WYVDGVEVHNAKTKPREEQFNSTYRVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYSRLTVDKSRWQEGNVFSCSVMHEAL<br>HNHYTQKSLSLSLGK |
| 117 | Human Cκ constant region | IGKC*01 | Human Cκ Light Chain Constant Region (IGKC*01) Nucleotide Sequence | cgtacggtggccgctccctccgtgttcatcttcccaccttccgacgagcagctgaagtccggcaccgcttctgtcgtg<br>tgcctgctgaacaacttctacccccgcgaggccaaggtgcagtggaaggtggacaacgccctgcagtccggcaactcc<br>caggaatccgtgaccgagcaggactccaaggacagcacctactccctgtcctccaccctgaccctgtccaaggccgac<br>tacgagaagcacaaggtgtacgcctgcgaagtgacccaccagggcctgtctagccccgtgaccaagtctttcaaccgg<br>ggcgagtgt |
| 118 | | | Cκ Light Chain Constant Region (IGKC*01) Amino Acid Sequence | RTVAAPSVFIFPPSDEQLKSGTASVVCLLNNFYPREAKVQWKVDNALQSGNSQESVTEQDSKDSTYSLSSTLTLSKAD<br>YEKHKVYACEVTHQGLSSPVTKSFNRGEC |

TABLE 9-continued

Sequences
Sequences for use in the present invention.

| Seq ID No: | | | Description | Sequence |
|---|---|---|---|---|
| 119 | Human Cκ constant region | IGKC*02 | Cκ Light Chain Constant Region (IGKC*02) Nucleotide Sequence | cgaactgtggctgcaccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggagagcaaggacagcacctacagcctcagcagcaccctgacgctgagcaaagcagactacgagaaacacaaagtctacgccggcgaagtcacccatcagggcctgagctcgcccgtcacaaagagcttcaacaggggagagtgt |
| 120 | | | Cκ Light Chain Constant Region (IGKC*02) Amino Acid Sequence | RTVAAPSVFIFPPSDEQLKSGTASVVCLLNNFYPREAKVQWKVDNALQSGNSQESVTEQESKDSTYSLSSTLTLSKADYEKHKVYAGEVTHQGLSSPVTKSFNRGEC |
| 121 | Human Cκ constant region | IGKC*03 | Cκ Light Chain Constant Region (IGKC*03) Nucleotide Sequence | cgaactgtggctgcaccatctgtcttcatcttcccgccatctgatgagcagttgaaatctggaactgcctctgttgtgtgcctgctgaataacttctatcccagagaggccaaagtacagcggaaggtggataacgccctccaatcgggtaactcccaggagagtgtcacagagcaggagagcaaggacagcacctacagcctcagcagcaccctgacgctgagcaaagcagactacgagaaacacaaagtctacgcctgcgaagtcacccatcagggcctgagctcgcccgtcacaaagagcttcaacaggggagagtgt |
| 122 | | | Cκ Light Chain Constant Region (IGKC*03) Amino Acid Sequence | RTVAAPSVFIFPPSDEQLKSGTASVVCLLNNFYPREAKVQRKVDNALQSGNSQESVTEQESKDSTYSLSSTLTLSKADYEKHKVYACEVTHQGLSSPVTKSFNRGEC |
| 123 | Human Cκ constant region | IGKC*04 | Cκ Light Chain Constant Region (IGKC*04) Nucleotide Sequence | cgaactgtggctgcaccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggacagcaaggacagcacctacagcctcagcagcaccctgacgctgagcaaagcagactacgagaaacacaaactctacgcctgcgaagtcacccatcagggcctgagctcgcccgtcacaaagagcttcaacaggggagagtgt |
| 124 | | | Cκ Light Chain Constant Region (IGKC*04) Amino Acid Sequence | RTVAAPSVFIFPPSDEQLKSGTASVVCLLNNFYPREAKVQWKVDNALQSGNSQESVTEQDSKDSTYSLSSTLTLSKADYEKHKLYACEVTHQGLSSPVTKSFNRGEC |
| 125 | Human Cκ constant region | IGKC*05 | Cκ Light Chain Constant Region (IGKC*05) Nucleotide Sequence | cgaactgtggctgcaccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggacagcaaggacagcacctacagcctcagcaacaccctgacgctgagcaaagcagactacgagaaacacaaagtctacgcctgcgaagtcacccatcagggcctgagctcgcccgtcacaaagagcttcaacaggggagagtgc |
| 126 | | | Cκ Light Chain Constant Region (IGKC*05) Amino Acid Sequence | RTVAAPSVFIFPPSDEQLKSGTASVVCLLNNFYPREAKVQWKVDNALQSGNSQESVTEQDSKDSTYSLSNTLTLSKADYEKHKVYACEVTHQGLSSPVTKSFNRGEC |
| 127 | Human Cλ constant region | IGLC1*01 | Cλ Light Chain Constant Region (IGLC1*01) Nucleotide Sequence (ENST00000390321.2) | cccaaggccaaccccacggtcactctgttcccgccctcctctgaggagctccaagccaacaaggccacactagtgtgtctgatcagtgacttctacccgggagctgtgacagtggcttggaaggcagatggcagccccgtcaaggcgggagtggagacgaccaaaccctccaaacagagcaacaacaagtacgcggccagcagctacctgagcctgacgcccgagcagtggaagtcccacagaagctacagctgccaggtcacgcatgaagggagcaccgtggagaagacagtggcccctacagaatgttca |
| 128 | | | Cλ Light Chain Constant Region (IGLC1*01) Amino Acid Sequence (A0A075B6K8) | PKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS |
| 129 | Human Cλ constant region | IGLC1*02 | Cλ Light Chain Constant Region (IGLC1*02) Nucleotide Sequence Version A | ggtcagcccaaggccaaccccactgtcactctgttcccgccctcctctgaggagctccaagccaacaaggccacactagtgtgtctgatcagtgacttctacccgggagctgtgacagtggcctggaaggcagatggcagccccgtcaaggcgggagtggagaccaccaaaccctccaaacagagcaacaacaagtacgcggccagcagctacctgagcctgacgcccgagcagtggaagtcccacagaagctacagctgccaggtcacgcatgaagggagcaccgtggagaagacagtggcccctacagaatgttca |

TABLE 9-continued

Sequences
Sequences for use in the present invention.

| Seq ID No: | | | Description | Sequence |
|---|---|---|---|---|
| 130 | | | Cλ Light Chain Constant Region (IGLC1*02) Nucleotide Sequence Version B | ggtcagcccaaggccaaccccactgtcactctgttcccgccctcctctgaggagctccaagccaacaaggccacacta gtgtgtctgatcagtgacttctacccgggagctgtgacagtggcctggaaggcagatggcagccccgtcaaggcggga gtggagaccaccaaaccctccaaacagagcaacaacaagtacgcggccagcagctacctgagcctgacgcccgagcag tggaagtcccacagaagctacagctgccaggtcacgcatgaagggagcaccgtggagaagacagtggcccctacagaa tgttca |
| 131 | | | Cλ Light Chain Constant Region (IGLC1*02) Amino Acid Sequence | GQPKANPTVTLFPPSSEELQANKATLVCLISDFYPGAVTVAWKADGSPVKAGVETTKPSKQSNNKYAASSYLSLTPEQ WKSHRSYSCQVTHEGSTVEKTVAPTECS |
| 132 | Human Cλ constant region | IGLC2*01 | Cλ Light Chain Constant Region (IGLC2*01) Nucleotide Sequence Version A | ggccagcctaaggccgctccttctgtgaccctgttcccccatcctccgaggaactgcaggctaacaaggccaccctc gtgtgcctgatcagcgacttctaccctggcgccgtgaccgtggcctggaaggctgatagctctcctgtgaaggccggc gtggaaaccaccaccccttccaagcagtccaacaacaaatacgccgcctcctcctacctgtccctgacccctgagcag tggaagtcccaccggtcctacagctgccaagtgacccacgagggctccaccgtggaaaagaccgtggctcctaccgag tgctcc |
| 133 | | | Cλ Light Chain Constant Region (IGLC2*01) Nucleotide Sequence Version B | ggccagcctaaagctgcccccagcgtcaccctgtttcctccctccagcgaggagctccaggccaacaaggccaccctc gtgtgcctgatctccgacttctatcccggcgctgtgaccgtggcttggaaagccgactccagccctgtcaaagccggc gtggagaccaccacaccctccaagcagtccaacaacaagtacgccgcctccagctatctctccctgacccctgagcag tggaagtcccaccggtcctactcctgtcaggtgacccacgagggctccaccgtggaaaagaccgtcgcccccaccgag tgctcc |
| 134 | | | Cλ Light Chain Constant Region (IGLC1*02) Amino Acid Sequence | GQPKAAPSVTLFPPSSEELQANKATLVCLISDFYPGAVTVAWKADSSPVKAGVETTTPSKQSNNKYAASSYLSLTPEQ WKSHRSYSCQVTHEGSTVEKTVAPTECS |
| 135 | Human Cλ constant region | IGLC2*02 or IGLC2*03 | Cλ Light Chain Constant Region (IGLC2*02 or IGLC2*03) Nucleotide Sequence | ggtcagcccaaggctgccccctcggtcactctgttcccgccctcctctgaggagcttcaagccaacaaggccacactg gtgtgtctcataagtgacttctacccgggagccgtgacagtggcctggaaggcagatagcagccccgtcaaggcggga gtggagaccaccacaccctccaaacaaagcaacaacaagtacgcggccagcagctatctgagcctgacgcctgagcag tggaagtcccacagaagctacagctgccaggtcacgcatgaagggagcaccgtggagaagacagtggcccctacagaa tgttca |
| 136 | | | Cλ Light Chain Constant Region (IGLC2*02) Amino Acid Sequence | GQPKAAPSVTLFPPSSEELQANKATLVCLISDFYPGAVTVAWKADSSPVKAGVETTTPSKQSNNKYAASSYLSLTPEQ WKSHRSYSCQVTHEGSTVEKTVAPTECS |
| 137 | Human Cλ constant region | IGLC3*01 | Cλ Light Chain Constant Region (IGLC3*01) Nucleotide Sequence | cccaaggctgccccctcggtcactctgttcccaccctcctctgaggagcttcaagccaacaaggccacactggtgtgt ctcataagtgacttctacccgggagccgtgacagttgcctggaaggcagatagcagccccgtcaaggcgggggtggag accaccacaccctccaaacaaagcaacaacaagtacgcggccagcagctacctgagcctgacgcctgagcagtggaag tcccacaaaagctacagctgccaggtcacgcatgaagggagcaccgtggagaagacagttgcccctacggaatgttca |
| 138 | | | Cλ Light Chain Constant Region IGLC3*01) Amino Acid Sequence | PKAAPSVTLFPPSSEELQANKATLVCLISDFYPGAVTVAWKADSSPVKAGVETTTPSKQSNNKYAASSYLSLTPEQWK SHKSYSCQVTHEGSTVEKTVAPTECS |
| 139 | Human Cλ constant region | IGLC3*02 | Cλ Light Chain Constant Region (IGLC3*02) Nucleotide Sequence | ggtcagcccaaggctgccccctcggtcactctgttcccaccctcctctgaggagcttcaagccaacaaggccacactg gtgtgtctcataagtgacttctacccggggccagtgacagttgcctggaaggcagatagcagccccgtcaaggcgggg gtggagaccaccacaccctccaaacaaagcaacaacaagtacgcggccagcagctacctgagcctgacgcctgagcag tggaagtcccacaaaagctacagctgccaggtcacgcatgaagggagcaccgtggagaagacagtggcccctacggaa tgttca |

TABLE 9-continued

Sequences
Sequences for use in the present invention.

| Seq ID No: | | | Description | Sequence |
|---|---|---|---|---|
| 140 | | | Cλ Light Chain Constant Region (IGLC1*02) Amino Acid Sequence | GQPKAAPSVTLFPPSSEELQANKATLVCLISDFYPGPVTVAWKADSSPVKAGVETTTPSKQSNNKYAASSYLSLTPEQ<br>WKSHKSYSCQVTHEGSTVEKTVAPTECS |
| 141 | Human Cλ constant region | IGLC3*03 | Cλ Light Chain Constant Region (IGLC3*03) Nucleotide Sequence | ggtcagcccaaggctgccccctcggtcactctgttcccaccctcctctgaggagcttcaagccaacaaggccacactg<br>gtgtgtctcataagtgacttctacccgggagccgtgacagtggcctggaaggcagatagcagccccgtcaaggcggga<br>gtggagaccaccacaccctccaaacaaagcaacaacaagtacgcggccagcagctacctgagcctgacgcctgagcag<br>tggaagtcccacaaaagctacagctgccaggtcacgcatgaagggagcaccgtggagaagacagtggcccctacagaa<br>tgttca |
| 142 | | | Cλ Light Chain Constant Region (IGLC3*03) Amino Acid Sequence | GQPKAAPSVTLFPPSSEELQANKATLVCLISDFYPGAVTVAWKADSSPVKAGVETTTPSKQSNNKYAASSYLSLTPEQ<br>WKSHKSYSCQVTHEGSTVEKTVAPTECS |
| 143 | Human Cλ constant region | IGLC3*04 | Cλ Light Chain Constant Region (IGLC3*04) Nucleotide Sequence | ggtcagcccaaggctgccccctcggtcactctgttcccgccctcctctgaggagcttcaagccaacaaggccacactg<br>gtgtgtctcataagtgacttctacccgggagccgtgacagtggcctggaaggcagatagcagccccgtcaaggcggga<br>gtggagaccaccacaccctccaaacaaagcaacaacaagtacgcggccagcagctacctgagcctgacgcctgagcag<br>tggaagtcccacagaagctacagctgccaggtcacgcatgaagggagcaccgtggagaagacagtggcccctacagaa<br>tgttca |
| 144 | | | Cλ Light Chain Constant Region (IGLC3*04) Amino Acid Sequence | GQPKAAPSVTLFPPSSEELQANKATLVCLISDFYPGAVTVAWKADSSPVKAGVETTTPSKQSNNKYAASSYLSLTPEQ<br>WKSHRSYSCQVTHEGSTVEKTVAPTECS |
| 145 | Human Cλ constant region | IGLC6*01 | Cλ Light Chain Constant Region (IGLC6*01) Nucleotide Sequence | ggtcagcccaaggctgccccatcggtcactctgttcccgccctcctctgaggagcttcaagccaacaaggccacactg<br>gtgtgcctgatcagtgacttctacccgggagctgtgaaagtggcctggaaggcagatggcagccccgtcaacacggga<br>gtggagaccaccacaccctccaaacagagcaacaacaagtacgcggccagcagctacctgagcctgacgcctgagcag<br>tggaagtcccacagaagctacagctgccaggtcacgcatgaagggagcaccgtggagaagacagtggcccctgcagaa<br>tgttca |
| 146 | | | Cλ Light Chain Constant Region (IGLC6*01) Amino Acid Sequence | GQPKAAPSVTLFPPSSEELQANKATLVCLISDFYPGAVKVAWKADGSPVNTGVETTTPSKQSNNKYAASSYLSLTPEQ<br>WKSHRSYSCQVTHEGSTVEKTVAPAECS |
| 147 | Human Cλ constant region | IGLC7*01 or IGLC7*02 | Cλ Light Chain Constant Region (IGLC7*01 or IGLC7*02) Nucleotide Sequence | ggtcagcccaaggctgccccatcggtcactctgttcccaccctcctctgaggagcttcaagccaacaaggccacactg<br>gtgtgtctcgtaagtgacttctacccgggagccgtgacagtggcctggaaggcagatggcagccccgtcaaggtggga<br>gtggagaccaccaaaccctccaaacaaagcaacaacaagtatgcggccagcagctacctgagcctgacgcccgagcag<br>tggaagtcccacagaagctacagctgccgggtcacgcatgaagggagcaccgtggagaagacagtggcccctgcagaa<br>tgctct |
| 148 | | | Cλ Light Chain Constant Region (IGLC7*01) Amino Acid Sequence | GQPKAAPSVTLFPPSSEELQANKATLVCLVSDFYPGAVTVAWKADGSPVKVGVETTKPSKQSNNKYAASSYLSLTPEQ<br>WKSHRSYSCRVTHEGSTVEKTVAPAECS |
| 149 | Human Cλ constant region | IGLC7*03 | Cλ Light Chain Constant Region (IGLC7*03) Nucleotide Sequence | GGTCAGCCCAAGGCTGCCCCCTCGGTCACTCTGTTCCCACCCTCCTCTGAGGAGCTTCAAGCCAACAAGGCCACACTG<br>GTGTGTCTCGTAAGTGACTTCAACCCGGGAGCCGTGACAGTGGCCTGGAAGGCAGATGGCAGCCCCGTCAAGGTGGGA<br>GTGGAGACCACCAAACCCTCCAAACAAAGCAACAACAAGTATGCGGCCAGCAGCTACCTGAGCCTGACGCCCGAGCAG<br>TGGAAGTCCCACAGAAGCTACAGCTGCCGGGTCACGCATGAAGGGAGCACCGTGGAGAAGACAGTGGCCCCTGCAGAA<br>TGCTCT |

TABLE 10

| GENE SEGMENT USAGE | | | | | | | |
|---|---|---|---|---|---|---|---|
| Antibody ID | IGH V gene | IGH D gene | IGH J gene | CDRH3 length (IMGT) | IGL V gene | IGL J gene | CDRL3 length (IMGT) |
| G09 | IGHV3-15*01 | IGHD3-9*01 | IGHJ6*02 | 20 | IGKV1D-39*01 | IGKJ4*01 | 13 |
| F05 | IGHV3-23*04 | IGHD3-9*01 | IGHJ5*02 | 18 | IGKV3-11*01 | IGKJ4*01 | 9 |
| C02 | IGHV3-23*04 | IGHD3-10*01 | IGHJ4*02 | 15 | IGKV1-16*02 | IGKJ4*01 | 9 |
| E04 | IGHV3-15*01 | IGH6-19*01 | IGHJ4*02 | 11 | IGKV1-5*03 | IGKJ1*01 | 9 |

The invention claimed is:

1. An antibody or fragment thereof which specifically binds to CD7 (Cluster of Differentiation 7) comprising:

(a) a VH domain which comprises a CDRH1 sequence identical to the amino acid sequence of SEQ ID NO: 1, a CDRH2 sequence identical to the amino acid sequence of SEQ ID NO: 2, and a CDRH3 sequence identical to the amino acid sequence of SEQ ID NO: 3; and a VL domain comprising a CDRL1 sequence identical to the amino acid sequence of SEQ ID NO: 11, a CDRL2 sequence identical to the amino acid sequence of SEQ ID NO: 12, and a CDRL3 sequence identical to the amino acid sequence of SEQ ID NO: 13, wherein the CDRH1, CDRH2, CDRH3, CDRL1, CDRL2 and CDRL3 sequences are defined according to the IMGT system; or (b) a VH domain which comprises a CDRH1 sequence identical to the amino acid sequence of SEQ ID NO: 4, a CDRH2 sequence identical to the amino acid sequence of SEQ ID NO: 5, and a CDRH3 identical to comprising the amino acid sequence of SEQ ID NO: 6; and a VL domain comprising a CDRL1 sequence identical to the amino acid sequence of SEQ ID NO: 14, a CDRL2 sequence identical to the amino acid sequence of SEQ ID NO: 15, and a CDRL3 sequence identical to the amino acid sequence of SEQ ID NO: 16, wherein the CDRH1, CDRH2, CDRH3, CDRL1, CDRL2 and CDRL3 sequences are defined according to the Kabat system.

2. The antibody or fragment of claim 1, wherein the VH domain comprises the amino acid sequence of SEQ ID NO: 7 or an amino acid sequence that is at least 70% identical thereto.

3. The antibody or fragment according to claim 1, wherein the VH domain comprises the amino acid sequence of SEQ ID NO: 7 and the VL domain comprises the amino acid sequence of SEQ ID NO: 17.

4. The antibody or fragment according to claim 1, which comprises (a) a heavy chain comprising the amino acid sequence of SEQ ID NO: 9 or an amino acid sequence that is at least 70% identical thereto; and/or (b) a light chain comprising the amino acid sequence of SEQ ID NO: 19 or an amino acid sequence that is at least 70% identical thereto.

5. The antibody or fragment according to claim 1, wherein the VL domain comprises the amino acid sequence of SEQ ID NO: 17 or an amino acid sequence that is at least 70% identical thereto.

6. The antibody or fragment according to claim 1, wherein the antibody or fragment comprises a human constant region that comprises the amino acid sequence of SEQ ID NO: 88, 90, 92, 94 or 96.

7. The antibody or fragment according to claim 1, further comprising an antigen-binding site that specifically binds another target antigen.

8. A pharmaceutical composition comprising the antibody or fragment as defined in claim 1 and a pharmaceutically acceptable excipient, diluent or carrier.

9. A method for treating a CD7-positive cancer in a subject, comprising administering the anti-CD7 antibody or fragment of claim 1 to the subject.

10. The method of claim 9, wherein the CD7-positive cancer is selected from a leukaemia, a lymphoma, a blood cancer and a myelodysplastic syndrome (MDS).

11. The method of claim 9, wherein the antibody or fragment is administered to the subject simultaneously or sequentially with chemotherapy or an immune checkpoint inhibitor.

12. A combination comprising the anti-CD7 antibody or fragment of claim 1 and a chemotherapeutic.

13. A method of treating a CD7-positive_leukaemia in a human comprising administering the anti-CD7 antibody or fragment of claim 1, wherein the antibody, fragment is administered to the human with an antagonist of human CD5, CD14 or CD19.

14. A nucleic acid that
a) comprises the nucleotide sequence of SEQ ID NO: 10; and the nucleotide sequence of SEQ ID NO: 20;
b) encodes a heavy chain and a light chain of an antibody or fragment as defined in claim 1; or
c) encodes (i) a heavy chain comprising the amino acid sequence of SEQ ID NO: 7 and (ii) a light chain comprising the amino acid sequence of SEQ ID NO: 17.

15. A host cell comprising the nucleic of claim 14.

16. A method of diagnosing a CD7-positive cancer in a subject, the method comprising combining the antibody or fragment of claim 1 with an isolated blood or serum sample and determining that cells comprised by the sample are specifically bound by the antibody or fragment.

17. An in vitro assay for detecting CD7-positive cells in a sample, the assay comprising combining the antibody or fragment of claim 1 with an isolated blood or serum sample and determining that cells comprised by the sample are specifically bound by the antibody or fragment.

18. The antibody or fragment according to claim 1, wherein the antibody or fragment comprises a constant region that enables an effector function.

19. The antibody or fragment according to claim 1, wherein the antibody or fragment comprises a human constant region that comprises the amino acid sequence of SEQ ID NO: 88.

20. The antibody or fragment according to claim 1, wherein the antibody or fragment comprises an IgG1 constant region.

21. The antibody or fragment of claim 20, wherein the constant region comprises a glycine at position 430, an arginine at position 356 and/or an arginine at position 357 (according to EU numbering).

22. The antibody or fragment of claim 20, wherein the constant region comprises a glycine at position 430 (according to EU numbering).

* * * * *